US012807731B2

(12) United States Patent
Waldenström et al.

(10) Patent No.: US 12,807,731 B2
(45) Date of Patent: Nov. 24, 2026

(54) METHOD AND COMPOUND FOR PROSTATE CANCER DIAGNOSIS

(71) Applicant: PROSMEDIC SWEDEN AB, Stockholm (SE)

(72) Inventors: Anders Waldenström, Stockholm (SE); Anders Larsson, Uppsala (SE)

(73) Assignee: PROSMEDIC SWEDEN AB, Stockholm (SE)

( * ) Notice: Subject to any disclaimer, the term of this patent is extended or adjusted under 35 U.S.C. 154(b) by 1003 days.

(21) Appl. No.: 17/908,291

(22) PCT Filed: Mar. 1, 2021

(86) PCT No.: PCT/EP2021/055061
§ 371 (c)(1),
(2) Date: Aug. 31, 2022

(87) PCT Pub. No.: WO2021/175788
PCT Pub. Date: Sep. 10, 2021

(65) Prior Publication Data
US 2023/0093265 A1 Mar. 23, 2023

(30) Foreign Application Priority Data
Mar. 3, 2020 (EP) .................................... 20160712

(51) Int. Cl.
*C07K 16/30* (2006.01)
*G01N 33/575* (2026.01)
*G01N 33/57555* (2026.01)

(52) U.S. Cl.
CPC ... *C07K 16/3076* (2013.01); *G01N 33/57555* (2026.01); *G01N 33/57585* (2026.01); *C07K 2317/21* (2013.01); *C07K 2317/622* (2013.01)

(58) Field of Classification Search
CPC .................................................. C07K 16/3076
USPC ....................................................... 424/133.1
See application file for complete search history.

(56) References Cited

U.S. PATENT DOCUMENTS

2013/0196316 A1 8/2013 Moghaddam

FOREIGN PATENT DOCUMENTS

| | | | |
|---|---|---|---|
| JP | 2013-525761 A | | 6/2013 |
| WO | WO 99/12553 | * | 3/1999 |
| WO | 2011/129762 A1 | | 4/2011 |

OTHER PUBLICATIONS

Nakajima et al (Oncotarget, 2017, 11: 17643-17650).*
Carlsson et al., Dominant prostasome immunogens for sperm-agglutinating autoantibodies of infertile men, Journal of Andrology, 25(5):699-705 (2004).
International Application No. PCT/EP2021/055061, International Preliminary Report on Patentability, mailed Sep. 15, 2022.
International Application No. PCT/EP2021/055061, International Search Report and Written Opinion, mailed Jul. 19, 2021.
Ishii et al., Isolation of Pathogenic Monoclonal Anti-Desmoglein 1 Human Antibodies by Phage Display of Pemphigus Foliaceus Autoantibodies, Journal Of Investigative Dermatology, 128(4):939-948 (2008).
Kumar et al., Beneficial effects of seminal prostasomes on sperm functional parameters, J. Entomology and Zoology Studies, 6(5):2464-2471 (2008).
Minelli et al., Antiprostasome antibody titres in benign and malignant prostate disease, Anticancer Res., 25(6C):4399-402 (2005).
Persson et al., A focused antibody library for improved hapten recognition, J. Mol. Biol., 357(2):607-620 (2006).
Ronquist et al., Prostasomal DNA characterization and transfer into human sperm, Mol. Reprod Dev., 78(7):467-76 (2011).
Sall et al., Generation and analyses of human synthetic antibody libraries and their application for protein microarrays, Protein Eng. Des. Sel., 29(10):427-437 (2016).
Tavoosidana et al., Multiple recognition assay reveals prostasomes as promising plasma biomarkers for prostate cancer, PNAS, 108(21):8809-8814 (2011).
Yu et al., Electrical and Label-Free Quantification of Exosomes with a Reduced Graphene Oxide Field Effect Transistor Biosensor, Anal. Chem., 91(16):10679-10686 (2019).

* cited by examiner

*Primary Examiner* — Sean E Aeder
(74) *Attorney, Agent, or Firm* — MARSHALL, GERSTEIN & BORUN LLP

(57) ABSTRACT

The present disclosure relates human antibodies, or antigen binding fragments thereof, able to bind prostasomes, and to prostate cancer diagnosis and prognosis. More specifically, the proposed technique relates to methods for diagnosing prostate cancer using human antibodies, or antigen binding fragments thereof, for detecting prostasomes in body fluids. The disclosure comprises human antibodies able to specifically and selectively detect prostasomes in body fluids, and methods for diagnosing prostate cancer using the human antibodies. The disclosure further comprises providing prognosis, evaluating the severity of the prostate cancer and determining the efficacy of a medical treatment of the prostate cancer.

8 Claims, 10 Drawing Sheets

Specification includes a Sequence Listing.

CDR-H1

| | 27 | 28 | 29 | 30 | 35 | 36 | 37 | 38 | 39 | 40 | CDR lengths |
|---|---|---|---|---|---|---|---|---|---|---|---|
| HelL-11/HelL13 | G | F | T | F | YSG | YSG | YSG | YSG | M | YSG | 8 |

CDR-H2

| | 55 | 56 | 57 | 58 | 59 | 62 | 63 | 64 | 65 | 66 | CDR lengths |
|---|---|---|---|---|---|---|---|---|---|---|---|
| HelL-11/HelL13 | YSG | I | YSG | YSG | YSG | YSG | YSG | YSG | T | YSG | 8 |

CDR-H3

| | 105 | 106 | 107 | 108 | 109 | 110 | 111 | 112 | 113 | 114 | 115 | 116 | 117 | CDR lengths |
|---|---|---|---|---|---|---|---|---|---|---|---|---|---|---|
| HelL11 | A | R | X | X | X | X | X | X | X | X | FILM | D | Y | 8-22 |
| HelL13 | A | R | J | J | J | J | J | J | J | J | FILM | D | Y | 8-17 |

CDR-L3

| | 105 | 106 | 107 | 108 | 114 | 115 | 116 | 117 | CDR lengths |
|---|---|---|---|---|---|---|---|---|---|
| HelL11 | Q | Q | X | X | X | PL | HPLYSF | T | 8-12 |
| HelL13 | Q | Q | J | J | J | PL | HPLYSF | T | 8-10 |

Fig. 3a

| Amino acid | X (%) | J (%) |
|---|---|---|
| Tyr | 25 | 25 |
| Gly | 15 | 20 |
| Ser | 15 | 15 |
| Trp | 10 | 5 |
| Ala | 5 | 5 |
| Phe | 5 | 5 |
| His | 5 | 5 |
| Pro | 5 | 5 |
| Val | 5 | 5 |
| Asp | 3 | 5 |
| Asn | 3 | 3 |
| Thr | 3 | 3 |
| Arg | 1 | 1 |

Figure 3b

*HeIL-11 scaffold*

*EVQLLESGGGLVQPGGSLRLSCAASGFTFSSYAMSWVRQAPGKGLEWVSAISGSGGSTYYADSV*
*KGRFTISRDNSKNTLYLQMNSLRAEDTVAVYYCAR***YFDYWGQGTLVTVSSGGGGSGGGGSGGG*
*GSDIQMTQSPSSLSASVGDRVTITCRASQSISSYLNWYQQKPGKAPKLLIYAASSLQSGVPSRFSG*
*SGSGTDFTLTISSLQPEDFATYYCQQS***YTFGQGTKLEIKR*

*HeIL-13 scaffold*

*EVQLLESGGGLVQPGGSLRLSCAASGFTFSSYAMSWVRQAPGKGLEWVSAISGSGGSTYYADSV*
*KGRFTISRDNSKNTLYLQMNSLRAEDTVAVYYCAR****LEYFDYWGQGTLVTVSSGGGGSGGGGS*
*GGGGSDIQMTQSPSSLSASVGDRVTITCRASQSISSYLNWYQQKPGKAPKLLIYAASSLQSGVPSR*
*FSGSGSGTDFTLTISSLQPEDFATYYCQQSYSTPYTFGQGTKLEIKR*

*Fig. 4a*

METHOD AND COMPOUND FOR PROSTATE CANCER DIAGNOSIS

TECHNICAL FIELD

The present disclosure relates human antibodies, or antigen binding fragments thereof, able to bind prostasomes, and to prostate cancer diagnosis and prognosis. More specifically, the proposed technique relates to methods for diagnosing prostate cancer using human antibodies, or antigen binding fragments thereof, for detecting prostasomes in body fluids. The disclosure comprises human antibodies able to specifically and selectively detect prostasomes in body fluids, and methods for diagnosing prostate cancer using the human antibodies. The disclosure further comprises providing prognosis, evaluating the severity of the prostate cancer and determining the efficacy of a medical treatment of the prostate cancer.

BACKGROUND

Cancer is one of the most prevalent deadly diseases, which despite recent advances in diagnosis and treatment still accounts for a substantial number of deaths each year.

Prostate cancer, as an example, is the most prevalent cancer disease in men exhibiting symptoms derived from a local tumor or metastatic spread of a tumor, such as dysfunctional voiding or bone pain, and the disease is often at an advanced stage at the time of diagnosis.

Measurement of prostate specific antigen (PSA) has changed the pattern of diagnosis of prostate cancer with more cases detected at an early stage and fewer cases at advanced stages. However, since serum PSA is not a prostate cancer specific marker in serum it is not the ideal diagnostic marker and therefore not accommodated for screening of prostate cancer. The PSA test cannot discriminate between benign prostatic hyperplasia and prostate cancer at an early stage and, what is more, between prostate cancer with high metastasizing potential (aggressive prostate cancer) and such cancer with no or weak aggressiveness (indolent prostate cancer).

It has previously been shown that cells excrete small vesicles called exosomes, released from the cell when multivesicular bodies fuse with the plasma membrane. Such vesicles are derived mainly from the raft part of the membrane of the cell of origin with a protein conformation specific for the cell of origin. Exosomes are present in many eukaryotic fluids, including blood, urine, and medium of cell cultures, etc. Exosomes contain various molecular constituents of their cell of origin, including proteins and RNA. Although the exosomal protein composition varies with the cell and tissue of origin, most exosomes contain an evolutionarily-conserved common set of protein molecules. The protein content of a single exosome can be about 20,000 molecules, and may be representative of the cell from which it originated, i.e. it may be possible to conclude which cell type that secreted an exosome by looking at its protein content. Exosomes have also been shown to carry double-stranded DNA. Evidence further suggest that exosomes have specialized functions and play a key role in processes such as coagulation, intercellular signaling, and waste management. Consequently, there is a growing interest in the clinical applications of exosomes. Exosomes can potentially be used for prognosis, for therapy, and as biomarkers for health and disease.

It has previously been discovered that submicron membranous vesicles are secreted by the prostate gland acinar cells into seminal fluid. These submicron membranous vesicles are a type of exosomes called prostasomes. Altered tissue architecture in malignancy facilitates the release of prostasomes to the interstitial space rather than to the acinar lumen of the prostate. Thus, prostasomes also leak into the external blood stream. It has been demonstrated that malignant prostate cells secrete prostasomes, and that presence of malignant prostate tumors increase the number of prostasomes present in peripheral blood (Tavoosidana et al. PNAS, May 24, 2011, vol. 108, no. 21, 8809-8814). It has thus been speculated that prostasomes may be a potential biomarker of prostate cancer.

SUMMARY

An object of the present disclosure is to provide methods and antibodies or fragments thereof which seek to mitigate, alleviate, or eliminate the above-identified deficiencies in the art and disadvantages singly or in any combination. This object is obtained by novel human antibodies or antigen binding fragments thereof, including synthetic fragments, for use in determining prostasome levels in a fluid body sample of a subject in need thereof.

In one aspect is provided a human monoclonal antibody or antigen binding fragment thereof, including synthetic fragments, which selectively binds prostasomes. In some aspects, the human monoclonal antibody or antigen binding fragment thereof is a full-length antibody, an antigen binding (Fab) fragment, or an antigen binding single chain Fv (scFv) fragment, such as a human synthetic scFv fragment.

In a further aspect, the human monoclonal antibody or antigen binding fragment thereof selectively binds prostasomes by binding one or more prostasome surface antigens, the prostasome surface antigens being selected from the group consisting of SEQ ID NO: 60-104, as defined in table 3.

In some aspects, the monoclonal antibody or antigen binding fragment thereof selectively binds prostasomes by binding a plurality of prostasome surface antigens. In some aspects, the monoclonal antibody or antigen binding fragment thereof selectively binds prostasomes by binding a plurality of prostasome surface antigens, wherein the prostasome surface antigens form a cluster or conglomerate on the prostasome membrane, which cluster is identified and bound by the monoclonal antibody or antigen binding fragment thereof.

In one embodiment, the human monoclonal antibody or antigen binding fragment thereof bind a conglomerate of proteins/antigens, wherein the conglomerate comprise at least five antigens selected from the proteins in table 11. For each respective scFv fragment 1-12, at least five proteins/antigens are present in the conglomerate bound, as defined for each respective fragment in table 11.

In some aspects, the antibody or antigen binding fragment thereof enable a sensitivity of at least 10 nano grams per milli liter (ng/ml) in an immunoassay using the human monoclonal antibody or antigen binding fragment thereof as a capturing antibody in the immunoassay.

In some embodiments, the human monoclonal antibody or antigen binding fragment thereof comprises at least six complementary determining regions (CDRs) in any combination of CDR-H1, CDR-H2, CDR-H3, CDR-L1, CDR-L2 and CDR-L3, wherein the CDRs are selected from the group comprising:

CDR-H1 selected from SEQ ID NO: 25, 27 and 28;

CDR-H2 selected from SEQ ID NO: 26, 29 and 30;

CDR-H3 selected from SEQ ID NO: 1, 2, 3, 4, 5, 6, 7, 8, 9, 10, 11 and 12;
CDR-L1 is selected from any variant of SEQ ID NO: 56 and 57;
CDR-L2 is selected from any variant of SEQ ID NO: 58 and 59;
CDR-L3 selected from SEQ ID NO: 13, 14, 15, 16, 17, 18, 19, 20, 21, 22, 23 and 24.

In a related embodiment the human monoclonal antibody or antigen binding fragment thereof may comprise at least six CDRs as described above, where CDR-H1, CDR-H2 and CDR-H3 are comprised in a heavy chain variable region (VH) sequence selected from the group consisting of SEQ ID NO: 32-43 and sequences having 70% or more, such as 75%, 80%, 85%, 90%, 95% or more, identity thereto, and CDR-L1, CDR-L2 and CDR-L3 is comprised in a light chain variable region (VL) sequence selected from the group consisting of SEQ ID NO: 44-55 and 56-59, and sequences having 70% or more, such as 75%, 80%, 85%, 90%, 95% or more, identity thereto.

In some embodiments, the human monoclonal antibody or antigen binding fragment thereof comprises at least four complementary determining regions (CDRs) in any combination of CDR-H1, CDR-H2, CDR-H3 and CDR-L3, wherein the CDRs are selected from the group comprising:
CDR-H1 selected from SEQ ID NO: 25, 27 and 28;
CDR-H2 selected from SEQ ID NO: 26, 29 and 30;
CDR-H3 selected from SEQ ID NO: 1, 2, 3, 4, 5, 6, 7, 8, 9, 10, 11 and 12;
CDR-L3 selected from SEQ ID NO: 13, 14, 15, 16, 17, 18, 19, 20, 21, 22, 23, and CDR sequences having 95% or more, such as 96%, 97%, 98%, 99% or more, identity thereto.

In a related embodiment the human monoclonal antibody or antigen binding fragment thereof may comprise at least four CDRs as described above, where CDR-H1, CDR-H2 and CDR-H3 are comprised in a heavy chain variable region (VH) sequence selected from the group consisting of SEQ ID NO: 32-43 and sequences having 70% or more, such as 75%, 80%, 85%, 90%, 95% or more, identity thereto, and CDR-L3 is comprised in a light chain variable region (VL) sequence selected from the group consisting of SEQ ID NO: 44-55 and sequences having 70% or more, such as 75%, 80%, 85%, 90%, 95% or more, identity thereto.

In one embodiment, the human antibody or antigen binding fragment thereof is a synthetic scFv fragment selected from the group comprising:

i) an scFv fragment having
CDR-H1 as defined by SEQ ID NO: 25
CDR-H2 as defined by SEQ ID NO: 26
CDR-H3 as defined by SEQ ID NO:4 and
CDR-L3 as defined by SEQ ID NO:16, il) an scFv fragment having
CDR-H1 as defined by SEQ ID NO: 25
CDR-H2 as defined by SEQ ID NO: 26
CDR-H3 as defined by SEQ ID NO:7 and
CDR-L3 as defined by SEQ ID NO:19, iii) an scFv fragment having
CDR-H1 as defined by SEQ ID NO: 25
CDR-H2 as defined by SEQ ID NO: 26
CDR-H3 as defined by SEQ ID NO:1 and
CDR-L3 as defined by SEQ ID NO:13, iv) an scFv fragment having
CDR-H1 as defined by SEQ ID NO: 25
CDR-H2 as defined by SEQ ID NO: 26.
CDR-H3 as defined by SEQ ID NO:2 and
CDR-L3 as defined by SEQ ID NO:14, v) an scFv fragment having
CDR-H1 as defined by SEQ ID NO: 25
CDR-H2 as defined by SEQ ID NO: 26
CDR-H3 as defined by SEQ ID NO:3 and
CDR-L3 as defined by SEQ ID NO:15, vi) an scFv fragment having
CDR-H1 as defined by SEQ ID NO: 25
CDR-H2 as defined by SEQ ID NO: 26
CDR-H3 as defined by SEQ ID NO:5 and
CDR-L3 as defined by SEQ ID NO:17, vii) an scFv fragment having
CDR-H1 as defined by SEQ ID NO: 25
CDR-H2 as defined by SEQ ID NO: 26
CDR-H3 as defined by SEQ ID NO:6 and
CDR-L3 as defined by SEQ ID NO:18, viii) an scFv fragment having
CDR-H1 as defined by SEQ ID NO: 25
CDR-H2 as defined by SEQ ID NO: 26
CDR-H3 as defined by SEQ ID NO:8 and
CDR-L3 as defined by SEQ ID NO:20, ix) an scFv fragment having
CDR-H1 as defined by SEQ ID NO: 25
CDR-H2 as defined by SEQ ID NO: 26
CDR-H3 as defined by SEQ ID NO:9 and
CDR-L3 as defined by SEQ ID NO:21, x) an scFv fragment having
CDR-H1 as defined by SEQ ID NO: 25
CDR-H2 as defined by SEQ ID NO: 26
CDR-H3 as defined by SEQ ID NO:10 and
CDR-L3 as defined by SEQ ID NO:22, xi) an scFv fragment having
CDR-H1 as defined by SEQ ID NO: 25
CDR-H2 as defined by SEQ ID NO: 26
CDR-H3 as defined by SEQ ID NO:11 and
CDR-L3 as defined by SEQ ID NO:23, xii) an scFv fragment having
CDR-H1 as defined by SEQ ID NO: 25
CDR-H2 as defined by SEQ ID NO: 26
CDR-H3 as defined by SEQ ID NO:12 and
CDR-L3 as defined by SEQ ID NO:24.

In one embodiment, the human antibody or antigen binding fragment thereof is a synthetic scFv fragment comprising the CDR:s as above, the fragment having a variable heavy chain, VH, and a variable light chain, VL, connected via a linker, wherein the fragments are selected from the group comprising and further selected from the group comprising:

i) an scFv fragment having
a VH as defined by SEQ ID NO:35 and
a VL as defined by SEQ ID NO:47, ii) an scFv fragment having
a VH as defined by SEQ ID NO:38 and
a VL as defined by SEQ ID NO:50, iii) an scFv fragment having
a VH as defined by SEQ ID NO:32 and
a VL as defined by SEQ ID NO:44, iv) an scFv fragment having
a VH as defined by SEQ ID NO:33 and
a VL as defined by SEQ ID NO:45, v) an scFv fragment having
a VH as defined by SEQ ID NO:34 and
a VL as defined by SEQ ID NO:46, vi) an scFv fragment having
a VH as defined by SEQ ID NO:36 and
a VL as defined by SEQ ID NO:48, vii) an scFv fragment having
a VH as defined by SEQ ID NO:37 and
a VL as defined by SEQ ID NO:49,
viii) an scFv fragment having
a VH as defined by SEQ ID NO:39 and
a VL as defined by SEQ ID NO:51,
ix) an scFv fragment having
a VH as defined by SEQ ID NO:40 and
a VL as defined by SEQ ID NO:52,
x) an scFv fragment having
a VH as defined by SEQ ID NO:41 and
a VL as defined by SEQ ID NO:53,
xi) an scFv fragment having
a VH as defined by SEQ ID NO:42 and
a VL as defined by SEQ ID NO:54,
xii) an scFv fragment having
a VH as defined by SEQ ID NO:43 and
a VL as defined by SEQ ID NO:55.

In one aspect is provided an in vitro method for determining whether prostate cancer is present in a subject, the method comprising: providing a human monoclonal antibody or antigen binding fragment thereof which selectively binds human prostasomes; reacting the human monoclonal antibody or antigen binding fragment thereof with a sample comprising prostasomes from a subject; detecting any prostasomes bound by the human monoclonal antibody or antigen binding fragment thereof to obtain a level of prostasomes; comparing said level of prostasomes detected with a predetermined threshold; and determining that prostate cancer is present in the subject if the detected level of prostasomes is higher than the predetermined threshold.

In a further aspect, detecting any prostasomes bound by the human monoclonal antibody or antigen binding fragment thereof comprises detecting the prostasomes using an anti-prostasome detection antibody or antigen binding fragment thereof.

In yet a further aspect, the method is a sandwich immunoassay and detecting prostasomes bound by the human monoclonal antibody or antigen binding fragment thereof comprises detecting the anti-prostasome detection antibody using a further detection antibody, wherein the human monoclonal antibody or binding fragment thereof is a capture antibody, the anti-prostasome detection antibody is a primary detection antibody and the further detection antibody is a secondary detection antibody.

In one aspect is provided a method in vitro for providing a prognosis of a prostate cancer in a subject in need thereof, the method comprising: providing a human monoclonal antibody or antigen binding fragment thereof which selectively binds prostasomes; reacting the human monoclonal antibody or antigen binding fragment thereof with a sample from a subject comprising prostasomes; detecting prostasomes bound by the human monoclonal antibody or antigen binding fragment thereof to obtain a level of prostasomes; comparing said level of prostasomes detected with a first and second predetermined threshold; and providing a prognosis of the prostate cancer, wherein prognosis of the prostate cancer is provided to be poor if the detected level of prostasomes are above a first predetermined threshold, and provided to be good if the detected level of prostasomes are below a second threshold.

In one aspect is provided a method in vitro for evaluating severity of a prostate cancer in a subject in need thereof, the method comprising: providing a human monoclonal antibody or antigen binding fragment thereof which selectively binds prostasomes; reacting the human monoclonal antibody or antigen binding fragment thereof with a sample from a subject comprising prostasomes; detecting prostasomes bound by the human monoclonal antibody or antigen binding fragment thereof to obtain a level of prostasomes; comparing said level of prostasomes detected with a first and second predetermined threshold; and evaluating the severity of the prostate cancer, wherein the prostate cancer is evaluated to be severe if the detected levels of prostasomes are above a first threshold, evaluated to be moderate if the detected levels of prostasomes are below a first threshold but above a second threshold, and evaluated to be light if the detected levels of prostasomes are below a second threshold.

In one aspect is provided a method in vitro of evaluating the efficacy of a prostate cancer treatment in a subject in need thereof, the method comprising: detecting a level of prostasomes in a sample from a subject before a prostate cancer treatment; providing an anti-prostate cancer treatment to the subject; detecting a level of prostasomes in a sample from the subject after said prostate cancer treatment; comparing the level of prostasomes before the treatment to the levels after the treatment; and determining the efficacy of the treatment, where the treatment is determined to be effective if the level of prostasomes after the treatment have decreased compared to the level before the treatment, and determined to be ineffective if the level of prostasomes have remained the same or increased. In some aspects, detecting a level of prostasomes in a sample from a subject comprises: providing a human monoclonal antibody or antigen binding fragment thereof which selectively binds prostasomes; reacting the human monoclonal antibody or antigen binding fragment thereof with a sample from a subject comprising prostasomes; and detecting prostasomes bound by the human monoclonal antibody or antigen binding fragment thereof to obtain a level of prostasomes.

In some embodiments, the sample from the subject is a body fluid sample, selected from the group consisting of blood, serum, plasma, urine, cerebrospinal fluid and a cell suspension.

In some embodiments, the predetermined threshold used in the diagnostic method is 10 ng prostasomes per mL of body fluid sample, and the first predetermined threshold is 10 ng prostasomes per mL of body fluid sample and the second predetermined threshold is 1 ng prostasomes per mL of body fluid sample, as used in the method for providing a prognosis or severity of a prostate cancer disease.

In some aspects, the human monoclonal antibody or antigen binding fragment thereof used in the methods is an antibody or antigen binding fragment as described above.

In another aspect is provided the antibody or antigen binding fragment thereof according as above for use in the methods above.

It is noted that the invention relates to all possible combinations of features recited in the claims. The mere fact that certain measures are recited in mutually different dependent claims does not indicate that a combination of these measures cannot be used to advantage.

Other objects and advantages will become apparent to those skilled in the art from a review of the ensuing detailed description, which proceeds with reference to the following illustrative drawings, and the attendant claims.

A feature described in relation to one aspect may also be incorporated in other aspects, and the advantage of the feature is applicable to all aspects in which it is incorporated.

Other objectives, features and advantages of the present inventive concept will appear from the following detailed disclosure, from the attached claims as well as from the drawings.

Generally, all terms used in the claims are to be interpreted according to their ordinary meaning in the technical field, unless explicitly defined otherwise herein. Further, the use of terms "first", "second", and the like, herein do not denote any order, quantity, or importance, but rather are used to distinguish one element from another. All references to "a/an/the [element, device, component, means, step, etc.]" are to be interpreted openly as referring to at least one instance of said element, device, component, means, step, etc., unless explicitly stated otherwise. The steps of any method disclosed herein do not have to be performed in the exact order disclosed, unless explicitly stated.

BRIEF DESCRIPTION OF THE DRAWINGS

The above, as well as additional objects, features and advantages of the present inventive concept, will be better understood through the following illustrative and non-limiting detailed description of different embodiments of the present inventive concept, with reference to the appended drawings, wherein:

FIG. 3 shows an example of the Hell-11 and Hell-13 synthetic scFv library designs, where FIG. 3*a* shows the CDRs and FIG. 3*b* shows the amino acid contents of the CDRs from example 1.

FIG. 4 illustrates the Hell-11 and Hell-13 library constructions where FIG. 4*a* shows the amino acid sequence of the Hell library scaffolds.

Figure 1:
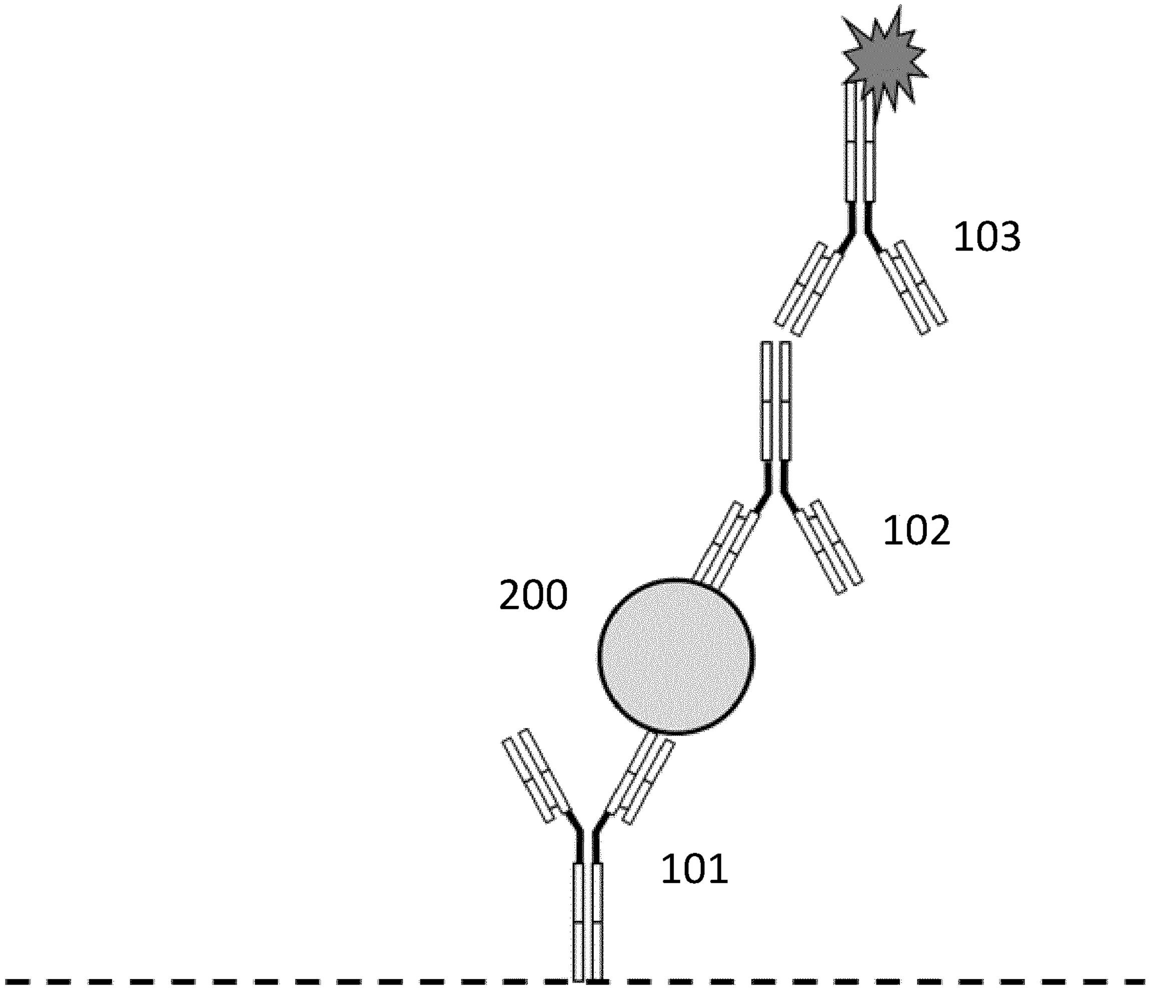
FIG. 1 illustrates an exemplary assay using an antibody of the invention.

The figures are not necessarily to scale, and generally only show parts that are necessary in order to elucidate the inventive concept, wherein other parts may be omitted or merely suggested.

DETAILED DESCRIPTION

The present disclosure relates to new monoclonal antibodies or antigen binding fragments which selectively bind prostasomes, and to prostate cancer diagnosis and prognosis using these monoclonal antibodies or fragments specific for prostasomes. Aspects of the present disclosure will be described more fully hereinafter with reference to the accompanying drawings. The antibodies and method disclosed herein can, however, be realized in many different forms and should not be construed as being limited to the aspects set forth herein. Like numbers in the drawings refer to like elements throughout.

The terminology used herein is for the purpose of describing particular aspects of the disclosure only, and is not intended to limit the disclosure. As used herein, the singular forms "a", "an" and "the" are intended to include the plural forms as well, unless the context clearly indicates otherwise. Initially, some terminology may be defined to provide clarification for the following disclosure.

In some embodiments a non-limiting terms "antibody" or "antigen binding fragment thereof" is used. The term "antibody" is used herein in its broadest sense, including both monoclonal and polyclonal antibodies. As is well known, antibodies are immunoglobulin molecules capable of specific binding to a target (an antigen), such as a protein, carbohydrate, polynucleotide, lipid, polypeptide or other, through at least one antigen recognition site located in the variable region of the immunoglobulin molecule. The human monoclonal antibodies herein, typically phage display antibodies, can be any type of human antibodies or human antigen binding fragments of antibodies which are capable of selectively binding the prostasomes.

As used herein, the term "antibody" or "an antigen binding fragment thereof" encompasses not only full-length or intact polyclonal or monoclonal antibodies, but also antigen-binding fragments thereof, such as Fab, Fab', F(ab')2, Fab3, Fv and variants thereof, fusion proteins comprising one or more antibody portions, humanized antibodies, chimeric antibodies, minibodies, diabodies, triabodies, tetrabodies, linear antibodies, single chain antibodies, multispecific antibodies (e.g. bispecific antibodies) and any other modified configuration of the immunoglobulin molecule that comprises an antigen recognition site of the required specificity, including glycosylation variants of antibodies, amino acid sequence variants of antibodies and covalently modified antibodies. A full-length antibody comprises two heavy chains and two light chains. Each heavy chain contains a heavy chain variable region (VH) and first, second and third constant regions (CH1, CH2 and CH3). Each light chain contains a light chain variable region (VL) and a light chain constant region (CL). Depending on the amino acid sequence of the constant domain of its heavy chains, antibodies are assigned to different classes. There are six major classes of antibodies: IgA, IgD, IgE, IgG, IgM and IgY, and several of these may be further divided into subclasses, e.g., lgG1, lgG2, lgG3, lgG4, IgA1 and IgA2. The term "full-length antibody" as used herein, refers to an antibody of any class, such as IgD, IgE, IgG, IgA, IgM or IgY (or any sub-class thereof). The subunit structures and three-dimensional configurations of different classes of antibodies are well known. The term "antigen binding fragment" refers to a portion or region of an antibody molecule, or a derivative thereof, that retains all or a significant part of the antigen binding of the corresponding full-length antibody. An antigen binding fragment may comprise the heavy chain variable region (VH), the light chain variable region (VL), or both. Each of the VH and VL typically contains three complementarity determining regions CDR1, CDR2 and CDR3, denoted CDR-H1, CDR-H2 and CDR-H3 for the CDRs from the VH domain and CDR-L1, CDR-L2 and CDR-L3 for the CDRs from the VL domain. The three CDRs in VH or VL are flanked by framework regions (FR1, FR2, FR3 and FR4). As briefly listed above, examples of antigen binding fragments include, but are not limited to: (1) a Fab fragment, which is a monovalent fragment having a VL-CL chain and a VH-CH chain; (2) a Fab' fragment, which is a Fab fragment with the heavy chain hinge region, (3) a F(ab')2 fragment, which is a dimer of Fab' fragments joined by the heavy chain hinge region, for example linked by a disulfide bridge at the hinge region; (4) an Fc fragment; (5) an Fv fragment, which is the minimum antibody fragment having the VL and VH domains of a single arm of an antibody; (6) a single chain Fv (scFv) fragment, which is a single polypeptide chain in which the VH and VL domains of an scFv are linked by a peptide linker; (7) an (scFv) 2, which comprises two VH domains and two VL domains, which are associated through the two VH domains via disulfide bridges and (8) domain antibodies, which can be antibody single variable domain (VH or VL) polypeptides that specifically bind antigens. Antigen binding fragments can be prepared via routine methods. For example, F(ab') 2 fragments can be produced by pepsin digestion of a full-length antibody molecule, and Fab fragments can be generated by reducing the disulfide bridges of F(ab') 2 fragments. Alternatively, fragments can be prepared via recombinant technology by expressing the heavy and light chain fragments in suitable host cells (e.g., *E. coli*, yeast, mammalian, plant or insect cells) and having them assembled to form the desired antigen-binding fragments either in vivo or in vitro. A single-chain antibody can be prepared via recombinant technology by linking a nucleotide sequence coding for a heavy chain variable region and a nucleotide sequence coding for a light chain variable region. For example, a flexible linker may be incorporated between the two variable regions. In one embodiment, CDRs present on a library scaffold are linked via a linker to form a synthetic scFv fragment. The term "antibody or antigen binding fragment thereof" as used herein thus also encompasses synthetic binding fragments, such as human synthetic scFv fragments. Accordingly, throughout the description the generic term "antibody" or "human antibody" is used. These terms are used in their broadest sense and thus also incorporate all variants and fragments described above and below. Thus, the term "human antibody" also encompass a human binding fragment of an antibody.

The term "human monoclonal antibodies" or "human antibodies" refers to fully human sequence derived antibodies or related fragments that have no murine sequence, and encompasses also fragments of antibodies, and synthetic scFv fragments. The human antibodies largely produced via two sources: phage display technologies and transgenic mice. The human antibodies of the invention do not encompass humanized antibodies, where for example a murine-monoclonal antibody has been treated to become more human. Humanization is the replacement of mouse constant regions and variable (V) framework regions for human sequences, and results in an antibody where only the complementarity determining regions (CDRs) of the variable (V) regions are of mouse-sequence origin. In contrast, human monoclonal antibodies are fully human, compared to humanized antibodies which still comprises a binding epitope which is non-human.

As used herein, the term "capable of binding X", wherein X is an antigen, refer to a property of an antibody or binding fragment thereof which may be tested for example by ELISA, by use of surface plasmon resonance (SPR) technology, by use of the Kinetic Exclusion Assay (KinExA®) or by bio-layer interferometry (BLI). The skilled person is aware of said methods and others.

Also in some embodiments generic terminology "immunoassay", is used. It can be any kind of immunoassay, such as Lateral Flow Immunochromatographic assays, Immunomagnetic Separation and Electrochemiluminescence (IMS-ECL) assays, Fluorescence immunoassays, Time-resolved Fluorescence (TRF) assays, Radioimmunoassays (RIA) or Enzyme-linked Immunosorbent (ELISA) assays, which use the monoclonal antibodies of the invention for detecting levels or amounts of prostasomes in a sample from a subject, where the "sample" may be a body fluid sample from a subject, such as a blood sample, plasma, serum, urine, cerebrospinal fluid or a cell suspension, wherein the cell suspension may be derived e.g. from a biopsy.

The term "conglomerate" may be used herein as referring to an entity comprising a plurality of prostasome antigens forming a three dimensional conformation of antigens bound to a prostate membrane or prostate membrane fragment. The conglomerate of protein antigens is present on the surface of the prostate membrane. In one embodiment, the antibodies or fragments thereof according to the invention bind a plurality of prostasome surface antigens, wherein the prostasome surface antigens form a conglomerate on the prostasome membrane, which conglomerate is identified by the monoclonal antibody or antigen binding fragment thereof. In some embodiments, monoclonal antibody or antigen binding fragment thereof bind a plurality of antigens, wherein the antigens are selected from Table 11. In some embodiments, the term "cluster", "structure", or "agglomerate" may be used synonymously when referring to an entity comprising a plurality of prostasome antigens forming a three dimensional conformation of antigens.

The term "sensitivity" refers to, in the context of a diagnostic assay for example, the true positive rate of the condition of interest, which is the probability of detection, and measures the proportion of actual positives that are correctly identified as such (e.g., the percentage of sick people who are correctly identified as having the condition). A high sensitivity will give a low number of false negatives, i.e. subject identified as not having the condition while they in reality do. "Sensitivity" in the context of antibodies, such as a "sensitive antibody" is an antibody which is able to detect also low amounts of an intended antigen. The sensitivity could thus be defined in relation to the lowest concentration of the antigen that may be detected in an assay using the antibody.

The term "specificity", sometimes referred to as "selectivity", refers to the true negative rate of the condition of interest and measures the proportion of actual negatives that are correctly identified as such (e.g., the percentage of healthy people who are correctly identified as not having the condition). A high specificity in an assay will give a low number of false positives, i.e. subject identified as having the condition while they in reality do not. A selective or specific antibody will not, or to a low extent, cross-react with other targets than the intended antigen. Thus, a prostasome specific antibody or binding fragment thereof of the invention will specifically or selectively bind to prostasomes or prostasome antigens, but not to other antigens such as antigens present on other types of exosomes or cells.

With the term "diagnosis" or "diagnosing" as used herein is meant a process of determining if a disease or condition, in this case prostate cancer, is present in a subject tested. A diagnosis, in the sense of diagnostic procedure, can be regarded as an attempt at classification of an individual's condition into separate and distinct categories that allow medical decisions about treatment and prognosis to be made. Subsequently, a diagnostic opinion is often described in terms of a disease or other condition. The initial task is to detect a medical indication to perform a diagnostic procedure, such as detection of any deviation from what is known to be normal, in this case the levels of prostasomes in peripheral blood. Typically, an aggressive prostate cancer will be detected and diagnosed in the present assays, in comparison with an indolent one.

With the term "prognosis" or "prognosing" as used herein is meant a prediction or estimate of the chance of recovery or survival from a disease. Prognosis with cancer can depend on several factors, such as the stage of disease at diagnosis, type and subtype of cancer, the molecular profile of the tumor, and even gender. The prognosis of the prostate cancer of the invention may be correlated to the levels of the prostasomes in the sample from the subject being tested, where high levels are indicative of a poor prognosis (i.e. a high likelihood of a negative outcome of the disease) and low levels are indicative of a good prognosis (i.e. high likelihood of a positive outcome of the disease).

With "prostasome" is meant submicron membranous vesicles, also called exosomes, which are secreted by the prostate gland epithelial cells into seminal fluid. Thus, the prostasome is a type of exosome. The prostasome is characterized by a size between 50 and 500 nm, surrounded by a lipid plasma membrane bilayer with exceptionally high cholesterol/phospholipid ratio and characteristic proteins like caveolin-1, prostate stem cell antigen, prostate specific membrane antigen (PSMA), CD 10, CD 13, and CD 26 on said surface membrane, while comprising RNA and DNA within (Beneficial effects of seminal prostasomes on sperm functional parameters, Amit Kumar, Sujata Pandita, Subha Ganguly, Simson Soren and Nileshkumar Pagrut J Entomology and Zoology Studies 2008; 6 (5): 2464-2471). Based on this information and the information of the cited paper, the skilled person would be able to distinguish a prostasome from a micro vesicle or from any other type of exosome if encountered in isolation or in peripheral blood. Due to the specific characteristics of prostasomes, prostasome specific antibodies not cross reacting with other exosomes are possible to obtain. The prostasomes typically display one or more protein antigens, as listed in table 2 in the specification below.

The term "prostate cancer", in the context of a subject suffering from prostate cancer is meant in the broadest sense the presence of one prostate cancer cell. Even though one cell will not be enough for having detectable prostasomes levels in body fluids outside of the seminal fluid above a threshold, early diagnosis of prostate cancer is possible. A detected or diagnosed prostate cancer of the invention could typically be at a stage where it could be possible to make a biopsy to retrieve cancer cells, and is preferably not metastasized but only present in the prostate, and thus possible to remove surgically. Accordingly, early detection of prostate cancer using the method gives a technical effect of an increased amount of cancers that will be possible to treat with surgery, and could also be used as a decision support for determining which cancers that will be possible to perform surgery on. Typically, a detected level of prostasomes in a sample of a subject being 10 ng/ml or less would be considered as treatable by surgery, while a level above 100 ng/ml would be considered as untreatable by surgery. A detected level of prostasomes between 10 ng/ml and 100 ng/ml could be used as an indication that further characterization of the prostate cancer is needed before deciding on the method of treatment to be performed. To be able to perform surgery the prostate cancer must remain in the prostate, and should not have metastasized, and high levels detected in the assays of the invention can thus predict that it is no longer possible to perform surgery.

PSA is the most used marker for detection of prostate cancer today, but unfortunately this biomarker is not specific enough. Thus, there is a need for a better marker for screening of prostate cancer. The preferred marker should be specific both for the organ prostate and for the cancer disease. One promising marker is the prostasome, a small vesicle emanating from acinar cells in the prostate.

The inventors have previously demonstrated that malignant prostate cells secrete prostasomes, and that presence of malignant prostate tumors increase the number of prostasomes present in peripheral blood, which indicates that prostasomes may be a potential biomarker of prostate cancer. However, developing a method which is simple, robust, reliable, selective and sensitive enough to diagnose prostate cancer using prostasomes as a biomarker has been difficult.

Methods of using monoclonal antibodies against prostasomes for prostate cancer diagnosis have been previously described, however none of these methods seem to have the sensitivity to detect small amounts of prostasomes in blood, serum or plasma using a single capture antibody. Also, the specificity to detect prostasomes and not exosomes in general seems to be lacking. Hence, there is a need for new robust methods which may be used for prostate cancer diagnosis, which are both sensitive and specific enough to avoid false negatives and positives when performing the diagnosis.

As presented in the current disclosure, the above-mentioned problems and drawbacks of the prior art have been overcome by the use of fully human monoclonal antibodies or binding fragments thereof in the diagnosis of prostate cancer. The fully human monoclonal antibodies or binding fragments of the invention will achieve the desired sensitivity and specificity/selectivity to actually be able to perform prostate cancer diagnosis on serum and plasma samples from a patient using a single capture antibody. The current disclosure thus relates to a method for diagnosing or providing a prognosis of a subject suspected of suffering from prostate cancer, comprising in vitro detection of prostasomes in a peripheral blood sample from the subject, where the detected levels of prostasomes may be compared to a threshold or to a reference value derived from healthy subject(s). The thresholds and reference values may be predetermined, or may be calibrated for a specific test.

Previous methods for detecting prostasomes for prostate cancer diagnosis have been using monoclonal antibodies which are typically murine or, at best, humanized. These methods have failed to provide the specificity and sensitivity needed to be able to efficiently diagnose and prognose prostate cancer. The biggest problem is probably the sensitivity, where the antibodies cannot detect small amounts of prostasomes in a sample, hence generating false negatives. For example, in a previous study an enzyme-linked immunosorbent assay (ELISA) was set up to test a number of antibodies for their ability to work as suitable capture or detection antibodies for prostasomes (E. Thermaenius et al, DIVA, id: diva2:544923). Two surface proteins specific for prostasomes were used in the study as capture antigens, and a prostasomal surface-bound protein was used as antigen for the secondary antibody in the assay. With this experimental setup the detection limit was 2500 ng/ml, which was not considered enough to detect prostasomes in cancer. In another previous study (Tavoosidana et al. *PNAS*, May 24, 2011, vol. 108, no. 21, 8809-8814) prostasome levels were detected in serum, which requested using five antibodies combined for reaching a fairly sufficient level of sensitivity and specificity for use in diagnosis. In contrast, the current invention provides method which only requires using one monoclonal antibody in the detection assay to specifically and selectively detect prostasomes for diagnosis. The use of the antibodies of the invention thus provides a far simpler assay, which can easily be scaled up and which are cheaper to produce.

There could also be a problem in the assays with false positives if the antibodies used is not specific enough. The antibodies used in an assay may for example react with other exosomes, since all exosomes share common epitopes. As shown by the Human Protein Atlas, a program aimed at mapping all the human proteins in cells, tissues and organs, a random antibody shows a large cross-reactivity with different tissues. It has previously been shown that prostasome surface antigens are the primary auto-antigens causing immunologic infertility and anti-sperm antibodies (see e.g. L. Carlsson et al. Journal of Andrology, Vol. 25, No. 5, September/October 2004 and A. Minelli et al. ANTICANCER RESEARCH 25:4399-4402 (2005)), i.e. auto-antibodies against prostasomes are common within men with clinical infertility. One thing that characterizes immunologic infertility is that the man affected is infertile, but generally without any further diseases. This has been interpreted by the inventors as that these auto-antibodies, which are antibodies that the human subject himself are producing, are specific for prostasomes and do not react with other types of cells or tissues. Hence, using human antibodies from human DNA libraries will attain better and more specific/selective prostasome antibodies than using murine monoclonal antibodies or humanized antibodies. Thus, using human antibodies or antibody fragments based on human antigen-binding epitopes for detecting prostasomes as a biomarker for cancer will achieve a higher specificity and selectivity compared to the antibodies suggested in the prior art.

In contrast to the prior art, the current disclosure provides new monoclonal antibodies or binding fragments, which are fully human, and which are specific enough to avoid false positives and sensitive enough to detect small amounts of prostasomes in body fluids. These prostasome specific antibodies may be used in different detection assays for detecting levels of prostasomes in body fluids, such as blood, serum or plasma. Upon performing a biopsy or prostate massage, also a cell suspension from the biopsy or urine comprising prostasomes due to the massage may be used as sample body fluids. Prostasomes are secreted by the prostate gland cells into seminal fluid, hence, in a healthy subject the prostasomes are generally present in seminal fluid, with only a very small fraction leaking out into the external blood stream. However, prostasomes are also secreted by malignant prostate cells, which increases the number of prostasomes present in peripheral blood. It has been found that the reason that the levels of prostasomes in peripheral blood rises fast when cancer cells secrete them is not only that the number and thus leakage increases, but in fact that the prostate cells loses their polarity when they become cancer cells, hence secreting prostasomes into the blood. Thus, also a slightly elevated level of prostasomes in the peripheral blood is indicative of prostate cancer. To be able to efficiently detect and diagnose and prognose prostate cancer, including also early stage prostate cancer which might have only slightly increased levels of prostasomes in peripheral blood, a very sensitive assay is needed.

The assays of the invention use fully human monoclonal antibodies or binding fragments thereof for detecting the presence of elevated levels of prostasomes in the blood, and thus the presence of malignant prostate cancer cells. A body fluid sample, such as a blood sample, is taken from a subject potentially in need of a diagnosis, such as a patient in a hospital or at a clinic, and the sample is either directly screened for elevated amounts of prostasomes, or first treated to obtain a serum or plasma sample which is then screened in the assay. The amount of detected prostasomes in the body fluid is compared to a predetermined threshold or reference value, where an increased detected value above the threshold or compared to the reference value is indicative of the presence of prostate cancer in the subject being tested. Typically, a level (concentration) of prostasomes of about 1-2 nanogram (ng) per milli liter (mL or ml) body fluid sample is indicative of cancer, and a level above 10 ng/ml may be used for definite diagnosis. The level of detected prostasomes compared to one or more thresholds or one or more reference values may also be used in prognosis of prostate cancer, where for example a higher detected level compared to a reference value is indicative of a later stage prostate cancer and thus a worse prognosis, while a lower detected value compared to the reference value is indicative of an earlier stage prostate cancer and thus a better prognosis. The prognosis could also be defined by certain thresholds, where being above or below the certain thresholds indicates different prognosis. For example, if the levels of prostasomes are above a certain threshold, such as a first predetermined threshold, the prognosis of the prostate cancer is prognosed to be poor, while if the level is below a certain threshold, such as a second predetermined threshold, the prognosis of the prostate cancer is prognosed to be good. The first threshold may be 10 ng prostasomes per mL of sample, and the second threshold may be 1 ng prostasomes per ml of sample. The level of prostasomes may also be indicative of the severity of the prostate cancer, which may be linked to possible treatments, such as surgery or no surgery. The cancer progression and treatment efficacy may also be determined, by making measurements of the prostasome levels in the same subject at different points in time, where a decrease in the amount of prostasomes is indicative of tumor regression and high treatment efficacy while an increase of the amount is indicative of tumor progression and low treatment efficacy. The efficacy of a treatment may thus be determined by measuring the levels of prostasomes before and after a treatment regime, where a lowering of the prostasome levels is indicative of an effective treatment. The treatment may be for example a surgery, administration of a medical substance to the subject, or radiation therapy. The medical substance may be for example an oral drug or a substance administered through injections or infusions.

The assays of the invention may be any assay suitable for detecting an analyte within a fluid sample using a monoclonal antibody. The assays may be immunoassays which rely on the ability of an antibody to recognize and bind a specific macromolecule in a sample which comprise a complex mixture of macromolecules. In immunology the particular macromolecule bound by an antibody is referred to as an antigen and the area on an antigen to which the antibody binds is called an epitope. In addition to the binding of an antibody to its antigen, the other key feature of all immunoassays is a means to produce a measurable signal in response to the binding. Most, though not all, immunoassays involve chemically linking antibodies or antigens with some kind of detectable label. A large number of labels exist in modern immunoassays, and they allow for detection through different means. Many labels are detectable because they either emit radiation, produce a color change in a solution, fluoresce under light, or can be induced to emit light. The assays of the invention may be for example Lateral Flow Immunochromatographic assays, Immunomagnetic Separation and Electrochemiluminescence (IMS-ECL) assays, Time-resolved Fluorescence (TRF) assays, or Enzyme-linked Immunosorbent (ELISA) assays. In one embodiment, the assay is an immunoassay or immunocapturing assay, such as a sandwich immunoassay, where the monoclonal antibodies of the invention are used to capture the prostasomes within the fluid sample (the body fluid extracted from the subject potentially in need of a diagnosis or prognosis), and then detected. For example, the assay may be a Sandwich ELISA, where a surface is prepared to which a known quantity of the capture antibody is bound, i.e. one of the monoclonal antibodies of the invention, to which the fluid sample comprising the prostasomes is applied. The prostasomes are captured by the capture antibody, the surface is washed and a primary detection antibody is applied, which binds to the prostasomes. Enzyme-linked secondary antibodies are applied as detection antibodies that also bind specifically to the antibody's Fc region, thereby detecting the presence of the primary detection antibodies and thus the bound prostasomes. The surface is washed to remove the unbound antibody-enzyme conjugates, and a chemical is added to be converted by the enzyme into a color or fluorescent or electrochemical signal. The absorbance or fluorescence or electrochemical signal (e.g., current) of the plate wells is measured to determine the presence and quantity of the analyte, i.e. prostasomes. The quantity of the prostasomes may then be compared to a reference value, and an increased level be linked to the presence of malignant prostate cancer cells in the subject being diagnosed. The primary detection antibodies may be for example chicken anti-PSA or anti-prostasome antibodies, and the secondary detection antibody may be an anti-chicken antibody, which may be HRP (Horseradish Peroxide) labelled. A commonly used enzymatic marker in ELISA assays is for example OPD (o-phenylenediamine dihydrochloride), which turns amber to detect HRP, which is often used to as a conjugated protein. Also, TMB (3,3',5,5'-tetramethylbenzidine) may be used, which turns blue when detecting HRP and turns yellow after the addition of sulfuric or phosphoric acid, or ABTS (2,2'-Azinobis [3-ethylbenzothiazoline-6-sulfonic acid]-diammonium salt), which turns green when detecting HRP. FIG. 1 shows an example where the human monoclonal antibody or antigen binding fragment thereof of the present disclosure (101) is used as a capture entity (capture antibody), which captures prostasomes (200), after which bound prostasomes (200) may be detected using a primary detection antibody (102) binding the prostasomes and being detected by a secondary detection antibody (103). The primary detection antibody (102) may be an anti-prostasome or anti-PSA antibody and may be of chicken origin (chicken anti-prostasome or chicken anti-PSA), and the secondary detection antibody (103) may be a Horseradish peroxidase (HRP) labelled antibody and will be anti the species of the primary detection antibody, i.e. anti-chicken if the primary detection antibody is chicken (HRP labelled anti-chicken antibody). The current invention thus provides assays for detecting prostasome levels and diagnosing prostate cancer, which are sensitive enough to use a single capturing antibody and a single primary detection antibody, together with a secondary detection antibody, which has not been possible in the prior art. Thus, in one embodiment a single capturing antibody is used in an immunoassay for detecting levels of prostasomes in a sample. In another embodiment, a plurality of capture antibodies are used, such as two, three or four capture antibodies of the invention, but less than five capture antibodies.

The antibodies or fragments of the invention are fully human monoclonal antibodies of fragments which are prostasome specific (selective for prostasomes compared to other cells or exosomes), and sensitive enough to be able to detect small levels of prostasomes in a sample. The sensitivity needed in an assay for an antibody to work as a single capture antibody in said assay, such as an ELISA, is typically at least 10 nanogram (ng) prostasomes per milli liter (mL). Thus, the assays of the invention makes it possible to detect levels of prostasomes of 10 ng/ml or lower. This sensitivity may be obtained using the antibodies or antigen binding fragment thereof of the invention. The sensitivity may be even higher than 10 ng/ml, where a sensitivity range of 1-2 ng/ml may be attained. No antibodies present in the prior art has been shown to enable this sensitivity in similar assays, hence, there is no antibodies in the art that could be used as a single capture antibody in a detection assay to detect prostasomes for adequate prostate cancer diagnosis.

The antibodies or fragments thereof according to the present invention bind clusters of protein antigens present on the surface of the prostate membrane. The agglomerated antigens form a three dimensional structure, a conglomerate of antigens and prostate membrane, which is identified by the antibodies or fragments thereof according to the present invention. Accordingly, the present antibodies or fragments thereof are ideal for measuring the presence of whole prostasomes in a sample, compared to prior art antibodies. The antibodies or fragments according to the present invention thus both have greater specificity and sensitivity compared to other antibodies or binding fragments. Accordingly, an assay sensitivity of detecting prostasomes in a sample, such as a blood or serum sample, of 10 ng prostasomes per mL, or even higher, such as 1-2 ng/mL, using a single one of these antibodies and fragments may be attained. This is not possible using any of the antibodies in the prior art.

Thus, in contrast to the prior art antibodies for use in prostate cancer diagnosis, the present antibodies are fully human and bind several prostasome antigens, such as a cluster of antigens. Further, the specificity and sensitivity is higher than in the prior art. For example, in Tavoosidana et al., as shown in FIG. 1, several antibodies (five more specifically) must be used in combination in an assay to attain a sensitivity in the range of what is attained using a single antibody or fragment of the invention. To state that an anti-CD 13 antibody achieves a detection sensitivity of 0.5 mg/mL is simply not correct. 5 antibodies and DNA fragments are used in Tavoosidana et al. (see FIG. 1), hence also requiring a further PCR step in the method. As several antibodies and a DNA fragment are needed to attain the sensitivity, it cannot be said that the antibodies in Tavoosidana et al, enable a sensitivity of at least 10 ng/ml in an immunoassay using the antibody as a single capturing antibody in the immunoassay. Hence, the individual antibodies of Tavoosidana et al, are not fully human, do not bind to several prostasome antigens, or a cluster of antigens on the prostasome membrane, nor do they individually achieve the specificity of the antibodies/fragments of the invention. The methods of the present invention also have further advantages over the method in Tavoosidana et al, since they are simpler, cheaper, and more efficient.

Regarding the method in document Yu et al., ("Electrical and Label-Free 1-18 Quantification of Exosomes with a Reduced Graphene Oxide Field Effect Transistor Biosensor", ANALYTICAL CHEMISTRY, vol. 91, no. 16, 23 Jul. 2019 (2019-07-23), pages 10679-10686), also this method as Tavoosidana et al. is built on analysis of DNA (PNA), which is a much more complex outline than a simple immune assay, and further DNA analyses and immunological analyses are fundamentally different from each other. Usually, DNA tests may achieve a high sensitivity, but immunological, e.g. antibody based, tests are simpler and cheaper. Further, regarding Yu et al., the anti-CD 63 antibody used have very low tissue specificity (see e.g. the protein atlas, URL https://www.proteinatlas.org/ENSG00000135404-CD63), which means that it cannot distinguish prostasomes from other types of exosomes, nor prostasomes from whole cells (as the anti-CD 63 antibody will react to whole cells). The antibody in Yu et al. is used to detect exosomes in a pure sample, and to detect non-specific occurrence of cancer, based merely on the fact that cancer produce more exosomes. There is no specificity in a diagnose based on just number of unspecified exosomes in blood. Further, in a sample, such as a blood sample of the invention, the antibody would not only detect all exosomes present, which may signify the presence of a broad variation of cancers or other disorders, but would also detect whole cells. Thus, the antibody would not be able to distinguish prostasomes or prostate cancer, nor would it be able to distinguish exosomes in a blood sample. Accordingly, the antibody in Yu et al. would not be able to be used in a method for detecting prostate cancer in patient samples. Thus, the antibody in Yu et al. is not fully human, it does not selectively bind prostasomes, nor does it bind to several prostasome antigens, or a cluster of antigens on the prostasome membrane, nor achieve the sensitivity of the antibodies/fragments of the invention in a simple immunoassay.

A human monoclonal antibody or antigen binding fragment thereof according to the invention is selected from the group consisting of full-length antibodies, Fab fragments, Fab' fragments, F(ab') 2 fragments, Fc fragments, Fv fragments, single chain Fv fragments, (scFv) 2 and domain antibodies. In one embodiment, said antibody or antigen binding fragment thereof is selected from full-length antibodies, Fab fragments and synthetic scFv fragments. In one embodiment, the antibody comprises twelve complementary determining regions (CDRs). In another embodiment, the antibody or antigen binding fragment thereof comprises six CDRs, CDR-H1/CDR-H2/CDR-H3/CDRL1/CDR-L2/CDR-L3. In a more specific such embodiment, the antibody or antigen binding fragment thereof comprises at least three complementarity determining regions (CDRs), where the CDRs may be for example from the heavy chain, CDR-H1, CDR-H2 and CDR-H3, or from the light chain, CDR-L1, CDR-L2 and CDR-L3.

In one embodiment, the human monoclonal antibody of the invention is an antigen-binding fragment (Fab) of an antibody. The antigen-binding fragment (Fab) is a region on an antibody that binds to antigens. It is composed of one constant and one variable domain of each of the heavy and the light chain. The variable domain contains the paratope (the antigen-binding site), comprising a set of complementarity determining regions, at the amino terminal end of the monomer.

Figure 2:
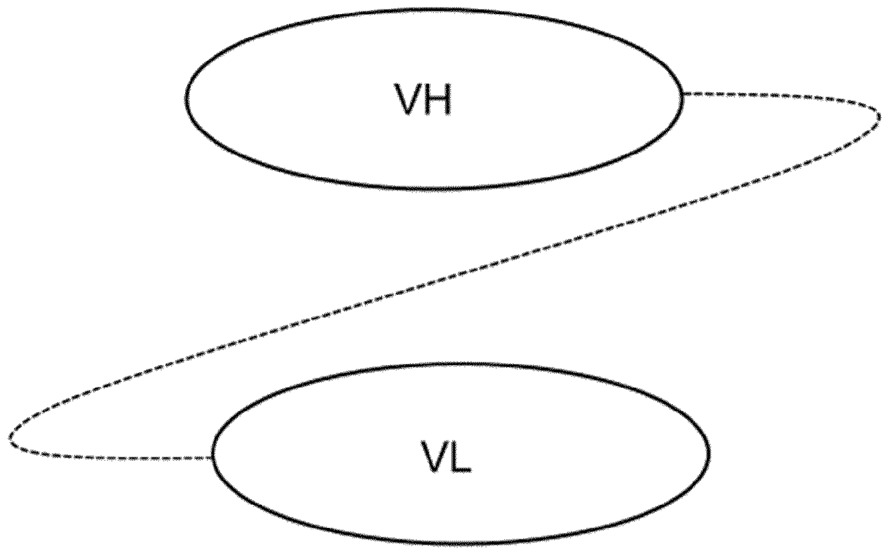
FIG. 2 illustrates an scFv fragment of the invention.

In one embodiment, the human monoclonal antibody of the invention is a single-chain variable fragment (scFv) of an antibody. The single-chain variable fragments lack the constant Fc region found in complete antibody molecules, and is not actually a fragment of an antibody, but instead is a fusion protein of the variable regions of the heavy (VH) and light chains (VL) of immunoglobulins, connected with a short linker peptide of ten to about 25 amino acids. These molecules maintain the same binding functionality that full-length antibodies but possess several advantageous features as quickness to penetrate the tissues, easy manipulation, fast elimination of their immunocomplex and the possibility of being produced in simple expression systems like bacteria and yeast. FIG. 2 shows a schematic figure of an scFv fragment of the invention, having a VH part comprising the heavy CDRs (CDR-H1, CDR-H2 and/or CDR-H3) and a VL part comprising the light CDR(s) (CDR-L1, CDR-L2 and/or CDR-L3), jointed together using a linker (dotted line of FIG. 2).

In one embodiment, the human monoclonal antibody of the invention is a human synthetic single-chain variable fragment (scFv) of an antibody. The scFv fragments may have a molecule weight of about 30 kDa, and comprise a heavy and a light chain linked via a linker. The heavy and light chains may have constant and variable parts, where the loops may be referred to as CDRs, which may be variable. In some embodiments, at least four variable CDRs are present, where typically the CDR-H3 and CDR-L3 are most variable since they form the most exposed part of the binding molecule or fragment. CDR-L1 and CDR-L2 may be lacking (may be constant), while CDR-H1 and CDR-H2 may have slight variations. In some embodiments, the synthetic scFv fragments comprise short heavy chain sequences of CDR-H1, CDR-H2 and/or CDR-H3 on a VH scaffold in combination with a short light chain sequence from CDR-L3 on a VL scaffold, which are linked using a linker to form a scFv fragment. The synthetic scFv fragments may arise from human synthetic scFv libraries, where the CDRs are present on a library scaffold, such as from a Hell-11 or Hell-13 scaffold library (Säll et al., Generation and analyses of human synthetic antibody libraries and their application for protein microarrays. Protein Eng Des Sel. 2016 October;29 (10): 427-437) or from a similar MAW-16 library. The length of the CDR-H3 is typically 8 to 22 amino acids, and the lengths of the CDR-L3 8-12 amino acids. The total scFv fragment comprising both the library scaffold, the heavy and light CDR parts and the linker is typically around 250-300 amino acids, such as 273 amino acids. The scFv fragments may be modified by attaching the fragment to another structure. These other structures may be e.g. an antibody or part of an antibody, a HIS-tag, FLAG or biotin etc. The CDRs may also be mounted on a full-size antibody, using the constant regions of CDR-L1 and CDR-L2 as corresponding antibody CDRs.

The human antibodies or binding fragments of the invention may be produced using different methods, such as using phage display and libraries. Monoclonal antibody production based on phage display technology represents an attractive alternative to traditional hybridoma technology. A gene sequence coding for a particular antibody is integrated into the DNA sequence of a filamentous bacteriophage, which allows its expression on the surface of the bacteriophage capsid. This peculiarity establishes a link between the genotype and the phenotype. The phage infects *Escherichia coli* and uses its inner replication system to continuously display new phage, without killing the host cell. This enables fast production of antibodies, in large numbers. A library of naïve or immune phage is therefore constituted and can be used to detect an antigen-antibody interaction of interest thanks to screening methods. Libraries can be generated from humans giving access to the human antibody repertoire.

For specific antibodies to prostasomes, the human genome offers clear advantages. Autoantibodies to prostasome are frequently occurring and when present they cause immunological infertility. Apart from the infertility the antibodies do not cause damage to other organs in the body. This is a strong indication that human antibodies to prostasomes are highly specific. The high selectivity is a clear advantage when detecting prostasomes in e.g. blood where other cell types will be present. One way of producing the antibodies or fragments of the invention is thus to use phage display technology to develop human scFv antibodies to human prostasomes. Another advantage of using antibodies from the same species is the immunological tolerance that should reduce the number of antibodies to antigens generally presented in the body. Immunological tolerance is a complex series of mechanisms that impair the immune system to mount responses against self-antigens. Studies of the scFv antibodies also indicates that they are superior to mouse antibodies as binders when used to detect prostasomes, allowing for the detection of much lower amounts of prostasomes. This is surprising since it is contrary to general beliefs that claim that the affinity of phage display antibodies often have lower affinity than hybridoma antibodies. A hypothesis for this finding is that it could be related to the fact that the antibodies are directed to prostasomes.

In one embodiment, the antibody or binding fragment thereof originates from a library which has been screened for binding capacities towards prostasomes (full size whole prostasomes). There exist numerous approaches to create antibody libraries from which binders can be selected, and these can be divided into natural or synthetic, depending on the source of the genetic diversity. Natural antibody repertoires take advantage of the ability of the immune system to generate diversity, while diversity in synthetic repertoires is introduced artificially at defined regions of the antibody sequence. Synthetic libraries generate high genetic diversity, but these have not been selected for function. In order to maximize function, the trend within synthetic library design has therefore been to try to mimic the diversity found in natural antibodies while still trying to boost the genetic diversity.

In the examples, below, we describe the generation of synthetic scFv libraries, which may be used to screen for the synthetic scFv fragments described herein. Two human synthetic antibody fragment libraries have previously been developed, made as part of a two-step process through which initial experience with the first-generation library (HelL-11) was utilized to design a second-generation library (HelL-13) (see Säll et al. Generation and analyses of human synthetic antibody libraries and their application for protein microarrays. Protein Eng Des Sel. 2016 October;29 (10): 427-437). Although differing slightly in the design of CDR-H3 and CDR-L3 (FIG. 3), both template scFv genes used as scaffolds for the Hell-11 and Hell-13 libraries were built on the human IGHV3-23 and IGKV1-39 genes, in which kappa light chain IGKV1-39 and heavy chain IGHV3-23 were used as scaffolds for library construction. Antibodies consisting of these genes are among the most frequently found in natural antibody repertoires and this particular VH/VL combination has been shown favorable. Alternatively to Hell-11 and Hell-13, a MAW-16 library may be used, in which the variable heavy chain is also based on IGHV3-23, and the light variable chain is also based on IGKV1-39.

Figure 4B:
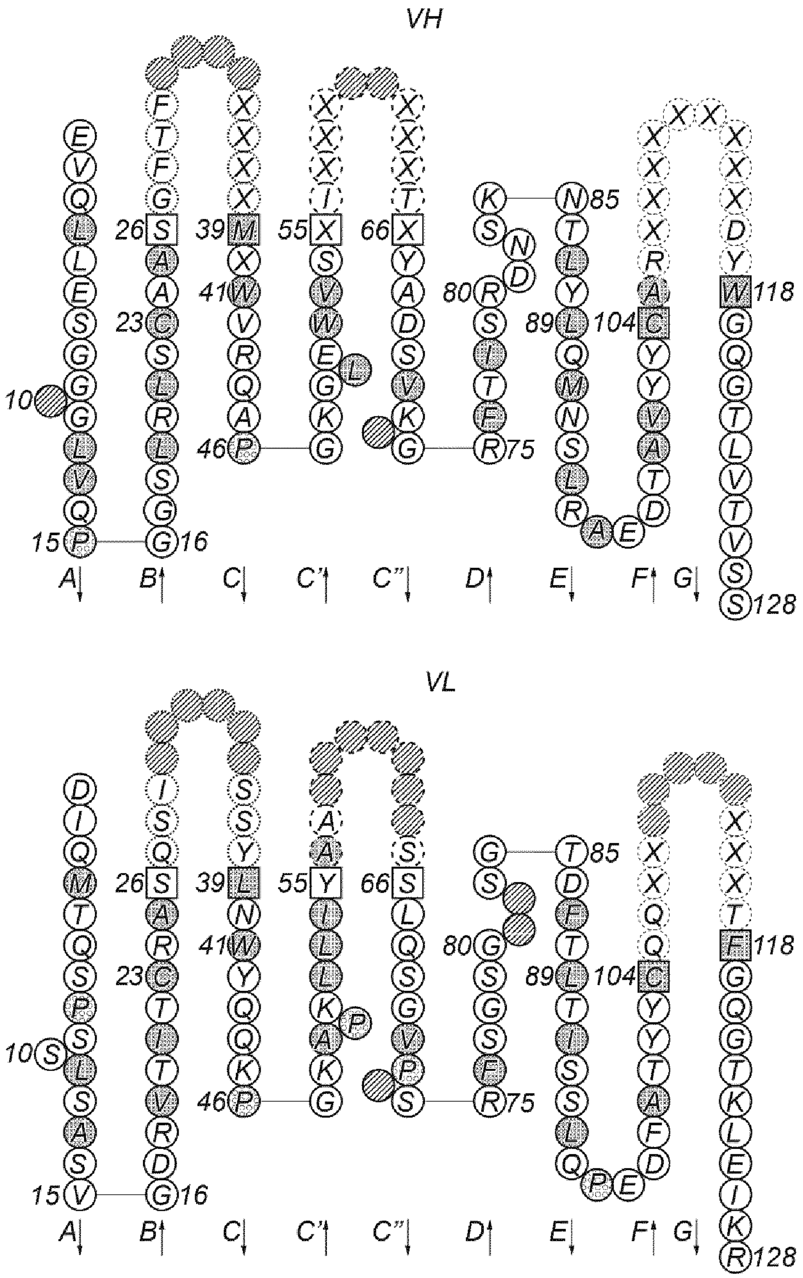
FIG. 4*b* shows the defining positions that are carriers of diversity (X) in the design of VH and VL of Hell-11 and Hell-13 antibody libraries.

Diversity was introduced at defined positions in four of the six CDR loops; CDR-H1, CDR-H2, CDR-H3 and CDR-L3, and residues distributed in CDR-H1, CDR-H2, CDR-H3 and CDR-L3 loops were chosen for diversification. The scFv fragments of the different libraries are shown in FIG. 4*a*, and the VH and VL parts are shown in FIG. 4*b*. One primer was used each for CDR-H1 and CDR-H2, while three or five and 10 or 15 primers, one primer for each of the allowed lengths of these loops, were used to diversify CDR-L3 and CDR-H3 of HelL-13 and Hell-11, respectively. The introduced diversity was biased for tyrosine, serine and glycine since these amino acids are highly abundant in antigen-binding sites and their preferred role in antigen recognition has been demonstrated in several studies. Targeted residues of CDR-H1 and CDRH2 were restricted to this trimer code. Although biased for tyrosine, serine and glycine, CDR-H3 and CDR-L3 were allowed a much more complex chemical diversity based on the knowledge of what is commonly found in natural antibodies of CDR-H3. Solvent accessible residues of CDR-H1 and CDR-H2 were restricted to tyrosine, serine and glycine, whereas a more complex diversity scheme was allowed in CDR-H3 and CDR-L3. The allowed lengths of CDR-H3 and CDR-L3 of HelL-11 were 8-22 and 8-12 residues, respectively. In Hell-13 the corresponding lengths were 8-17 and 8-10 residues. The variability introduced here was mainly restricted to amino acids commonly found in natural antibodies at these positions. In Hell-11 the lengths of CDR-H3 and CDR-L3 were allowed to vary from 8 to 22 and 8 to 12, respectively, thereby covering >90% of the most frequently occurring lengths of natural antibodies. The Hell-13 library was designed to contain CDR-H3 loop lengths of 8-17 and CDR-L3 of 8-10, thereby covering ~90% of the functional selected binders derived from Hell-11. To further increase the fraction of functional binders in the naïve repertoire of Hell-13 a CDR-L3 loop without stop-codons was included. The IGKV1-39 germline sequence was chosen as template for CDR-L3 (position 105-115). In position 116, which is naturally derived from the J-segment, a tyrosine was included because of its general favorable binding properties.

In one embodiment, the human monoclonal antibody of the invention is a human synthetic single-chain variable fragment (scFv) of an antibody. The technology for developing the library and screening for the antibody fragments utilizes a focused single chain antibody fragment (scFv) repertoire (Persson et al., (2006) Creating a focused antibody library for improved hapten recognition. J Mol Biol 357, 607-620. (Abstract) (GenBank)). The template scFv genes used as scaffolds for the HelL-11 and Hell-13 libraries were built on the human Immunoglobulin heavy variable 3-23 precursor (IGHV3-23) and Immunoglobulin kappa variable 1-39 precursor (IGKV1-39) genes. The phagemid vector backbone was pFab5c. Residues distributed in CDR-H1, CDR-H2, CDR-H3 and CDR-L3 were cloned and the sequences were introduced into the library scaffold genes, as shown in FIG. 3*a*. The lengths of CDR-H1 and H2 were 8 amino acid residues for both Hell-11 and Hell-13. The lengths of CDR-H3 and CDR-L3 of Hell-11 were 8-22 and 8-12 amino acid residues, respectively. In Hell-13 the corresponding lengths were 8-17 and 8-10 residues. (Säll et al., Generation and analyses of human synthetic antibody libraries and their application for protein microarrays. Protein Eng Des Sel. 2016 October;29 (10): 427-437).

The library was screened, using phage display, against a panel of different prostasomes, yielding diverse and highly specific binders to prostasomes. Analysis has shown that members selected from such populations are excellent sources to develop high affinity binders following affinity maturation by random mutagenesis and stringent phage display selection. Mutations in high affinity variants were scattered throughout the scaffold and could not easily have been predicted.

The synthetic scFv fragments of the invention may include one VH part comprising CDR H1, CDR H2, and CDR H3, and one VL part comprising CDR L3 or CDR L1, CDR L2 and CDR L3. The CDR-L1 and CDR-L2 could be seen as CDR:s present in the synthetic scFv fragments, the location of the CDR-L1 and CDR-L2 being shown in FIG. 4*b*. But as they do not differ between the different fragments of the invention, they could also be seen as part of the scaffold. Thus, in one embodiment only CDR H1, CDR H2, CDR H3 and CDR L3 is defined for each fragment. In other embodiments, such as when using the CDR:s in an antibody, all six CDR:s may be defined, including CDR L1 and CDR L2.

The synthetic scFv fragments of the invention may include one VH part comprising CDR H1, CDR H2, and CDR H3, and one VL part comprising CDR L3, which VH and VL parts are combined using a linker. This may be a gly-ser sequence of about 15 amino acids, such as GGGGSGGGGSGGGGS as shown in SEQ ID NO: 31. In some embodiments, the VH fragments is 128 amino acids, the VL fragment is 128 amino acids and the total scFv fragment is 273 amino acids. In some embodiments, the fragments may be shorter due to omission of some amino acids, as shown as dotted circles in FIG. 4*b*.

In one embodiment the antibody or antigen binding fragment may comprise a CDR of the VH part, such as a heavy chain CDR which may be referred to as CDR-H3, and a CDR of the VL part, such as a light chain CDR which may be referred to as CDR-L3, wherein:

CDR-H3 selected from SEQ ID NO: 1, 2, 3, 4, 5, 6, 7, 8, 9, 10, 11 and 12; CDR-L3 selected from SEQ ID NO: 13, 14, 15, 16, 17, 18, 19, 20, 21, 22, 23 and 24, and CDR sequences having 95% or more, such as 96%, 97%, 98%, 99% or more, identity thereto.

The most important variable parts constitutes the CDR-H3 and CDR-L3 parts. The CDR-H1, CDR-H2, CDR-L1 and CDR-L2 parts may be constant or vary, as show in table 1 below.

TABLE 1

| SEQUENCE | VL CDR L1 |
|---|---|
| SEQ ID NO: 56 | SQSISSYL |
| SEQ ID NO: 57 | SQSI$X_5X_6X_7X_8X_9X_{10}$SSYL |
| **SEQUENCE** | **VL CDR L2** |
| SEQ ID NO: 58 | YAASS |
| SEQ ID NO: 59 | YAA$X_4X_5X_6X_7X_8X_9X_{10}$SS |
| **SEQUENCE** | **VH CDR H1** |
| SEQ ID NO: 25 | GFTFSSYA |
| SEQ ID NO: 27 | GFTF $X_5X_6X_7X_8$M$X_{10}$ |
| SEQ ID NO: 28 | GFTF$X_5X_6X_7X_8$SSYA |
| **SEQUENCE** | **VH CDR H2** |
| SEQ ID NO: 26 | ISGSGGST |
| SEQ ID NO: 29 | GFTF $X_5X_6X_7X_8$T$X_{10}$ |
| SEQ ID NO: 30 | ISGS $X_5X_6$GGST |

The amino acids denoted as X may be any natural occurring amino acids. However, in a preferred embodiment the amino acids X are chosen from Y, S or G.

In one embodiment the antibody or antigen binding fragment comprises at least three heavy CDRs (CDR-H1, CDR-H2, CDR-H3) and one light CDR (CDR-L3), in any combination thereof, wherein:

CDR-H1 is selected from any variant of SEQ ID NO:25 and 27-28;

CDR-H2 is selected from any variant of SEQ ID NO:26 and 28;

CDR-H3 selected from SEQ ID NO: 1, 2, 3, 4, 5, 6, 7, 8, 9, 10, 11 and 12;

CDR-L3 selected from SEQ ID NO: 13, 14, 15, 16, 17, 18, 19, 20, 21, 22, 23 and 24, and CDR sequences having 95% or more, such as 96%, 97%, 98%, 99% or more, identity thereto.

In some embodiments, the antibody or antigen binding fragment comprises at least two CDRs; CDR-H3 and CDR-L3, or at least four CDRs; CDR-H1, CDR-H2, CDR-H3 and CDR-L3, or at least six CDRs; CDR-H1, CDR-H2, CDR-H3, CDR-L1, CDR-L2 and CDR-L3, wherein:

CDR-H1 is selected from any variant of SEQ ID NO: 25, 27 and 28;

CDR-H2 is selected from any variant of SEQ ID NO: 26, 29, and 30;

CDR-H3 selected from SEQ ID NO: 1, 2, 3, 4, 5, 6, 7, 8, 9, 10, 11 and 12;

CDR-L1 is selected from any variant of SEQ ID NO: 56 and 57;

CDR-L2 is selected from any variant of SEQ ID NO: 58 and 59;

CDR-L3 selected from SEQ ID NO: 13, 14, 15, 16, 17, 18, 19, 20, 21, 22, 23 and 24, and CDR sequences having 95% or more, such as 96%, 97%, 98%, 99% or more, identity thereto. The CDRs may be grafted on any suitable human antibody or antibody scaffold, such as built on the human IGHV3-23 and IGKV1-39 genes, in which kappa light chain IGKV1-39 and heavy chain IGHV3-23 are used as scaffolds.

In another embodiment, the antibody or antigen binding fragment thereof comprises a heavy chain variable region (VH) sequence selected from the group consisting of SEQ ID NO: 32-43 and sequences having 80% or more, such as 85%, 90%, 95% or more, identity thereto. In another embodiment, the antibody or antigen binding fragment thereof comprises a light chain variable region (VL) sequence selected from the group consisting of SEQ ID NO: 44-55 and sequences having 80% or more, such as 85%, 90%, 95% or more, identity thereto.

In some embodiments, the antigen binding fragment is an scFv fragment comprising a VH part selected from SEQ ID NO: 32-43 and a VL part selected from SEQ ID NO: 44-55, joined via a linker, such as the linker of SEQ ID NO: 31.

In one embodiment, the human monoclonal antibody or binding fragment thereof is a synthetic scFv fragment, built e.g. on the HelL-11 or HelL.13 scaffold, and comprising the CDRs chosen from the 12 scFv fragments of table 2, where VH CDR-H1 for fragment scFv 1 to scFv 12 corresponds to SEQ ID NO: 25, VH CDR-H2 for fragment scFv 1 to scFv 12 corresponds to SEQ ID NO: 26, VH CDR-H3 for fragment scFv 1 to scFv 12 corresponds to SEQ ID NO: 1-12, VL CDR-L3 for fragment scFv 1 to scFv 12 corresponds to SEQ ID NO: 13-24, and the linker between the fragments correspond to SEQ ID NO: 31.

TABLE 2

| Synthetic scFv fragment | VH CDR H1 | VH CDR H2 | VH CDR H3 | VL CDR L3 |
|---|---|---|---|---|
| scFv 1 | GFTF SSYA | ISGS GGST | CARH YYNW ASGY FDYW | CQQG WYPP TF |
| scFv 2 | GFTF SSYA | ISGS GGST | CART TSYY GYSA HFID YW | CQQG YGPF TF |
| scFv 3 | GFTF SSYA | ISGS GGST | CARV YYHY YYYG SFDY W | CQQS THLS TF |

TABLE 2-continued

| Synthetic scFv fragment | VH CDR H1 | VH CDR H2 | VH CDR H3 | VL CDR L3 |
|---|---|---|---|---|
| scFv 4 | GFTF SSYA | ISGS GGST | CARY SYYY AGSY YFDY W | CQQS YSTP YTF |
| scFv 5 | GFTF SSYA | ISGS GGST | CARS YSWY SRGP SLDY W | CQQA FYAH LLTF |
| scFv 6 | GFTF SSYA | ISGS GGST | CARY VRGY GYGY LDYW | CQQA PAYS PFTF |
| scFv 7 | GFTF SSYA | ISGS GGST | CARY THST YGYR LDYW | CQQD AYHP PTF |
| scFv 8 | GFTF SSYA | ISGS GGST | CARV FYYG PYYF SYHF DYW | CQQD DRGL PTF |

TABLE 2-continued

| Synthetic scFv fragment | VH CDR H1 | VH CDR H2 | VH CDR H3 | VL CDR L3 |
|---|---|---|---|---|
| scFv 9 | GFTF SSYA | ISGS GGST | CARS HYGS LDYW | CQQF SYTL STF |
| scFv 10 | GFTF SSYA | ISGS GGST | CARY SYYY TWLD YW | CQQF YPSL HTF |
| scFv 11 | GFTF SSYA | ISGS GGST | CARY TYYV GGFD YW | CQQG FVLS TF |
| scFv 12 | GFTF SSYA | ISGS GGST | CART YYYF YPYG YYFD YW | CQQG FYLP TF |

The human antibodies and binding fragments of the invention are capable of binding prostasomes, and thus to be used as a capture antibody in an assay for diagnosing prostate cancer. The antibodies or binding fragments thereof may recognize and bind any possible epitope of the prostasomes, which epitopes are known in the art. Some of the relevant epitopes are summarized in table 3 below.

TABLE 3

| Protein | Uniprot code | SEQ ID NO |
|---|---|---|
| 14-3-3 protein | P62258 | SEQ ID NO: 60 |
| Actin, | P60709 | SEQ ID NO: 61 |
| Alpha-actinin-2 | P35609 | SEQ ID NO: 62 |
| Aminopeptidase N | P15144 | SEQ ID NO: 63 |
| Annexin A2 | P07355 | SEQ ID NO: 64 |
| Clusterin | P10909 | SEQ ID NO: 65 |
| Desmoglein-1 | Q02413 | SEQ ID NO: 66 |
| Desmoplakin | P15924 | SEQ ID NO: 67 |
| Dipeptidyl peptidase 4 | P27487 | SEQ ID NO: 68 |
| Epiplakin | P58107 | SEQ ID NO: 69 |
| Ezrin | P15311 | SEQ ID NO: 70 |
| Filaggrin-2 | Q5D862 | SEQ ID NO: 71 |
| Flotillin-1 | O75955 | SEQ ID NO: 72 |
| Flotillin-2 | Q14254 | SEQ ID NO: 73 |
| Glyceraldehyde-3-phosphate dehydrogenase | P04406 | SEQ ID NO: 74 |
| G-protein coupled receptor | Q8IZP9 | SEQ ID NO: 75 |
| Heat shock 70 kDa protein | P0DMV8 | SEQ ID NO: 76 |
| Heat shock cognate 71 kDa protein | P11142 | SEQ ID NO: 77 |
| Heat shock protein HSP 90-alpha | P07900 | SEQ ID NO: 78 |
| Heat shock protein HSP 90-beta | P08238 | SEQ ID NO: 79 |
| High affinity immunoglobulin gamma Fc receptor I | P12314 | SEQ ID NO: 80 |
| Histidine-rich glycoprotein | P04196 | SEQ ID NO: 81 |
| Histidine--tRNA ligase | P12081 | SEQ ID NO: 82 |
| Immunoglobulin lambda-like polypeptide | B9A064 | SEQ ID NO: 83 |
| Intelectin-1 | Q8WWA0 | SEQ ID NO: 84 |
| Intelectin-2 | Q8WWU7 | SEQ ID NO: 85 |
| Junction plakoglobin | P14923 | SEQ ID NO: 86 |
| Kallikrein-2 | P20151 | SEQ ID NO: 87 |
| Myosin-1 | P12882 | SEQ ID NO: 88 |
| Myosin-2 | Q9UKX2 | SEQ ID NO: 89 |
| Nebulin | P20929 | SEQ ID NO: 90 |
| Programmed cell death 6-interacting protein | Q8WUM4 | SEQ ID NO: 91 |
| Prolactin-inducible protein (PIP) | P12273 | SEQ ID NO: 92 |
| Prostate-specific antigen | P07288 | SEQ ID NO: 93 |
| Prostatic acid phosphatase | P15309 | SEQ ID NO: 94 |
| Protein-glutamine gamma-glutamyltransferase | Q08188 | SEQ ID NO: 95 |
| Ras-related protein Rab | Q9BZG1 | SEQ ID NO: 96 |
| Semenogelin-1 | P04279 | SEQ ID NO: 97 |
| Semenogelin-2 | Q02383 | SEQ ID NO: 98 |
| Serine--tRNA ligase | P49591 | SEQ ID NO: 99 |

TABLE 3-continued

| Protein | Uniprot code | SEQ ID NO |
|---|---|---|
| Sorbitol dehydrogenase | Q00796 | SEQ ID NO: 100 |
| Titin | Q8WZ42 | SEQ ID NO: 101 |
| Tubulin alpha 1C | Q9BQE3 | SEQ ID NO: 102 |
| Tubulin alpha 4A | P68366 | SEQ ID NO: 103 |
| Tubulin beta | P07437 | SEQ ID NO: 104 |

A method for diagnosing, prognosing, evaluating severity or treatment efficacy of a prostate cancer according to the inventive concept will now be described with reference to FIGS. 5-8. For clarity and simplicity, the method will be described in terms of 'steps'. It is emphasized that steps are not necessarily processes that are delimited in time or separate from each other, and more than one 'step' may be performed at the same time in a parallel fashion.

The inventive concept has mainly been described above with reference to a few embodiments. However, as is readily appreciated by a person skilled in the art, other embodiments than the ones disclosed above are equally possible within the scope of the inventive concept, as defined by the appended patent claims.

Example Operations

The proposed methods will now be described in more detail referring to FIGS. 5-8. It should be appreciated that the operations do not need to be performed in order. Furthermore, it should be appreciated that not all of the operations need to be performed.

Figure 5:
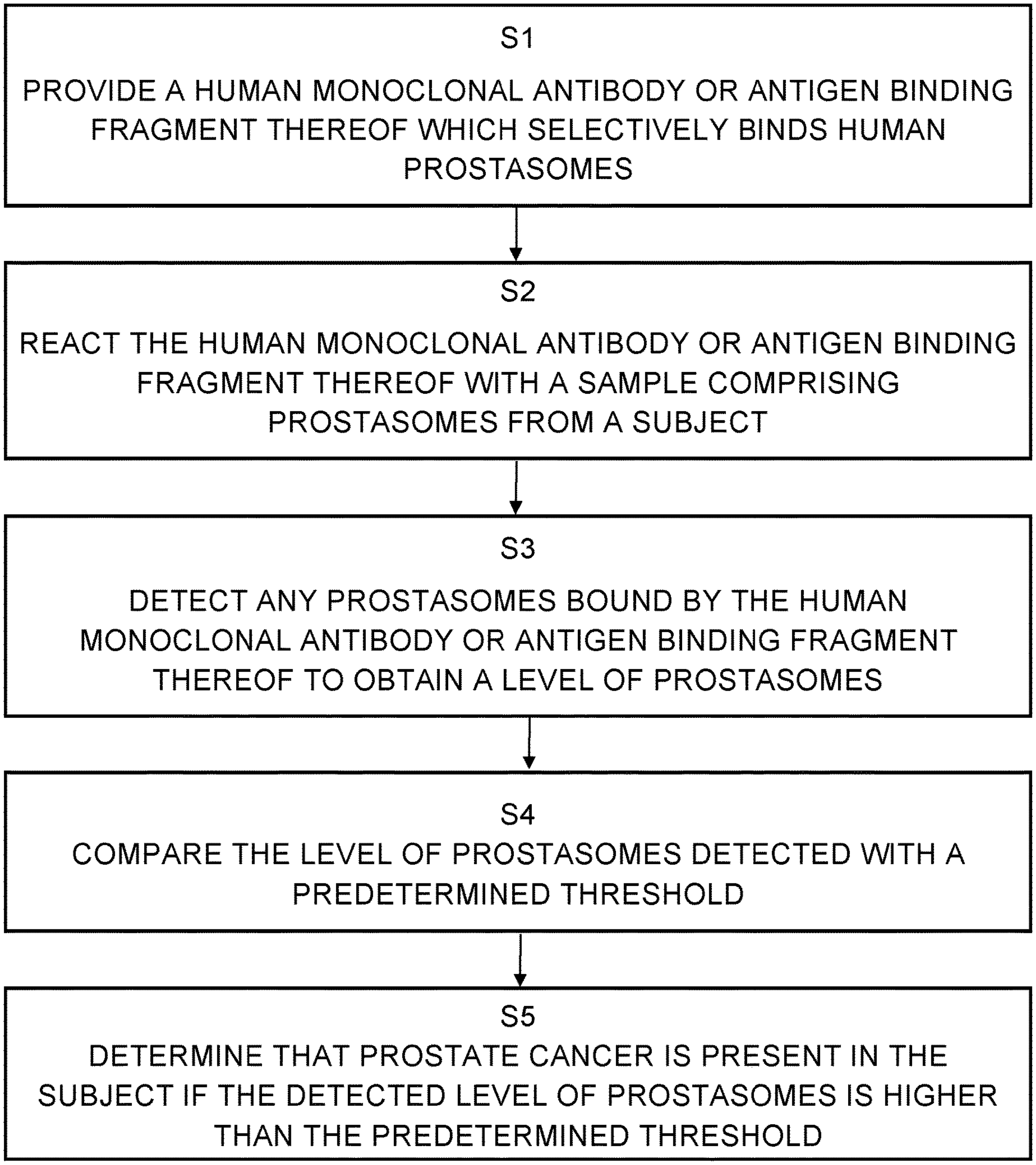
FIG. 5 shows a flowchart of a method of the present disclosure for diagnosing a prostate cancer in a subject.

FIG. 5 illustrates an in vitro method for determining whether prostate cancer is present in a subject, the method comprising the steps of: providing (S1) a human monoclonal antibody or antigen binding fragment thereof which selectively binds human prostasomes, reacting (S2) the human monoclonal antibody or antigen binding fragment thereof with a sample comprising prostasomes from a subject, detecting (S3) any prostasomes bound by the human monoclonal antibody or antigen binding fragment thereof to obtain a level of prostasomes, comparing (S4) said level of prostasomes detected with a predetermined threshold; and determining (S5) that prostate cancer is present in the subject if the detected level of prostasomes is higher than the predetermined threshold. Determining that prostate cancer is not present in this regard includes determining that no clinically detectable prostate cancer is present, i.e. that any potentially existing cancer cells are too few to be detected or labelled as an existing prostate cancer. However, a few cancer cells may of course be present, which will develop into a detectable prostate cancer eventually. However, these low amounts will be considered as that prostate cancer is not present at the time of diagnosis.

The predetermined threshold may correspond to a level of 10 ng prostasomes per mL sample. In another embodiment, the predetermined threshold is as low as 1-2 ng prostasomes per mL sample. The threshold may also be 3, 4, 5, 6, 7, 8, or 9 ng/ml.

In one aspect, detecting (S3) any prostasomes bound by the human monoclonal antibody or antigen binding fragment thereof comprises detecting the prostasomes using an anti-prostasome detection antibody or antigen binding fragment thereof. Typically, a low amount of prostasomes are always present in the sample if the subject is male. In a further aspect, the method is a sandwich immunoassay and detecting (S3) prostasomes (200) bound by the human monoclonal antibody or antigen binding fragment thereof (101) comprises detecting the anti-prostasome detection antibody (102) using a further detection antibody (103), wherein the human monoclonal antibody or binding fragment thereof (101) is a capture antibody, the anti-prostasome detection antibody (102) is a primary detection antibody and the further detection antibody (103) is a secondary detection antibody. In one further aspect, the primary detection antibody (102) is a chicken antibody and the secondary detection antibody (103) is an anti-chicken antibody. In one aspect, the sample from the subject is a body fluid sample. In a further aspect, the body fluid sample from the subject is selected from the group consisting of blood, serum, plasma, urine cerebrospinal fluid and a cell suspension. The blood, serum and plasma arise from a blood sample of peripheral blood taken from the patient, while the cell suspension typically arise from a biopsy. The urine may be used after e.g. a prostate massage has been performed, where after prostasomes may leak into the urine. In one aspect, the human monoclonal antibody or antigen binding fragment thereof is an antibody or antigen binding fragment of the present disclosure.

Figure 6:
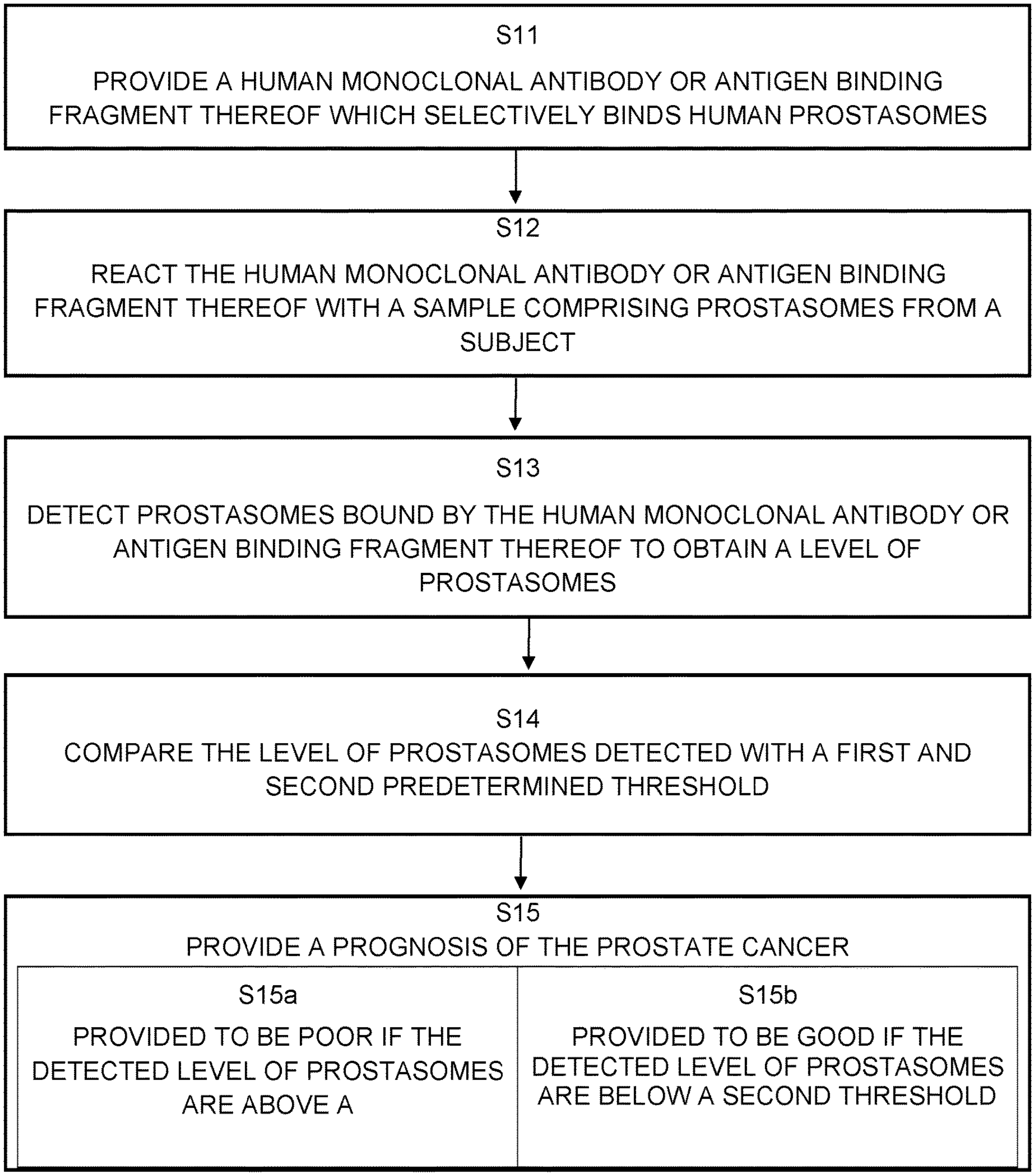
FIG. 6 shows a flowchart of a method of the present disclosure for prognosing prostate cancer in a subject.

FIG. 6 illustrates an in vitro method for providing a prognosis of a prostate cancer in a subject in need thereof, the method comprising the steps of: providing (S11) a human monoclonal antibody or antigen binding fragment thereof which selectively binds prostasomes, reacting (S12) the human monoclonal antibody or antigen binding fragment thereof with a sample from a subject comprising prostasomes, detecting (S13) prostasomes bound by the human monoclonal antibody or antigen binding fragment thereof to obtain a level of prostasomes, comparing (S14) said level of prostasomes detected with a first and second predetermined threshold, and providing (S15) a prognosis of the prostate cancer, wherein prognosis of the prostate cancer is provided (S15*a*) to be poor if the detected level of prostasomes are above a first predetermined threshold, and provided (S15*b*) to be good if the detected level of prostasomes are below a second threshold. In one embodiment, the first threshold is 10 ng prostasomes per mL sample and the second threshold is 1 ng prostasomes per ml sample.

In one aspect, the detecting (S13) prostasomes bound by the human monoclonal antibody or antigen binding fragment thereof comprises detecting the prostasomes using an anti-prostasome detection antibody or antigen binding fragment thereof. In a further aspect, the method is a sandwich immunoassay and detecting (S13) prostasomes (200) bound by the human monoclonal antibody or antigen binding fragment thereof (101) comprises detecting the anti-prostasome detection antibody (102) using a further detection antibody (103), wherein the human monoclonal antibody or binding fragment thereof (101) is a capture antibody, the anti-prostasome detection antibody (102) is a primary detection antibody and the further detection antibody (103) is a secondary detection antibody. In one further aspect, the primary detection antibody (102) is a chicken antibody and the secondary detection antibody (103) is an anti-chicken antibody. In one aspect, the sample from the subject is a body fluid sample. In a further aspect, the body fluid sample from the subject is selected from the group consisting of blood, serum, plasma, urine, cerebrospinal fluid and a cell suspension. In one aspect, the human monoclonal antibody or antigen binding fragment thereof is an antibody or antigen binding fragment of the present disclosure.

Figure 7:
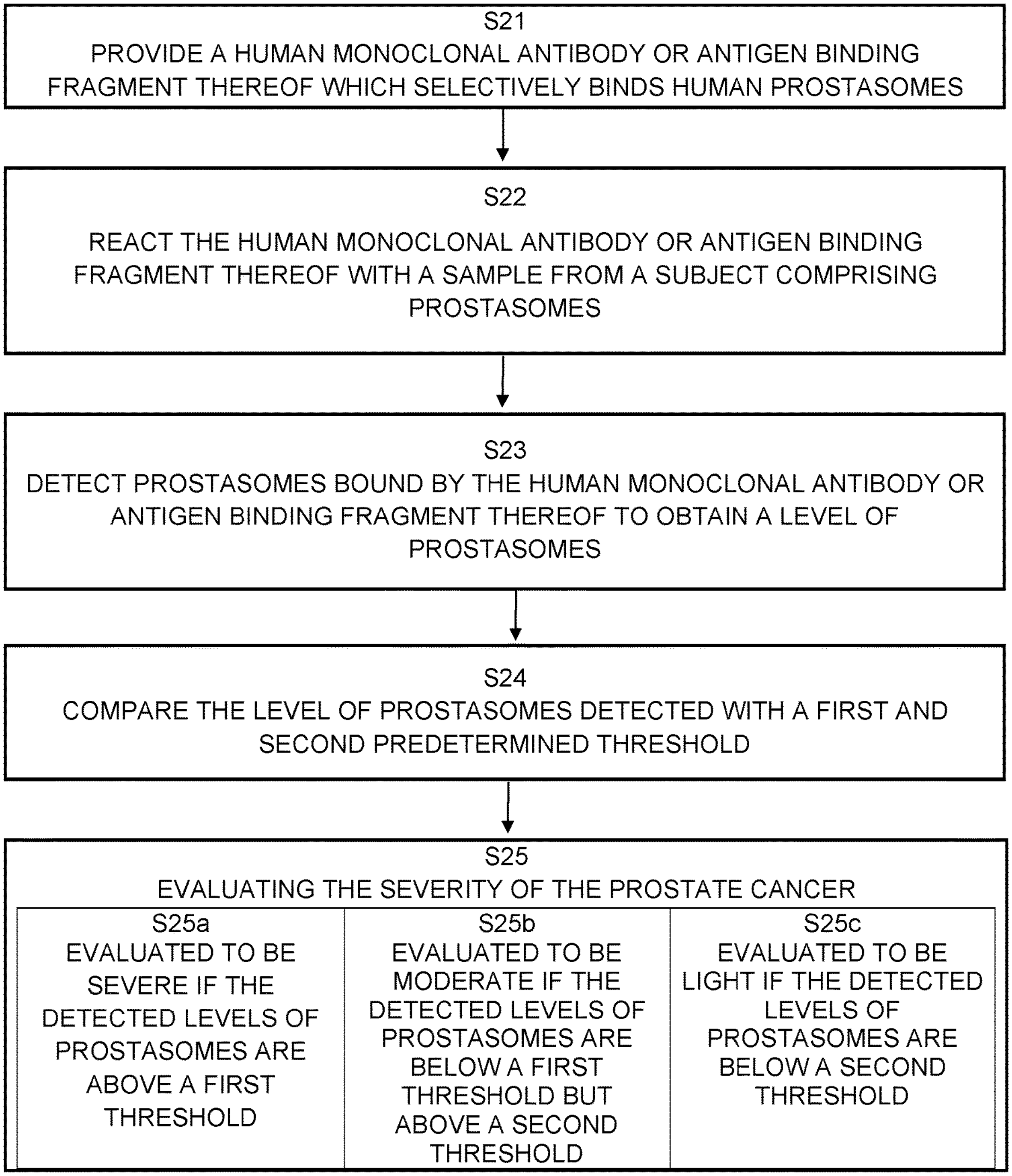
FIG. 7 shows a flowchart of a method of the present disclosure for evaluating the severity of a prostate cancer in a subject.

FIG. 7 illustrates an in vitro method for evaluating severity of a prostate cancer in a subject in need thereof, the method comprising the steps of: providing (S21) a human monoclonal antibody or antigen binding fragment thereof which selectively binds prostasomes; reacting (S22) the human monoclonal antibody or antigen binding fragment thereof with a sample from a subject comprising prostasomes; detecting (S23) prostasomes bound by the human monoclonal antibody or antigen binding fragment thereof to obtain a level of prostasomes; comparing (S24) said level of prostasomes detected with a first and second predetermined threshold; and evaluating (S25) the severity of the prostate cancer, wherein the prostate cancer is evaluated (S25*a*) to be severe if the detected levels of prostasomes are above a first threshold, evaluated (S25*b*) to be moderate if the detected levels of prostasomes are below a first threshold but above a second threshold, and evaluated (S25*c*) to be light if the detected levels of prostasomes are below a second threshold. In one embodiment, the first threshold is 10 ng prostasomes per mL sample and the second threshold is 1 ng prostasomes per ml sample.

In one aspect, the detecting (S23) prostasomes bound by the human monoclonal antibody or antigen binding fragment thereof comprises detecting the prostasomes using an anti-prostasome detection antibody or antigen binding fragment thereof. In a further aspect, the method is a sandwich immunoassay and detecting (S23) prostasomes (200) bound by the human monoclonal antibody or antigen binding fragment thereof (101) comprises detecting the anti-prostasome detection antibody (102) using a further detection antibody (103), wherein the human monoclonal antibody or binding fragment thereof (101) is a capture antibody, the anti-prostasome detection antibody (102) is a primary detection antibody and the further detection antibody (103) is a secondary detection antibody. In one further aspect, the primary detection antibody (102) is a chicken antibody and the secondary detection antibody (103) is an anti-chicken antibody. In one aspect, the sample from the subject is a body fluid sample. In a further aspect, the body fluid sample from the subject is selected from the group consisting of blood, serum, plasma, urine, cerebrospinal fluid and a cell suspension. In one aspect, the human monoclonal antibody or antigen binding fragment thereof is an antibody or antigen binding fragment of the present disclosure. The severity of the prostate cancer is usually described in the art in relation to a Gleason score, which may be linked to both aggressiveness and severity, as well as prognosis. Men with a biochemical recurrence and a PSA doubling time <12 months and/or a biopsy Gleason score of 8-10 are considered to have an indication for androgen deprivation therapy (ADT) according to the European Association of Urology (EAU) guidelines. The prostasome assay of the invention distinguished patients with high and medium Gleason scores (8/9 and 7, respectively) from those with low score (≤6), thus reflecting disease aggressiveness. Thus, a determined level of prostasomes above 1 ng/ml could be said to correspond to a Gleason score of above 6.

Figure 8:
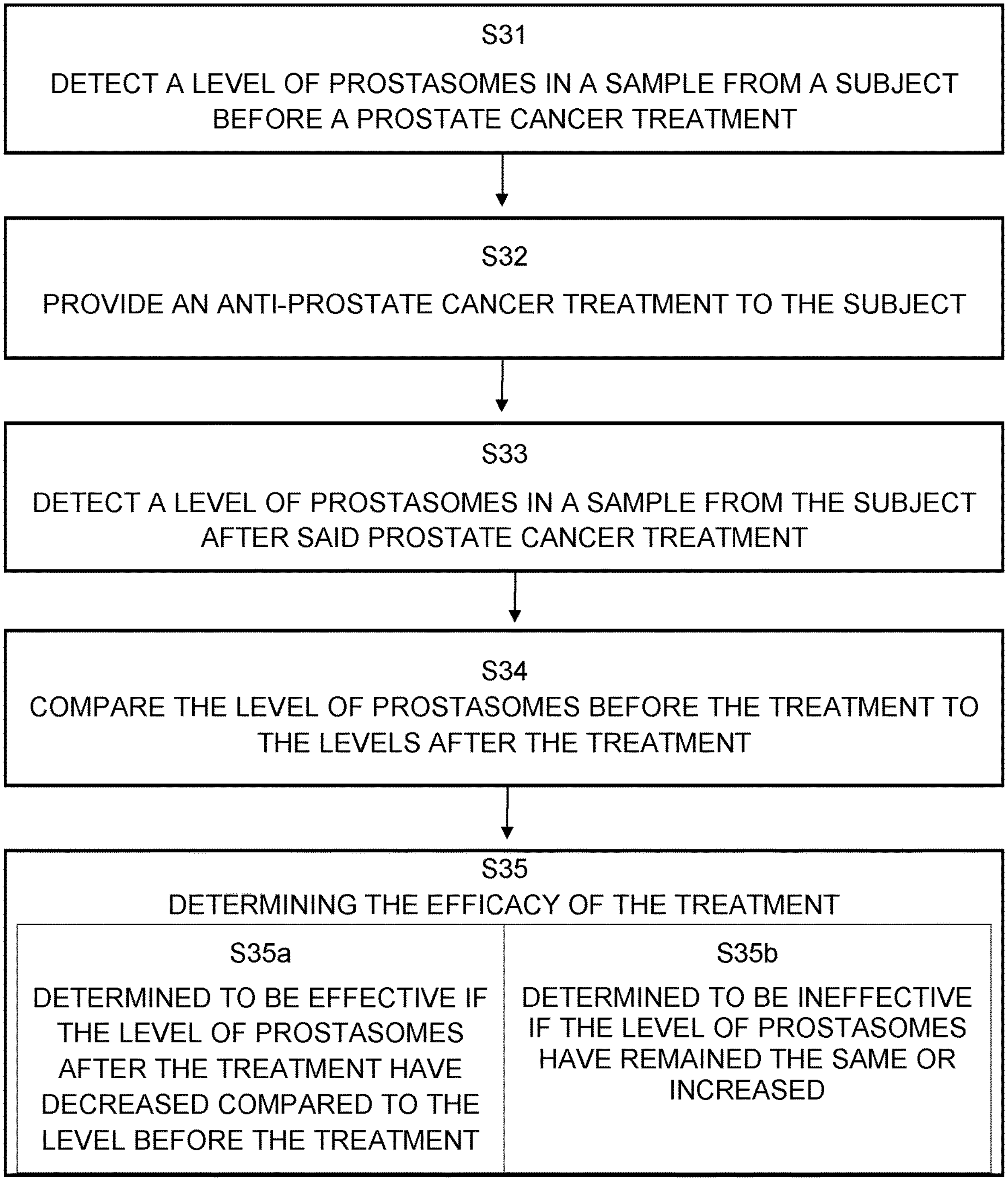
FIG. 8 shows a flowchart of a method of the present disclosure for determining the efficacy of a prostate cancer treatment of a subject.

FIG. 8 illustrates an in vitro method for evaluating the efficacy of a prostate cancer treatment in a subject in need thereof, the method comprising the steps of: detecting (S31) a level of prostasomes in a sample from a subject before a prostate cancer treatment, providing (S32) an anti-prostate cancer treatment to the subject, detecting (S33) a level of prostasomes in a sample from the subject after said prostate cancer treatment, comparing (S34) the level of prostasomes before the treatment to the levels after the treatment, and determining (S35) the efficacy of the treatment, where the treatment is determined to be effective (S35*a*) if the level of prostasomes after the treatment have decreased compared to the level before the treatment, and determined as ineffective (S35*b*) if the level of prostasomes have remained the same or increased.

In one aspect, the detecting (S33) prostasomes bound by the human monoclonal antibody or antigen binding fragment thereof comprises detecting the prostasomes using an anti-prostasome detection antibody or antigen binding fragment thereof. In a further aspect, the method is a sandwich immunoassay and detecting (S33) prostasomes (200) bound by the human monoclonal antibody or antigen binding fragment thereof (101) comprises detecting the anti-prostasome detection antibody (102) using a further detection antibody (103), wherein the human monoclonal antibody or binding fragment thereof (101) is a capture antibody, the anti-prostasome detection antibody (102) is a primary detection antibody and the further detection antibody (103) is a secondary detection antibody. In one further aspect, the primary detection antibody (102) is a chicken antibody and the secondary detection antibody (103) is an anti-chicken antibody. In one aspect, the sample from the subject is a body fluid sample. In a further aspect, the body fluid sample from the subject is selected from the group consisting of blood, serum, plasma, urine, cerebrospinal fluid and a cell suspension. In one aspect, the human monoclonal antibody or antigen binding fragment thereof is an antibody or antigen binding fragment of the present disclosure.

The content of this disclosure thus enables to diagnose prostate cancer, to determine the prognosis of the prostate cancer, which is linked to the stage and aggressiveness of the cancer, to evaluate the severity of the cancer, which may be used as a decision support for selecting treatment, such as performing surgery or not, and to evaluate a treatment regimen of the prostate cancer in a subject, the subject typically being a male human being. The treatment regimen may be evaluating the efficacy of the treatment by measuring the levels of prostasomes in a sample before and after said treatment, the treatment including both surgery, radiation therapy and administration of a medical substance. Thus, the method may comprise measuring the prostasome levels according to the invention, administering a therapeutic drug, and measuring the levels of prostasomes again after the drug has been administered and has had time to affect the cancer, the time depending on the drug used, which would be apparent to a skilled person depending on the treatment used.

In the drawings and specification, there have been disclosed exemplary aspects of the disclosure. However, many variations and modifications can be made to these aspects without substantially departing from the principles of the present disclosure. Thus, the disclosure should be regarded as illustrative rather than restrictive, and not as being limited to the particular aspects discussed above. Accordingly, although specific terms are employed, they are used in a generic and descriptive sense only and not for purposes of limitation. The description of the example embodiments provided herein have been presented for purposes of illustration. The description is not intended to be exhaustive or to limit example embodiments to the precise form disclosed, and modifications and variations are possible in light of the above teachings or may be acquired from practice of various alternatives to the provided embodiments. The examples discussed herein were chosen and described in order to explain the principles and the nature of various example embodiments and its practical application to enable one skilled in the art to utilize the example embodiments in various manners and with various modifications as are suited to the particular use contemplated. The features of the embodiments described herein may be combined in all possible combinations of methods, products, and systems. It should be appreciated that the example embodiments presented herein may be practiced in any combination with each other.

It should be noted that the word "comprising" does not necessarily exclude the presence of other elements or steps than those listed and the words "a" or "an" preceding an element do not exclude the presence of a plurality of such elements. It should further be noted that any reference signs do not limit the scope of the claims, that the example embodiments may be realized in the broadest sense of the claims.

While the invention has been described with reference to various exemplary aspects and embodiments, it will be understood by those skilled in the art that various changes may be made, and equivalents may be substituted for elements thereof without departing from the scope of the invention. In addition, many modifications may be made to adapt a particular situation to the teachings of the invention without departing from the essential scope thereof. Therefore, it is intended that the invention not be limited to any particular embodiment, but that the invention will include all embodiments falling within the scope of the appended claims. The invention will be further illustrated by the following non-limiting Examples.

EXAMPLES

Example 1 Synthetic Antibody Fragment Library Construction

The synthetical scFv fragments scFv 1-12 of the invention originates from the human synthetic antibody fragment libraries HeIL-11 and HeIL-13 produced by Säll et al. (Säll et al., Generation and analyses of human synthetic antibody libraries and their application for protein microarrays. Protein Eng Des Sel. 2016 October;29(10): 427-437), aspects of the method are summarized below.

Residues distributed in CDR-H1, CDR-H2, CDR-H3 and CDR-L3 were chosen for diversification and oligonucleotides targeting these loops were made using custom-made trimer phosphoramidite mixes (TriLink BioTechnologies, San Diego, CA, USA), encoding the amino acid compositions shown in FIG. 3. One primer was used each for CDR-H1 and CDR-H2, while three or five and 10 or 15 primers, one primer for each of the allowed lengths of these loops, were used to diversify CDR-L3 and CDR-H3 of HeIL-13 and Hell-11, respectively. The primer encoded sequences were introduced into the library scaffold genes using an optimized Kunkel mutagenesis methodology, and the Kunkel DNA was subsequently electrocorporated into E-*coli* cells. Ultimately the scFv displaying phages were harvested. Phage selection based on specific antigens could then be performed to attain specific antigen binding fragments.

Thus, FIG. 3 shows the Hell-11 and Hell-13 library designs. The two libraries have similar designs and are both build on the human scFv scaffold based on heavy chain variable gene IGHV3-23 and kappa light chain variable gene IGKV1-39 (for full sequences of these, see Sall et al., Generation and analyses of human synthetic antibody libraries and their application for protein microarrays. Protein Eng Des Sel. 2016 October;29 (10): 427-437), as shown in FIG. 3*a*. The libraries were constructed to contain diversity, denoted with the standard one letter code, in selected positions within and in immediate proximity to CDR-H1, CDR-H2, CDR-H3 and CDR-L3. Solvent accessible residues of CDR-H1 and CDR-H2 were restricted to tyrosine, serine and glycine, whereas a more complex diversity scheme was allowed in CDR-H3 and CDR-L3. X and J each denote a mixture of 13 amino acids introduced at proportions as described in FIG. 3*b*. The allowed lengths of CDR-H3 and CDR-L3 of Hell-11 were 8-22 and 8-12 residues, respectively. In Hell-13 the corresponding lengths were 8-17 and 8-10 residues. (Boundaries for CDRs and residue numbering are as defined by the IMGT nomenclature).

The library design and construction is further depicted in FIG. 4. FIG. 4*a* shows the amino acid sequence of the Hell library scaffolds. Hell-11 and Hell-13 are synthetic scFv libraries based on the human scaffold based on heavy chain variable gene IGHV3-23 and kappa light chain variable gene IGKV1-39, connected by a 15 amino acid long Gly-Ser linker (underlined). CDR-H1, H2, H3 and L3 are marked with a box, and randomized positions are highlighted in grey. Since the Kunkel cloning procedure is not 100% efficient, stop-codons were introduced in CDR-H3 and CDR-L3 of the Hell-11 template and in the CDR-H3 of the HelL-13 template gene (indicated with *). This ensures that only clones mutagenized in these regions are displayed on phage. Stop-codons were not introduced in any of the other CDR loops and hence non-mutated versions of these loops will be found in the displayed library. The template sequence of the first and second CDRs of both the heavy and light chains were chosen to mimic that found in the germline genes. Likewise, the sequence of IGKV1-39 was chosen for CDR-L3 (position 105-115) of the Hell-13 scaffold gene. In position 116 of VL, which is naturally derived from the J-segment, a tyrosine was incorporated because of the general favorable binding properties of this residue.

In FIG. 4*b* is shown Collier de Perles defining positions that are carriers of diversity (X) in the design of VH and VL of HelL-11 and Hell-13 antibody libraries. The present illustrations demonstrate sequences with CDR3 lengths of 13 (VH) and 8 (VL) residues, but the library design allows for length variation in these hypervariable loops. Residues defined by the IMGT numbering scheme but not present in these VH and VL sequences are represented by dashed circles.

Examples 2-5 below show different prostasome detection tests. Human monoclonal synthetic scFv fragments were produced (see example 1 above) and screened against micro titer plates coated with prostasomes. 64 positive clones were sequenced and according to the DNA sequences the positive selected clones represented 60 different human monoclonals.

Example 2 Testing of Human Monoclonals as Detectors, scFv Fragments 1-12

Purified prostasomes (1 mg/mL) were diluted 1:250 in PBS (phosphate buffered saline) and 100 μL were added per well in a microtitre plate. It was incubated for 2 h at room temperature, and washed three times with PBS containing 0.05% Tween 20. 120 μL 1% bovine serum albumin (BSA)

was added to the wells, which were incubated over night at room temperature. The wells were washed three times with PBS containing 0.05% Tween 20. Addition of biotinylated human synthetic scFv fragments 1:250 in row A were made and then 1:5 dilutions downwards. The plates were then incubated for 2 h at room temperature and then washed three times with PBS containing 0.05% Tween 20. 100 μL Streptavidine-HRP was added to the wells and incubated for 2 h at room temperature. The wells were washed three times with PBS containing 0.05% Tween 20. 100 μL TMB (tetramethylbenzidine) substrate was added to the wells, and incubated for 20 min and 25 μL 1 M H2SO4 was added to the plate. The plate was read at 450 nm.

Seminal plasma was collected from the Reproduction Centre at Akademiska Hospital. (Uppsala, Sweden) following previously described routines (Ronquist, G. K., et al., Prostasomal DNA characterization and transfer into human sperm. Mol Reprod Dev, 2011. 78(7): p. 467-76.). The seminal plasma was thawed and centrifuged at 3,000 g for 12 min. The supernatants were collected and centrifuged at 10,000 g for 30 min. The supernatants were then transferred to new tubes and ultra-centrifuged using a 90Ti rotor (Beckman Coulter, Brea, CA, USA) at 100,000 g for 2 h. The pellets were resuspended in 0.02 M NaH2PO4, 0.15 M NaCl, pH 7.2 (PBS), overnight at 4 °C. The resuspended pellets were then loaded on a chromatography column (XK 60/70, GE Healthcare, Uppsala, Sweden) packed with Superdex 200 gel. Fractions were collected at a flow rate of 5 mL/h. The fractions were then measured with a spectrophotometer where peaks at both 260 nm (nucleic acid) and 280 nm (proteins) corresponds to prostasomes. These fractions were collected and pooled and ultra-centrifuged at 100,000 g. The obtained pellet was resuspended in PBS. The purified prostasomes (1 mg/ml were diluted 1:250 in PBS and 100 ul were added per well in a F96 Polysorb NUNC Immunoplate (Thermo Fisher Scientific, Uppsala, Sweden). The plates were incubated for 2 h at ambient temperature and then washed three times with PBS containing 0.05% Tween 20 (P1379, Sigma-Aldrich). 120 μL 1% bovine serum albumin (BSA, Sigma-Aldrich) in PBS were added to the wells and the plate was incubated over night at ambient temperature. The plate was washed three times with PBS containing 0.05% Tween 20. 100 μL of the biotinylated monoclonal antibodies were added in dilution of 4 μg/mL in PBS to the wells. The plate was incubated for two hours at ambient temperature and the wells were then washed three times with PBS containing 0.05% Tween 20. 100 μL Streptavidine-HRP (43-8322, Thermo Fisher Scientific) diluted 1:2000 in PBS was added to the plates. The plate was incubated for two hours at ambient temperature and the wells were then washed three times with PBS containing 0.05% Tween 20. 100 μL TMB substrate (EC-Blue Enhanced TMB substrate, *Medicago*, Uppsala, Sweden) was added to the plates and the plates were incubated for 20 min at ambient temperature in darkness. 25 μL of 1 M H2SO4 was added to each well and the plate was read at 450 nm in a SpectraMax 250 ELISA reader.

The results for individual human monoclonal scFv fragments 1-12 are presented in table 4 below.

TABLE 4

| scFv fragment no: | Dilution | Absorbance |
|---|---|---|
| 1 | 4 μg/mL | 0.643 |
| 2 | 4 μg/mL | 0.394 |
| 3 | 4 μg/mL | 0.903 |
| 4 | 4 μg/mL | 0.653 |

TABLE 4-continued

| scFv fragment no: | Dilution | Absorbance |
|---|---|---|
| 5 | 4 μg/mL | 0.617 |
| 6 | 4 μg/mL | 0.556 |
| 7 | 4 μg/mL | 1.36 |
| 8 | 4 μg/mL | 0.653 |
| 9 | 4 μg/mL | 1.291 |
| 10 | 4 μg/mL | 1.643 |
| 11 | 4 μg/mL | 0.066 |
| 12 | 4 μg/mL | 0.954 |

A conclusion from the experiment is that all synthetic scFv fragments give a positive response as detector antibodies when tested against purified prostasomes.

Example 3 Testing of Chicken Polyclonals as Detectors

Purified prostasomes (1 mg/mL) were diluted 1:250 in PBS and 100 μL were added per well in a microtitre plate. The plate was incubated for 2 h at room temperature, and washed three times with PBS containing 0.05% Tween 20. 120 μL 1% bovine serum albumin (BSA) was added to the wells, which were incubated over night at room temperature. The wells were washed three times with PBS containing 0.05% Tween 20. Addition of chicken anti-prostasome antibodies to row 1 and 2 and chicken anti-PSA antibodies to row 3 and 4 was made. Initial dilution 1:125 in row A and then 1:5 dilutions downwards were used, where the dilution was made in PBS-tween. The plates were then incubated for 1 h at room temperature and then washed three times with PBS containing 0.05% Tween 20. 100 μL anti-chicken IgY-HRP was added to the wells diluted in PBS-tween, and incubated for 1 h at room temperature. The wells were washed three times with PBS containing 0.05% Tween 20. 100 μL TMB substrate was added to the wells, and incubated for 10 min and thereafter 25 μL 1 M $H_2SO4$ was added to the plate. The plate was read at 450 nm.

Purified prostasomes (1 mg/mL) were diluted 1:250 in PBS and 100 μL were added per well in a F96 Polysorb NUNC Immunoplate (Thermo Fisher Scientific, Uppsala, Sweden). The plates were incubated for 2 h at ambient temperature and then washed three times with PBS containing 0.05% Tween 20 (P1379, Sigma-Aldrich). 120 μL 1% bovine serum albumin (BSA, Sigma-Aldrich) in PBS were added to the wells and the plate was incubated over night at ambient temperature. The plate was washed three times with PBS containing 0.05% Tween 20. 100 μL of chicken anti-prostasome and chicken anti-PSA antibodies (Immunsystem AB, Uppsala, Sweden) were added to the wells in dilution 1:125 in PBS containing 0.05% tween 20. The plate was incubated for one hour at ambient temperature and the wells were then washed three times with PBS containing 0.05% Tween 20. 100 μL chicken anti-IgY-HRP (A16130, Novex, Frederick, MD, USA) diluted 1:2000 in PBS-tween was added to the plates. The plate was incubated for one hour at ambient temperature and the wells were then washed three times with PBS containing 0.05% Tween 20. 100 μL TMB substrate (EC-Blue Enhanced TMB substrate, Medicago, Uppsala, Sweden) was added to the plates and the plates were incubated for 20 min at ambient temperature in darkness. 25 μL of 1 M H2SO4 was added to each well and the plate was read at 450 nm in a SpectraMax 250 ELISA reader. The results for the antibodies are presented in table 5 below.

TABLE 5

| Chicken Antibody | Dilution | Absorbance |
|---|---|---|
| anti-prostasome | 125× | 3.685 |
| anti-prostasome | 125× | 3.915 |
| anti-PSA | 125× | 3.364 |
| anti-PSA | 125× | 3.217 |

A conclusion from the experiment is that both chicken antibodies give a positive response as detector antibodies when tested against purified prostasomes. The tested antibodies give a strong response due to polyclonal antibodies having many epitopes, which gives a strong signal. Thus, the polyclonal chicken antibodies are well suited for use as a primary detection antibody for detection prostasomes bound to a capture antibody of the inventions.

Example 4 Testing of Purified Prostasomes Added to Normal Plasma

Human synthetic scFv fragment 4 (2 μg/mL) and human synthetic scFv fragment 7 (2 μg/mL) was coated in PBS. 100 μL were added per well and incubated for 2 h at room temperature, and then washed three times with PBS containing 0.05% Tween 20. 120 μL 1% bovine serum albumin (BSA) was added to the wells, which were incubated over night at room temperature. After incubation the wells were washed three times with PBS containing 0.05% Tween 20. Addition of 100 μL prostasomes 1 ng/ml diluted in plasma from female blood donor was made. 100 μL was added to row 1 and incubated for 2 h at room temperature. Addition of chicken anti-prostasome antibodies and chicken anti-PSA antibodies both in dilution 1:1000 were made, diluted in PBS-tween. The plate was incubated for 2 h at room temperature and washed three times with PBS containing 0.05% Tween 20. 100 UL anti-chicken IgY-HRP was added to the wells diluted in PBS-tween and incubated for 2 h at room temperature and then washed three times with PBS containing 0.05% Tween 20. 100 μL TMB substrate was added to the wells and incubated for 10 min where after 20 μL 1 M H2SO4 was added to the plate. The plate was read at 450 nm. 100 μL of human synthetic scFv fragment 4 (final concentration 2 μg/mL in PBS) and scFv fragment 7 (final concentration 2 μg/mL in PBS) were added separately per well in a F96 Polysorb NUNC Immunoplate (Thermo Fisher Scientific, Uppsala, Sweden). The plates were incubated for 2 h at ambient temperature and then washed three times with PBS containing 0.05% Tween 20 (P1379, Sigma-Aldrich). 120 UL 1% bovine serum albumin (BSA, Sigma-Aldrich) in PBS were added to the wells and the plate was incubated over night at ambient temperature. The plate was washed three times with PBS containing 0.05% Tween 20. 1 ng/ml purified prostasomes (final concentration) were diluted in female human blood donor plasma and 100 μL were added to the wells. The plate was incubated for two hours at ambient temperature and the wells were then washed three times with PBS containing 0.05% Tween 20. 100 μL of chicken anti-prostasome and chicken anti-PSA antibodies (Immunsystem AB, Uppsala, Sweden) were added separately to the wells in dilution 1:1000 in PBS containing 0.05% tween 20. The plate was incubated for two hours at ambient temperature and the wells were then washed three times with PBS containing 0.05% Tween 20. 100 μl anti-IgY-HRP (A16130, Novex, Frederick, MD, USA) diluted 1:2000 in PBS-tween was added to the plates. The plate was incubated for two hours at ambient temperature and the wells were then washed three times with PBS containing 0.05% Tween 20. 100 μL TMB substrate (EC-Blue Enhanced TMB substrate, Medicago, Uppsala, Sweden) was added to the plates and the plates were incubated for 20 min at ambient temperature in darkness. 25 μL of 1 M $H_2SO4$ was added to each well and the plate was read at 450 nm in a SpectraMax 250 ELISA reader. The results for the scFv fragments are presented in table 6 below.

TABLE 6

| Capture Antibody | Chicken ab | Absorbance |
|---|---|---|
| scFv fragment 4 | anti-prostasome | 1.212 |
| scFv fragment 7 | anti-prostasome | 1.053 |
| scFv fragment 4 | anti-PSA | 1.41 |
| scFv fragment 7 | anti-PSA | 1.346 |

In the previous experiment we tested the use of the chicken detection antibodies using purified prostasomes. In the present example we tested how well the antibodies work when the prostasomes are diluted in a sample, such as serum or plasma. A conclusion from the experiment is that both chicken antibodies tested give a positive response also in the presence of human plasma indicating that they can be used to detect prostasomes also in plasma.

Example 5 Testing of Patient Samples, Patients with Elevated PSA (>50), Female Blood Donors and Male Blood Donors <35 Years Human synthetic scFv fragment 4 (2 μg/mL) and human synthetic scFv fragment 7 (2 μg/mL), human synthetic scFv fragment 10 (2 μg/mL) was coated in PBS. 100 μL was added per well and incubated for 2 h at room temperature, and then washed three times with PBS containing 0.05% Tween 20. 120 μL 1% bovine serum albumin (BSA) was added to the wells, and incubated over night at room temperature, and then washed three times with PBS containing 0.05% Tween 20. Addition of 100 L patient samples was made, and the plates then incubated for 2 h at room temperature. Addition of chicken anti-PSA both in dilution 1:1000 was made, diluted in PBS-tween, and incubated for 2 h at room temperature and then washed three times with PBS containing 0.05% Tween 20. 100 μL anti-chicken IgY-HRP 1:2000 was added to the wells diluted in PBS-tween, and then incubated for 2 h at room temperature and then and washed three times with PBS containing 0.05% Tween 20. 100 μL TMB substrate was added to the wells and incubated for 10 min where after 20 μl 1 M H2SO4 was added to the plate. The plate was read at 450 nm.

100 μL of human synthetic scFv fragment 4 (final concentration 2 μg/mL in PBS), human synthetic scFv fragment 7 (final concentration 2 μg/mL in PBS) and human synthetic scFv fragment 10 (final concentration 2 μg/mL in PBS) were added per well in a F96 Polysorb NUNC Immunoplate (Thermo Fisher Scientific, Uppsala, Sweden). The plates were incubated for 2 h at ambient temperature and then washed three times with PBS containing 0.05% Tween 20 (P1379, Sigma-Aldrich). 120 μL 1% bovine serum albumin (BSA, Sigma-Aldrich) in PBS were added to the wells and the plate was incubated over night at ambient temperature. The plate was washed three times with PBS containing 0.05% Tween 20. 100 μL of samples from patients with elevated PSA (>50 μg/L, labeled PSA in the table), female blood donors (control) and male blood donors <35 years (young male blood donors very rarely have prostate cancer and thus served as a negative control) were added to the wells. The plate was incubated for two hours at ambient temperature and the wells were then washed three times with PBS containing 0.05% Tween 20. 100 μL of chicken anti-prostasome and chicken anti-PSA antibodies (Immunsystem AB, Uppsala, Sweden) were added to the wells in dilution 1:1000 in PBS containing 0.05% tween 20. The plate was incubated for two hours at ambient temperature and the wells were then washed three times with PBS containing 0.05% Tween 20. 100 μL anti-IgY-HRP (A16130, Novex, Frederick, MD, USA) diluted 1:2000 in PBS-tween was added to the plates. The plate was incubated for two hours at ambient temperature and the wells were then washed three times with PBS containing 0.05% Tween 20. 100 μL TMB substrate (EC-Blue Enhanced TMB substrate, Medicago, Uppsala, Sweden) was added to the plates and the plates were incubated for 20 min at ambient temperature in darkness. 25 μL of 1 M $H_2SO4$ was added to each well and the plate was read at 450 nm in a SpectraMax 250 ELISA reader. The results for the scFv fragments are presented in tables 7-9 below.

TABLE 7

| Capture Antibody | Chicken ab | Sample | Absorbance |
|---|---|---|---|
| scFv fragment 4 | anti-PSA | PSA | 1.414 |
| scFv fragment 4 | anti-PSA | PSA | 1.409 |
| scFv fragment 4 | anti-PSA | PSA | 0.985 |
| scFv fragment 4 | anti-PSA | PSA | 1.762 |
| scFv fragment 4 | anti-PSA | Female | 0.781 |
| scFv fragment 4 | anti-PSA | Female | 0.782 |
| scFv fragment 4 | anti-PSA | Female | 0.800 |
| scFv fragment 4 | anti-PSA | Female | 0.714 |
| scFv fragment 4 | anti-PSA | Male<35 | 0.678 |
| scFv fragment 4 | anti-PSA | Male<35 | 0.934 |
| scFv fragment 4 | anti-PSA | Male<35 | 0.751 |
| scFv fragment 4 | anti-PSA | Male<35 | 0.823 |

TABLE 8

| Capture Antibody | Chicken ab | Sample | Absorbance |
|---|---|---|---|
| scFv fragment 7 | anti-PSA | PSA | 0.795 |
| scFv fragment 7 | anti-PSA | PSA | 0.833 |
| scFv fragment 7 | anti-PSA | PSA | 0.671 |
| scFv fragment 7 | anti-PSA | PSA | 1.094 |
| scFv fragment 7 | anti-PSA | Female | 0.527 |
| scFv fragment 7 | anti-PSA | Female | 0.543 |
| scFv fragment 7 | anti-PSA | Female | 0.597 |
| scFv fragment 7 | anti-PSA | Female | 0.546 |
| scFv fragment 7 | anti-PSA | Male<35 | 0.518 |
| scFv fragment 7 | anti-PSA | Male<35 | 0.641 |
| scFv fragment 7 | anti-PSA | Male<35 | 0.623 |
| scFv fragment 7 | Anti-PSA | Male<35 | 0.526 |

TABLE 9

| Capture Antibody | Chicken ab | Sample | Absorbance |
|---|---|---|---|
| scFv fragment 10 | anti-PSA | PSA | 0.502 |
| scFv fragment 10 | anti-PSA | PSA | 0.508 |
| scFv fragment 10 | anti-PSA | PSA | 0.36 |
| scFv fragment 10 | anti-PSA | PSA | 0.783 |
| scFv fragment 10 | anti-PSA | Female | 0.364 |
| scFv fragment 10 | anti-PSA | Female | 0.404 |
| scFv fragment 10 | anti-PSA | Female | 0.431 |
| scFv fragment 10 | anti-PSA | Female | 0.416 |
| scFv fragment 10 | anti-PSA | Male<35 | 0.333 |
| scFv fragment 10 | anti-PSA | Male<35 | 0.433 |
| scFv fragment 10 | anti-PSA | Male<35 | 0.365 |
| scFv fragment 10 | anti-PSA | Male<35 | 0.377 |

A conclusion from the experiment is that we get higher values for PSA positive plasma samples compared to females and younger male blood donors, indicating it as a marker for prostate cancer.

Example 6 Testing of Mouse Monoclonals as Detectors in the Prostasome ELISA

Seminal plasma was collected from the Reproduction Centre at Akademiska Hospital (Uppsala, Sweden) following previously described routines (Ronquist, G. K., et al., Prostasomal DNA characterization and transfer into human sperm. Mol Reprod Dev, 2011. 78(7): p. 467-76.). The seminal plasma was thawed and centrifuged at 3,000 g for 12 min. The supernatants were collected and centrifuged at 10,000 g for 30 min. The supernatants were then transferred to new tubes and ultra-centrifuged using a 90Ti rotor (Beckman Coulter, Brea, CA, USA) at 100,000 g for 2 h. The pellets were resuspended in 0.02 M NaH2PO4, 0.15 M NaCl, pH 7.2 (PBS), overnight at 4 °C.

The resuspended pellets were then loaded on a chromatography column (XK 60/70, GE Healthcare, Uppsala, Sweden) packed with Superdex 200 gel. Fractions were collected at a flowrate of 5 mL/h. The fractions were then measured with a spectrophotometer where peaks at both 260 nm (nucleic acid) and 280 nm (proteins) corresponds to prostasomes. These fractions were collected and pooled and ultra-centrifuged at 100,000 g. The obtained pellet was resuspended in PBS.

100 μL of monoclonal antibodies at a final concentration of 1 μg/mL in PBS were added per well in duplicates in a F96 Polysorb NUNC Immunoplate (Thermo Fisher Scientific, Uppsala, Sweden). The mouse monoclonal antibodies used for coating were anti-CD10, (0112, Immunotech, Marseille, France), anti-CD46 (0846, Immunotech), anti-CD38 (Sanquin, Amsterdam, The Netherlands), anti-CD59 (Sanquin), anti-CD13, (C8589, Sigma-Aldrich, St Louis, MI, USA) and anti-PSMA (Invitrogen, Carlsbad, CA). The plates were incubated for 2 h at ambient temperature and then washed three times with PBS containing 0.05% Tween 20 (P1379, Sigma-Aldrich). 120 μL 1% bovine serum albumin (BSA, Sigma-Aldrich) in PBS were added to the wells and the plate was incubated over night at ambient temperature. The plate was washed three times with PBS containing 0.05% Tween 20. 100 μL of the purified prostasomes, diluted to 100 ng/ml in PBS, were added to the wells. According to a previous study (Tavoosidana et al. *PNAS*, May 24, 2011, vol. 108, no. 21, 8809-8814), the sensitivity for detecting prostasomes in the blood from prostate cancer patients is around 1 ng/ml. The tested concentration is thus well above this level.

The plate was incubated for two hours at ambient temperature and the wells were then washed three times with PBS containing 0.05% Tween 20. 100 μL of chicken anti-PSA antibodies (Immunsystem AB, Uppsala, Sweden) were added to the wells in dilution 1:1000 in PBS containing 0.05% Tween 20. The plate was incubated for two hours at ambient temperature and the wells were then washed three times with PBS containing 0.05% Tween 20. 100 μl anti- IgY-HRP (A16130, Novex, Frederick, MD, USA) diluted 1:2000 in PBS-Tween was added to the plates. The plate was incubated for two hours at ambient temperature and the wells were then washed three times with PBS containing 0.05% Tween 20. 100 μL TMB substrate (EC-Blue Enhanced TMB substrate, *Medicago*, Uppsala, Sweden) was added to the plates and the plates were incubated for 20 min at ambient temperature in darkness. 25 μL of 1 M $H_2SO_4$ was added to each well and the plate was read at 450 nm in a SpectraMax 250 ELISA reader. None of the tested antibodies gave a positive reaction.

Thus, the examples contained herein proves the efficacy of the proposed human monoclonal antibodies or binding fragments thereof in selectively detecting prostasomes at low concentrations in a sample, while murine counterparts are shown not to be able to detect low levels of prostasomes, thus not being suitable for use in prostate cancer diagnosis.

Example 7 Testing of Prognostic Efficacy of Fragment 4 and 7

A study was performed to evaluate the potential to prognosticate severity and outcome for a patient/subject based on the measured levels of prostasomes performed according to an embodiment of the present disclosure. The efficacy of fragment 4 and 7 were evaluated.

Blood samples were collected prior to surgery from patients with prostate cancer. The samples were collected in the years 1991-2001. After centrifugation, the obtained serum samples were stored at −70C. Follow-up data on death and cause of death were extracted from the patient files in February 2021. The endpoint used was death at the time of the follow up after exclusion of documented lack of tumor recurrence. Eighty-one samples were thawed and analyzed using ScFv fragment 4 (AK4) and ScFv fragment 7 (AK7) as capture antibodies (capture ScFv fragments) and chicken anti-prostasome antibody as detector. Fifty-one of these samples were also analyzed using AK4 and AK7 as capture antibodies (capture ScFv fragments) and chicken anti-PSA antibody as detector.

For both experiments using AK4 and AK7 in combination with the anti-prostasome antibody (Pros) as detector, measured relatively higher levels of prostasomes were correlated with death, and relatively lower levels with survival after 20 years or more. AK7 in combination with the anti-PSA antibody (PSA) as detector was significantly associated with predicted death or survival after 20 years or more. The results are presented in table 10 below.

TABLE 10

| Fragment and Antibody used | p-value | N alive | N dead |
|---|---|---|---|
| scFv 4-Pros | 0.007063 | 42 | 39 |
| scFv 4-Pros | 0.040716 | 42 | 39 |
| scFv 4-PSA | 0.650606 | 27 | 24 |
| scFv 7-PSA | 0.000018 | 27 | 24 |

Example 8 Evaluation of Fragment Binding Targets Using Immunoprecipitation Mass Spectrometry By using immunoprecipitation in combination with mass spectrometry (IP-MS) it is possible to verify that an antibody interacts specifically with an intended target. To determine the targets on the prostasomes to which the respective fragments 1-12 bind, the binding of the fragments to lysed prostasomes were studied using liquid chromatography (LC)-IP-MS analysis.

Purified prostasomes were lysed in high-salt buffer by a freeze-thaw and sonication procedure. Debris was removed by centrifugation and the prostasome solution was mixed with magnetic beads each coated with one of antibody fragments 1-12. After incubation for 2 h at 4 °C the beads were washed three times with buffer containing 10 mM Tris-HCl, pH 7.9, 100 mM NaCl, 0.1% (v/v) Nonidet P-40 and two times with the same buffer without detergent. The samples were eluted from the beads with 0.5 M $NH_4OH$ in water. The eluates were dried in a Speed-Vac and then reconstituted in 50 μL of 50 mM ammonium bicarbonate. The samples were subsequently reduced with 100 mM TCEP-HCl and alkylated with 500 mM iodoacetamide followed by digestion with trypsin.

Subsequently, the samples were subjected to liquid chromatography (LC)-MS analysis. The enzyme specificity was set to trypsin and the search was performed against human proteins. The top 5 identified proteins (*Homo sapiens*) that were present in the complexes bound by each antibody fragment (1-12) are listed in table 11 below.

TABLE 11

| scFv fragment | Accession No. | Name |
|---|---|---|
| 1 | O75955 | Flotillin-1 |
| | P10909-2 | Isoform 2 of Clusterin |
| | P15309-2 | Isoform 2 of Prostatic acid phosphatase |
| | P04279 | Semenogelin-1 |
| | Q02383 | Semenogelin-2 |
| 2 | P60709 | Actin, cytoplasmic 1 |
| | P02751 | Fibronectin |
| | Q8WWA0 | Intelectin-1 |
| | P04279 | Semenogelin-1 |
| | Q02383 | Semenogelin-2 |
| 3 | P15144 | Aminopeptidase N |
| | P02751 | Fibronectin |
| | P10909-2 | Isoform 2 of Clusterin |
| | P04279 | Semenogelin-1 |
| | Q02383 | Semenogelin-2 |
| 4 | Q8WZ42-12 | Isoform 12 of Titin |
| | P12882 | Myosin-1 |
| | Q9UKX2 | Myosin-2 |
| | Q9Y623 | Myosin-4 |
| | P13535 | Myosin-8 |

TABLE 11-continued

| scFv fragment | Accession No. | Name |
|---|---|---|
| 5 | P58107 | Epiplakin |
| | E9PPU0 | Epiplakin |
| | P04279 | Semenogelin-1 |
| | Q02383 | Semenogelin-2 |
| | Q5T5C7 | Serine--tRNA ligase, cytoplasmic |
| 6 | P68133 | Actin, alpha skeletal muscle |
| | P12882 | Myosin-1 |
| | Q9UKX2 | Myosin-2 |
| 6 | Q9Y623 | Myosin-4 |
| | P04279 | Semenogelin-1 |
| 7 | P02751 | Fibronectin |
| | Q8WWA0 | Intelectin-1 |
| | P04279 | Semenogelin-1 |
| | Q02383 | Semenogelin-2 |
| | P02768 | Serum albumin |
| 8 | P02751 | Fibronectin |
| | Q8WWA0 | Intelectin-1 |
| | P04279 | Semenogelin-1 |
| | Q02383 | Semenogelin-2 |
| | P02768 | Serum albumin |
| 9 | P60709 | Actin, cytoplasmic 1 |
| | P15924 | Desmoplakin |
| | P10909-2 | Isoform 2 of Clusterin |
| | P04279 | Semenogelin-1 |
| | Q02383 | Semenogelin-2 |
| 10 | P02751 | Fibronectin |
| | Q8WWA0 | Intelectin-1 |
| | P10909-2 | Isoform 2 of Clusterin |
| | P04279 | Semenogelin-1 |
| | Q02383 | Semenogelin-2 |
| 11 | P60709 | Actin, cytoplasmic 1 |
| | P08107 | Heat shock 70 kDa protein 1A/1B |
| | P08238 | Heat shock protein HSP 90-beta |
| | P04279 | Semenogelin-1 |
| | Q02383 | Semenogelin-2 |
| 12 | P60709 | Actin, cytoplasmic 1 |
| | P12314 | High affinity immunoglobulin gamma Fc receptor I |
| | P15309-2 | Isoform 2 of Prostatic acid phosphatase |
| | P04279 | Semenogelin-1 |
| | Q02383 | Semenogelin-2 |

The result showed that each individual fragment 1-12 of the invention, respectively, does not bind one single target protein/lipid/carbohydrate, but binds several targets. The identified top targets in the IP-MS analysis revealed that the targets bound by the fragments were not individual targets, but complexes formed by several individual proteins/lipids/carbohydrates. The binding strength to the pure antigens, the respective individual targets in the lysed prostasome samples, were much weaker than the binding to the complexes, where the complexes were comprised of several individual targets agglomerated or bound to a prostasome membrane fragment, indicating that the scFv fragments indeed bind to a three-dimensional structure or three-dimensional conformation of target proteins on the surface of the prostasome. Thus, the antigens bound by the scFv fragments of the invention are structures on the surface of the prostasome membrane, conglomerates or complexes of antigens bound to a prostasome membrane fragment, instead of binding individual isolated antigens, thereby being ideal for measuring whole prostasomes in a sample. Hence, the proteins of table 11 should not be viewed as individual targets/antigens that the respective fragment binds, but as being part of a complex that the respective fragment binds.

ITEMIZED LIST OF EMBODIMENTS

1. A human monoclonal antibody or antigen binding fragment thereof, which selectively binds prostasomes.

2. The human monoclonal antibody or antigen binding fragment thereof according to item 1, wherein the human monoclonal antibody or antigen binding fragment thereof is a full-length antibody, an antigen binding (Fab) fragment, or an antigen binding single chain Fv (scFv) fragment.

3. The human monoclonal antibody or antigen binding fragment thereof according to items 1 or 2, wherein the human monoclonal antibody or antigen binding fragment thereof is a human synthetic scFv fragment.

4. The human monoclonal antibody or antigen binding fragment thereof according to any one of items1-3, wherein the antibody or antigen binding fragment thereof enable a sensitivity of at least 10 ng/ml in an immunoassay using the human monoclonal antibody or antigen binding fragment thereof as a capturing antibody in the immunoassay.

5. The human monoclonal antibody or antigen binding fragment thereof according to any one of items 1-4, wherein the monoclonal antibody or antigen binding fragment thereof selectively binds prostasomes by binding one or more prostasome surface antigens, the prostasome surface antigens being selected from SEQ ID NO: 60-104.

6. The human monoclonal antibody or antigen binding fragment thereof according to any one of items 1-5, wherein the monoclonal antibody or antigen binding fragment thereof comprises a heavy chain complementary determining region (CDR) being selected from SEQ ID NO: 1-12, and a light chain CDR being selected from SEQ ID NO: 13-24, and CDR sequences having 95% or more, such as 96%, 97%, 98%, 99% or more, identity thereto.

7. The human monoclonal antibody or antigen binding fragment thereof according to any one of items 1-6, wherein the antibody or antigen binding fragment thereof comprises at least four complementary determining regions (CDRs) in any combination of CDR-H1, CDR-H2, CDR-H3 and CDR-L3, wherein the CDRs are selected from the group comprising:

CDR-H1 selected from SEQ ID NO: 25, 27 and 28;
CDR-H2 selected from SEQ ID NO: 26, 29 and 30;
CDR-H3 selected from SEQ ID NO: 1, 2, 3, 4, 5, 6, 7, 8, 9, 10, 11 and 12;
CDR-L3 selected from SEQ ID NO: 13, 14, 15, 16, 17, 18, 19, 20, 21, 22, 23 and 24, and CDR sequences having 95% or more, such as 96%, 97%, 98%, 99% or more, identity thereto.

8. The human monoclonal antibody or antigen binding fragment thereof according to any one of items 1-7, wherein the antibody or antigen binding fragment thereof comprises at least six complementary determining regions (CDRs) in any combination of CDR-H1, CDR-H2, CDR-H3, CDR-L1, CDR-L2 and CDR-L3, wherein the CDRs are selected from the group comprising:

CDR-H1 selected from SEQ ID NO: 25, 27 and 28;
CDR-H2 selected from SEQ ID NO: 26, 29 and 30;
CDR-H3 selected from SEQ ID NO: 1, 2, 3, 4, 5, 6, 7, 8, 9, 10, 11 and 12;
CDR-L1 is selected from any variant of SEQ ID NO: 56 and 57;
CDR-L2 is selected from any variant of SEQ ID NO: 58 and 59;
CDR-L3 selected from SEQ ID NO: 13, 14, 15, 16, 17, 18, 19, 20, 21, 22, 23 and 24, and CDR sequences having 95% or more, such as 96%, 97%, 98%, 99% or more, identity thereto.

9. The human monoclonal antibody or antigen binding fragment thereof according to any one of items 1-8, wherein the antibody or antigen binding fragment thereof comprises a heavy chain variable region (VH) sequence selected from the group consisting of SEQ ID NO: 32-43 and sequences having 80% or more, such as 85%, 90%, 95% or more, identity thereto.

10. The human monoclonal antibody or antigen binding fragment thereof according to any one of items 1-8, wherein the antibody or antigen binding fragment thereof comprises a light chain variable region (VL) sequence selected from the group consisting of SEQ ID NO: 44-55 and sequences having 80% or more, such as 85%, 90%, 95% or more, identity thereto.

11. The human monoclonal antibody or antigen binding fragment thereof according to items 9 and 10, wherein the antibody or antigen binding fragment thereof is a synthetical scFv fragment comprising a VH fragment according to item 9, a VL fragment according to item 10, and a linker.

12. The human monoclonal antibody or antigen binding fragment thereof according to any one of items 1-11, wherein the antibody or antigen binding fragment thereof is a synthetic scFv fragment selected from the group of scFv fragment 4, scFv fragment 1, scFv fragment 2, scFv fragment 3, scFv fragment 5, scFv fragment 6, scFv fragment 7, scFv fragment 8, scFv fragment 9, scFv fragment 10, scFv fragment 11 and scFv fragment 12.

13. The human monoclonal antibody or antigen binding fragment thereof according to any one of items 1-12, wherein the antibody or antigen binding fragment thereof is scFv fragment 4.

14. An in vitro method for determining whether prostate cancer is present in a subject, the method comprising:

providing (S1) a human monoclonal antibody or antigen binding fragment thereof which selectively binds human prostasomes;
reacting (S2) the human monoclonal antibody or antigen binding fragment thereof with a sample comprising prostasomes from a subject;
detecting (S3) any prostasomes bound by the human monoclonal antibody or antigen binding fragment thereof to obtain a level of prostasomes;
comparing (S4) said level of prostasomes detected with a predetermined threshold; and
determining (S5) that prostate cancer is present in the subject if the detected level of prostasomes is higher than the predetermined threshold.

15. The method according to item 14, further comprising:
determining (S5) that prostate cancer is not present in the subject if the detected level of prostasomes is lower than the predetermined threshold.

16. The method according to items 14 or 15, wherein detecting (S3) any prostasomes bound by the human monoclonal antibody or antigen binding fragment thereof comprises detecting the prostasomes using an anti-prostasome detection antibody or antigen binding fragment thereof.

17. The method according to item 16, wherein the method is a sandwich immunoassay and detecting (S3) prostasomes (200) bound by the human monoclonal antibody or antigen binding fragment thereof (101) comprises detecting the anti-prostasome detection antibody (102) using a further detection antibody (103), wherein the human monoclonal antibody or binding fragment thereof (101) is a capture antibody, the anti-prostasome detection antibody (102) is a primary detection antibody and the further detection antibody (103) is a secondary detection antibody.

18. The method according to item 17, wherein the primary detection antibody (102) is a chicken antibody and the secondary detection antibody (103) is an anti-chicken antibody.

19. The method according to any one of items 14-18, wherein the sample from the subject is a body fluid sample.

20. The method according to item 19, wherein the body fluid sample from the subject is selected from the group consisting of blood, serum, plasma, urine, cerebrospinal fluid and a cell suspension.

21. The method according to any one of items 19 or 20, wherein the predetermined threshold is 10 ng prostasomes per mL of body fluid sample.

22. The method according to any one of items 14-21, wherein the human monoclonal antibody or antigen binding fragment thereof is an antibody or antigen binding fragment thereof according to any one of items 1-13.

23. A method in vitro for providing a prognosis of a prostate cancer in a subject in need thereof, the method comprising:

providing (S11) a human monoclonal antibody or antigen binding fragment thereof which selectively binds prostasomes;
reacting (S12) the human monoclonal antibody or antigen binding fragment thereof with a sample from a subject comprising prostasomes;
detecting (S13) prostasomes bound by the human monoclonal antibody or antigen binding fragment thereof to obtain a level of prostasomes;
comparing (S14) said level of prostasomes detected with a first and second predetermined threshold; and
providing (S15) a prognosis of the prostate cancer, wherein prognosis of the prostate cancer is provided (S15*a*) to be poor if the detected level of prostasomes are above a first predetermined threshold, and provided (S15*b*) to be good if the detected level of prostasomes are below a second threshold.

24. The method according to item 23, wherein the sample from the subject is a body fluid sample 25. The method according to item 24, wherein the body fluid sample from the subject is selected from the group consisting of blood, serum, plasma, urine, cerebrospinal fluid and a cell suspension.

26. The method according to any one of items 24-25, wherein the first predetermined threshold is 10 ng prostasomes per mL of body fluid sample and the second predetermined threshold is 1 ng prostasomes per mL of body fluid sample.

27. The method according to any one of items 23-26, wherein the human monoclonal antibody or antigen binding fragment thereof is an antibody or antigen binding fragment thereof according to any one of items 1-13.

28. A method in vitro for evaluating severity of a prostate cancer in a subject in need thereof, the method comprising:

providing (S21) a human monoclonal antibody or antigen binding fragment thereof which selectively binds prostasomes;

reacting (S22) the human monoclonal antibody or antigen binding fragment thereof with a sample from a subject comprising prostasomes;

detecting (S23) prostasomes bound by the human monoclonal antibody or antigen binding fragment thereof to obtain a level of prostasomes;

comparing (S24) said level of prostasomes detected with a first and second predetermined threshold; and evaluating (S25) the severity of the prostate cancer, wherein the prostate cancer is evaluated (S25*a*) to be severe if the detected levels of prostasomes are above a first threshold, evaluated (S25*b*) to be moderate if the detected levels of prostasomes are below a first threshold but above a second threshold, and evaluated (S25*c*) to be light if the detected levels of prostasomes are below a second threshold.

29. The method according to item 28, wherein the sample from the subject is a body fluid sample.

30. The method according to item 29 wherein the body fluid sample from the subject is selected from the group consisting of blood, serum, plasma, urine, cerebrospinal fluid and a cell suspension.

31. The method according to any one of items 29-30, wherein the first predetermined threshold is 10 ng prostasomes per ml of body fluid sample and the second predetermined threshold is 1 ng prostasomes per mL of body fluid sample.

32. The method according to any one of items 28-31, wherein the human monoclonal antibody or antigen binding fragment thereof is an antibody or antigen binding fragment thereof according to any one of items 1-14.

33. A method in vitro of evaluating the efficacy of a prostate cancer treatment in a subject in need thereof, the method comprising:

detecting (S31) a level of prostasomes in a sample from a subject before a prostate cancer treatment;

providing (S32) an anti-prostate cancer treatment to the subject;

detecting (S33) a level of prostasomes in a sample from the subject after said prostate cancer treatment;

comparing (S34) the level of prostasomes before the treatment to the levels after the treatment; and determining (S35) the efficacy of the treatment, where the treatment is determined to be effective (S35*a*) if the level of prostasomes after the treatment have decreased compared to the level before the treatment, and determined as ineffective (S35*b*) if the level of prostasomes have remained the same or increased.

34. The method according to item 33, wherein detecting (S31, S33) a level of prostasomes in a sample from a subject comprises:

providing (S31*a*, S33*a*) a human monoclonal antibody or antigen binding fragment thereof which selectively binds prostasomes;

reacting (S31*b*, S33*b*) the human monoclonal antibody or antigen binding fragment thereof with a sample from a subject comprising prostasomes; and detecting (S31*c*, S33*c*) prostasomes bound by the human monoclonal antibody or antigen binding fragment thereof to obtain a level of prostasomes.

35. The method according to any one of items 33 or 34, wherein the sample from the subject is a body fluid sample.

36. The method according to item 35, wherein the body fluid sample from the subject is selected from the group consisting of blood, serum, plasma, urine, cerebrospinal fluid and a cell suspension.

37. The method according to any one of items 34-36, wherein the human monoclonal antibody or antigen binding fragment thereof is an antibody or antigen binding fragment thereof according to any one of items 1-13.

38. The antibody or antigen binding fragment thereof according to any one of items 1-13 for use in the methods according to any one of items 14-37.

39. A method of treating a subject having prostate cancer, the method comprising:

having provided a human monoclonal antibody or antigen binding fragment thereof which selectively binds human prostasomes;

having reacted the human monoclonal antibody or antigen binding fragment thereof with a sample comprising prostasomes from a subject;

having detected prostasomes bound by the human monoclonal antibody or antigen binding fragment thereof to obtain a level of prostasomes;

having compared said level of prostasomes detected with a predetermined first threshold;

having determined that prostate cancer is present in the subject if the detected level of prostasomes is higher than the first predetermined threshold;

having determined that the level of prostasomes are lower than a second predetermined threshold;

treating the subject in need thereof by performing surgery on the prostate cancer.

All references cited herein are incorporated by reference to the extent allowed.

The invention claimed is:

1. A human monoclonal antibody or antigen binding fragment thereof, wherein the antibody or antigen binding fragment thereof binds a conglomerate of prostasome antigens, and wherein the antibody or antigen binding fragment thereof is a synthetic scFv fragment selected from the group consisting of:

i) an scFv fragment having
 CDR-H1 as defined by SEQ ID NO: 25,
 CDR-H2 as defined by SEQ ID NO: 26,
 CDR-H3 as defined by SEQ ID NO: 4, and
 CDR-L3 as defined by SEQ ID NO: 16;
ii) an scFv fragment having
 CDR-H1 as defined by SEQ ID NO: 25,
 CDR-H2 as defined by SEQ ID NO: 26,
 CDR-H3 as defined by SEQ ID NO: 7, and
 CDR-L3 as defined by SEQ ID NO: 19;
iii) an scFv fragment having
 CDR-H1 as defined by SEQ ID NO: 25,
 CDR-H2 as defined by SEQ ID NO: 26,
 CDR-H3 as defined by SEQ ID NO: 1, and
 CDR-L3 as defined by SEQ ID NO: 13;
iv) an scFv fragment having
 CDR-H1 as defined by SEQ ID NO: 25,
 CDR-H2 as defined by SEQ ID NO: 26,
 CDR-H3 as defined by SEQ ID NO: 2, and
 CDR-L3 as defined by SEQ ID NO: 14;
v) an scFv fragment having
 CDR-H1 as defined by SEQ ID NO: 25,
 CDR-H2 as defined by SEQ ID NO: 26,
 CDR-H3 as defined by SEQ ID NO: 3, and
 CDR-L3 as defined by SEQ ID NO: 15;
vi) an scFv fragment having
 CDR-H1 as defined by SEQ ID NO: 25,
 CDR-H2 as defined by SEQ ID NO: 26,
 CDR-H3 as defined by SEQ ID NO: 5, and
 CDR-L3 as defined by SEQ ID NO: 17;
vii) an scFv fragment having
 CDR-H1 as defined by SEQ ID NO: 25,
 CDR-H2 as defined by SEQ ID NO: 26,
 CDR-H3 as defined by SEQ ID NO: 6, and
 CDR-L3 as defined by SEQ ID NO:18;
viii) an scFv fragment having
 CDR-H1 as defined by SEQ ID NO: 25,
 CDR-H2 as defined by SEQ ID NO: 26,
 CDR-H3 as defined by SEQ ID NO: 8, and
 CDR-L3 as defined by SEQ ID NO: 20;
ix) an scFv fragment having
 CDR-H1 as defined by SEQ ID NO: 25,
 CDR-H2 as defined by SEQ ID NO: 26,
 CDR-H3 as defined by SEQ ID NO: 9, and
 CDR-L3 as defined by SEQ ID NO: 21;
x) an scFv fragment having
 CDR-H1 as defined by SEQ ID NO: 25,
 CDR-H2 as defined by SEQ ID NO: 26,
 CDR-H3 as defined by SEQ ID NO: 10, and
 CDR-L3 as defined by SEQ ID NO: 22;
xi) an scFv fragment having
 CDR-H1 as defined by SEQ ID NO: 25,
 CDR-H2 as defined by SEQ ID NO: 26,
 CDR-H3 as defined by SEQ ID NO: 11, and
 CDR-L3 as defined by SEQ ID NO:23;and
xii) an scFv fragment having
 CDR-H1 as defined by SEQ ID NO: 25,
 CDR-H2 as defined by SEQ ID NO: 26, CDR-H3 as defined by SEQ ID NO: 12, and
CDR-L3 as defined by SEQ ID NO: 24.

2. The antibody or antigen binding fragment thereof according to claim 1, wherein the scFv fragment is a synthetic scFv fragment having a variable heavy chain, VH, and a variable light chain, VL, connected via a linker, wherein the VH and VL are selected from the group consisting of:

i) a VH as defined by SEQ ID NO:35 and a VL as defined by SEQ ID NO:47;
ii) a VH as defined by SEQ ID NO:38 and a VL as defined by SEQ ID NO:50;
iii) a VH as defined by SEQ ID NO:32 and a VL as defined by SEQ ID NO:44;
iv) a VH as defined by SEQ ID NO:33 and a VL as defined by SEQ ID NO:45;
v) a VH as defined by SEQ ID NO:34 and a VL as defined by SEQ ID NO:46;
vi) a VH as defined by SEQ ID NO:36 and a VL as defined by SEQ ID NO:48;
vii) a VH as defined by SEQ ID NO:37 and a VL as defined by SEQ ID NO:49;
viii) a VH as defined by SEQ ID NO:39 and a VL as defined by SEQ ID NO:51;
ix) a VH as defined by SEQ ID NO:40 and a VL as defined by SEQ ID NO:52;
x) a VH as defined by SEQ ID NO:41 and a VL as defined by SEQ ID NO:53;
xi) a VH as defined by SEQ ID NO:42 and a VL as defined by SEQ ID NO:54; and
xii) a VH as defined by SEQ ID NO:43 and a VL as defined by SEQ ID NO:55.

3. The antibody or antigen binding fragment thereof according to claim 1, wherein the antibody or antigen binding fragment thereof binds a conglomerate of prostasome antigens comprising Myosin-1, Myosin-2, Myosin-4, Myosin-8, and Isoform 12 of Titin, and wherein the antibody or antigen binding fragment thereof is a synthetic scFv fragment having CDR-H1 as defined by SEQ ID NO: 25,
CDR-H2 as defined by SEQ ID NO: 26,
CDR-H3 as defined by SEQ ID NO: 4, and
CDR-L3 as defined by SEQ ID NO: 16.

4. An in vitro method for determining a prostasome level in a sample from a subject, the method comprising:

reacting the human monoclonal antibody or antigen binding fragment thereof of claim 1 with the sample; and
determining the prostasome level in the sample.

5. The method according to claim 4, wherein determining the prostasome level is carried out by an immunoassay.

6. The antibody or antigen binding fragment thereof according to claim 1, wherein the antibody or antigen binding fragment thereof enables a sensitivity of at least 10 ng/ml in an immunoassay wherein the antibody or antigen binding fragment thereof functions as a capturing antibody.

7. The method according to claim 4, wherein the sample from the subject is a body fluid sample selected from the group consisting of: blood, serum, plasma, urine, cerebrospinal fluid, and a cell suspension.

8. The method according to claim 5, wherein the immunoassay is a sandwich immunoassay, a lateral flow immunochromatographic assay, an immunomagnetic separation and electrochemiluminescence (IMS-ECL) assay, a fluorescence immunoassay, a time-resolved fluorescence (TRF) assay, a radioimmunoassay, or an enzyme-linked immunosorbent (ELISA) assay.

* * * * *

SEQUENCE LISTING

```
<160> NUMBER OF SEQ ID NOS: 104

<210> SEQ ID NO 1
```

<211> LENGTH: 16
<212> TYPE: PRT
<213> ORGANISM: Artificial Sequence
<220> FEATURE:
<223> OTHER INFORMATION: synthetic sequence

<400> SEQUENCE: 1

Cys Ala Arg His Tyr Tyr Asn Trp Ala Ser Gly Tyr Phe Asp Tyr Trp
1 5 10 15

<210> SEQ ID NO 2
<211> LENGTH: 18
<212> TYPE: PRT
<213> ORGANISM: Artificial Sequence
<220> FEATURE:
<223> OTHER INFORMATION: synthetic sequence

<400> SEQUENCE: 2

Cys Ala Arg Thr Thr Ser Tyr Tyr Gly Tyr Ser Ala His Phe Ile Asp
1 5 10 15

Tyr Trp

<210> SEQ ID NO 3
<211> LENGTH: 17
<212> TYPE: PRT
<213> ORGANISM: Artificial Sequence
<220> FEATURE:
<223> OTHER INFORMATION: synthetic sequence

<400> SEQUENCE: 3

Cys Ala Arg Val Tyr Tyr His Tyr Tyr Tyr Tyr Gly Ser Phe Asp Tyr
1 5 10 15

Trp

<210> SEQ ID NO 4
<211> LENGTH: 17
<212> TYPE: PRT
<213> ORGANISM: Artificial Sequence
<220> FEATURE:
<223> OTHER INFORMATION: synthetic sequence

<400> SEQUENCE: 4

Cys Ala Arg Tyr Ser Tyr Tyr Tyr Ala Gly Ser Tyr Tyr Phe Asp Tyr
1 5 10 15

Trp

<210> SEQ ID NO 5
<211> LENGTH: 17
<212> TYPE: PRT
<213> ORGANISM: Artificial Sequence
<220> FEATURE:
<223> OTHER INFORMATION: synthetic sequence

<400> SEQUENCE: 5

Cys Ala Arg Ser Tyr Ser Trp Tyr Ser Arg Gly Pro Ser Leu Asp Tyr
1 5 10 15

Trp

<210> SEQ ID NO 6
<211> LENGTH: 16
<212> TYPE: PRT
<213> ORGANISM: Artificial Sequence
<220> FEATURE:
<223> OTHER INFORMATION: synthetic sequence

<400> SEQUENCE: 6

Cys Ala Arg Tyr Val Arg Gly Tyr Gly Tyr Gly Tyr Leu Asp Tyr Trp
1 5 10 15

<210> SEQ ID NO 7
<211> LENGTH: 16
<212> TYPE: PRT
<213> ORGANISM: Artificial Sequence
<220> FEATURE:
<223> OTHER INFORMATION: synthetic sequence

<400> SEQUENCE: 7

Cys Ala Arg Tyr Thr His Ser Thr Tyr Gly Tyr Arg Leu Asp Tyr Trp
1 5 10 15

<210> SEQ ID NO 8
<211> LENGTH: 19
<212> TYPE: PRT
<213> ORGANISM: Artificial Sequence
<220> FEATURE:
<223> OTHER INFORMATION: synthetic sequence

<400> SEQUENCE: 8

Cys Ala Arg Val Phe Tyr Tyr Gly Pro Tyr Tyr Phe Ser Tyr His Phe
1 5 10 15

Asp Tyr Trp

<210> SEQ ID NO 9
<211> LENGTH: 12
<212> TYPE: PRT
<213> ORGANISM: Artificial Sequence
<220> FEATURE:
<223> OTHER INFORMATION: synthetic sequence

<400> SEQUENCE: 9

Cys Ala Arg Ser His Tyr Gly Ser Leu Asp Tyr Trp
1 5 10

<210> SEQ ID NO 10
<211> LENGTH: 14
<212> TYPE: PRT
<213> ORGANISM: Artificial Sequence
<220> FEATURE:
<223> OTHER INFORMATION: synthetic sequence

<400> SEQUENCE: 10

Cys Ala Arg Tyr Ser Tyr Tyr Tyr Thr Trp Leu Asp Tyr Trp
1 5 10

<210> SEQ ID NO 11
<211> LENGTH: 14
<212> TYPE: PRT
<213> ORGANISM: Artificial Sequence
<220> FEATURE:
<223> OTHER INFORMATION: synthetic sequence

<400> SEQUENCE: 11

Cys Ala Arg Tyr Thr Tyr Tyr Val Gly Gly Phe Asp Tyr Trp
1 5 10

<210> SEQ ID NO 12
<211> LENGTH: 18
<212> TYPE: PRT
<213> ORGANISM: Artificial Sequence
<220> FEATURE:
<223> OTHER INFORMATION: synthetic sequence

<400> SEQUENCE: 12

Cys Ala Arg Thr Tyr Tyr Tyr Phe Tyr Pro Tyr Gly Tyr Tyr Phe Asp
1 5 10 15

Tyr Trp

<210> SEQ ID NO 13
<211> LENGTH: 10
<212> TYPE: PRT
<213> ORGANISM: Artificial Sequence
<220> FEATURE:
<223> OTHER INFORMATION: synthetic sequence

<400> SEQUENCE: 13

Cys Gln Gln Gly Trp Tyr Pro Pro Thr Phe
1 5 10

<210> SEQ ID NO 14
<211> LENGTH: 10
<212> TYPE: PRT
<213> ORGANISM: Artificial Sequence
<220> FEATURE:
<223> OTHER INFORMATION: synthetic sequence

<400> SEQUENCE: 14

Cys Gln Gln Gly Tyr Gly Pro Phe Thr Phe
1 5 10

<210> SEQ ID NO 15
<211> LENGTH: 10
<212> TYPE: PRT
<213> ORGANISM: Artificial Sequence
<220> FEATURE:
<223> OTHER INFORMATION: synthetic sequence

<400> SEQUENCE: 15

Cys Gln Gln Ser Thr His Leu Ser Thr Phe
1 5 10

<210> SEQ ID NO 16
<211> LENGTH: 11
<212> TYPE: PRT
<213> ORGANISM: Artificial Sequence
<220> FEATURE:
<223> OTHER INFORMATION: synthetic sequence

<400> SEQUENCE: 16

Cys Gln Gln Ser Tyr Ser Thr Pro Tyr Thr Phe
1 5 10

<210> SEQ ID NO 17
<211> LENGTH: 12
<212> TYPE: PRT
<213> ORGANISM: Artificial Sequence
<220> FEATURE:
<223> OTHER INFORMATION: synthetic sequence

<400> SEQUENCE: 17

Cys Gln Gln Ala Phe Tyr Ala His Leu Leu Thr Phe
1 5 10

<210> SEQ ID NO 18
<211> LENGTH: 12
<212> TYPE: PRT
<213> ORGANISM: Artificial Sequence
<220> FEATURE:

<223> OTHER INFORMATION: synthetic sequence

<400> SEQUENCE: 18

Cys Gln Gln Ala Pro Ala Tyr Ser Pro Phe Thr Phe
1 5 10

<210> SEQ ID NO 19
<211> LENGTH: 11
<212> TYPE: PRT
<213> ORGANISM: Artificial Sequence
<220> FEATURE:
<223> OTHER INFORMATION: synthetic sequence

<400> SEQUENCE: 19

Cys Gln Gln Asp Ala Tyr His Pro Pro Thr Phe
1 5 10

<210> SEQ ID NO 20
<211> LENGTH: 11
<212> TYPE: PRT
<213> ORGANISM: Artificial Sequence
<220> FEATURE:
<223> OTHER INFORMATION: synthetic sequence

<400> SEQUENCE: 20

Cys Gln Gln Asp Asp Arg Gly Leu Pro Thr Phe
1 5 10

<210> SEQ ID NO 21
<211> LENGTH: 11
<212> TYPE: PRT
<213> ORGANISM: Artificial Sequence
<220> FEATURE:
<223> OTHER INFORMATION: synthetic sequence

<400> SEQUENCE: 21

Cys Gln Gln Phe Ser Tyr Thr Leu Ser Thr Phe
1 5 10

<210> SEQ ID NO 22
<211> LENGTH: 11
<212> TYPE: PRT
<213> ORGANISM: Artificial Sequence
<220> FEATURE:
<223> OTHER INFORMATION: synthetic sequence

<400> SEQUENCE: 22

Cys Gln Gln Phe Tyr Pro Ser Leu His Thr Phe
1 5 10

<210> SEQ ID NO 23
<211> LENGTH: 10
<212> TYPE: PRT
<213> ORGANISM: Artificial Sequence
<220> FEATURE:
<223> OTHER INFORMATION: synthetic sequence

<400> SEQUENCE: 23

Cys Gln Gln Gly Phe Val Leu Ser Thr Phe
1 5 10

<210> SEQ ID NO 24
<211> LENGTH: 10
<212> TYPE: PRT
<213> ORGANISM: Artificial Sequence
<220> FEATURE:
<223> OTHER INFORMATION: synthetic sequence

```
<400> SEQUENCE: 24

Cys Gln Gln Gly Phe Tyr Leu Pro Thr Phe
1               5                   10


<210> SEQ ID NO 25
<211> LENGTH: 8
<212> TYPE: PRT
<213> ORGANISM: Artificial Sequence
<220> FEATURE:
<223> OTHER INFORMATION: synthetic sequence

<400> SEQUENCE: 25

Gly Phe Thr Phe Ser Ser Tyr Ala
1               5


<210> SEQ ID NO 26
<211> LENGTH: 8
<212> TYPE: PRT
<213> ORGANISM: Artificial Sequence
<220> FEATURE:
<223> OTHER INFORMATION: synthetic sequence

<400> SEQUENCE: 26

Ile Ser Gly Ser Gly Gly Ser Thr
1               5


<210> SEQ ID NO 27
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (5)..(8)
<223> OTHER INFORMATION: Xaa is Y, S or G
<220> FEATURE:
<221> NAME/KEY: VARIANT
<222> LOCATION: (10)..(10)
<223> OTHER INFORMATION: Xaa is Y, S or G

<400> SEQUENCE: 27

Gly Phe Thr Phe Xaa Xaa Xaa Xaa Met Xaa
1               5                   10


<210> SEQ ID NO 28
<211> LENGTH: 12
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (5)..(8)
<223> OTHER INFORMATION: Xaa is Y, S or G

<400> SEQUENCE: 28

Gly Phe Thr Phe Xaa Xaa Xaa Xaa Ser Ser Tyr Ala
1               5                   10


<210> SEQ ID NO 29
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
```

<222> LOCATION: (5)..(8)
<223> OTHER INFORMATION: Xaa is Y, S or G
<220> FEATURE:
<221> NAME/KEY: VARIANT
<222> LOCATION: (10)..(10)
<223> OTHER INFORMATION: Xaa is Y, S or G

<400> SEQUENCE: 29

Gly Phe Thr Phe Xaa Xaa Xaa Xaa Thr Xaa
1               5                   10

<210> SEQ ID NO 30
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (5)..(6)
<223> OTHER INFORMATION: Xaa is Y, S or G

<400> SEQUENCE: 30

Ile Ser Gly Ser Xaa Xaa Gly Gly Ser Thr
1               5                   10

<210> SEQ ID NO 31
<211> LENGTH: 15
<212> TYPE: PRT
<213> ORGANISM: Artificial Sequence
<220> FEATURE:
<223> OTHER INFORMATION: synthetic sequence

<400> SEQUENCE: 31

Gly Gly Gly Gly Ser Gly Gly Gly Gly Ser Gly Gly Gly Gly Ser
1               5                   10                  15

<210> SEQ ID NO 32
<211> LENGTH: 120
<212> TYPE: PRT
<213> ORGANISM: Artificial Sequence
<220> FEATURE:
<223> OTHER INFORMATION: synthetic sequence

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg His Tyr Tyr Asn Trp Ala Ser Gly Tyr Phe Asp Tyr Trp Gly Gln
            100                 105                 110

Gly Thr Leu Val Thr Val Ser Ser
        115                 120

<210> SEQ ID NO 33
<211> LENGTH: 122

<212> TYPE: PRT
<213> ORGANISM: Artificial Sequence
<220> FEATURE:
<223> OTHER INFORMATION: synthetic sequence

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Thr Thr Ser Tyr Tyr Gly Tyr Ser Ala His Phe Ile Asp Tyr Trp
            100                 105                 110

Gly Gln Gly Thr Leu Val Thr Val Ser Ser
        115                 120

<210> SEQ ID NO 34
<211> LENGTH: 121
<212> TYPE: PRT
<213> ORGANISM: Artificial Sequence
<220> FEATURE:
<223> OTHER INFORMATION: synthetic sequence

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Val Tyr Tyr His Tyr Tyr Tyr Tyr Gly Ser Phe Asp Tyr Trp Gly
            100                 105                 110

Gln Gly Thr Leu Val Thr Val Ser Ser
        115                 120

<210> SEQ ID NO 35
<211> LENGTH: 121
<212> TYPE: PRT
<213> ORGANISM: Artificial Sequence
<220> FEATURE:
<223> OTHER INFORMATION: synthetic sequence

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr

```
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Ser Tyr Tyr Tyr Ala Gly Ser Tyr Tyr Phe Asp Tyr Trp Gly
            100                 105                 110

Gln Gly Thr Leu Val Thr Val Ser Ser
        115                 120


<210> SEQ ID NO 36
<211> LENGTH: 121
<212> TYPE: PRT
<213> ORGANISM: Artificial Sequence
<220> FEATURE:
<223> OTHER INFORMATION: synthetic sequence

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ser Tyr Ser Trp Tyr Ser Arg Gly Pro Ser Leu Asp Tyr Trp Gly
            100                 105                 110

Gln Gly Thr Leu Val Thr Val Ser Ser
        115                 120


<210> SEQ ID NO 37
<211> LENGTH: 120
<212> TYPE: PRT
<213> ORGANISM: Artificial Sequence
<220> FEATURE:
<223> OTHER INFORMATION: synthetic sequence

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Ser Val Lys
    50                  55                  60

Gly Arg Phe Thr Ile Ser Arg Asp Asn Ser Lys Asn Thr Leu Tyr Leu
65                  70                  75                  80
```

```
Gln Met Asn Ser Leu Arg Ala Glu Asp Thr Ala Val Tyr Tyr Cys Ala
                85                  90                  95

Arg Tyr Val Arg Gly Tyr Gly Tyr Gly Tyr Leu Asp Tyr Trp Gly Gln
            100                 105                 110

Gly Thr Leu Val Thr Val Ser Ser
        115                 120


<210> SEQ ID NO 38
<211> LENGTH: 120
<212> TYPE: PRT
<213> ORGANISM: Artificial Sequence
<220> FEATURE:
<223> OTHER INFORMATION: synthetic sequence

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Thr His Ser Thr Tyr Gly Tyr Arg Leu Asp Tyr Trp Gly Gln
            100                 105                 110

Gly Thr Leu Val Thr Val Ser Ser
        115                 120


<210> SEQ ID NO 39
<211> LENGTH: 123
<212> TYPE: PRT
<213> ORGANISM: Artificial Sequence
<220> FEATURE:
<223> OTHER INFORMATION: synthetic sequence

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Val Phe Tyr Tyr Gly Pro Tyr Tyr Phe Ser Tyr His Phe Asp Tyr
            100                 105                 110

Trp Gly Gln Gly Thr Leu Val Thr Val Ser Ser
        115                 120


<210> SEQ ID NO 40
```

<211> LENGTH: 116
<212> TYPE: PRT
<213> ORGANISM: Artificial Sequence
<220> FEATURE:
<223> OTHER INFORMATION: synthetic sequence

<400> SEQUENCE: 40

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Ser His Tyr Gly Ser Leu Asp Tyr Trp Gly Gln Gly Thr Leu Val
100 105 110

Thr Val Ser Ser
115

<210> SEQ ID NO 41
<211> LENGTH: 118
<212> TYPE: PRT
<213> ORGANISM: Artificial Sequence
<220> FEATURE:
<223> OTHER INFORMATION: synthetic sequence

<400> SEQUENCE: 41

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Tyr Ser Tyr Tyr Tyr Thr Trp Leu Asp Tyr Trp Gly Gln Gly Thr
100 105 110

Leu Val Thr Val Ser Ser
115

<210> SEQ ID NO 42
<211> LENGTH: 118
<212> TYPE: PRT
<213> ORGANISM: Artificial Sequence
<220> FEATURE:
<223> OTHER INFORMATION: synthetic sequence

<400> SEQUENCE: 42

Glu Val Gln Leu Leu Glu Ser Gly Gly Gly Leu Val Gln Pro Gly Gly
1 5 10 15

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Thr Tyr Tyr Val Gly Gly Phe Asp Tyr Trp Gly Gln Gly Thr
            100                 105                 110

Leu Val Thr Val Ser Ser
        115


<210> SEQ ID NO 43
<211> LENGTH: 122
<212> TYPE: PRT
<213> ORGANISM: Artificial Sequence
<220> FEATURE:
<223> OTHER INFORMATION: synthetic sequence

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Thr Tyr Tyr Tyr Phe Tyr Pro Tyr Gly Tyr Tyr Phe Asp Tyr Trp
            100                 105                 110

Gly Gln Gly Thr Leu Val Thr Val Ser Ser
        115                 120


<210> SEQ ID NO 44
<211> LENGTH: 107
<212> TYPE: PRT
<213> ORGANISM: Artificial Sequence
<220> FEATURE:
<223> OTHER INFORMATION: synthetic sequence

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Gly Trp Tyr Pro Pro Thr
                85                  90                  95

Phe Gly Gln Gly Thr Lys Leu Glu Ile Lys Arg
            100                 105


<210> SEQ ID NO 45
<211> LENGTH: 107
<212> TYPE: PRT
<213> ORGANISM: Artificial Sequence
<220> FEATURE:
<223> OTHER INFORMATION: synthetic sequence

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Gly Pro Phe Thr
                85                  90                  95

Phe Gly Gln Gly Thr Lys Leu Glu Ile Lys Arg
            100                 105


<210> SEQ ID NO 46
<211> LENGTH: 107
<212> TYPE: PRT
<213> ORGANISM: Artificial Sequence
<220> FEATURE:
<223> OTHER INFORMATION: synthetic sequence

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Thr His Leu Ser Thr
                85                  90                  95

Phe Gly Gln Gly Thr Lys Leu Glu Ile Lys Arg
            100                 105


<210> SEQ ID NO 47
<211> LENGTH: 108
<212> TYPE: PRT
<213> ORGANISM: Artificial Sequence
<220> FEATURE:
<223> OTHER INFORMATION: synthetic sequence

<400> SEQUENCE: 47
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys Arg
            100                 105


<210> SEQ ID NO 48
<211> LENGTH: 109
<212> TYPE: PRT
<213> ORGANISM: Artificial Sequence
<220> FEATURE:
<223> OTHER INFORMATION: synthetic sequence

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Phe Tyr Ala His Leu
                85                  90                  95

Leu Thr Phe Gly Gln Gly Thr Lys Leu Glu Ile Lys Arg
            100                 105


<210> SEQ ID NO 49
<211> LENGTH: 109
<212> TYPE: PRT
<213> ORGANISM: Artificial Sequence
<220> FEATURE:
<223> OTHER INFORMATION: synthetic sequence

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Pro Ala Tyr Ser Pro
                85                  90                  95
```

```
Phe Thr Phe Gly Gln Gly Thr Lys Leu Glu Ile Lys Arg
            100                 105


<210> SEQ ID NO 50
<211> LENGTH: 108
<212> TYPE: PRT
<213> ORGANISM: Artificial Sequence
<220> FEATURE:
<223> OTHER INFORMATION: synthetic sequence

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Ala Tyr His Pro Pro
                85                  90                  95

Thr Phe Gly Gln Gly Thr Lys Leu Glu Ile Lys Arg
            100                 105


<210> SEQ ID NO 51
<211> LENGTH: 108
<212> TYPE: PRT
<213> ORGANISM: Artificial Sequence
<220> FEATURE:
<223> OTHER INFORMATION: synthetic sequence

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Asp Arg Gly Leu Pro
                85                  90                  95

Thr Phe Gly Gln Gly Thr Lys Leu Glu Ile Lys Arg
            100                 105


<210> SEQ ID NO 52
<211> LENGTH: 108
<212> TYPE: PRT
<213> ORGANISM: Artificial Sequence
<220> FEATURE:
<223> OTHER INFORMATION: synthetic sequence

<400> SEQUENCE: 52

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe Ser Tyr Thr Leu Ser
85 90 95

Thr Phe Gly Gln Gly Thr Lys Leu Glu Ile Lys Arg
100 105

<210> SEQ ID NO 53
<211> LENGTH: 108
<212> TYPE: PRT
<213> ORGANISM: Artificial Sequence
<220> FEATURE:
<223> OTHER INFORMATION: synthetic sequence

<400> SEQUENCE: 53

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe Tyr Pro Ser Leu His
85 90 95

Thr Phe Gly Gln Gly Thr Lys Leu Glu Ile Lys Arg
100 105

<210> SEQ ID NO 54
<211> LENGTH: 107
<212> TYPE: PRT
<213> ORGANISM: Artificial Sequence
<220> FEATURE:
<223> OTHER INFORMATION: synthetic sequence

<400> SEQUENCE: 54

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Gly Phe Val Leu Ser Thr
85 90 95

Phe Gly Gln Gly Thr Lys Leu Glu Ile Lys Arg
100 105

<210> SEQ ID NO 55
<211> LENGTH: 107
<212> TYPE: PRT
<213> ORGANISM: Artificial Sequence
<220> FEATURE:
<223> OTHER INFORMATION: synthetic sequence

<400> SEQUENCE: 55

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Phe Tyr Leu Pro Thr
                85                  90                  95

Phe Gly Gln Gly Thr Lys Leu Glu Ile Lys Arg
            100                 105
```

<210> SEQ ID NO 56
<211> LENGTH: 8
<212> TYPE: PRT
<213> ORGANISM: Artificial Sequence
<220> FEATURE:
<223> OTHER INFORMATION: synthetic sequence

<400> SEQUENCE: 56

```
Ser Gln Ser Ile Ser Ser Tyr Leu
1               5
```

<210> SEQ ID NO 57
<211> LENGTH: 14
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (5)..(10)
<223> OTHER INFORMATION: Xaa is Y, S or G

<400> SEQUENCE: 57

```
Ser Gln Ser Ile Xaa Xaa Xaa Xaa Xaa Xaa Ser Ser Tyr Leu
1               5                   10
```

<210> SEQ ID NO 58
<211> LENGTH: 5
<212> TYPE: PRT
<213> ORGANISM: Artificial Sequence
<220> FEATURE:
<223> OTHER INFORMATION: synthetic sequence

<400> SEQUENCE: 58

```
Tyr Ala Ala Ser Ser
1               5
```

<210> SEQ ID NO 59
<211> LENGTH: 12
<212> TYPE: PRT

<213> ORGANISM: Artificial Sequence
<220> FEATURE:
<223> OTHER INFORMATION: synthetic sequence
<220> FEATURE:
<221> NAME/KEY: VARIANT
<222> LOCATION: (4)..(10)
<223> OTHER INFORMATION: Xaa is Y, S or G

<400> SEQUENCE: 59

```
Tyr Ala Ala Xaa Xaa Xaa Xaa Xaa Xaa Xaa Ser Ser
1               5                   10
```

<210> SEQ ID NO 60
<211> LENGTH: 255
<212> TYPE: PRT
<213> ORGANISM: Homo sapiens

<400> SEQUENCE: 60

```
Met Asp Asp Arg Glu Asp Leu Val Tyr Gln Ala Lys Leu Ala Glu Gln
1               5                   10                  15

Ala Glu Arg Tyr Asp Glu Met Val Glu Ser Met Lys Lys Val Ala Gly
            20                  25                  30

Met Asp Val Glu Leu Thr Val Glu Glu Arg Asn Leu Leu Ser Val Ala
        35                  40                  45

Tyr Lys Asn Val Ile Gly Ala Arg Arg Ala Ser Trp Arg Ile Ile Ser
    50                  55                  60

Ser Ile Glu Gln Lys Glu Glu Asn Lys Gly Gly Glu Asp Lys Leu Lys
65                  70                  75                  80

Met Ile Arg Glu Tyr Arg Gln Met Val Glu Thr Glu Leu Lys Leu Ile
                85                  90                  95

Cys Cys Asp Ile Leu Asp Val Leu Asp Lys His Leu Ile Pro Ala Ala
            100                 105                 110

Asn Thr Gly Glu Ser Lys Val Phe Tyr Tyr Lys Met Lys Gly Asp Tyr
        115                 120                 125

His Arg Tyr Leu Ala Glu Phe Ala Thr Gly Asn Asp Arg Lys Glu Ala
    130                 135                 140

Ala Glu Asn Ser Leu Val Ala Tyr Lys Ala Ala Ser Asp Ile Ala Met
145                 150                 155                 160

Thr Glu Leu Pro Pro Thr His Pro Ile Arg Leu Gly Leu Ala Leu Asn
                165                 170                 175

Phe Ser Val Phe Tyr Tyr Glu Ile Leu Asn Ser Pro Asp Arg Ala Cys
            180                 185                 190

Arg Leu Ala Lys Ala Ala Phe Asp Asp Ala Ile Ala Glu Leu Asp Thr
        195                 200                 205

Leu Ser Glu Glu Ser Tyr Lys Asp Ser Thr Leu Ile Met Gln Leu Leu
    210                 215                 220

Arg Asp Asn Leu Thr Leu Trp Thr Ser Asp Met Gln Gly Asp Gly Glu
225                 230                 235                 240

Glu Gln Asn Lys Glu Ala Leu Gln Asp Val Glu Asp Glu Asn Gln
                245                 250                 255
```

<210> SEQ ID NO 61
<211> LENGTH: 375
<212> TYPE: PRT
<213> ORGANISM: Homo sapiens

<400> SEQUENCE: 61

```
Met Asp Asp Asp Ile Ala Ala Leu Val Val Asp Asn Gly Ser Gly Met
1               5                   10                  15
```

Cys Lys Ala Gly Phe Ala Gly Asp Asp Ala Pro Arg Ala Val Phe Pro
20 25 30

Ser Ile Val Gly Arg Pro Arg His Gln Gly Val Met Val Gly Met Gly
35 40 45

Gln Lys Asp Ser Tyr Val Gly Asp Glu Ala Gln Ser Lys Arg Gly Ile
50 55 60

Leu Thr Leu Lys Tyr Pro Ile Glu His Gly Ile Val Thr Asn Trp Asp
65 70 75 80

Asp Met Glu Lys Ile Trp His His Thr Phe Tyr Asn Glu Leu Arg Val
85 90 95

Ala Pro Glu Glu His Pro Val Leu Leu Thr Glu Ala Pro Leu Asn Pro
100 105 110

Lys Ala Asn Arg Glu Lys Met Thr Gln Ile Met Phe Glu Thr Phe Asn
115 120 125

Thr Pro Ala Met Tyr Val Ala Ile Gln Ala Val Leu Ser Leu Tyr Ala
130 135 140

Ser Gly Arg Thr Thr Gly Ile Val Met Asp Ser Gly Asp Gly Val Thr
145 150 155 160

His Thr Val Pro Ile Tyr Glu Gly Tyr Ala Leu Pro His Ala Ile Leu
165 170 175

Arg Leu Asp Leu Ala Gly Arg Asp Leu Thr Asp Tyr Leu Met Lys Ile
180 185 190

Leu Thr Glu Arg Gly Tyr Ser Phe Thr Thr Thr Ala Glu Arg Glu Ile
195 200 205

Val Arg Asp Ile Lys Glu Lys Leu Cys Tyr Val Ala Leu Asp Phe Glu
210 215 220

Gln Glu Met Ala Thr Ala Ala Ser Ser Ser Ser Leu Glu Lys Ser Tyr
225 230 235 240

Glu Leu Pro Asp Gly Gln Val Ile Thr Ile Gly Asn Glu Arg Phe Arg
245 250 255

Cys Pro Glu Ala Leu Phe Gln Pro Ser Phe Leu Gly Met Glu Ser Cys
260 265 270

Gly Ile His Glu Thr Thr Phe Asn Ser Ile Met Lys Cys Asp Val Asp
275 280 285

Ile Arg Lys Asp Leu Tyr Ala Asn Thr Val Leu Ser Gly Gly Thr Thr
290 295 300

Met Tyr Pro Gly Ile Ala Asp Arg Met Gln Lys Glu Ile Thr Ala Leu
305 310 315 320

Ala Pro Ser Thr Met Lys Ile Lys Ile Ile Ala Pro Pro Glu Arg Lys
325 330 335

Tyr Ser Val Trp Ile Gly Gly Ser Ile Leu Ala Ser Leu Ser Thr Phe
340 345 350

Gln Gln Met Trp Ile Ser Lys Gln Glu Tyr Asp Glu Ser Gly Pro Ser
355 360 365

Ile Val His Arg Lys Cys Phe
370 375

<210> SEQ ID NO 62
<211> LENGTH: 894
<212> TYPE: PRT
<213> ORGANISM: Homo sapiens

<400> SEQUENCE: 62

Met Asn Gln Ile Glu Pro Gly Val Gln Tyr Asn Tyr Val Tyr Asp Glu

-continued

```
1               5                   10                  15

Asp Glu Tyr Met Ile Gln Glu Glu Glu Trp Asp Arg Asp Leu Leu Leu
            20                  25                  30

Asp Pro Ala Trp Glu Lys Gln Gln Arg Lys Thr Phe Thr Ala Trp Cys
        35                  40                  45

Asn Ser His Leu Arg Lys Ala Gly Thr Gln Ile Glu Asn Ile Glu Glu
    50                  55                  60

Asp Phe Arg Asn Gly Leu Lys Leu Met Leu Leu Leu Glu Val Ile Ser
65                  70                  75                  80

Gly Glu Arg Leu Pro Lys Pro Asp Arg Gly Lys Met Arg Phe His Lys
                85                  90                  95

Ile Ala Asn Val Asn Lys Ala Leu Asp Tyr Ile Ala Ser Lys Gly Val
            100                 105                 110

Lys Leu Val Ser Ile Gly Ala Glu Glu Ile Val Asp Gly Asn Val Lys
        115                 120                 125

Met Thr Leu Gly Met Ile Trp Thr Ile Ile Leu Arg Phe Ala Ile Gln
    130                 135                 140

Asp Ile Ser Val Glu Glu Thr Ser Ala Lys Glu Gly Leu Leu Leu Trp
145                 150                 155                 160

Cys Gln Arg Lys Thr Ala Pro Tyr Arg Asn Val Asn Ile Gln Asn Phe
                165                 170                 175

His Thr Ser Trp Lys Asp Gly Leu Gly Leu Cys Ala Leu Ile His Arg
            180                 185                 190

His Arg Pro Asp Leu Ile Asp Tyr Ser Lys Leu Asn Lys Asp Asp Pro
        195                 200                 205

Ile Gly Asn Ile Asn Leu Ala Met Glu Ile Ala Glu Lys His Leu Asp
    210                 215                 220

Ile Pro Lys Met Leu Asp Ala Glu Asp Ile Val Asn Thr Pro Lys Pro
225                 230                 235                 240

Asp Glu Arg Ala Ile Met Thr Tyr Val Ser Cys Phe Tyr His Ala Phe
                245                 250                 255

Ala Gly Ala Glu Gln Ala Glu Thr Ala Ala Asn Arg Ile Cys Lys Val
            260                 265                 270

Leu Ala Val Asn Gln Glu Asn Glu Arg Leu Met Glu Glu Tyr Glu Arg
        275                 280                 285

Leu Ala Ser Glu Leu Leu Glu Trp Ile Arg Arg Thr Ile Pro Trp Leu
    290                 295                 300

Glu Asn Arg Thr Pro Glu Lys Thr Met Gln Ala Met Gln Lys Lys Leu
305                 310                 315                 320

Glu Asp Phe Arg Asp Tyr Arg Arg Lys His Lys Pro Pro Lys Val Gln
                325                 330                 335

Glu Lys Cys Gln Leu Glu Ile Asn Phe Asn Thr Leu Gln Thr Lys Leu
            340                 345                 350

Arg Ile Ser Asn Arg Pro Ala Phe Met Pro Ser Glu Gly Lys Met Val
        355                 360                 365

Ser Asp Ile Ala Gly Ala Trp Gln Arg Leu Glu Gln Ala Glu Lys Gly
    370                 375                 380

Tyr Glu Glu Trp Leu Leu Asn Glu Ile Arg Arg Leu Glu Arg Leu Glu
385                 390                 395                 400

His Leu Ala Glu Lys Phe Arg Gln Lys Ala Ser Thr His Glu Thr Trp
                405                 410                 415

Ala Tyr Gly Lys Glu Gln Ile Leu Leu Gln Lys Asp Tyr Glu Ser Ala
            420                 425                 430
```

```
Ser Leu Thr Glu Val Arg Ala Leu Leu Arg Lys His Glu Ala Phe Glu
        435                 440                 445

Ser Asp Leu Ala Ala His Gln Asp Arg Val Glu Gln Ile Ala Ala Ile
    450                 455                 460

Ala Gln Glu Leu Asn Glu Leu Asp Tyr His Asp Ala Val Asn Val Asn
465                 470                 475                 480

Asp Arg Cys Gln Lys Ile Cys Asp Gln Trp Asp Arg Leu Gly Thr Leu
                485                 490                 495

Thr Gln Lys Arg Arg Glu Ala Leu Glu Arg Met Glu Lys Leu Leu Glu
            500                 505                 510

Thr Ile Asp Gln Leu His Leu Glu Phe Ala Lys Arg Ala Ala Pro Phe
        515                 520                 525

Asn Asn Trp Met Glu Gly Ala Met Glu Asp Leu Gln Asp Met Phe Ile
    530                 535                 540

Val His Ser Ile Glu Glu Ile Gln Ser Leu Ile Thr Ala His Glu Gln
545                 550                 555                 560

Phe Lys Ala Thr Leu Pro Glu Ala Asp Gly Glu Arg Gln Ser Ile Met
                565                 570                 575

Ala Ile Gln Asn Glu Val Glu Lys Val Ile Gln Ser Tyr Asn Ile Arg
            580                 585                 590

Ile Ser Ser Ser Asn Pro Tyr Ser Thr Val Thr Met Asp Glu Leu Arg
        595                 600                 605

Thr Lys Trp Asp Lys Val Lys Gln Leu Val Pro Ile Arg Asp Gln Ser
    610                 615                 620

Leu Gln Glu Glu Leu Ala Arg Gln His Ala Asn Glu Arg Leu Arg Arg
625                 630                 635                 640

Gln Phe Ala Ala Gln Ala Asn Ala Ile Gly Pro Trp Ile Gln Asn Lys
                645                 650                 655

Met Glu Glu Ile Ala Arg Ser Ser Ile Gln Ile Thr Gly Ala Leu Glu
            660                 665                 670

Asp Gln Met Asn Gln Leu Lys Gln Tyr Glu His Asn Ile Ile Asn Tyr
        675                 680                 685

Lys Asn Asn Ile Asp Lys Leu Glu Gly Asp His Gln Leu Ile Gln Glu
    690                 695                 700

Ala Leu Val Phe Asp Asn Lys His Thr Asn Tyr Thr Met Glu His Ile
705                 710                 715                 720

Arg Val Gly Trp Glu Leu Leu Leu Thr Thr Ile Ala Arg Thr Ile Asn
                725                 730                 735

Glu Val Glu Thr Gln Ile Leu Thr Arg Asp Ala Lys Gly Ile Thr Gln
            740                 745                 750

Glu Gln Met Asn Glu Phe Arg Ala Ser Phe Asn His Phe Asp Arg Arg
        755                 760                 765

Lys Asn Gly Leu Met Asp His Glu Asp Phe Arg Ala Cys Leu Ile Ser
    770                 775                 780

Met Gly Tyr Asp Leu Gly Glu Ala Glu Phe Ala Arg Ile Met Thr Leu
785                 790                 795                 800

Val Asp Pro Asn Gly Gln Gly Thr Val Thr Phe Gln Ser Phe Ile Asp
                805                 810                 815

Phe Met Thr Arg Glu Thr Ala Asp Thr Asp Thr Ala Glu Gln Val Ile
            820                 825                 830

Ala Ser Phe Arg Ile Leu Ala Ser Asp Lys Pro Tyr Ile Leu Ala Glu
        835                 840                 845
```

```
Glu Leu Arg Arg Glu Leu Pro Pro Asp Gln Ala Gln Tyr Cys Ile Lys
    850                 855                 860

Arg Met Pro Ala Tyr Ser Gly Pro Gly Ser Val Pro Gly Ala Leu Asp
865                 870                 875                 880

Tyr Ala Ala Phe Ser Ser Ala Leu Tyr Gly Glu Ser Asp Leu
                885                 890


<210> SEQ ID NO 63
<211> LENGTH: 967
<212> TYPE: PRT
<213> ORGANISM: Homo sapiens

<400> SEQUENCE: 63

Met Ala Lys Gly Phe Tyr Ile Ser Lys Ser Leu Gly Ile Leu Gly Ile
1               5                   10                  15

Leu Leu Gly Val Ala Ala Val Cys Thr Ile Ile Ala Leu Ser Val Val
            20                  25                  30

Tyr Ser Gln Glu Lys Asn Lys Asn Ala Asn Ser Ser Pro Val Ala Ser
        35                  40                  45

Thr Thr Pro Ser Ala Ser Ala Thr Thr Asn Pro Ala Ser Ala Thr Thr
    50                  55                  60

Leu Asp Gln Ser Lys Ala Trp Asn Arg Tyr Arg Leu Pro Asn Thr Leu
65                  70                  75                  80

Lys Pro Asp Ser Tyr Arg Val Thr Leu Arg Pro Tyr Leu Thr Pro Asn
                85                  90                  95

Asp Arg Gly Leu Tyr Val Phe Lys Gly Ser Ser Thr Val Arg Phe Thr
            100                 105                 110

Cys Lys Glu Ala Thr Asp Val Ile Ile Ile His Ser Lys Lys Leu Asn
        115                 120                 125

Tyr Thr Leu Ser Gln Gly His Arg Val Val Leu Arg Gly Val Gly Gly
    130                 135                 140

Ser Gln Pro Pro Asp Ile Asp Lys Thr Glu Leu Val Glu Pro Thr Glu
145                 150                 155                 160

Tyr Leu Val Val His Leu Lys Gly Ser Leu Val Lys Asp Ser Gln Tyr
                165                 170                 175

Glu Met Asp Ser Glu Phe Glu Gly Glu Leu Ala Asp Asp Leu Ala Gly
            180                 185                 190

Phe Tyr Arg Ser Glu Tyr Met Glu Gly Asn Val Arg Lys Val Val Ala
        195                 200                 205

Thr Thr Gln Met Gln Ala Ala Asp Ala Arg Lys Ser Phe Pro Cys Phe
    210                 215                 220

Asp Glu Pro Ala Met Lys Ala Glu Phe Asn Ile Thr Leu Ile His Pro
225                 230                 235                 240

Lys Asp Leu Thr Ala Leu Ser Asn Met Leu Pro Lys Gly Pro Ser Thr
                245                 250                 255

Pro Leu Pro Glu Asp Pro Asn Trp Asn Val Thr Glu Phe His Thr Thr
            260                 265                 270

Pro Lys Met Ser Thr Tyr Leu Leu Ala Phe Ile Val Ser Glu Phe Asp
        275                 280                 285

Tyr Val Glu Lys Gln Ala Ser Asn Gly Val Leu Ile Arg Ile Trp Ala
    290                 295                 300

Arg Pro Ser Ala Ile Ala Ala Gly His Gly Asp Tyr Ala Leu Asn Val
305                 310                 315                 320

Thr Gly Pro Ile Leu Asn Phe Phe Ala Gly His Tyr Asp Thr Pro Tyr
                325                 330                 335
```

```
Pro Leu Pro Lys Ser Asp Gln Ile Gly Leu Pro Asp Phe Asn Ala Gly
            340                 345                 350

Ala Met Glu Asn Trp Gly Leu Val Thr Tyr Arg Glu Asn Ser Leu Leu
        355                 360                 365

Phe Asp Pro Leu Ser Ser Ser Ser Ser Asn Lys Glu Arg Val Val Thr
    370                 375                 380

Val Ile Ala His Glu Leu Ala His Gln Trp Phe Gly Asn Leu Val Thr
385                 390                 395                 400

Ile Glu Trp Trp Asn Asp Leu Trp Leu Asn Glu Gly Phe Ala Ser Tyr
                405                 410                 415

Val Glu Tyr Leu Gly Ala Asp Tyr Ala Glu Pro Thr Trp Asn Leu Lys
            420                 425                 430

Asp Leu Met Val Leu Asn Asp Val Tyr Arg Val Met Ala Val Asp Ala
        435                 440                 445

Leu Ala Ser Ser His Pro Leu Ser Thr Pro Ala Ser Glu Ile Asn Thr
    450                 455                 460

Pro Ala Gln Ile Ser Glu Leu Phe Asp Ala Ile Ser Tyr Ser Lys Gly
465                 470                 475                 480

Ala Ser Val Leu Arg Met Leu Ser Ser Phe Leu Ser Glu Asp Val Phe
                485                 490                 495

Lys Gln Gly Leu Ala Ser Tyr Leu His Thr Phe Ala Tyr Gln Asn Thr
            500                 505                 510

Ile Tyr Leu Asn Leu Trp Asp His Leu Gln Glu Ala Val Asn Asn Arg
        515                 520                 525

Ser Ile Gln Leu Pro Thr Thr Val Arg Asp Ile Met Asn Arg Trp Thr
    530                 535                 540

Leu Gln Met Gly Phe Pro Val Ile Thr Val Asp Thr Ser Thr Gly Thr
545                 550                 555                 560

Leu Ser Gln Glu His Phe Leu Leu Asp Pro Asp Ser Asn Val Thr Arg
                565                 570                 575

Pro Ser Glu Phe Asn Tyr Val Trp Ile Val Pro Ile Thr Ser Ile Arg
            580                 585                 590

Asp Gly Arg Gln Gln Gln Asp Tyr Trp Leu Ile Asp Val Arg Ala Gln
        595                 600                 605

Asn Asp Leu Phe Ser Thr Ser Gly Asn Glu Trp Val Leu Leu Asn Leu
    610                 615                 620

Asn Val Thr Gly Tyr Tyr Arg Val Asn Tyr Asp Glu Glu Asn Trp Arg
625                 630                 635                 640

Lys Ile Gln Thr Gln Leu Gln Arg Asp His Ser Ala Ile Pro Val Ile
                645                 650                 655

Asn Arg Ala Gln Ile Ile Asn Asp Ala Phe Asn Leu Ala Ser Ala His
            660                 665                 670

Lys Val Pro Val Thr Leu Ala Leu Asn Asn Thr Leu Phe Leu Ile Glu
        675                 680                 685

Glu Arg Gln Tyr Met Pro Trp Glu Ala Ala Leu Ser Ser Leu Ser Tyr
    690                 695                 700

Phe Lys Leu Met Phe Asp Arg Ser Glu Val Tyr Gly Pro Met Lys Asn
705                 710                 715                 720

Tyr Leu Lys Lys Gln Val Thr Pro Leu Phe Ile His Phe Arg Asn Asn
                725                 730                 735

Thr Asn Asn Trp Arg Glu Ile Pro Glu Asn Leu Met Asp Gln Tyr Ser
            740                 745                 750
```

```
Glu Val Asn Ala Ile Ser Thr Ala Cys Ser Asn Gly Val Pro Glu Cys
        755                 760                 765

Glu Glu Met Val Ser Gly Leu Phe Lys Gln Trp Met Glu Asn Pro Asn
    770                 775                 780

Asn Asn Pro Ile His Pro Asn Leu Arg Ser Thr Val Tyr Cys Asn Ala
785                 790                 795                 800

Ile Ala Gln Gly Gly Glu Glu Glu Trp Asp Phe Ala Trp Glu Gln Phe
                805                 810                 815

Arg Asn Ala Thr Leu Val Asn Glu Ala Asp Lys Leu Arg Ala Ala Leu
            820                 825                 830

Ala Cys Ser Lys Glu Leu Trp Ile Leu Asn Arg Tyr Leu Ser Tyr Thr
        835                 840                 845

Leu Asn Pro Asp Leu Ile Arg Lys Gln Asp Ala Thr Ser Thr Ile Ile
    850                 855                 860

Ser Ile Thr Asn Asn Val Ile Gly Gln Gly Leu Val Trp Asp Phe Val
865                 870                 875                 880

Gln Ser Asn Trp Lys Lys Leu Phe Asn Asp Tyr Gly Gly Gly Ser Phe
                885                 890                 895

Ser Phe Ser Asn Leu Ile Gln Ala Val Thr Arg Arg Phe Ser Thr Glu
            900                 905                 910

Tyr Glu Leu Gln Gln Leu Glu Gln Phe Lys Lys Asp Asn Glu Glu Thr
        915                 920                 925

Gly Phe Gly Ser Gly Thr Arg Ala Leu Glu Gln Ala Leu Glu Lys Thr
    930                 935                 940

Lys Ala Asn Ile Lys Trp Val Lys Glu Asn Lys Glu Val Val Leu Gln
945                 950                 955                 960

Trp Phe Thr Glu Asn Ser Lys
                965


<210> SEQ ID NO 64
<211> LENGTH: 339
<212> TYPE: PRT
<213> ORGANISM: Homo sapiens

<400> SEQUENCE: 64

Met Ser Thr Val His Glu Ile Leu Cys Lys Leu Ser Leu Glu Gly Asp
1               5                   10                  15

His Ser Thr Pro Pro Ser Ala Tyr Gly Ser Val Lys Ala Tyr Thr Asn
            20                  25                  30

Phe Asp Ala Glu Arg Asp Ala Leu Asn Ile Glu Thr Ala Ile Lys Thr
        35                  40                  45

Lys Gly Val Asp Glu Val Thr Ile Val Asn Ile Leu Thr Asn Arg Ser
    50                  55                  60

Asn Ala Gln Arg Gln Asp Ile Ala Phe Ala Tyr Gln Arg Arg Thr Lys
65                  70                  75                  80

Lys Glu Leu Ala Ser Ala Leu Lys Ser Ala Leu Ser Gly His Leu Glu
                85                  90                  95

Thr Val Ile Leu Gly Leu Leu Lys Thr Pro Ala Gln Tyr Asp Ala Ser
            100                 105                 110

Glu Leu Lys Ala Ser Met Lys Gly Leu Gly Thr Asp Glu Asp Ser Leu
        115                 120                 125

Ile Glu Ile Ile Cys Ser Arg Thr Asn Gln Glu Leu Gln Glu Ile Asn
    130                 135                 140

Arg Val Tyr Lys Glu Met Tyr Lys Thr Asp Leu Glu Lys Asp Ile Ile
145                 150                 155                 160
```

```
Ser Asp Thr Ser Gly Asp Phe Arg Lys Leu Met Val Ala Leu Ala Lys
                165                 170                 175

Gly Arg Arg Ala Glu Asp Gly Ser Val Ile Asp Tyr Glu Leu Ile Asp
            180                 185                 190

Gln Asp Ala Arg Asp Leu Tyr Asp Ala Gly Val Lys Arg Lys Gly Thr
        195                 200                 205

Asp Val Pro Lys Trp Ile Ser Ile Met Thr Glu Arg Ser Val Pro His
    210                 215                 220

Leu Gln Lys Val Phe Asp Arg Tyr Lys Ser Tyr Ser Pro Tyr Asp Met
225                 230                 235                 240

Leu Glu Ser Ile Arg Lys Glu Val Lys Gly Asp Leu Glu Asn Ala Phe
                245                 250                 255

Leu Asn Leu Val Gln Cys Ile Gln Asn Lys Pro Leu Tyr Phe Ala Asp
            260                 265                 270

Arg Leu Tyr Asp Ser Met Lys Gly Lys Gly Thr Arg Asp Lys Val Leu
        275                 280                 285

Ile Arg Ile Met Val Ser Arg Ser Glu Val Asp Met Leu Lys Ile Arg
    290                 295                 300

Ser Glu Phe Lys Arg Lys Tyr Gly Lys Ser Leu Tyr Tyr Tyr Ile Gln
305                 310                 315                 320

Gln Asp Thr Lys Gly Asp Tyr Gln Lys Ala Leu Leu Tyr Leu Cys Gly
                325                 330                 335

Gly Asp Asp


<210> SEQ ID NO 65
<211> LENGTH: 449
<212> TYPE: PRT
<213> ORGANISM: Homo sapiens

<400> SEQUENCE: 65

Met Met Lys Thr Leu Leu Leu Phe Val Gly Leu Leu Leu Thr Trp Glu
1               5                   10                  15

Ser Gly Gln Val Leu Gly Asp Gln Thr Val Ser Asp Asn Glu Leu Gln
            20                  25                  30

Glu Met Ser Asn Gln Gly Ser Lys Tyr Val Asn Lys Glu Ile Gln Asn
        35                  40                  45

Ala Val Asn Gly Val Lys Gln Ile Lys Thr Leu Ile Glu Lys Thr Asn
    50                  55                  60

Glu Glu Arg Lys Thr Leu Leu Ser Asn Leu Glu Glu Ala Lys Lys Lys
65                  70                  75                  80

Lys Glu Asp Ala Leu Asn Glu Thr Arg Glu Ser Glu Thr Lys Leu Lys
                85                  90                  95

Glu Leu Pro Gly Val Cys Asn Glu Thr Met Met Ala Leu Trp Glu Glu
            100                 105                 110

Cys Lys Pro Cys Leu Lys Gln Thr Cys Met Lys Phe Tyr Ala Arg Val
        115                 120                 125

Cys Arg Ser Gly Ser Gly Leu Val Gly Arg Gln Leu Glu Glu Phe Leu
    130                 135                 140

Asn Gln Ser Ser Pro Phe Tyr Phe Trp Met Asn Gly Asp Arg Ile Asp
145                 150                 155                 160

Ser Leu Leu Glu Asn Asp Arg Gln Gln Thr His Met Leu Asp Val Met
                165                 170                 175

Gln Asp His Phe Ser Arg Ala Ser Ser Ile Ile Asp Glu Leu Phe Gln
            180                 185                 190
```

Asp Arg Phe Phe Thr Arg Glu Pro Gln Asp Thr Tyr His Tyr Leu Pro
195 200 205

Phe Ser Leu Pro His Arg Arg Pro His Phe Phe Phe Pro Lys Ser Arg
210 215 220

Ile Val Arg Ser Leu Met Pro Phe Ser Pro Tyr Glu Pro Leu Asn Phe
225 230 235 240

His Ala Met Phe Gln Pro Phe Leu Glu Met Ile His Glu Ala Gln Gln
245 250 255

Ala Met Asp Ile His Phe His Ser Pro Ala Phe Gln His Pro Pro Thr
260 265 270

Glu Phe Ile Arg Glu Gly Asp Asp Asp Arg Thr Val Cys Arg Glu Ile
275 280 285

Arg His Asn Ser Thr Gly Cys Leu Arg Met Lys Asp Gln Cys Asp Lys
290 295 300

Cys Arg Glu Ile Leu Ser Val Asp Cys Ser Thr Asn Asn Pro Ser Gln
305 310 315 320

Ala Lys Leu Arg Arg Glu Leu Asp Glu Ser Leu Gln Val Ala Glu Arg
325 330 335

Leu Thr Arg Lys Tyr Asn Glu Leu Leu Lys Ser Tyr Gln Trp Lys Met
340 345 350

Leu Asn Thr Ser Ser Leu Leu Glu Gln Leu Asn Glu Gln Phe Asn Trp
355 360 365

Val Ser Arg Leu Ala Asn Leu Thr Gln Gly Glu Asp Gln Tyr Tyr Leu
370 375 380

Arg Val Thr Thr Val Ala Ser His Thr Ser Asp Ser Asp Val Pro Ser
385 390 395 400

Gly Val Thr Glu Val Val Val Lys Leu Phe Asp Ser Asp Pro Ile Thr
405 410 415

Val Thr Val Pro Val Glu Val Ser Arg Lys Asn Pro Lys Phe Met Glu
420 425 430

Thr Val Ala Glu Lys Ala Leu Gln Glu Tyr Arg Lys Lys His Arg Glu
435 440 445

Glu

<210> SEQ ID NO 66
<211> LENGTH: 1049
<212> TYPE: PRT
<213> ORGANISM: Homo sapiens

<400> SEQUENCE: 66

Met Asp Trp Ser Phe Phe Arg Val Val Ala Met Leu Phe Ile Phe Leu
1 5 10 15

Val Val Val Glu Val Asn Ser Glu Phe Arg Ile Gln Val Arg Asp Tyr
20 25 30

Asn Thr Lys Asn Gly Thr Ile Lys Trp His Ser Ile Arg Arg Gln Lys
35 40 45

Arg Glu Trp Ile Lys Phe Ala Ala Ala Cys Arg Glu Gly Glu Asp Asn
50 55 60

Ser Lys Arg Asn Pro Ile Ala Lys Ile His Ser Asp Cys Ala Ala Asn
65 70 75 80

Gln Gln Val Thr Tyr Arg Ile Ser Gly Val Gly Ile Asp Gln Pro Pro
85 90 95

Tyr Gly Ile Phe Val Ile Asn Gln Lys Thr Gly Glu Ile Asn Ile Thr
100 105 110

```
Ser Ile Val Asp Arg Glu Val Thr Pro Phe Phe Ile Ile Tyr Cys Arg
        115                 120                 125

Ala Leu Asn Ser Met Gly Gln Asp Leu Glu Arg Pro Leu Glu Leu Arg
    130                 135                 140

Val Arg Val Leu Asp Ile Asn Asp Asn Pro Pro Val Phe Ser Met Ala
145                 150                 155                 160

Thr Phe Ala Gly Gln Ile Glu Glu Asn Ser Asn Ala Asn Thr Leu Val
                165                 170                 175

Met Ile Leu Asn Ala Thr Asp Ala Asp Glu Pro Asn Asn Leu Asn Ser
            180                 185                 190

Lys Ile Ala Phe Lys Ile Ile Arg Gln Glu Pro Ser Asp Ser Pro Met
        195                 200                 205

Phe Ile Ile Asn Arg Asn Thr Gly Glu Ile Arg Thr Met Asn Asn Phe
    210                 215                 220

Leu Asp Arg Glu Gln Tyr Gly Gln Tyr Ala Leu Ala Val Arg Gly Ser
225                 230                 235                 240

Asp Arg Asp Gly Gly Ala Asp Gly Met Ser Ala Glu Cys Glu Cys Asn
                245                 250                 255

Ile Lys Ile Leu Asp Val Asn Asp Asn Ile Pro Tyr Met Glu Gln Ser
            260                 265                 270

Ser Tyr Thr Ile Glu Ile Gln Glu Asn Thr Leu Asn Ser Asn Leu Leu
        275                 280                 285

Glu Ile Arg Val Ile Asp Leu Asp Glu Glu Phe Ser Ala Asn Trp Met
    290                 295                 300

Ala Val Ile Phe Phe Ile Ser Gly Asn Glu Gly Asn Trp Phe Glu Ile
305                 310                 315                 320

Glu Met Asn Glu Arg Thr Asn Val Gly Ile Leu Lys Val Val Lys Pro
                325                 330                 335

Leu Asp Tyr Glu Ala Met Gln Ser Leu Gln Leu Ser Ile Gly Val Arg
            340                 345                 350

Asn Lys Ala Glu Phe His His Ser Ile Met Ser Gln Tyr Lys Leu Lys
        355                 360                 365

Ala Ser Ala Ile Ser Val Thr Val Leu Asn Val Ile Glu Gly Pro Val
    370                 375                 380

Phe Arg Pro Gly Ser Lys Thr Tyr Val Val Thr Gly Asn Met Gly Ser
385                 390                 395                 400

Asn Asp Lys Val Gly Asp Phe Val Ala Thr Asp Leu Asp Thr Gly Arg
                405                 410                 415

Pro Ser Thr Thr Val Arg Tyr Val Met Gly Asn Asn Pro Ala Asp Leu
            420                 425                 430

Leu Ala Val Asp Ser Arg Thr Gly Lys Leu Thr Leu Lys Asn Lys Val
        435                 440                 445

Thr Lys Glu Gln Tyr Asn Met Leu Gly Gly Lys Tyr Gln Gly Thr Ile
    450                 455                 460

Leu Ser Ile Asp Asp Asn Leu Gln Arg Thr Cys Thr Gly Thr Ile Asn
465                 470                 475                 480

Ile Asn Ile Gln Ser Phe Gly Asn Asp Asp Arg Thr Asn Thr Glu Pro
                485                 490                 495

Asn Thr Lys Ile Thr Thr Asn Thr Gly Arg Gln Glu Ser Thr Ser Ser
            500                 505                 510

Thr Asn Tyr Asp Thr Ser Thr Thr Ser Thr Asp Ser Ser Gln Val Tyr
        515                 520                 525
```

```
Ser Ser Glu Pro Gly Asn Gly Ala Lys Asp Leu Leu Ser Asp Asn Val
    530                 535                 540

His Phe Gly Pro Ala Gly Ile Gly Leu Leu Ile Met Gly Phe Leu Val
545                 550                 555                 560

Leu Gly Leu Val Pro Phe Leu Met Ile Cys Cys Asp Cys Gly Gly Ala
                565                 570                 575

Pro Arg Ser Ala Ala Gly Phe Glu Pro Val Pro Glu Cys Ser Asp Gly
            580                 585                 590

Ala Ile His Ser Trp Ala Val Glu Gly Pro Gln Pro Glu Pro Arg Asp
        595                 600                 605

Ile Thr Thr Val Ile Pro Gln Ile Pro Pro Asp Asn Ala Asn Ile Ile
    610                 615                 620

Glu Cys Ile Asp Asn Ser Gly Val Tyr Thr Asn Glu Tyr Gly Gly Arg
625                 630                 635                 640

Glu Met Gln Asp Leu Gly Gly Gly Glu Arg Met Thr Gly Phe Glu Leu
                645                 650                 655

Thr Glu Gly Val Lys Thr Ser Gly Met Pro Glu Ile Cys Gln Glu Tyr
            660                 665                 670

Ser Gly Thr Leu Arg Arg Asn Ser Met Arg Glu Cys Arg Glu Gly Gly
        675                 680                 685

Leu Asn Met Asn Phe Met Glu Ser Tyr Phe Cys Gln Lys Ala Tyr Ala
    690                 695                 700

Tyr Ala Asp Glu Asp Glu Gly Arg Pro Ser Asn Asp Cys Leu Leu Ile
705                 710                 715                 720

Tyr Asp Ile Glu Gly Val Gly Ser Pro Ala Gly Ser Val Gly Cys Cys
                725                 730                 735

Ser Phe Ile Gly Glu Asp Leu Asp Asp Ser Phe Leu Asp Thr Leu Gly
            740                 745                 750

Pro Lys Phe Lys Lys Leu Ala Asp Ile Ser Leu Gly Lys Glu Ser Tyr
        755                 760                 765

Pro Asp Leu Asp Pro Ser Trp Pro Pro Gln Ser Thr Glu Pro Val Cys
    770                 775                 780

Leu Pro Gln Glu Thr Glu Pro Val Val Ser Gly His Pro Pro Ile Ser
785                 790                 795                 800

Pro His Phe Gly Thr Thr Thr Val Ile Ser Glu Ser Thr Tyr Pro Ser
                805                 810                 815

Gly Pro Gly Val Leu His Pro Lys Pro Ile Leu Asp Pro Leu Gly Tyr
            820                 825                 830

Gly Asn Val Thr Val Thr Glu Ser Tyr Thr Thr Ser Asp Thr Leu Lys
        835                 840                 845

Pro Ser Val His Val His Asp Asn Arg Pro Ala Ser Asn Val Val Val
    850                 855                 860

Thr Glu Arg Val Val Gly Pro Ile Ser Gly Ala Asp Leu His Gly Met
865                 870                 875                 880

Leu Glu Met Pro Asp Leu Arg Asp Gly Ser Asn Val Ile Val Thr Glu
                885                 890                 895

Arg Val Ile Ala Pro Ser Ser Ser Leu Pro Thr Ser Leu Thr Ile His
            900                 905                 910

His Pro Arg Glu Ser Ser Asn Val Val Val Thr Glu Arg Val Ile Gln
        915                 920                 925

Pro Thr Ser Gly Met Ile Gly Ser Leu Ser Met His Pro Glu Leu Ala
    930                 935                 940

Asn Ala His Asn Val Ile Val Thr Glu Arg Val Val Ser Gly Ala Gly
```

945 950 955 960

Val Thr Gly Ile Ser Gly Thr Thr Gly Ile Ser Gly Gly Ile Gly Ser
965 970 975

Ser Gly Leu Val Gly Thr Ser Met Gly Ala Gly Ser Gly Ala Leu Ser
980 985 990

Gly Ala Gly Ile Ser Gly Gly Gly Ile Gly Leu Ser Ser Leu Gly Gly
995 1000 1005

Thr Ala Ser Ile Gly His Met Arg Ser Ser Ser Asp His His Phe
1010 1015 1020

Asn Gln Thr Ile Gly Ser Ala Ser Pro Ser Thr Ala Arg Ser Arg
1025 1030 1035

Ile Thr Lys Tyr Ser Thr Val Gln Tyr Ser Lys
1040 1045

<210> SEQ ID NO 67
<211> LENGTH: 2871
<212> TYPE: PRT
<213> ORGANISM: Homo sapiens

<400> SEQUENCE: 67

Met Ser Cys Asn Gly Gly Ser His Pro Arg Ile Asn Thr Leu Gly Arg
1 5 10 15

Met Ile Arg Ala Glu Ser Gly Pro Asp Leu Arg Tyr Glu Val Thr Ser
20 25 30

Gly Gly Gly Gly Thr Ser Arg Met Tyr Tyr Ser Arg Arg Gly Val Ile
35 40 45

Thr Asp Gln Asn Ser Asp Gly Tyr Cys Gln Thr Gly Thr Met Ser Arg
50 55 60

His Gln Asn Gln Asn Thr Ile Gln Glu Leu Leu Gln Asn Cys Ser Asp
65 70 75 80

Cys Leu Met Arg Ala Glu Leu Ile Val Gln Pro Glu Leu Lys Tyr Gly
85 90 95

Asp Gly Ile Gln Leu Thr Arg Ser Arg Glu Leu Asp Glu Cys Phe Ala
100 105 110

Gln Ala Asn Asp Gln Met Glu Ile Leu Asp Ser Leu Ile Arg Glu Met
115 120 125

Arg Gln Met Gly Gln Pro Cys Asp Ala Tyr Gln Lys Arg Leu Leu Gln
130 135 140

Leu Gln Glu Gln Met Arg Ala Leu Tyr Lys Ala Ile Ser Val Pro Arg
145 150 155 160

Val Arg Arg Ala Ser Ser Lys Gly Gly Gly Gly Tyr Thr Cys Gln Ser
165 170 175

Gly Ser Gly Trp Asp Glu Phe Thr Lys His Val Thr Ser Glu Cys Leu
180 185 190

Gly Trp Met Arg Gln Gln Arg Ala Glu Met Asp Met Val Ala Trp Gly
195 200 205

Val Asp Leu Ala Ser Val Glu Gln His Ile Asn Ser His Arg Gly Ile
210 215 220

His Asn Ser Ile Gly Asp Tyr Arg Trp Gln Leu Asp Lys Ile Lys Ala
225 230 235 240

Asp Leu Arg Glu Lys Ser Ala Ile Tyr Gln Leu Glu Glu Glu Tyr Glu
245 250 255

Asn Leu Leu Lys Ala Ser Phe Glu Arg Met Asp His Leu Arg Gln Leu
260 265 270

```
Gln Asn Ile Ile Gln Ala Thr Ser Arg Glu Ile Met Trp Ile Asn Asp
        275                 280                 285

Cys Glu Glu Glu Glu Leu Leu Tyr Asp Trp Ser Asp Lys Asn Thr Asn
    290                 295                 300

Ile Ala Gln Lys Gln Glu Ala Phe Ser Ile Arg Met Ser Gln Leu Glu
305                 310                 315                 320

Val Lys Glu Lys Glu Leu Asn Lys Leu Lys Gln Glu Ser Asp Gln Leu
                325                 330                 335

Val Leu Asn Gln His Pro Ala Ser Asp Lys Ile Glu Ala Tyr Met Asp
            340                 345                 350

Thr Leu Gln Thr Gln Trp Ser Trp Ile Leu Gln Ile Thr Lys Cys Ile
        355                 360                 365

Asp Val His Leu Lys Glu Asn Ala Ala Tyr Phe Gln Phe Phe Glu Glu
    370                 375                 380

Ala Gln Ser Thr Glu Ala Tyr Leu Lys Gly Leu Gln Asp Ser Ile Arg
385                 390                 395                 400

Lys Lys Tyr Pro Cys Asp Lys Asn Met Pro Leu Gln His Leu Leu Glu
                405                 410                 415

Gln Ile Lys Glu Leu Glu Lys Glu Arg Glu Lys Ile Leu Glu Tyr Lys
            420                 425                 430

Arg Gln Val Gln Asn Leu Val Asn Lys Ser Lys Lys Ile Val Gln Leu
        435                 440                 445

Lys Pro Arg Asn Pro Asp Tyr Arg Ser Asn Lys Pro Ile Ile Leu Arg
    450                 455                 460

Ala Leu Cys Asp Tyr Lys Gln Asp Gln Lys Ile Val His Lys Gly Asp
465                 470                 475                 480

Glu Cys Ile Leu Lys Asp Asn Asn Glu Arg Ser Lys Trp Tyr Val Thr
                485                 490                 495

Gly Pro Gly Gly Val Asp Met Leu Val Pro Ser Val Gly Leu Ile Ile
            500                 505                 510

Pro Pro Pro Asn Pro Leu Ala Val Asp Leu Ser Cys Lys Ile Glu Gln
        515                 520                 525

Tyr Tyr Glu Ala Ile Leu Ala Leu Trp Asn Gln Leu Tyr Ile Asn Met
    530                 535                 540

Lys Ser Leu Val Ser Trp His Tyr Cys Met Ile Asp Ile Glu Lys Ile
545                 550                 555                 560

Arg Ala Met Thr Ile Ala Lys Leu Lys Thr Met Arg Gln Glu Asp Tyr
                565                 570                 575

Met Lys Thr Ile Ala Asp Leu Glu Leu His Tyr Gln Glu Phe Ile Arg
            580                 585                 590

Asn Ser Gln Gly Ser Glu Met Phe Gly Asp Asp Asp Lys Arg Lys Ile
        595                 600                 605

Gln Ser Gln Phe Thr Asp Ala Gln Lys His Tyr Gln Thr Leu Val Ile
    610                 615                 620

Gln Leu Pro Gly Tyr Pro Gln His Gln Thr Val Thr Thr Thr Glu Ile
625                 630                 635                 640

Thr His His Gly Thr Cys Gln Asp Val Asn His Asn Lys Val Ile Glu
                645                 650                 655

Thr Asn Arg Glu Asn Asp Lys Gln Glu Thr Trp Met Leu Met Glu Leu
            660                 665                 670

Gln Lys Ile Arg Arg Gln Ile Glu His Cys Glu Gly Arg Met Thr Leu
        675                 680                 685

Lys Asn Leu Pro Leu Ala Asp Gln Gly Ser Ser His His Ile Thr Val
```

```
    690                 695                 700

Lys Ile Asn Glu Leu Lys Ser Val Gln Asn Asp Ser Gln Ala Ile Ala
705                 710                 715                 720

Glu Val Leu Asn Gln Leu Lys Asp Met Leu Ala Asn Phe Arg Gly Ser
                725                 730                 735

Glu Lys Tyr Cys Tyr Leu Gln Asn Glu Val Phe Gly Leu Phe Gln Lys
            740                 745                 750

Leu Glu Asn Ile Asn Gly Val Thr Asp Gly Tyr Leu Asn Ser Leu Cys
        755                 760                 765

Thr Val Arg Ala Leu Leu Gln Ala Ile Leu Gln Thr Glu Asp Met Leu
    770                 775                 780

Lys Val Tyr Glu Ala Arg Leu Thr Glu Glu Glu Thr Val Cys Leu Asp
785                 790                 795                 800

Leu Asp Lys Val Glu Ala Tyr Arg Cys Gly Leu Lys Lys Ile Lys Asn
                805                 810                 815

Asp Leu Asn Leu Lys Lys Ser Leu Leu Ala Thr Met Lys Thr Glu Leu
            820                 825                 830

Gln Lys Ala Gln Gln Ile His Ser Gln Thr Ser Gln Gln Tyr Pro Leu
        835                 840                 845

Tyr Asp Leu Asp Leu Gly Lys Phe Gly Glu Lys Val Thr Gln Leu Thr
    850                 855                 860

Asp Arg Trp Gln Arg Ile Asp Lys Gln Ile Asp Phe Arg Leu Trp Asp
865                 870                 875                 880

Leu Glu Lys Gln Ile Lys Gln Leu Arg Asn Tyr Arg Asp Asn Tyr Gln
                885                 890                 895

Ala Phe Cys Lys Trp Leu Tyr Asp Ala Lys Arg Arg Gln Asp Ser Leu
            900                 905                 910

Glu Ser Met Lys Phe Gly Asp Ser Asn Thr Val Met Arg Phe Leu Asn
        915                 920                 925

Glu Gln Lys Asn Leu His Ser Glu Ile Ser Gly Lys Arg Asp Lys Ser
    930                 935                 940

Glu Glu Val Gln Lys Ile Ala Glu Leu Cys Ala Asn Ser Ile Lys Asp
945                 950                 955                 960

Tyr Glu Leu Gln Leu Ala Ser Tyr Thr Ser Gly Leu Glu Thr Leu Leu
                965                 970                 975

Asn Ile Pro Ile Lys Arg Thr Met Ile Gln Ser Pro Ser Gly Val Ile
            980                 985                 990

Leu Gln Glu Ala Ala Asp Val His  Ala Arg Tyr Ile Glu  Leu Leu Thr
        995                 1000                1005

Arg Ser  Gly Asp Tyr Tyr Arg  Phe Leu Ser Glu Met  Leu Lys Ser
    1010                1015                1020

Leu Glu  Asp Leu Lys Leu Lys  Asn Thr Lys Ile Glu  Val Leu Glu
    1025                1030                1035

Glu Glu  Leu Arg Leu Ala Arg  Asp Ala Asn Ser Glu  Asn Cys Asn
    1040                1045                1050

Lys Asn  Lys Phe Leu Asp Gln  Asn Leu Gln Lys Tyr  Gln Ala Glu
    1055                1060                1065

Cys Ser  Gln Phe Lys Ala Lys  Leu Ala Ser Leu Glu  Glu Leu Lys
    1070                1075                1080

Arg Gln  Ala Glu Leu Asp Gly  Lys Ser Ala Lys Gln  Asn Leu Asp
    1085                1090                1095

Lys Cys  Tyr Gly Gln Ile Lys  Glu Leu Asn Glu Lys  Ile Thr Arg
    1100                1105                1110
```

Leu Thr Tyr Glu Ile Glu Asp Glu Lys Arg Arg Arg Lys Ser Val
1115 1120 1125

Glu Asp Arg Phe Asp Gln Gln Lys Asn Asp Tyr Asp Gln Leu Gln
1130 1135 1140

Lys Ala Arg Gln Cys Glu Lys Glu Asn Leu Gly Trp Gln Lys Leu
1145 1150 1155

Glu Ser Glu Lys Ala Ile Lys Glu Lys Glu Tyr Glu Ile Glu Arg
1160 1165 1170

Leu Arg Val Leu Leu Gln Glu Glu Gly Thr Arg Lys Arg Glu Tyr
1175 1180 1185

Glu Asn Glu Leu Ala Lys Val Arg Asn His Tyr Asn Glu Glu Met
1190 1195 1200

Ser Asn Leu Arg Asn Lys Tyr Glu Thr Glu Ile Asn Ile Thr Lys
1205 1210 1215

Thr Thr Ile Lys Glu Ile Ser Met Gln Lys Glu Asp Asp Ser Lys
1220 1225 1230

Asn Leu Arg Asn Gln Leu Asp Arg Leu Ser Arg Glu Asn Arg Asp
1235 1240 1245

Leu Lys Asp Glu Ile Val Arg Leu Asn Asp Ser Ile Leu Gln Ala
1250 1255 1260

Thr Glu Gln Arg Arg Arg Ala Glu Glu Asn Ala Leu Gln Gln Lys
1265 1270 1275

Ala Cys Gly Ser Glu Ile Met Gln Lys Lys Gln His Leu Glu Ile
1280 1285 1290

Glu Leu Lys Gln Val Met Gln Gln Arg Ser Glu Asp Asn Ala Arg
1295 1300 1305

His Lys Gln Ser Leu Glu Glu Ala Ala Lys Thr Ile Gln Asp Lys
1310 1315 1320

Asn Lys Glu Ile Glu Arg Leu Lys Ala Glu Phe Gln Glu Glu Ala
1325 1330 1335

Lys Arg Arg Trp Glu Tyr Glu Asn Glu Leu Ser Lys Val Arg Asn
1340 1345 1350

Asn Tyr Asp Glu Glu Ile Ile Ser Leu Lys Asn Gln Phe Glu Thr
1355 1360 1365

Glu Ile Asn Ile Thr Lys Thr Thr Ile His Gln Leu Thr Met Gln
1370 1375 1380

Lys Glu Glu Asp Thr Ser Gly Tyr Arg Ala Gln Ile Asp Asn Leu
1385 1390 1395

Thr Arg Glu Asn Arg Ser Leu Ser Glu Glu Ile Lys Arg Leu Lys
1400 1405 1410

Asn Thr Leu Thr Gln Thr Thr Glu Asn Leu Arg Arg Val Glu Glu
1415 1420 1425

Asp Ile Gln Gln Gln Lys Ala Thr Gly Ser Glu Val Ser Gln Arg
1430 1435 1440

Lys Gln Gln Leu Glu Val Glu Leu Arg Gln Val Thr Gln Met Arg
1445 1450 1455

Thr Glu Glu Ser Val Arg Tyr Lys Gln Ser Leu Asp Asp Ala Ala
1460 1465 1470

Lys Thr Ile Gln Asp Lys Asn Lys Glu Ile Glu Arg Leu Lys Gln
1475 1480 1485

Leu Ile Asp Lys Glu Thr Asn Asp Arg Lys Cys Leu Glu Asp Glu
1490 1495 1500

```
Asn Ala  Arg Leu Gln Arg Val  Gln Tyr Asp Leu Gln  Lys Ala Asn
    1505                 1510                 1515

Ser Ser  Ala Thr Glu Thr Ile  Asn Lys Leu Lys Val  Gln Glu Gln
    1520                 1525                 1530

Glu Leu  Thr Arg Leu Arg Ile  Asp Tyr Glu Arg Val  Ser Gln Glu
    1535                 1540                 1545

Arg Thr  Val Lys Asp Gln Asp  Ile Thr Arg Phe Gln  Asn Ser Leu
    1550                 1555                 1560

Lys Glu  Leu Gln Leu Gln Lys  Gln Lys Val Glu Glu  Glu Leu Asn
    1565                 1570                 1575

Arg Leu  Lys Arg Thr Ala Ser  Glu Asp Ser Cys Lys  Arg Lys Lys
    1580                 1585                 1590

Leu Glu  Glu Glu Leu Glu Gly  Met Arg Arg Ser Leu  Lys Glu Gln
    1595                 1600                 1605

Ala Ile  Lys Ile Thr Asn Leu  Thr Gln Gln Leu Glu  Gln Ala Ser
    1610                 1615                 1620

Ile Val  Lys Lys Arg Ser Glu  Asp Asp Leu Arg Gln  Gln Arg Asp
    1625                 1630                 1635

Val Leu  Asp Gly His Leu Arg  Glu Lys Gln Arg Thr  Gln Glu Glu
    1640                 1645                 1650

Leu Arg  Arg Leu Ser Ser Glu  Val Glu Ala Leu Arg  Arg Gln Leu
    1655                 1660                 1665

Leu Gln  Glu Gln Glu Ser Val  Lys Gln Ala His Leu  Arg Asn Glu
    1670                 1675                 1680

His Phe  Gln Lys Ala Ile Glu  Asp Lys Ser Arg Ser  Leu Asn Glu
    1685                 1690                 1695

Ser Lys  Ile Glu Ile Glu Arg  Leu Gln Ser Leu Thr  Glu Asn Leu
    1700                 1705                 1710

Thr Lys  Glu His Leu Met Leu  Glu Glu Glu Leu Arg  Asn Leu Arg
    1715                 1720                 1725

Leu Glu  Tyr Asp Asp Leu Arg  Arg Gly Arg Ser Glu  Ala Asp Ser
    1730                 1735                 1740

Asp Lys  Asn Ala Thr Ile Leu  Glu Leu Arg Ser Gln  Leu Gln Ile
    1745                 1750                 1755

Ser Asn  Asn Arg Thr Leu Glu  Leu Gln Gly Leu Ile  Asn Asp Leu
    1760                 1765                 1770

Gln Arg  Glu Arg Glu Asn Leu  Arg Gln Glu Ile Glu  Lys Phe Gln
    1775                 1780                 1785

Lys Gln  Ala Leu Glu Ala Ser  Asn Arg Ile Gln Glu  Ser Lys Asn
    1790                 1795                 1800

Gln Cys  Thr Gln Val Val Gln  Glu Arg Glu Ser Leu  Leu Val Lys
    1805                 1810                 1815

Ile Lys  Val Leu Glu Gln Asp  Lys Ala Arg Leu Gln  Arg Leu Glu
    1820                 1825                 1830

Asp Glu  Leu Asn Arg Ala Lys  Ser Thr Leu Glu Ala  Glu Thr Arg
    1835                 1840                 1845

Val Lys  Gln Arg Leu Glu Cys  Glu Lys Gln Gln Ile  Gln Asn Asp
    1850                 1855                 1860

Leu Asn  Gln Trp Lys Thr Gln  Tyr Ser Arg Lys Glu  Glu Ala Ile
    1865                 1870                 1875

Arg Lys  Ile Glu Ser Glu Arg  Glu Lys Ser Glu Arg  Glu Lys Asn
    1880                 1885                 1890

Ser Leu  Arg Ser Glu Ile Glu  Arg Leu Gln Ala Glu  Ile Lys Arg
```

```
    1895                1900                1905

Ile Glu  Glu Arg Cys Arg Arg  Lys Leu Glu Asp Ser  Thr Arg Glu
    1910                1915                1920

Thr Gln  Ser Gln Leu Glu Thr  Glu Arg Ser Arg Tyr  Gln Arg Glu
    1925                1930                1935

Ile Asp  Lys Leu Arg Gln Arg  Pro Tyr Gly Ser His  Arg Glu Thr
    1940                1945                1950

Gln Thr  Glu Cys Glu Trp Thr  Val Asp Thr Ser Lys  Leu Val Phe
    1955                1960                1965

Asp Gly  Leu Arg Lys Lys Val  Thr Ala Met Gln Leu  Tyr Glu Cys
    1970                1975                1980

Gln Leu  Ile Asp Lys Thr Thr  Leu Asp Lys Leu Leu  Lys Gly Lys
    1985                1990                1995

Lys Ser  Val Glu Glu Val Ala  Ser Glu Ile Gln Pro  Phe Leu Arg
    2000                2005                2010

Gly Ala  Gly Ser Ile Ala Gly  Ala Ser Ala Ser Pro  Lys Glu Lys
    2015                2020                2025

Tyr Ser  Leu Val Glu Ala Lys  Arg Lys Lys Leu Ile  Ser Pro Glu
    2030                2035                2040

Ser Thr  Val Met Leu Leu Glu  Ala Gln Ala Ala Thr  Gly Gly Ile
    2045                2050                2055

Ile Asp  Pro His Arg Asn Glu  Lys Leu Thr Val Asp  Ser Ala Ile
    2060                2065                2070

Ala Arg  Asp Leu Ile Asp Phe  Asp Asp Arg Gln Gln  Ile Tyr Ala
    2075                2080                2085

Ala Glu  Lys Ala Ile Thr Gly  Phe Asp Asp Pro Phe  Ser Gly Lys
    2090                2095                2100

Thr Val  Ser Val Ser Glu Ala  Ile Lys Lys Asn Leu  Ile Asp Arg
    2105                2110                2115

Glu Thr  Gly Met Arg Leu Leu  Glu Ala Gln Ile Ala  Ser Gly Gly
    2120                2125                2130

Val Val  Asp Pro Val Asn Ser  Val Phe Leu Pro Lys  Asp Val Ala
    2135                2140                2145

Leu Ala  Arg Gly Leu Ile Asp  Arg Asp Leu Tyr Arg  Ser Leu Asn
    2150                2155                2160

Asp Pro  Arg Asp Ser Gln Lys  Asn Phe Val Asp Pro  Val Thr Lys
    2165                2170                2175

Lys Lys  Val Ser Tyr Val Gln  Leu Lys Glu Arg Cys  Arg Ile Glu
    2180                2185                2190

Pro His  Thr Gly Leu Leu Leu  Leu Ser Val Gln Lys  Arg Ser Met
    2195                2200                2205

Ser Phe  Gln Gly Ile Arg Gln  Pro Val Thr Val Thr  Glu Leu Val
    2210                2215                2220

Asp Ser  Gly Ile Leu Arg Pro  Ser Thr Val Asn Glu  Leu Glu Ser
    2225                2230                2235

Gly Gln  Ile Ser Tyr Asp Glu  Val Gly Glu Arg Ile  Lys Asp Phe
    2240                2245                2250

Leu Gln  Gly Ser Ser Cys Ile  Ala Gly Ile Tyr Asn  Glu Thr Thr
    2255                2260                2265

Lys Gln  Lys Leu Gly Ile Tyr  Glu Ala Met Lys Ile  Gly Leu Val
    2270                2275                2280

Arg Pro  Gly Thr Ala Leu Glu  Leu Leu Glu Ala Gln  Ala Ala Thr
    2285                2290                2295
```

Gly Phe Ile Val Asp Pro Val Ser Asn Leu Arg Leu Pro Val Glu
2300 2305 2310

Glu Ala Tyr Lys Arg Gly Leu Val Gly Ile Glu Phe Lys Glu Lys
2315 2320 2325

Leu Leu Ser Ala Glu Arg Ala Val Thr Gly Tyr Asn Asp Pro Glu
2330 2335 2340

Thr Gly Asn Ile Ile Ser Leu Phe Gln Ala Met Asn Lys Glu Leu
2345 2350 2355

Ile Glu Lys Gly His Gly Ile Arg Leu Leu Glu Ala Gln Ile Ala
2360 2365 2370

Thr Gly Gly Ile Ile Asp Pro Lys Glu Ser His Arg Leu Pro Val
2375 2380 2385

Asp Ile Ala Tyr Lys Arg Gly Tyr Phe Asn Glu Glu Leu Ser Glu
2390 2395 2400

Ile Leu Ser Asp Pro Ser Asp Asp Thr Lys Gly Phe Phe Asp Pro
2405 2410 2415

Asn Thr Glu Glu Asn Leu Thr Tyr Leu Gln Leu Lys Glu Arg Cys
2420 2425 2430

Ile Lys Asp Glu Glu Thr Gly Leu Cys Leu Leu Pro Leu Lys Glu
2435 2440 2445

Lys Lys Lys Gln Val Gln Thr Ser Gln Lys Asn Thr Leu Arg Lys
2450 2455 2460

Arg Arg Val Val Ile Val Asp Pro Glu Thr Asn Lys Glu Met Ser
2465 2470 2475

Val Gln Glu Ala Tyr Lys Lys Gly Leu Ile Asp Tyr Glu Thr Phe
2480 2485 2490

Lys Glu Leu Cys Glu Gln Glu Cys Glu Trp Glu Glu Ile Thr Ile
2495 2500 2505

Thr Gly Ser Asp Gly Ser Thr Arg Val Val Leu Val Asp Arg Lys
2510 2515 2520

Thr Gly Ser Gln Tyr Asp Ile Gln Asp Ala Ile Asp Lys Gly Leu
2525 2530 2535

Val Asp Arg Lys Phe Phe Asp Gln Tyr Arg Ser Gly Ser Leu Ser
2540 2545 2550

Leu Thr Gln Phe Ala Asp Met Ile Ser Leu Lys Asn Gly Val Gly
2555 2560 2565

Thr Ser Ser Ser Met Gly Ser Gly Val Ser Asp Asp Val Phe Ser
2570 2575 2580

Ser Ser Arg His Glu Ser Val Ser Lys Ile Ser Thr Ile Ser Ser
2585 2590 2595

Val Arg Asn Leu Thr Ile Arg Ser Ser Ser Phe Ser Asp Thr Leu
2600 2605 2610

Glu Glu Ser Ser Pro Ile Ala Ala Ile Phe Asp Thr Glu Asn Leu
2615 2620 2625

Glu Lys Ile Ser Ile Thr Glu Gly Ile Glu Arg Gly Ile Val Asp
2630 2635 2640

Ser Ile Thr Gly Gln Arg Leu Leu Glu Ala Gln Ala Cys Thr Gly
2645 2650 2655

Gly Ile Ile His Pro Thr Thr Gly Gln Lys Leu Ser Leu Gln Asp
2660 2665 2670

Ala Val Ser Gln Gly Val Ile Asp Gln Asp Met Ala Thr Arg Leu
2675 2680 2685

```
Lys Pro  Ala Gln Lys Ala Phe  Ile Gly Phe Glu Gly  Val Lys Gly
    2690                 2695                 2700

Lys Lys  Lys Met Ser Ala Ala  Glu Ala Val Lys Glu  Lys Trp Leu
    2705                 2710                 2715

Pro Tyr  Glu Ala Gly Gln Arg  Phe Leu Glu Phe Gln  Tyr Leu Thr
    2720                 2725                 2730

Gly Gly  Leu Val Asp Pro Glu  Val His Gly Arg Ile  Ser Thr Glu
    2735                 2740                 2745

Glu Ala  Ile Arg Lys Gly Phe  Ile Asp Gly Arg Ala  Ala Gln Arg
    2750                 2755                 2760

Leu Gln  Asp Thr Ser Ser Tyr  Ala Lys Ile Leu Thr  Cys Pro Lys
    2765                 2770                 2775

Thr Lys  Leu Lys Ile Ser Tyr  Lys Asp Ala Ile Asn  Arg Ser Met
    2780                 2785                 2790

Val Glu  Asp Ile Thr Gly Leu  Arg Leu Leu Glu Ala  Ala Ser Val
    2795                 2800                 2805

Ser Ser  Lys Gly Leu Pro Ser  Pro Tyr Asn Met Ser  Ser Ala Pro
    2810                 2815                 2820

Gly Ser  Arg Ser Gly Ser Arg  Ser Gly Ser Arg Ser  Gly Ser Arg
    2825                 2830                 2835

Ser Gly  Ser Arg Ser Gly Ser  Arg Arg Gly Ser Phe  Asp Ala Thr
    2840                 2845                 2850

Gly Asn  Ser Ser Tyr Ser Tyr  Ser Tyr Ser Phe Ser  Ser Ser Ser
    2855                 2860                 2865

Ile Gly  His
    2870
```

<210> SEQ ID NO 68
<211> LENGTH: 766
<212> TYPE: PRT
<213> ORGANISM: Homo sapiens

<400> SEQUENCE: 68

```
Met Lys Thr Pro Trp Lys Val Leu Leu Gly Leu Leu Gly Ala Ala Ala
1               5                   10                  15

Leu Val Thr Ile Ile Thr Val Pro Val Val Leu Leu Asn Lys Gly Thr
            20                  25                  30

Asp Asp Ala Thr Ala Asp Ser Arg Lys Thr Tyr Thr Leu Thr Asp Tyr
        35                  40                  45

Leu Lys Asn Thr Tyr Arg Leu Lys Leu Tyr Ser Leu Arg Trp Ile Ser
    50                  55                  60

Asp His Glu Tyr Leu Tyr Lys Gln Glu Asn Asn Ile Leu Val Phe Asn
65                  70                  75                  80

Ala Glu Tyr Gly Asn Ser Ser Val Phe Leu Glu Asn Ser Thr Phe Asp
                85                  90                  95

Glu Phe Gly His Ser Ile Asn Asp Tyr Ser Ile Ser Pro Asp Gly Gln
            100                 105                 110

Phe Ile Leu Leu Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
    130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175
```

```
Glu Pro Asn Leu Pro Ser Tyr Arg Ile Thr Trp Thr Gly Lys Glu Asp
            180                 185                 190

Ile Ile Tyr Asn Gly Ile Thr Asp Trp Val Tyr Glu Glu Glu Val Phe
        195                 200                 205

Ser Ala Tyr Ser Ala Leu Trp Trp Ser Pro Asn Gly Thr Phe Leu Ala
    210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
            260                 265                 270

Thr Asp Ser Leu Ser Ser Val Thr Asn Ala Thr Ser Ile Gln Ile Thr
        275                 280                 285

Ala Pro Ala Ser Met Leu Ile Gly Asp His Tyr Leu Cys Asp Val Thr
    290                 295                 300

Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
                325                 330                 335

Trp Asn Cys Leu Val Ala Arg Gln His Ile Glu Met Ser Thr Thr Gly
            340                 345                 350

Trp Val Gly Arg Phe Arg Pro Ser Glu Pro His Phe Thr Leu Asp Gly
        355                 360                 365

Asn Ser Phe Tyr Lys Ile Ile Ser Asn Glu Glu Gly Tyr Arg His Ile
    370                 375                 380

Cys Tyr Phe Gln Ile Asp Lys Lys Asp Cys Thr Phe Ile Thr Lys Gly
385                 390                 395                 400

Thr Trp Glu Val Ile Gly Ile Glu Ala Leu Thr Ser Asp Tyr Leu Tyr
                405                 410                 415

Tyr Ile Ser Asn Glu Tyr Lys Gly Met Pro Gly Gly Arg Asn Leu Tyr
            420                 425                 430

Lys Ile Gln Leu Ser Asp Tyr Thr Lys Val Thr Cys Leu Ser Cys Glu
        435                 440                 445

Leu Asn Pro Glu Arg Cys Gln Tyr Tyr Ser Val Ser Phe Ser Lys Glu
    450                 455                 460

Ala Lys Tyr Tyr Gln Leu Arg Cys Ser Gly Pro Gly Leu Pro Leu Tyr
465                 470                 475                 480

Thr Leu His Ser Ser Val Asn Asp Lys Gly Leu Arg Val Leu Glu Asp
                485                 490                 495

Asn Ser Ala Leu Asp Lys Met Leu Gln Asn Val Gln Met Pro Ser Lys
            500                 505                 510

Lys Leu Asp Phe Ile Ile Leu Asn Glu Thr Lys Phe Trp Tyr Gln Met
        515                 520                 525

Ile Leu Pro Pro His Phe Asp Lys Ser Lys Lys Tyr Pro Leu Leu Leu
    530                 535                 540

Asp Val Tyr Ala Gly Pro Cys Ser Gln Lys Ala Asp Thr Val Phe Arg
545                 550                 555                 560

Leu Asn Trp Ala Thr Tyr Leu Ala Ser Thr Glu Asn Ile Ile Val Ala
                565                 570                 575

Ser Phe Asp Gly Arg Gly Ser Gly Tyr Gln Gly Asp Lys Ile Met His
            580                 585                 590
```

Ala Ile Asn Arg Arg Leu Gly Thr Phe Glu Val Glu Asp Gln Ile Glu
595 600 605

Ala Ala Arg Gln Phe Ser Lys Met Gly Phe Val Asp Asn Lys Arg Ile
610 615 620

Ala Ile Trp Gly Trp Ser Tyr Gly Gly Tyr Val Thr Ser Met Val Leu
625 630 635 640

Gly Ser Gly Ser Gly Val Phe Lys Cys Gly Ile Ala Val Ala Pro Val
645 650 655

Ser Arg Trp Glu Tyr Tyr Asp Ser Val Tyr Thr Glu Arg Tyr Met Gly
660 665 670

Leu Pro Thr Pro Glu Asp Asn Leu Asp His Tyr Arg Asn Ser Thr Val
675 680 685

Met Ser Arg Ala Glu Asn Phe Lys Gln Val Glu Tyr Leu Leu Ile His
690 695 700

Gly Thr Ala Asp Asp Asn Val His Phe Gln Gln Ser Ala Gln Ile Ser
705 710 715 720

Lys Ala Leu Val Asp Val Gly Val Asp Phe Gln Ala Met Trp Tyr Thr
725 730 735

Asp Glu Asp His Gly Ile Ala Ser Ser Thr Ala His Gln His Ile Tyr
740 745 750

Thr His Met Ser His Phe Ile Lys Gln Cys Phe Ser Leu Pro
755 760 765

<210> SEQ ID NO 69
<211> LENGTH: 5088
<212> TYPE: PRT
<213> ORGANISM: Homo sapiens

<400> SEQUENCE: 69

Met Ser Gly His Thr Leu Pro Pro Leu Pro Val Pro Gly Thr Asn Ser
1 5 10 15

Thr Glu Gln Ala Ser Val Pro Arg Ala Met Ala Ala Thr Leu Gly Ala
20 25 30

Gly Thr Pro Pro Arg Pro Gln Ala Arg Ser Ile Ala Gly Val Tyr Val
35 40 45

Glu Ala Ser Gly Gln Ala Gln Ser Val Tyr Ala Ala Met Glu Gln Gly
50 55 60

Leu Leu Pro Ala Gly Leu Gly Gln Ala Leu Leu Glu Ala Gln Ala Ala
65 70 75 80

Thr Gly Gly Leu Val Asp Leu Ala Arg Gly Gln Leu Leu Pro Val Ser
85 90 95

Lys Ala Leu Gln Gln Gly Leu Val Gly Leu Glu Leu Lys Glu Lys Leu
100 105 110

Leu Ala Ala Glu Arg Ala Thr Thr Gly Tyr Pro Asp Pro Tyr Gly Gly
115 120 125

Glu Lys Leu Ala Leu Phe Gln Ala Ile Gly Lys Glu Val Val Asp Arg
130 135 140

Ala Leu Gly Gln Ser Trp Leu Glu Val Gln Leu Ala Thr Gly Gly Leu
145 150 155 160

Val Asp Pro Ala Gln Gly Val Leu Val Ala Pro Glu Pro Ala Cys His
165 170 175

Gln Gly Leu Leu Asp Arg Glu Thr Trp His Lys Leu Ser Glu Leu Glu
180 185 190

Pro Gly Thr Gly Asp Leu Arg Phe Leu Asp Pro Asn Thr Leu Glu Arg
195 200 205

```
Leu Thr Tyr His Gln Leu Leu Glu Arg Cys Val Arg Ala Pro Gly Ser
    210                 215                 220

Gly Leu Ala Leu Leu Pro Leu Lys Ile Thr Phe Arg Ser Met Gly Gly
225                 230                 235                 240

Ala Val Ser Ala Ala Glu Leu Leu Glu Val Gly Ile Leu Asp Glu Gln
                245                 250                 255

Ala Val Gln Gly Leu Arg Glu Gly Arg Leu Ala Ala Val Asp Val Ser
            260                 265                 270

Ala Arg Ala Glu Val Arg Arg Tyr Leu Glu Gly Thr Gly Ser Val Ala
        275                 280                 285

Gly Val Val Leu Leu Pro Glu Gly His Lys Lys Ser Phe Phe Gln Ala
    290                 295                 300

Ala Thr Glu His Leu Leu Pro Met Gly Thr Ala Leu Pro Leu Leu Glu
305                 310                 315                 320

Ala Gln Ala Ala Thr His Thr Leu Val Asp Pro Ile Thr Gly Gln Arg
                325                 330                 335

Leu Trp Val Asp Glu Ala Val Arg Ala Gly Leu Val Ser Pro Glu Leu
            340                 345                 350

His Glu Gln Leu Leu Val Ala Glu Gln Ala Val Thr Gly His His Asp
        355                 360                 365

Pro Phe Ser Gly Ser Gln Ile Pro Leu Phe Gln Ala Met Lys Lys Gly
    370                 375                 380

Leu Val Asp Arg Pro Leu Ala Leu Arg Leu Leu Asp Ala Gln Leu Ala
385                 390                 395                 400

Thr Gly Gly Leu Val Cys Pro Ala Arg Arg Leu Arg Leu Pro Leu Glu
                405                 410                 415

Ala Ala Leu Arg Cys Gly Cys Leu Asp Glu Asp Thr Gln Arg Gln Leu
            420                 425                 430

Ser Gln Ala Gly Ser Phe Ser Asp Gly Thr His Gly Gly Leu Arg Tyr
        435                 440                 445

Glu Gln Leu Leu Ala Leu Cys Val Thr Asp Pro Glu Thr Gly Leu Ala
    450                 455                 460

Phe Leu Pro Leu Ser Gly Gly Pro Arg Gly Gly Glu Pro Gln Gly Pro
465                 470                 475                 480

Pro Phe Ile Lys Tyr Ser Thr Arg Gln Ala Leu Ser Thr Ala Thr Ala
                485                 490                 495

Thr Val Ser Val Gly Lys Phe Arg Gly Arg Pro Val Ser Leu Trp Glu
            500                 505                 510

Leu Leu Phe Ser Glu Ala Ile Ser Ser Glu Gln Arg Ala Met Leu Ala
        515                 520                 525

Gln Gln Tyr Gln Glu Gly Thr Leu Ser Val Glu Lys Leu Ala Ala Lys
    530                 535                 540

Leu Ser Ala Thr Leu Glu Gln Ala Ala Ala Thr Ala Arg Val Thr Phe
545                 550                 555                 560

Ser Gly Leu Arg Asp Thr Val Thr Pro Gly Glu Leu Leu Lys Ala Glu
                565                 570                 575

Ile Ile Asp Gln Asp Leu Tyr Glu Arg Leu Glu His Gly Gln Ala Thr
            580                 585                 590

Ala Lys Asp Val Gly Ser Leu Ala Ser Val Gln Arg Tyr Leu Gln Gly
        595                 600                 605

Thr Gly Cys Ile Ala Gly Leu Leu Leu Pro Gly Ser Gln Glu Arg Leu
    610                 615                 620
```

-continued

```
Ser Ile Tyr Glu Ala Arg Cys Lys Gly Leu Leu Arg Pro Gly Thr Ala
625                 630                 635                 640

Leu Ile Leu Leu Glu Ala Gln Ala Ala Thr Gly Phe Ile Ile Asp Pro
                645                 650                 655

Lys Ala Asn Lys Gly His Ser Val Glu Glu Ala Leu Arg Ala Ala Val
            660                 665                 670

Ile Gly Pro Asp Val Phe Ala Lys Leu Leu Ser Ala Glu Arg Ala Val
        675                 680                 685

Thr Gly Tyr Thr Asp Pro Tyr Thr Gly Gln Gln Ile Ser Leu Phe Gln
    690                 695                 700

Ala Met Gln Lys Gly Leu Ile Val Arg Glu His Gly Ile Arg Leu Leu
705                 710                 715                 720

Glu Ala Gln Ile Ala Thr Gly Gly Val Ile Asp Pro Val His Ser His
                725                 730                 735

Arg Val Pro Val Asp Val Ala Tyr Arg Arg Gly Tyr Phe Asp Gln Met
            740                 745                 750

Leu Asn Leu Ile Leu Leu Asp Pro Ser Asp Asp Thr Lys Gly Phe Phe
        755                 760                 765

Asp Pro Asn Thr His Glu Asn Leu Thr Tyr Leu Gln Leu Leu Glu Arg
    770                 775                 780

Cys Val Arg Asp Pro Glu Thr Gly Leu Tyr Leu Leu Pro Leu Ser Ser
785                 790                 795                 800

Thr Gln Ser Pro Leu Val Asp Ser Ala Thr Gln Gln Ala Phe Gln Asn
                805                 810                 815

Leu Leu Leu Ser Val Lys Tyr Gly Arg Phe Gln Gly Gln Arg Val Ser
            820                 825                 830

Ala Trp Glu Leu Ile Asn Ser Glu Tyr Phe Ser Glu Gly Arg Arg Arg
        835                 840                 845

Gln Leu Leu Arg Arg Tyr Arg Gln Arg Glu Val Thr Leu Gly Gln Val
    850                 855                 860

Ala Lys Leu Leu Glu Ala Glu Thr Gln Arg Gln Ala Asp Ile Met Leu
865                 870                 875                 880

Pro Ala Leu Arg Ser Arg Val Thr Val His Gln Leu Leu Glu Ala Gly
                885                 890                 895

Ile Ile Asp Gln Gln Leu Leu Asp Gln Val Leu Ala Gly Thr Ile Ser
            900                 905                 910

Pro Glu Ala Leu Leu Leu Met Asp Gly Val Arg Arg Tyr Leu Cys Gly
        915                 920                 925

Leu Gly Ala Val Gly Gly Val Arg Leu Leu Pro Ser Gly Gln Arg Leu
    930                 935                 940

Ser Leu Tyr Gln Ala Met Arg Gln Lys Leu Leu Gly Pro Arg Val Ala
945                 950                 955                 960

Leu Ala Leu Leu Glu Ala Gln Ala Ala Thr Gly Thr Ile Met Asp Pro
                965                 970                 975

His Ser Pro Glu Ser Leu Ser Val Asp Glu Ala Val Arg Arg Gly Val
            980                 985                 990

Val Gly Pro Glu Leu Tyr Gly Arg  Leu Lys Arg Ala Glu  Gly Ala Ile
        995                 1000                 1005

Ala Gly  Phe Arg Asp Pro Phe  Ser Gly Lys Gln Val  Ser Val Phe
    1010                 1015                 1020

Gln Ala  Met Lys Lys Gly Leu  Ile Pro Trp Glu Gln  Ala Ala Arg
    1025                 1030                 1035

Leu Leu  Glu Ala Gln Val Ala  Thr Gly Gly Ile Ile  Asp Pro Thr
```

```
    1040                1045                1050

Ser His  His His Leu Pro Met  Pro Val Ala Ile Gln  Arg Gly Tyr
    1055                1060                1065

Val Asp  Gln Glu Met Glu Thr  Ala Leu Ser Ser Ser  Ser Glu Thr
    1070                1075                1080

Phe Pro  Thr Pro Asp Gly Gln  Gly Arg Thr Ser Tyr  Ala Gln Leu
    1085                1090                1095

Leu Glu  Glu Cys Pro Arg Asp  Glu Thr Ser Gly Leu  His Leu Leu
    1100                1105                1110

Pro Leu  Pro Glu Ser Ala Pro  Ala Leu Pro Thr Glu  Glu Gln Val
    1115                1120                1125

Gln Arg  Ser Leu Gln Ala Val  Pro Gly Ala Lys Asp  Gly Thr Ser
    1130                1135                1140

Leu Trp  Asp Leu Leu Ser Ser  Cys His Phe Thr Glu  Glu Gln Arg
    1145                1150                1155

Arg Gly  Leu Leu Glu Asp Val  Gln Glu Gly Arg Thr  Thr Val Pro
    1160                1165                1170

Gln Leu  Leu Ala Ser Val Gln  Arg Trp Val Gln Glu  Thr Lys Leu
    1175                1180                1185

Leu Ala  Gln Ala Arg Val Met  Val Pro Gly Pro Arg  Gly Glu Val
    1190                1195                1200

Pro Ala  Val Trp Leu Leu Asp  Ala Gly Ile Ile Thr  Gln Glu Thr
    1205                1210                1215

Leu Glu  Ala Leu Ala Gln Gly  Thr Gln Ser Pro Ala  Gln Val Ala
    1220                1225                1230

Glu Gln  Pro Ala Val Lys Ala  Cys Leu Trp Gly Thr  Gly Cys Val
    1235                1240                1245

Ala Gly  Val Leu Leu Gln Pro  Ser Gly Ala Lys Ala  Ser Ile Ala
    1250                1255                1260

Gln Ala  Val Arg Asp Gly Leu  Leu Pro Thr Gly Leu  Gly Gln Arg
    1265                1270                1275

Leu Leu  Glu Ala Gln Val Ala  Ser Gly Phe Leu Val  Asp Pro Leu
    1280                1285                1290

Asn Asn  Gln Arg Leu Ser Val  Glu Asp Ala Val Lys  Val Gly Leu
    1295                1300                1305

Val Gly  Arg Glu Leu Ser Glu  Gln Leu Gly Gln Ala  Glu Arg Ala
    1310                1315                1320

Ala Ala  Gly Tyr Pro Asp Pro  Tyr Ser Arg Ala Ser  Leu Ser Leu
    1325                1330                1335

Trp Gln  Ala Met Glu Lys Gly  Leu Val Pro Gln Asn  Glu Gly Leu
    1340                1345                1350

Pro Leu  Leu Gln Val Gln Leu  Ala Thr Gly Gly Val  Val Asp Pro
    1355                1360                1365

Val His  Gly Val His Leu Pro  Gln Ala Ala Ala Cys  Arg Leu Gly
    1370                1375                1380

Leu Leu  Asp Thr Gln Thr Ser  Gln Val Leu Thr Ala  Val Asp Lys
    1385                1390                1395

Asp Asn  Lys Phe Phe Phe Asp  Pro Ser Ala Arg Asp  Gln Val Thr
    1400                1405                1410

Tyr Gln  Gln Leu Arg Glu Arg  Cys Val Cys Asp Ser  Glu Thr Gly
    1415                1420                1425

Leu Leu  Leu Leu Pro Leu Pro  Ser Asp Thr Val Leu  Glu Val Asp
    1430                1435                1440
```

```
Asp His Thr Ala Val Ala Leu Arg Ala Met Lys Val Pro Val Ser
    1445                1450                1455

Thr Gly Arg Phe Lys Gly Cys Ser Val Ser Leu Trp Asp Leu Leu
    1460                1465                1470

Leu Ser Glu Tyr Val Gly Ala Asp Lys Arg Arg Glu Leu Val Ala
    1475                1480                1485

Leu Cys Arg Ser Gly Arg Ala Ala Ala Leu Arg Gln Val Val Ser
    1490                1495                1500

Ala Val Thr Thr Leu Val Glu Ala Ala Glu Arg Gln Pro Leu Gln
    1505                1510                1515

Ala Thr Phe Arg Gly Leu Arg Lys Gln Val Ser Ala Arg Asp Leu
    1520                1525                1530

Phe Arg Ala Gln Leu Ile Ser Arg Lys Thr Leu Asp Glu Leu Ser
    1535                1540                1545

Gln Gly Thr Thr Thr Val Lys Glu Val Ala Glu Met Asp Ser Val
    1550                1555                1560

Lys Arg Ser Leu Glu Gly Gly Asn Phe Ile Ala Gly Val Leu Ile
    1565                1570                1575

Gln Gly Thr Gln Glu Arg Met Ser Ile Pro Glu Ala Leu Arg Arg
    1580                1585                1590

His Ile Leu Arg Pro Gly Thr Ala Leu Val Leu Leu Glu Ala Gln
    1595                1600                1605

Ala Ala Thr Gly Phe Ile Ile Asp Pro Val Glu Asn Arg Lys Leu
    1610                1615                1620

Thr Val Glu Glu Ala Phe Lys Ala Gly Met Phe Gly Lys Glu Thr
    1625                1630                1635

Tyr Val Lys Leu Leu Ser Ala Glu Arg Ala Val Thr Gly Tyr Thr
    1640                1645                1650

Asp Pro Tyr Thr Gly Gln Gln Ile Ser Leu Phe Gln Ala Met Gln
    1655                1660                1665

Lys Asp Leu Ile Val Arg Glu His Gly Ile Arg Leu Leu Glu Ala
    1670                1675                1680

Gln Ile Ala Thr Gly Gly Ile Ile Asp Pro Val His Ser His Arg
    1685                1690                1695

Val Pro Val Asp Val Ala Tyr Arg Cys Gly Tyr Phe Asp Glu Glu
    1700                1705                1710

Met Asn Arg Ile Leu Ala Asp Pro Ser Asp Asp Thr Lys Gly Phe
    1715                1720                1725

Phe Asp Pro Asn Thr His Glu Asn Leu Thr Tyr Leu Gln Leu Leu
    1730                1735                1740

Glu Arg Cys Val Glu Asp Pro Glu Thr Gly Leu Tyr Leu Leu Gln
    1745                1750                1755

Ile Ile Lys Lys Gly Glu Asn Tyr Val Tyr Ile Asn Glu Ala Thr
    1760                1765                1770

Arg His Val Leu Gln Ser Arg Thr Ala Lys Met Arg Val Gly Arg
    1775                1780                1785

Phe Ala Asp Gln Val Val Ser Phe Trp Asp Leu Leu Ser Ser Pro
    1790                1795                1800

Tyr Phe Thr Glu Asp Arg Lys Arg Glu Leu Ile Gln Glu Tyr Gly
    1805                1810                1815

Ala Gln Ser Gly Gly Leu Glu Lys Leu Leu Glu Ile Ile Thr Thr
    1820                1825                1830
```

```
Thr Ile  Glu Glu Thr Glu Thr  Gln Asn Gln Gly Ile  Lys Val Ala
    1835                 1840                 1845

Ala Ile  Arg Gly Glu Val Thr  Ala Ala Asp Leu Phe  Asn Ser Arg
    1850                 1855                 1860

Val Ile  Asp Gln Lys Thr Leu  His Thr Leu Arg Val  Gly Arg Thr
    1865                 1870                 1875

Gly Gly  Gln Ala Leu Ser Thr  Leu Glu Cys Val Lys  Pro Tyr Leu
    1880                 1885                 1890

Glu Gly  Ser Gly Cys Ile Ala  Gly Val Thr Val Pro  Ser Thr Arg
    1895                 1900                 1905

Glu Val  Met Ser Leu His Glu  Ala Ser Arg Lys Glu  Leu Ile Pro
    1910                 1915                 1920

Ala Ala  Phe Ala Thr Trp Leu  Leu Glu Ala Gln Ala  Ala Thr Gly
    1925                 1930                 1935

Phe Leu  Leu Asp Pro Cys Thr  Arg Gln Lys Leu Ser  Val Asp Glu
    1940                 1945                 1950

Ala Val  Asp Val Gly Leu Val  Asn Glu Glu Leu Arg  Glu Arg Leu
    1955                 1960                 1965

Leu Lys  Ala Glu Arg Ala Ala  Thr Gly Tyr Arg Asp  Pro Ala Thr
    1970                 1975                 1980

Gly Asp  Thr Ile Pro Leu Phe  Gln Ala Met Gln Lys  Gln Leu Ile
    1985                 1990                 1995

Glu Lys  Ala Glu Ala Leu Arg  Leu Leu Glu Val Gln  Val Ala Thr
    2000                 2005                 2010

Gly Gly  Val Ile Asp Pro Gln  His His His Arg Leu  Pro Leu Glu
    2015                 2020                 2025

Thr Ala  Tyr Arg Arg Gly Cys  Leu His Lys Asp Ile  Tyr Ala Leu
    2030                 2035                 2040

Ile Ser  Asp Gln Lys His Met  Arg Lys Arg Phe Val  Asp Pro Asn
    2045                 2050                 2055

Thr Gln  Glu Lys Val Ser Tyr  Arg Glu Leu Gln Glu  Arg Cys Arg
    2060                 2065                 2070

Pro Gln  Glu Asp Thr Gly Trp  Leu Leu Phe Pro Val  Asn Lys Ala
    2075                 2080                 2085

Ala Arg  Asp Ser Glu His Ile  Asp Asp Glu Thr Arg  Arg Ala Leu
    2090                 2095                 2100

Glu Ala  Glu Gln Val Glu Ile  Thr Val Gly Arg Phe  Arg Gly Gln
    2105                 2110                 2115

Lys Pro  Thr Leu Trp Ala Leu  Leu Asn Ser Glu Tyr  Val Thr Glu
    2120                 2125                 2130

Glu Lys  Lys Leu Gln Leu Val  Arg Met Tyr Arg Thr  His Thr Arg
    2135                 2140                 2145

Arg Ala  Leu Gln Thr Val Ala  Gln Leu Ile Leu Glu  Leu Ile Glu
    2150                 2155                 2160

Lys Gln  Glu Thr Ser Asn Lys  His Leu Trp Phe Gln  Gly Ile Arg
    2165                 2170                 2175

Arg Gln  Ile Thr Ala Ser Glu  Leu Leu Ser Ser Ala  Ile Ile Thr
    2180                 2185                 2190

Glu Glu  Met Leu Gln Asp Leu  Glu Thr Gly Arg Ser  Thr Thr Gln
    2195                 2200                 2205

Glu Leu  Met Glu Asp Asp Arg  Val Lys Arg Tyr Leu  Glu Gly Thr
    2210                 2215                 2220

Ser Cys  Ile Ala Gly Val Leu  Val Pro Ala Lys Asp  Gln Pro Gly
```

```
    2225                2230                2235

Arg Gln  Glu Lys Met Ser Ile  Tyr Gln Ala Met Trp  Lys Gly Val
    2240                2245                2250

Leu Arg  Pro Gly Thr Ala Leu  Val Leu Leu Glu Ala  Gln Ala Ala
    2255                2260                2265

Thr Gly  Phe Val Ile Asp Pro  Val Arg Asn Leu Arg  Leu Ser Val
    2270                2275                2280

Glu Glu  Ala Val Ala Ala Gly  Val Val Gly Gly Glu  Ile Gln Glu
    2285                2290                2295

Lys Leu  Leu Ser Ala Glu Arg  Ala Val Thr Gly Tyr  Thr Asp Pro
    2300                2305                2310

Tyr Thr  Gly Gln Gln Ile Ser  Leu Phe Gln Ala Met  Gln Lys Asp
    2315                2320                2325

Leu Ile  Val Arg Glu His Gly  Ile Arg Leu Leu Glu  Ala Gln Ile
    2330                2335                2340

Ala Thr  Gly Gly Val Ile Asp  Pro Val His Ser His  Arg Val Pro
    2345                2350                2355

Val Asp  Val Ala Tyr Arg Arg  Gly Tyr Phe Asp Glu  Glu Met Asn
    2360                2365                2370

Arg Val  Leu Ala Asp Pro Ser  Asp Asp Thr Lys Gly  Phe Phe Asp
    2375                2380                2385

Pro Asn  Thr His Glu Asn Leu  Thr Tyr Val Gln Leu  Leu Arg Arg
    2390                2395                2400

Cys Val  Pro Asp Pro Asp Thr  Gly Leu Tyr Met Leu  Gln Leu Ala
    2405                2410                2415

Gly Arg  Gly Ser Ala Val His  Gln Leu Ser Glu Glu  Leu Arg Cys
    2420                2425                2430

Ala Leu  Arg Asp Ala Arg Val  Thr Pro Gly Ser Gly  Ala Leu Gln
    2435                2440                2445

Gly Gln  Ser Val Ser Val Trp  Glu Leu Leu Phe Tyr  Arg Glu Val
    2450                2455                2460

Ser Glu  Asp Arg Arg Gln Asp  Leu Leu Ser Arg Tyr  Arg Ala Gly
    2465                2470                2475

Thr Leu  Thr Val Glu Glu Leu  Gly Ala Thr Leu Thr  Ser Leu Leu
    2480                2485                2490

Ala Gln  Ala Gln Ala Gln Ala  Arg Ala Glu Ala Glu  Ala Gly Ser
    2495                2500                2505

Pro Arg  Pro Asp Pro Arg Glu  Ala Leu Arg Ala Ala  Thr Met Glu
    2510                2515                2520

Val Lys  Val Gly Arg Leu Arg  Gly Arg Ala Val Pro  Val Trp Asp
    2525                2530                2535

Val Leu  Ala Ser Gly Tyr Val  Ser Arg Ala Ala Arg  Glu Glu Leu
    2540                2545                2550

Leu Ala  Glu Phe Gly Ser Gly  Thr Leu Asp Leu Pro  Ala Leu Thr
    2555                2560                2565

Arg Arg  Leu Thr Ala Ile Ile  Glu Glu Ala Glu Glu  Ala Pro Gly
    2570                2575                2580

Ala Arg  Pro Gln Leu Gln Asp  Ala Trp Arg Gly Pro  Arg Glu Pro
    2585                2590                2595

Gly Pro  Ala Gly Arg Gly Asp  Gly Asp Ser Gly Arg  Ser Gln Arg
    2600                2605                2610

Glu Gly  Gln Gly Glu Gly Glu  Thr Gln Glu Ala Ala  Ala Ala Ala
    2615                2620                2625
```

```
Ala Ala Ala Ala Ala Arg Arg Gln Glu Gln Thr Leu Arg Asp Ala
    2630                2635                2640

Thr Met Glu Val Gln Arg Gly Gln Phe Gln Gly Arg Pro Val Ser
    2645                2650                2655

Val Trp Asp Val Leu Phe Ser Ser Tyr Leu Ser Glu Ala Arg Arg
    2660                2665                2670

Asp Glu Leu Leu Ala Gln His Ala Ala Gly Ala Leu Gly Leu Pro
    2675                2680                2685

Asp Leu Val Ala Val Leu Thr Arg Val Ile Glu Glu Thr Glu Glu
    2690                2695                2700

Arg Leu Ser Lys Val Ser Phe Arg Gly Leu Arg Arg Gln Val Ser
    2705                2710                2715

Ala Ser Glu Leu His Thr Ser Gly Ile Leu Gly Pro Glu Thr Leu
    2720                2725                2730

Arg Asp Leu Ala Gln Gly Thr Lys Thr Leu Gln Glu Val Thr Glu
    2735                2740                2745

Met Asp Ser Val Lys Arg Tyr Leu Glu Gly Thr Ser Cys Ile Ala
    2750                2755                2760

Gly Val Leu Val Pro Ala Lys Asp Gln Pro Gly Arg Gln Glu Lys
    2765                2770                2775

Met Ser Ile Tyr Gln Ala Met Trp Lys Gly Val Leu Arg Pro Gly
    2780                2785                2790

Thr Ala Leu Val Leu Leu Glu Ala Gln Ala Ala Thr Gly Phe Val
    2795                2800                2805

Ile Asp Pro Val Arg Asn Leu Arg Leu Ser Val Glu Glu Ala Val
    2810                2815                2820

Ala Ala Gly Val Val Gly Gly Glu Ile Gln Glu Lys Leu Leu Ser
    2825                2830                2835

Ala Glu Arg Ala Val Thr Gly Tyr Thr Asp Pro Tyr Thr Gly Gln
    2840                2845                2850

Gln Ile Ser Leu Phe Gln Ala Met Gln Lys Asp Leu Ile Val Arg
    2855                2860                2865

Glu His Gly Ile Arg Leu Leu Glu Ala Gln Ile Ala Thr Gly Gly
    2870                2875                2880

Val Ile Asp Pro Val His Ser His Arg Val Pro Val Asp Val Ala
    2885                2890                2895

Tyr Gln Arg Gly Tyr Phe Asp Glu Glu Met Asn Arg Val Leu Ala
    2900                2905                2910

Asp Pro Ser Asp Asp Thr Lys Gly Phe Phe Asp Pro Asn Thr His
    2915                2920                2925

Glu Asn Leu Thr Tyr Val Gln Leu Leu Arg Arg Cys Val Pro Asp
    2930                2935                2940

Pro Asp Thr Gly Leu Tyr Met Leu Gln Leu Ala Gly Arg Gly Ser
    2945                2950                2955

Ala Val His Gln Leu Ser Glu Glu Leu Arg Cys Ala Leu Arg Asp
    2960                2965                2970

Ala Arg Val Thr Pro Gly Ser Gly Ala Leu Gln Gly Gln Ser Val
    2975                2980                2985

Ser Val Trp Glu Leu Leu Phe Tyr Arg Glu Val Ser Glu Asp Arg
    2990                2995                3000

Arg Gln Asp Leu Leu Ser Arg Tyr Arg Ala Gly Thr Leu Thr Val
    3005                3010                3015
```

-continued

```
Glu Glu  Leu Gly Ala Thr Leu  Thr Ser Leu Leu Ala  Gln Ala Gln
    3020                 3025                 3030

Ala Gln  Ala Arg Ala Glu Ala  Glu Ala Gly Ser Pro  Arg Pro Asp
    3035                 3040                 3045

Pro Arg  Glu Ala Leu Arg Ala  Ala Thr Met Glu Val  Lys Val Gly
    3050                 3055                 3060

Arg Leu  Arg Gly Arg Ala Val  Pro Val Trp Asp Val  Leu Ala Ser
    3065                 3070                 3075

Gly Tyr  Val Ser Arg Ala Ala  Arg Glu Glu Leu Leu  Ala Glu Phe
    3080                 3085                 3090

Gly Ser  Gly Thr Leu Asp Leu  Pro Ala Leu Thr Arg  Arg Leu Thr
    3095                 3100                 3105

Ala Ile  Ile Glu Glu Ala Glu  Glu Ala Pro Gly Ala  Arg Pro Gln
    3110                 3115                 3120

Leu Gln  Asp Ala Trp Arg Gly  Pro Arg Glu Pro Gly  Pro Ala Gly
    3125                 3130                 3135

Arg Gly  Asp Gly Asp Ser Gly  Arg Ser Gln Arg Glu  Gly Gln Gly
    3140                 3145                 3150

Glu Gly  Glu Thr Gln Glu Ala  Ala Ala Ala Ala Arg  Arg Gln Glu
    3155                 3160                 3165

Gln Thr  Leu Arg Asp Ala Thr  Met Glu Val Gln Arg  Gly Gln Phe
    3170                 3175                 3180

Gln Gly  Arg Pro Val Ser Val  Trp Asp Val Leu Phe  Ser Ser Tyr
    3185                 3190                 3195

Leu Ser  Glu Ala Arg Arg Asp  Glu Leu Leu Ala Gln  His Ala Ala
    3200                 3205                 3210

Gly Ala  Leu Gly Leu Pro Asp  Leu Val Ala Val Leu  Thr Arg Val
    3215                 3220                 3225

Ile Glu  Glu Thr Glu Glu Arg  Leu Ser Lys Val Ser  Phe Arg Gly
    3230                 3235                 3240

Leu Arg  Cys Gln Val Ser Ala  Ser Glu Leu His Thr  Ser Gly Ile
    3245                 3250                 3255

Leu Gly  Pro Glu Thr Leu Arg  Asp Leu Ala Gln Gly  Thr Lys Thr
    3260                 3265                 3270

Leu Gln  Glu Val Thr Glu Met  Asp Ser Val Lys Arg  Tyr Leu Glu
    3275                 3280                 3285

Gly Thr  Ser Cys Ile Ala Gly  Val Leu Val Pro Ala  Lys Asp Gln
    3290                 3295                 3300

Pro Gly  Arg Gln Glu Lys Met  Ser Ile Tyr Gln Ala  Met Trp Lys
    3305                 3310                 3315

Gly Val  Leu Arg Pro Gly Thr  Ala Leu Val Leu Leu  Glu Ala Gln
    3320                 3325                 3330

Ala Ala  Thr Gly Phe Val Ile  Asp Pro Val Arg Asn  Leu Arg Leu
    3335                 3340                 3345

Ser Val  Glu Glu Ala Val Ala  Ala Gly Val Val Gly  Gly Glu Ile
    3350                 3355                 3360

Gln Glu  Lys Leu Leu Ser Ala  Glu Arg Ala Val Thr  Gly Tyr Thr
    3365                 3370                 3375

Asp Pro  Tyr Thr Gly Gln Gln  Ile Ser Leu Phe Gln  Ala Met Gln
    3380                 3385                 3390

Lys Asp  Leu Ile Val Arg Glu  His Gly Ile Arg Leu  Leu Glu Ala
    3395                 3400                 3405

Gln Ile  Ala Thr Gly Gly Val  Ile Asp Pro Val His  Ser His Arg
```

```
    3410                3415                3420

Val Pro Val Asp Val Ala Tyr Arg Arg Gly Tyr Phe Asp Glu Glu
    3425                3430                3435

Met Asn Arg Val Leu Ala Asp Pro Ser Asp Asp Thr Lys Gly Phe
    3440                3445                3450

Phe Asp Pro Asn Thr His Glu Asn Leu Thr Tyr Val Gln Leu Leu
    3455                3460                3465

Arg Arg Cys Val Pro Asp Pro Asp Thr Gly Leu Tyr Met Leu Gln
    3470                3475                3480

Leu Ala Gly Arg Gly Ser Ala Val His Gln Leu Ser Glu Glu Leu
    3485                3490                3495

Arg Cys Ala Leu Arg Asp Ala Arg Val Thr Pro Gly Ser Gly Ala
    3500                3505                3510

Leu Gln Gly Gln Ser Val Ser Val Trp Glu Leu Leu Phe Tyr Arg
    3515                3520                3525

Glu Val Ser Glu Asp Arg Arg Gln Asp Leu Leu Ser Arg Tyr Arg
    3530                3535                3540

Ala Gly Thr Leu Thr Val Glu Glu Leu Gly Ala Thr Leu Thr Ser
    3545                3550                3555

Leu Leu Ala Gln Ala Gln Ala Gln Ala Arg Ala Glu Ala Glu Ala
    3560                3565                3570

Gly Ser Pro Arg Pro Asp Pro Arg Glu Ala Leu Arg Ala Ala Thr
    3575                3580                3585

Met Glu Val Lys Val Gly Arg Leu Arg Gly Arg Ala Val Pro Val
    3590                3595                3600

Trp Asp Val Leu Ala Ser Gly Tyr Val Ser Arg Ala Ala Arg Glu
    3605                3610                3615

Glu Leu Leu Ala Glu Phe Gly Ser Gly Thr Leu Asp Leu Pro Ala
    3620                3625                3630

Leu Thr Arg Arg Leu Thr Ala Ile Ile Glu Glu Ala Glu Glu Ala
    3635                3640                3645

Pro Gly Ala Arg Pro Gln Leu Gln Asp Ala Trp Arg Gly Pro Arg
    3650                3655                3660

Glu Pro Gly Pro Ala Gly Arg Gly Asp Gly Asp Ser Gly Arg Ser
    3665                3670                3675

Gln Arg Glu Gly Gln Gly Glu Gly Glu Thr Gln Glu Ala Ala Ala
    3680                3685                3690

Ala Thr Ala Ala Ala Arg Arg Gln Glu Gln Thr Leu Arg Asp Ala
    3695                3700                3705

Thr Met Glu Val Gln Arg Gly Gln Phe Gln Gly Arg Pro Val Ser
    3710                3715                3720

Val Trp Asp Val Leu Phe Ser Ser Tyr Leu Ser Glu Ala Arg Arg
    3725                3730                3735

Asp Glu Leu Leu Ala Gln His Ala Ala Gly Ala Leu Gly Leu Pro
    3740                3745                3750

Asp Leu Val Ala Val Leu Thr Arg Val Ile Glu Glu Thr Glu Glu
    3755                3760                3765

Arg Leu Ser Lys Val Ser Phe Arg Gly Leu Arg Arg Gln Val Ser
    3770                3775                3780

Ala Ser Glu Leu His Thr Ser Gly Ile Leu Gly Pro Glu Thr Leu
    3785                3790                3795

Arg Asp Leu Ala Gln Gly Thr Lys Thr Leu Gln Glu Val Thr Glu
    3800                3805                3810
```

```
Met Asp Ser Val Lys Arg Tyr Leu Glu Gly Thr Ser Cys Ile Ala
    3815                3820                3825

Gly Val Leu Val Pro Ala Lys Asp Gln Pro Gly Arg Gln Glu Lys
    3830                3835                3840

Met Ser Ile Tyr Gln Ala Met Trp Lys Gly Val Leu Arg Pro Gly
    3845                3850                3855

Thr Ala Leu Val Leu Leu Glu Ala Gln Ala Ala Thr Gly Phe Val
    3860                3865                3870

Ile Asp Pro Val Arg Asn Leu Arg Leu Ser Val Glu Glu Ala Val
    3875                3880                3885

Ala Ala Gly Val Val Gly Gly Glu Ile Gln Glu Lys Leu Leu Ser
    3890                3895                3900

Ala Glu Arg Ala Val Thr Gly Tyr Thr Asp Pro Tyr Thr Gly Gln
    3905                3910                3915

Gln Ile Ser Leu Phe Gln Ala Met Gln Lys Asp Leu Ile Val Arg
    3920                3925                3930

Glu His Gly Ile Arg Leu Leu Glu Ala Gln Ile Ala Thr Gly Gly
    3935                3940                3945

Val Ile Asp Pro Val His Ser His Arg Val Pro Val Asp Val Ala
    3950                3955                3960

Tyr Arg Arg Gly Tyr Phe Asp Glu Glu Met Asn Arg Val Leu Ala
    3965                3970                3975

Asp Pro Ser Asp Asp Thr Lys Gly Phe Phe Asp Pro Asn Thr His
    3980                3985                3990

Glu Asn Leu Thr Tyr Val Gln Leu Leu Arg Arg Cys Val Pro Asp
    3995                4000                4005

Pro Asp Thr Gly Leu Tyr Met Leu Gln Leu Ala Gly Arg Gly Ser
    4010                4015                4020

Ala Val His Gln Leu Ser Glu Glu Leu Arg Cys Ala Leu Arg Asp
    4025                4030                4035

Ala Arg Val Thr Pro Gly Ser Gly Ala Leu Gln Gly Gln Ser Val
    4040                4045                4050

Ser Val Trp Glu Leu Leu Phe Tyr Arg Glu Val Ser Glu Asp Arg
    4055                4060                4065

Arg Gln Asp Leu Leu Ser Arg Tyr Arg Ala Gly Thr Leu Thr Val
    4070                4075                4080

Glu Glu Leu Gly Ala Thr Leu Thr Ser Leu Leu Ala Gln Ala Gln
    4085                4090                4095

Ala Gln Ala Arg Ala Glu Ala Glu Ala Gly Ser Pro Arg Pro Asp
    4100                4105                4110

Pro Arg Glu Ala Leu Arg Ala Ala Thr Met Glu Val Lys Val Gly
    4115                4120                4125

Arg Leu Arg Gly Arg Ala Val Pro Val Trp Asp Val Leu Ala Ser
    4130                4135                4140

Gly Tyr Val Ser Arg Ala Ala Arg Glu Glu Leu Leu Ala Glu Phe
    4145                4150                4155

Gly Ser Gly Thr Leu Asp Leu Pro Ala Leu Thr Arg Arg Leu Thr
    4160                4165                4170

Ala Ile Ile Glu Glu Ala Glu Glu Ala Pro Gly Ala Arg Pro Gln
    4175                4180                4185

Leu Gln Asp Ala Trp Arg Gly Pro Arg Glu Pro Gly Pro Ala Gly
    4190                4195                4200
```

Arg Gly Asp Gly Asp Ser Gly Arg Ser Gln Arg Glu Gly Gln Gly
4205 4210 4215

Glu Gly Glu Thr Gln Glu Ala Ala Ala Ala Thr Ala Ala Ala Arg
4220 4225 4230

Arg Gln Glu Gln Thr Leu Arg Asp Ala Thr Met Glu Val Gln Arg
4235 4240 4245

Gly Gln Phe Gln Gly Arg Pro Val Ser Val Trp Asp Val Leu Phe
4250 4255 4260

Ser Ser Tyr Leu Ser Glu Ala Arg Arg Asp Glu Leu Leu Ala Gln
4265 4270 4275

His Ala Ala Gly Ala Leu Gly Leu Pro Asp Leu Val Ala Val Leu
4280 4285 4290

Thr Arg Val Ile Glu Glu Thr Glu Glu Arg Leu Ser Lys Val Ser
4295 4300 4305

Phe Arg Gly Leu Arg Arg Gln Val Ser Ala Ser Glu Leu His Thr
4310 4315 4320

Ser Gly Ile Leu Gly Pro Glu Thr Leu Arg Asp Leu Ala Gln Gly
4325 4330 4335

Thr Lys Thr Leu Gln Glu Val Thr Glu Met Asp Ser Val Lys Arg
4340 4345 4350

Tyr Leu Glu Gly Thr Ser Cys Ile Ala Gly Val Leu Val Pro Ala
4355 4360 4365

Lys Asp Gln Pro Gly His Gln Glu Lys Met Ser Ile Tyr Gln Ala
4370 4375 4380

Met Trp Lys Gly Val Leu Arg Pro Gly Thr Ala Leu Val Leu Leu
4385 4390 4395

Glu Ala Gln Ala Ala Thr Gly Phe Val Ile Asp Pro Val Arg Asn
4400 4405 4410

Leu Arg Leu Ser Val Glu Glu Ala Val Ala Ala Gly Val Val Gly
4415 4420 4425

Gly Glu Ile Gln Glu Lys Leu Leu Ser Ala Glu Arg Ala Val Thr
4430 4435 4440

Gly Tyr Thr Asp Pro Tyr Thr Gly Gln Gln Ile Ser Leu Phe Gln
4445 4450 4455

Ala Met Gln Lys Asp Leu Ile Val Arg Glu His Gly Ile Arg Leu
4460 4465 4470

Leu Glu Ala Gln Ile Ala Thr Gly Gly Val Ile Asp Pro Val His
4475 4480 4485

Ser His Arg Val Pro Val Asp Val Ala Tyr Arg Arg Gly Tyr Phe
4490 4495 4500

Asp Glu Glu Met Asn Arg Val Leu Ala His Pro Ser Asp Asp Thr
4505 4510 4515

Lys Gly Phe Phe Asp Pro Asn Thr His Glu Asn Leu Thr Tyr Val
4520 4525 4530

Gln Leu Leu Arg Arg Cys Val Pro Asp Pro Asp Thr Gly Leu Tyr
4535 4540 4545

Met Leu Gln Leu Ala Gly Arg Gly Ser Ala Val His Gln Leu Ser
4550 4555 4560

Glu Glu Leu Arg Cys Ala Leu Arg Asp Ala Arg Val Met Pro Gly
4565 4570 4575

Ser Gly Ala Leu Gln Gly Gln Ser Val Ser Val Trp Glu Leu Leu
4580 4585 4590

Phe Tyr Arg Glu Val Ser Glu Asp Arg Arg Gln Asp Leu Leu Ser

```
    4595                4600                4605

Arg Tyr  Arg Ala Gly Thr Leu  Thr Val Glu Glu Leu  Gly Ala Thr
    4610                4615                4620

Leu Thr  Ser Leu Leu Ala Gln  Ala Gln Ala Gln Ala  Arg Ala Glu
    4625                4630                4635

Ala Glu  Ala Glu Ala Gly Ser  Pro Arg Pro Asp Pro  Arg Glu Ala
    4640                4645                4650

Leu Arg  Ala Ala Thr Met Glu  Val Lys Val Gly Arg  Leu Arg Gly
    4655                4660                4665

Arg Ala  Val Pro Val Trp Asp  Val Leu Ala Ser Gly  Tyr Val Ser
    4670                4675                4680

Gly Ala  Ala Arg Glu Glu Leu  Leu Ala Glu Phe Gly  Ser Gly Thr
    4685                4690                4695

Leu Asp  Leu Pro Ala Leu Thr  Arg Arg Leu Thr Ala  Ile Ile Glu
    4700                4705                4710

Glu Ala  Glu Glu Ala Pro Gly  Ala Arg Pro Gln Leu  Gln Asp Ala
    4715                4720                4725

Trp Arg  Gly Pro Arg Glu Pro  Gly Pro Ala Gly Arg  Gly Asp Gly
    4730                4735                4740

Asp Ser  Gly Arg Ser Gln Arg  Glu Gly Gln Gly Glu  Gly Glu Thr
    4745                4750                4755

Gln Glu  Ala Ala Ala Ala Ala  Arg Arg Gln Glu Gln  Thr Leu Arg
    4760                4765                4770

Asp Ala  Thr Met Glu Val Gln  Arg Gly Gln Phe Gln  Gly Arg Pro
    4775                4780                4785

Val Ser  Val Trp Asp Val Leu  Phe Ser Ser Tyr Leu  Ser Glu Ala
    4790                4795                4800

His Arg  Asp Glu Leu Leu Ala  Gln His Ala Ala Gly  Ala Leu Gly
    4805                4810                4815

Leu Pro  Asp Leu Val Ala Val  Leu Thr Arg Val Ile  Glu Glu Thr
    4820                4825                4830

Glu Glu  Arg Leu Ser Lys Val  Ser Phe Arg Gly Leu  Arg Arg Gln
    4835                4840                4845

Val Ser  Ala Ser Glu Leu His  Thr Ser Gly Ile Leu  Gly Pro Glu
    4850                4855                4860

Thr Leu  Arg Asp Leu Ala Gln  Gly Thr Lys Thr Leu  Gln Glu Val
    4865                4870                4875

Thr Glu  Met Asp Ser Val Lys  Arg Tyr Leu Glu Gly  Thr Ser Cys
    4880                4885                4890

Ile Ala  Gly Val Leu Val Pro  Ala Lys Asp Gln Pro  Gly Arg Gln
    4895                4900                4905

Glu Lys  Met Ser Ile Tyr Gln  Ala Met Trp Lys Gly  Val Leu Arg
    4910                4915                4920

Pro Gly  Thr Ala Leu Val Leu  Leu Glu Ala Gln Ala  Ala Thr Gly
    4925                4930                4935

Phe Val  Ile Asp Pro Val Arg  Asn Leu Arg Leu Ser  Val Glu Glu
    4940                4945                4950

Ala Val  Ala Ala Gly Val Val  Gly Gly Glu Ile Gln  Glu Lys Leu
    4955                4960                4965

Leu Ser  Ala Glu Arg Ala Val  Thr Gly Tyr Thr Asp  Pro Tyr Thr
    4970                4975                4980

Gly Gln  Gln Ile Ser Leu Phe  Gln Ala Met Gln Lys  Asp Leu Ile
    4985                4990                4995
```

```
Val Arg  Glu His Gly Ile Arg  Leu Leu Glu Ala Gln  Ile Ala Thr
    5000                 5005                 5010

Gly Gly  Val Ile Asp Pro Val  His Ser His Arg Val  Pro Val Asp
    5015                 5020                 5025

Val Ala  Tyr Arg Arg Gly Tyr  Phe Asp Glu Glu Met  Asn Arg Val
    5030                 5035                 5040

Leu Ala  Asp Pro Ser Asp Asp  Thr Lys Gly Phe Phe  Asp Pro Asn
    5045                 5050                 5055

Thr His  Glu Asn Leu Thr Tyr  Leu Gln Leu Leu Gln  Arg Ala Thr
    5060                 5065                 5070

Leu Asp  Pro Glu Thr Gly Leu  Leu Phe Leu Ser Leu  Ser Leu Gln
    5075                 5080                 5085
```

<210> SEQ ID NO 70
<211> LENGTH: 586
<212> TYPE: PRT
<213> ORGANISM: Homo sapiens

<400> SEQUENCE: 70

```
Met Pro Lys Pro Ile Asn Val Arg Val Thr Thr Met Asp Ala Glu Leu
1               5                   10                  15

Glu Phe Ala Ile Gln Pro Asn Thr Thr Gly Lys Gln Leu Phe Asp Gln
            20                  25                  30

Val Val Lys Thr Ile Gly Leu Arg Glu Val Trp Tyr Phe Gly Leu His
        35                  40                  45

Tyr Val Asp Asn Lys Gly Phe Pro Thr Trp Leu Lys Leu Asp Lys Lys
    50                  55                  60

Val Ser Ala Gln Glu Val Arg Lys Glu Asn Pro Leu Gln Phe Lys Phe
65                  70                  75                  80

Arg Ala Lys Phe Tyr Pro Glu Asp Val Ala Glu Glu Leu Ile Gln Asp
                85                  90                  95

Ile Thr Gln Lys Leu Phe Phe Leu Gln Val Lys Glu Gly Ile Leu Ser
            100                 105                 110

Asp Glu Ile Tyr Cys Pro Pro Glu Thr Ala Val Leu Leu Gly Ser Tyr
        115                 120                 125

Ala Val Gln Ala Lys Phe Gly Asp Tyr Asn Lys Glu Val His Lys Ser
    130                 135                 140

Gly Tyr Leu Ser Ser Glu Arg Leu Ile Pro Gln Arg Val Met Asp Gln
145                 150                 155                 160

His Lys Leu Thr Arg Asp Gln Trp Glu Asp Arg Ile Gln Val Trp His
                165                 170                 175

Ala Glu His Arg Gly Met Leu Lys Asp Asn Ala Met Leu Glu Tyr Leu
            180                 185                 190

Lys Ile Ala Gln Asp Leu Glu Met Tyr Gly Ile Asn Tyr Phe Glu Ile
        195                 200                 205

Lys Asn Lys Lys Gly Thr Asp Leu Trp Leu Gly Val Asp Ala Leu Gly
    210                 215                 220

Leu Asn Ile Tyr Glu Lys Asp Asp Lys Leu Thr Pro Lys Ile Gly Phe
225                 230                 235                 240

Pro Trp Ser Glu Ile Arg Asn Ile Ser Phe Asn Asp Lys Lys Phe Val
                245                 250                 255

Ile Lys Pro Ile Asp Lys Lys Ala Pro Asp Phe Val Phe Tyr Ala Pro
            260                 265                 270

Arg Leu Arg Ile Asn Lys Arg Ile Leu Gln Leu Cys Met Gly Asn His
```

```
        275                 280                 285

Glu Leu Tyr Met Arg Arg Arg Lys Pro Asp Thr Ile Glu Val Gln Gln
    290                 295                 300

Met Lys Ala Gln Ala Arg Glu Glu Lys His Gln Lys Gln Leu Glu Arg
305                 310                 315                 320

Gln Gln Leu Glu Thr Glu Lys Lys Arg Arg Glu Thr Val Glu Arg Glu
                325                 330                 335

Lys Glu Gln Met Met Arg Glu Lys Glu Glu Leu Met Leu Arg Leu Gln
            340                 345                 350

Asp Tyr Glu Glu Lys Thr Lys Lys Ala Glu Arg Glu Leu Ser Glu Gln
        355                 360                 365

Ile Gln Arg Ala Leu Gln Leu Glu Glu Glu Arg Lys Arg Ala Gln Glu
    370                 375                 380

Glu Ala Glu Arg Leu Glu Ala Asp Arg Met Ala Ala Leu Arg Ala Lys
385                 390                 395                 400

Glu Glu Leu Glu Arg Gln Ala Val Asp Gln Ile Lys Ser Gln Glu Gln
                405                 410                 415

Leu Ala Ala Glu Leu Ala Glu Tyr Thr Ala Lys Ile Ala Leu Leu Glu
            420                 425                 430

Glu Ala Arg Arg Arg Lys Glu Asp Glu Val Glu Glu Trp Gln His Arg
        435                 440                 445

Ala Lys Glu Ala Gln Asp Asp Leu Val Lys Thr Lys Glu Glu Leu His
    450                 455                 460

Leu Val Met Thr Ala Pro Pro Pro Pro Pro Pro Pro Val Tyr Glu Pro
465                 470                 475                 480

Val Ser Tyr His Val Gln Glu Ser Leu Gln Asp Glu Gly Ala Glu Pro
                485                 490                 495

Thr Gly Tyr Ser Ala Glu Leu Ser Ser Glu Gly Ile Arg Asp Asp Arg
            500                 505                 510

Asn Glu Glu Lys Arg Ile Thr Glu Ala Glu Lys Asn Glu Arg Val Gln
        515                 520                 525

Arg Gln Leu Leu Thr Leu Ser Ser Glu Leu Ser Gln Ala Arg Asp Glu
    530                 535                 540

Asn Lys Arg Thr His Asn Asp Ile Ile His Asn Glu Asn Met Arg Gln
545                 550                 555                 560

Gly Arg Asp Lys Tyr Lys Thr Leu Arg Gln Ile Arg Gln Gly Asn Thr
                565                 570                 575

Lys Gln Arg Ile Asp Glu Phe Glu Ala Leu
            580                 585


<210> SEQ ID NO 71
<211> LENGTH: 2391
<212> TYPE: PRT
<213> ORGANISM: Homo sapiens

<400> SEQUENCE: 71

Met Thr Asp Leu Leu Arg Ser Val Val Thr Val Ile Asp Val Phe Tyr
1               5                   10                  15

Lys Tyr Thr Lys Gln Asp Gly Glu Cys Gly Thr Leu Ser Lys Gly Glu
            20                  25                  30

Leu Lys Glu Leu Leu Glu Lys Glu Leu His Pro Val Leu Lys Asn Pro
        35                  40                  45

Asp Asp Pro Asp Thr Val Asp Val Ile Met His Met Leu Asp Arg Asp
    50                  55                  60
```

-continued

```
His Asp Arg Arg Leu Asp Phe Thr Glu Phe Leu Leu Met Ile Phe Lys
65                  70                  75                  80

Leu Thr Met Ala Cys Asn Lys Val Leu Ser Lys Glu Tyr Cys Lys Ala
                85                  90                  95

Ser Gly Ser Lys Lys His Arg Arg Gly His Arg His Gln Glu Glu Glu
            100                 105                 110

Ser Glu Thr Glu Glu Asp Glu Glu Asp Thr Pro Gly His Lys Ser Gly
        115                 120                 125

Tyr Arg His Ser Ser Trp Ser Glu Gly Glu Glu His Gly Tyr Ser Ser
    130                 135                 140

Gly His Ser Arg Gly Thr Val Lys Cys Arg His Gly Ser Asn Ser Arg
145                 150                 155                 160

Arg Leu Gly Arg Gln Gly Asn Leu Ser Ser Ser Gly Asn Gln Glu Gly
                165                 170                 175

Ser Gln Lys Arg Tyr His Arg Ser Ser Cys Gly His Ser Trp Ser Gly
            180                 185                 190

Gly Lys Asp Arg His Gly Ser Ser Ser Val Glu Leu Arg Glu Arg Ile
        195                 200                 205

Asn Lys Ser His Ile Ser Pro Ser Arg Glu Ser Gly Glu Glu Tyr Glu
    210                 215                 220

Ser Gly Ser Gly Ser Asn Ser Trp Glu Arg Lys Gly His Gly Gly Leu
225                 230                 235                 240

Ser Cys Gly Leu Glu Thr Ser Gly His Glu Ser Asn Ser Thr Gln Ser
                245                 250                 255

Arg Ile Arg Glu Gln Lys Leu Gly Ser Ser Cys Ser Gly Ser Gly Asp
            260                 265                 270

Ser Gly Arg Arg Ser His Ala Cys Gly Tyr Ser Asn Ser Ser Gly Cys
        275                 280                 285

Gly Arg Pro Gln Asn Ala Ser Ser Ser Cys Gln Ser His Arg Phe Gly
    290                 295                 300

Gly Gln Gly Asn Gln Phe Ser Tyr Ile Gln Ser Gly Cys Gln Ser Gly
305                 310                 315                 320

Ile Lys Gly Gly Gln Gly His Gly Cys Val Ser Gly Gly Gln Pro Ser
                325                 330                 335

Gly Cys Gly Gln Pro Glu Ser Asn Pro Cys Ser Gln Ser Tyr Ser Gln
            340                 345                 350

Arg Gly Tyr Gly Ala Arg Glu Asn Gly Gln Pro Gln Asn Cys Gly Gly
        355                 360                 365

Gln Trp Arg Thr Gly Ser Ser Gln Ser Ser Cys Cys Gly Gln Tyr Gly
    370                 375                 380

Ser Gly Gly Ser Gln Ser Cys Ser Asn Gly Gln His Glu Tyr Gly Ser
385                 390                 395                 400

Cys Gly Arg Phe Ser Asn Ser Ser Ser Ser Asn Glu Phe Ser Lys Cys
                405                 410                 415

Asp Gln Tyr Gly Ser Gly Ser Ser Gln Ser Thr Ser Phe Glu Gln His
            420                 425                 430

Gly Thr Gly Leu Ser Gln Ser Ser Gly Phe Glu Gln His Val Cys Gly
        435                 440                 445

Ser Gly Gln Thr Cys Gly Gln His Glu Ser Thr Ser Ser Gln Ser Leu
    450                 455                 460

Gly Tyr Asp Gln His Gly Ser Ser Ser Gly Lys Thr Ser Gly Phe Gly
465                 470                 475                 480

Gln His Gly Ser Gly Ser Gly Gln Ser Ser Gly Phe Gly Gln Cys Gly
```

```
                485                 490                 495

Ser Gly Ser Gly Gln Ser Ser Gly Phe Gly Gln His Gly Ser Val Ser
            500                 505                 510

Gly Gln Ser Ser Gly Phe Gly Gln His Gly Ser Val Ser Gly Gln Ser
        515                 520                 525

Ser Gly Phe Gly Gln His Glu Ser Arg Ser Arg Gln Ser Ser Tyr Gly
    530                 535                 540

Gln His Gly Ser Gly Ser Ser Gln Ser Ser Gly Tyr Gly Gln Tyr Gly
545                 550                 555                 560

Ser Arg Glu Thr Ser Gly Phe Gly Gln His Gly Leu Gly Ser Gly Gln
                565                 570                 575

Ser Thr Gly Phe Gly Gln Tyr Gly Ser Gly Ser Gly Gln Ser Ser Gly
            580                 585                 590

Phe Gly Gln His Gly Ser Gly Ser Gly Gln Ser Ser Gly Phe Gly Gln
        595                 600                 605

His Glu Ser Arg Ser Gly Gln Ser Ser Tyr Gly Gln His Ser Ser Gly
    610                 615                 620

Ser Ser Gln Ser Ser Gly Tyr Gly Gln His Gly Ser Arg Gln Thr Ser
625                 630                 635                 640

Gly Phe Gly Gln His Gly Ser Gly Ser Ser Gln Ser Thr Gly Phe Gly
                645                 650                 655

Gln Tyr Gly Ser Gly Ser Gly Gln Ser Ser Gly Phe Gly Gln His Val
            660                 665                 670

Ser Gly Ser Gly Gln Ser Ser Gly Phe Gly Gln His Glu Ser Arg Ser
        675                 680                 685

Gly His Ser Ser Tyr Gly Gln His Gly Phe Gly Ser Ser Gln Ser Ser
    690                 695                 700

Gly Tyr Gly Gln His Gly Ser Ser Ser Gly Gln Thr Ser Gly Phe Gly
705                 710                 715                 720

Gln His Glu Leu Ser Ser Gly Gln Ser Ser Ser Phe Gly Gln His Gly
                725                 730                 735

Ser Gly Ser Gly Gln Ser Ser Gly Phe Gly Gln His Gly Ser Gly Ser
            740                 745                 750

Gly Gln Ser Ser Gly Phe Gly Gln His Glu Ser Arg Ser Gly Gln Ser
        755                 760                 765

Ser Tyr Gly Gln His Ser Ser Gly Ser Ser Gln Ser Ser Gly Tyr Gly
    770                 775                 780

Gln His Gly Ser Arg Gln Thr Ser Gly Phe Gly Gln His Gly Ser Gly
785                 790                 795                 800

Ser Ser Gln Ser Thr Gly Phe Gly Gln Tyr Gly Ser Gly Ser Gly Gln
                805                 810                 815

Ser Ala Gly Phe Gly Gln His Gly Ser Gly Ser Gly Gln Ser Ser Gly
            820                 825                 830

Phe Gly Gln His Glu Ser Arg Ser His Gln Ser Ser Tyr Gly Gln His
        835                 840                 845

Gly Ser Gly Ser Ser Gln Ser Ser Gly Tyr Gly Gln His Gly Ser Ser
    850                 855                 860

Ser Gly Gln Thr Ser Gly Phe Gly Gln His Arg Ser Ser Ser Gly Gln
865                 870                 875                 880

Tyr Ser Gly Phe Gly Gln His Gly Ser Gly Ser Gly Gln Ser Ser Gly
                885                 890                 895

Phe Gly Gln His Gly Thr Gly Ser Gly Gln Tyr Ser Gly Phe Gly Gln
            900                 905                 910
```

```
His Glu Ser Arg Ser His Gln Ser Ser Tyr Gly Gln His Gly Ser Gly
        915                 920                 925

Ser Ser Gln Ser Ser Gly Tyr Gly Gln His Gly Ser Ser Ser Gly Gln
    930                 935                 940

Thr Phe Gly Phe Gly Gln His Arg Ser Gly Ser Gly Gln Ser Ser Gly
945                 950                 955                 960

Phe Gly Gln His Gly Ser Gly Ser Gly Gln Ser Ser Gly Phe Gly Gln
                965                 970                 975

His Glu Ser Gly Ser Gly Lys Ser Ser Gly Phe Gly Gln His Glu Ser
            980                 985                 990

Arg Ser Ser Gln Ser Asn Tyr Gly  Gln His Gly Ser Gly  Ser Ser Gln
        995                 1000                 1005

Ser Ser  Gly Tyr Gly Gln His  Gly Ser Ser Ser Gly  Gln Thr Thr
    1010                 1015                 1020

Gly Phe  Gly Gln His Arg Ser  Ser Ser Gly Gln Tyr  Ser Gly Phe
    1025                 1030                 1035

Gly Gln  His Gly Ser Gly Ser  Asp Gln Ser Ser Gly  Phe Gly Gln
    1040                 1045                 1050

His Gly  Thr Gly Ser Gly Gln  Ser Ser Gly Phe Gly  Gln Tyr Glu
    1055                 1060                 1065

Ser Arg  Ser Arg Gln Ser Ser  Tyr Gly Gln His Gly  Ser Gly Ser
    1070                 1075                 1080

Ser Gln  Ser Ser Gly Tyr Gly  Gln His Gly Ser Asn  Ser Gly Gln
    1085                 1090                 1095

Thr Ser  Gly Phe Gly Gln His  Arg Pro Gly Ser Gly  Gln Ser Ser
    1100                 1105                 1110

Gly Phe  Gly Gln Tyr Gly Ser  Gly Ser Gly Gln Ser  Ser Gly Phe
    1115                 1120                 1125

Gly Gln  His Gly Ser Gly Thr  Gly Lys Ser Ser Gly  Phe Ala Gln
    1130                 1135                 1140

His Glu  Tyr Arg Ser Gly Gln  Ser Ser Tyr Gly Gln  His Gly Thr
    1145                 1150                 1155

Gly Ser  Ser Gln Ser Ser Gly  Cys Gly Gln His Glu  Ser Gly Ser
    1160                 1165                 1170

Gly Pro  Thr Thr Ser Phe Gly  Gln His Val Ser Gly  Ser Asp Asn
    1175                 1180                 1185

Phe Ser  Ser Ser Gly Gln His  Ile Ser Asp Ser Gly  Gln Ser Thr
    1190                 1195                 1200

Gly Phe  Gly Gln Tyr Gly Ser  Gly Ser Gly Gln Ser  Thr Gly Leu
    1205                 1210                 1215

Gly Gln  Gly Glu Ser Gln Gln  Val Glu Ser Gly Ser  Thr Val His
    1220                 1225                 1230

Gly Arg  Gln Glu Thr Thr His  Gly Gln Thr Ile Asn  Thr Thr Arg
    1235                 1240                 1245

His Ser  Gln Ser Gly Gln Gly  Gln Ser Thr Gln Thr  Gly Ser Arg
    1250                 1255                 1260

Val Thr  Arg Arg Arg Arg Ser  Ser Gln Ser Glu Asn  Ser Asp Ser
    1265                 1270                 1275

Glu Val  His Ser Lys Val Ser  His Arg His Ser Glu  His Ile His
    1280                 1285                 1290

Thr Gln  Ala Gly Ser His Tyr  Pro Lys Ser Gly Ser  Thr Val Arg
    1295                 1300                 1305
```

```
Arg Arg Gln Gly Thr Thr His Gly Gln Arg Gly Asp Thr Thr Arg
    1310                1315                1320

His Gly His Ser Gly His Gly Gln Ser Thr Gln Thr Gly Ser Arg
    1325                1330                1335

Thr Ser Gly Arg Gln Arg Phe Ser His Ser Asp Ala Thr Asp Ser
    1340                1345                1350

Glu Val His Ser Gly Val Ser His Arg Pro His Ser Gln Glu Gln
    1355                1360                1365

Thr His Ser Gln Ala Gly Ser Gln His Gly Glu Ser Glu Ser Thr
    1370                1375                1380

Val His Glu Arg His Glu Thr Thr Tyr Gly Gln Thr Gly Glu Ala
    1385                1390                1395

Thr Gly His Gly His Ser Gly His Gly Gln Ser Thr Gln Arg Gly
    1400                1405                1410

Ser Arg Thr Thr Gly Arg Arg Gly Ser Gly His Ser Glu Ser Ser
    1415                1420                1425

Asp Ser Glu Val His Ser Gly Gly Ser His Arg Pro Gln Ser Gln
    1430                1435                1440

Glu Gln Thr His Gly Gln Ala Gly Ser Gln His Gly Glu Ser Gly
    1445                1450                1455

Ser Thr Val His Gly Arg His Gly Thr Thr His Gly Gln Thr Gly
    1460                1465                1470

Asp Thr Thr Arg His Ala His Tyr His His Gly Lys Ser Thr Gln
    1475                1480                1485

Arg Gly Ser Ser Thr Thr Gly Arg Arg Gly Ser Gly His Ser Glu
    1490                1495                1500

Ser Ser Asp Ser Glu Val His Ser Gly Gly Ser His Thr His Ser
    1505                1510                1515

Gly His Thr His Gly Gln Ser Gly Ser Gln His Gly Glu Ser Glu
    1520                1525                1530

Ser Ile Ile His Asp Arg His Arg Ile Thr His Gly Gln Thr Gly
    1535                1540                1545

Asp Thr Thr Arg His Ser Tyr Ser Gly His Glu Gln Thr Thr Gln
    1550                1555                1560

Thr Gly Ser Arg Thr Thr Gly Arg Gln Arg Thr Ser His Ser Glu
    1565                1570                1575

Ser Thr Asp Ser Glu Val His Ser Gly Gly Ser His Arg Pro His
    1580                1585                1590

Ser Arg Glu His Thr Tyr Gly Gln Ala Gly Ser Gln His Glu Glu
    1595                1600                1605

Pro Glu Phe Thr Val His Glu Arg His Gly Thr Thr His Gly Gln
    1610                1615                1620

Ile Gly Asp Thr Thr Gly His Ser His Ser Gly His Gly Gln Ser
    1625                1630                1635

Thr Gln Arg Gly Ser Arg Thr Thr Gly Arg Gln Arg Ser Ser His
    1640                1645                1650

Ser Glu Ser Ser Asp Ser Glu Val His Ser Gly Val Ser His Thr
    1655                1660                1665

His Thr Gly His Thr His Gly Gln Ala Gly Ser Gln His Gly Gln
    1670                1675                1680

Ser Glu Ser Ile Val Pro Glu Arg His Gly Thr Thr His Gly Gln
    1685                1690                1695

Thr Gly Asp Thr Thr Arg His Ala His Tyr His His Gly Leu Thr
```

```
    1700                1705                1710

Thr Gln  Thr Gly Ser Arg Thr  Thr Gly Arg Arg Gly  Ser Gly His
    1715                1720                1725

Ser Glu  Tyr Ser Asp Ser Glu  Gly Tyr Ser Gly Val  Ser His Thr
    1730                1735                1740

His Ser  Gly His Thr His Gly  Gln Ala Arg Ser Gln  His Gly Glu
    1745                1750                1755

Ser Glu  Ser Ile Val His Glu  Arg His Gly Thr Ile  His Gly Gln
    1760                1765                1770

Thr Gly  Asp Thr Thr Arg His  Ala His Ser Gly His  Gly Gln Ser
    1775                1780                1785

Thr Gln  Thr Gly Ser Arg Thr  Thr Gly Arg Arg Ser  Ser Gly His
    1790                1795                1800

Ser Glu  Tyr Ser Asp Ser Glu  Gly His Ser Gly Phe  Ser Gln Arg
    1805                1810                1815

Pro His  Ser Arg Gly His Thr  His Gly Gln Ala Gly  Ser Gln His
    1820                1825                1830

Gly Glu  Ser Glu Ser Ile Val  Asp Glu Arg His Gly  Thr Thr His
    1835                1840                1845

Gly Gln  Thr Gly Asp Thr Ser  Gly His Ser Gln Ser  Gly His Gly
    1850                1855                1860

Gln Ser  Thr Gln Ser Gly Ser  Ser Thr Thr Gly Arg  Arg Arg Ser
    1865                1870                1875

Gly His  Ser Glu Ser Ser Asp  Ser Glu Val His Ser  Gly Gly Ser
    1880                1885                1890

His Thr  His Ser Gly His Thr  His Ser Gln Ala Arg  Ser Gln His
    1895                1900                1905

Gly Glu  Ser Glu Ser Thr Val  His Lys Arg His Gln  Thr Thr His
    1910                1915                1920

Gly Gln  Thr Gly Asp Thr Thr  Glu His Gly His Pro  Ser His Gly
    1925                1930                1935

Gln Thr  Ile Gln Thr Gly Ser  Arg Thr Thr Gly Arg  Arg Gly Ser
    1940                1945                1950

Gly His  Ser Glu Tyr Ser Asp  Ser Glu Gly Pro Ser  Gly Val Ser
    1955                1960                1965

His Thr  His Ser Gly His Thr  His Gly Gln Ala Gly  Ser His Tyr
    1970                1975                1980

Pro Glu  Ser Gly Ser Ser Val  His Glu Arg His Gly  Thr Thr His
    1985                1990                1995

Gly Gln  Thr Ala Asp Thr Thr  Arg His Gly His Ser  Gly His Gly
    2000                2005                2010

Gln Ser  Thr Gln Arg Gly Ser  Arg Thr Thr Gly Arg  Arg Ala Ser
    2015                2020                2025

Gly His  Ser Glu Tyr Ser Asp  Ser Glu Gly His Ser  Gly Val Ser
    2030                2035                2040

His Thr  His Ser Gly His Ala  His Gly Gln Ala Gly  Ser Gln His
    2045                2050                2055

Gly Glu  Ser Gly Ser Ser Val  His Glu Arg His Gly  Thr Thr His
    2060                2065                2070

Gly Gln  Thr Gly Asp Thr Thr  Arg His Ala His Ser  Gly His Gly
    2075                2080                2085

Gln Ser  Thr Gln Arg Gly Ser  Arg Thr Ala Gly Arg  Arg Gly Ser
    2090                2095                2100
```

```
Gly His  Ser Glu Ser Ser Asp  Ser Glu Val His Ser  Gly Val Ser
    2105                 2110                 2115

His Thr  His Ser Gly His Thr  Tyr Gly Gln Ala Arg  Ser Gln His
    2120                 2125                 2130

Gly Glu  Ser Gly Ser Ala Ile  His Gly Arg Gln Gly  Thr Ile His
    2135                 2140                 2145

Gly Gln  Thr Gly Asp Thr Thr  Arg His Gly Gln Ser  Gly His Gly
    2150                 2155                 2160

Gln Ser  Thr Gln Thr Gly Ser  Arg Thr Thr Gly Arg  Gln Arg Ser
    2165                 2170                 2175

Ser His  Ser Glu Ser Ser Asp  Ser Glu Val His Ser  Glu Ala Ser
    2180                 2185                 2190

Pro Thr  His Ser Gly His Thr  His Ser Gln Ala Gly  Ser Arg His
    2195                 2200                 2205

Gly Gln  Ser Gly Ser Ser Gly  His Gly Arg Gln Gly  Thr Thr His
    2210                 2215                 2220

Gly Gln  Thr Gly Asp Thr Thr  Arg His Ala His Tyr  Gly Tyr Gly
    2225                 2230                 2235

Gln Ser  Thr Gln Arg Gly Ser  Arg Thr Thr Gly Arg  Arg Gly Ser
    2240                 2245                 2250

Gly His  Ser Glu Ser Ser Asp  Ser Glu Val His Ser  Trp Gly Ser
    2255                 2260                 2265

His Thr  His Ser Gly His Ile  Gln Gly Gln Ala Gly  Ser Gln Gln
    2270                 2275                 2280

Arg Gln  Pro Gly Ser Thr Val  His Gly Arg Leu Glu  Thr Thr His
    2285                 2290                 2295

Gly Gln  Thr Gly Asp Thr Thr  Arg His Gly His Ser  Gly Tyr Gly
    2300                 2305                 2310

Gln Ser  Thr Gln Thr Gly Ser  Arg Ser Ser Arg Ala  Ser His Phe
    2315                 2320                 2325

Gln Ser  His Ser Ser Glu Arg  Gln Arg His Gly Ser  Ser Gln Val
    2330                 2335                 2340

Trp Lys  His Gly Ser Tyr Gly  Pro Ala Glu Tyr Asp  Tyr Gly His
    2345                 2350                 2355

Thr Gly  Tyr Gly Pro Ser Gly  Gly Ser Arg Lys Ser  Ile Ser Asn
    2360                 2365                 2370

Ser His  Leu Ser Trp Ser Thr  Asp Ser Thr Ala Asn  Lys Gln Leu
    2375                 2380                 2385

Ser Arg  His
    2390


<210> SEQ ID NO 72
<211> LENGTH: 427
<212> TYPE: PRT
<213> ORGANISM: Homo sapiens

<400> SEQUENCE: 72

Met Phe Phe Thr Cys Gly Pro Asn Glu Ala Met Val Val Ser Gly Phe
1               5                   10                  15

Cys Arg Ser Pro Pro Val Met Val Ala Gly Gly Arg Val Phe Val Leu
            20                  25                  30

Pro Cys Ile Gln Gln Ile Gln Arg Ile Ser Leu Asn Thr Leu Thr Leu
        35                  40                  45

Asn Val Lys Ser Glu Lys Val Tyr Thr Arg His Gly Val Pro Ile Ser
```

```
    50                  55                  60

Val Thr Gly Ile Ala Gln Val Lys Ile Gln Gly Gln Asn Lys Glu Met
65                  70                  75                  80

Leu Ala Ala Ala Cys Gln Met Phe Leu Gly Lys Thr Glu Ala Glu Ile
                85                  90                  95

Ala His Ile Ala Leu Glu Thr Leu Glu Gly His Gln Arg Ala Ile Met
            100                 105                 110

Ala His Met Thr Val Glu Glu Ile Tyr Lys Asp Arg Gln Lys Phe Ser
        115                 120                 125

Glu Gln Val Phe Lys Val Ala Ser Ser Asp Leu Val Asn Met Gly Ile
    130                 135                 140

Ser Val Val Ser Tyr Thr Leu Lys Asp Ile His Asp Asp Gln Asp Tyr
145                 150                 155                 160

Leu His Ser Leu Gly Lys Ala Arg Thr Ala Gln Val Gln Lys Asp Ala
                165                 170                 175

Arg Ile Gly Glu Ala Glu Ala Lys Arg Asp Ala Gly Ile Arg Glu Ala
            180                 185                 190

Lys Ala Lys Gln Glu Lys Val Ser Ala Gln Tyr Leu Ser Glu Ile Glu
        195                 200                 205

Met Ala Lys Ala Gln Arg Asp Tyr Glu Leu Lys Lys Ala Ala Tyr Asp
    210                 215                 220

Ile Glu Val Asn Thr Arg Arg Ala Gln Ala Asp Leu Ala Tyr Gln Leu
225                 230                 235                 240

Gln Val Ala Lys Thr Lys Gln Gln Ile Glu Glu Gln Arg Val Gln Val
                245                 250                 255

Gln Val Val Glu Arg Ala Gln Gln Val Ala Val Gln Glu Gln Glu Ile
            260                 265                 270

Ala Arg Arg Glu Lys Glu Leu Glu Ala Arg Val Arg Lys Pro Ala Glu
        275                 280                 285

Ala Glu Arg Tyr Lys Leu Glu Arg Leu Ala Glu Ala Glu Lys Ser Gln
    290                 295                 300

Leu Ile Met Gln Ala Glu Ala Glu Ala Ala Ser Val Arg Met Arg Gly
305                 310                 315                 320

Glu Ala Glu Ala Phe Ala Ile Gly Ala Arg Ala Arg Ala Glu Ala Glu
                325                 330                 335

Gln Met Ala Lys Lys Ala Glu Ala Phe Gln Leu Tyr Gln Glu Ala Ala
            340                 345                 350

Gln Leu Asp Met Leu Leu Glu Lys Leu Pro Gln Val Ala Glu Glu Ile
        355                 360                 365

Ser Gly Pro Leu Thr Ser Ala Asn Lys Ile Thr Leu Val Ser Ser Gly
    370                 375                 380

Ser Gly Thr Met Gly Ala Ala Lys Val Thr Gly Glu Val Leu Asp Ile
385                 390                 395                 400

Leu Thr Arg Leu Pro Glu Ser Val Glu Arg Leu Thr Gly Val Ser Ile
                405                 410                 415

Ser Gln Val Asn His Lys Pro Leu Arg Thr Ala
            420                 425


<210> SEQ ID NO 73
<211> LENGTH: 428
<212> TYPE: PRT
<213> ORGANISM: Homo sapiens

<400> SEQUENCE: 73
```

```
Met Gly Asn Cys His Thr Val Gly Pro Asn Glu Ala Leu Val Val Ser
1               5                   10                  15

Gly Gly Cys Cys Gly Ser Asp Tyr Lys Gln Tyr Val Phe Gly Gly Trp
            20                  25                  30

Ala Trp Ala Trp Trp Cys Ile Ser Asp Thr Gln Arg Ile Ser Leu Glu
        35                  40                  45

Ile Met Thr Leu Gln Pro Arg Cys Glu Asp Val Glu Thr Ala Glu Gly
    50                  55                  60

Val Ala Leu Thr Val Thr Gly Val Ala Gln Val Lys Ile Met Thr Glu
65                  70                  75                  80

Lys Glu Leu Leu Ala Val Ala Cys Glu Gln Phe Leu Gly Lys Asn Val
                85                  90                  95

Gln Asp Ile Lys Asn Val Val Leu Gln Thr Leu Glu Gly His Leu Arg
            100                 105                 110

Ser Ile Leu Gly Thr Leu Thr Val Glu Gln Ile Tyr Gln Asp Arg Asp
        115                 120                 125

Gln Phe Ala Lys Leu Val Arg Glu Val Ala Ala Pro Asp Val Gly Arg
    130                 135                 140

Met Gly Ile Glu Ile Leu Ser Phe Thr Ile Lys Asp Val Tyr Asp Lys
145                 150                 155                 160

Val Asp Tyr Leu Ser Ser Leu Gly Lys Thr Gln Thr Ala Val Val Gln
                165                 170                 175

Arg Asp Ala Asp Ile Gly Val Ala Glu Ala Glu Arg Asp Ala Gly Ile
            180                 185                 190

Arg Glu Ala Glu Cys Lys Lys Glu Met Leu Asp Val Lys Phe Met Ala
        195                 200                 205

Asp Thr Lys Ile Ala Asp Ser Lys Arg Ala Phe Glu Leu Gln Lys Ser
    210                 215                 220

Ala Phe Ser Glu Glu Val Asn Ile Lys Thr Ala Glu Ala Gln Leu Ala
225                 230                 235                 240

Tyr Glu Leu Gln Gly Ala Arg Glu Gln Gln Lys Ile Arg Gln Glu Glu
                245                 250                 255

Ile Glu Ile Glu Val Val Gln Arg Lys Lys Gln Ile Ala Val Glu Ala
            260                 265                 270

Gln Glu Ile Leu Arg Thr Asp Lys Glu Leu Ile Ala Thr Val Arg Arg
        275                 280                 285

Pro Ala Glu Ala Glu Ala His Arg Ile Gln Gln Ile Ala Glu Gly Glu
    290                 295                 300

Lys Val Lys Gln Val Leu Leu Ala Gln Ala Glu Ala Glu Lys Ile Arg
305                 310                 315                 320

Lys Ile Gly Glu Ala Glu Ala Ala Val Ile Glu Ala Met Gly Lys Ala
                325                 330                 335

Glu Ala Glu Arg Met Lys Leu Lys Ala Glu Ala Tyr Gln Lys Tyr Gly
            340                 345                 350

Asp Ala Ala Lys Met Ala Leu Val Leu Glu Ala Leu Pro Gln Ile Ala
        355                 360                 365

Ala Lys Ile Ala Ala Pro Leu Thr Lys Val Asp Glu Ile Val Val Leu
    370                 375                 380

Ser Gly Asp Asn Ser Lys Val Thr Ser Glu Val Asn Arg Leu Leu Ala
385                 390                 395                 400

Glu Leu Pro Ala Ser Val His Ala Leu Thr Gly Val Asp Leu Ser Lys
                405                 410                 415

Ile Pro Leu Ile Lys Lys Ala Thr Gly Val Gln Val
```

420 425

<210> SEQ ID NO 74
<211> LENGTH: 335
<212> TYPE: PRT
<213> ORGANISM: Homo sapiens

<400> SEQUENCE: 74

Met Gly Lys Val Lys Val Gly Val Asn Gly Phe Gly Arg Ile Gly Arg
1 5 10 15

Leu Val Thr Arg Ala Ala Phe Asn Ser Gly Lys Val Asp Ile Val Ala
20 25 30

Ile Asn Asp Pro Phe Ile Asp Leu Asn Tyr Met Val Tyr Met Phe Gln
35 40 45

Tyr Asp Ser Thr His Gly Lys Phe His Gly Thr Val Lys Ala Glu Asn
50 55 60

Gly Lys Leu Val Ile Asn Gly Asn Pro Ile Thr Ile Phe Gln Glu Arg
65 70 75 80

Asp Pro Ser Lys Ile Lys Trp Gly Asp Ala Gly Ala Glu Tyr Val Val
85 90 95

Glu Ser Thr Gly Val Phe Thr Thr Met Glu Lys Ala Gly Ala His Leu
100 105 110

Gln Gly Gly Ala Lys Arg Val Ile Ile Ser Ala Pro Ser Ala Asp Ala
115 120 125

Pro Met Phe Val Met Gly Val Asn His Glu Lys Tyr Asp Asn Ser Leu
130 135 140

Lys Ile Ile Ser Asn Ala Ser Cys Thr Thr Asn Cys Leu Ala Pro Leu
145 150 155 160

Ala Lys Val Ile His Asp Asn Phe Gly Ile Val Glu Gly Leu Met Thr
165 170 175

Thr Val His Ala Ile Thr Ala Thr Gln Lys Thr Val Asp Gly Pro Ser
180 185 190

Gly Lys Leu Trp Arg Asp Gly Arg Gly Ala Leu Gln Asn Ile Ile Pro
195 200 205

Ala Ser Thr Gly Ala Ala Lys Ala Val Gly Lys Val Ile Pro Glu Leu
210 215 220

Asn Gly Lys Leu Thr Gly Met Ala Phe Arg Val Pro Thr Ala Asn Val
225 230 235 240

Ser Val Val Asp Leu Thr Cys Arg Leu Glu Lys Pro Ala Lys Tyr Asp
245 250 255

Asp Ile Lys Lys Val Val Lys Gln Ala Ser Glu Gly Pro Leu Lys Gly
260 265 270

Ile Leu Gly Tyr Thr Glu His Gln Val Val Ser Ser Asp Phe Asn Ser
275 280 285

Asp Thr His Ser Ser Thr Phe Asp Ala Gly Ala Gly Ile Ala Leu Asn
290 295 300

Asp His Phe Val Lys Leu Ile Ser Trp Tyr Asp Asn Glu Phe Gly Tyr
305 310 315 320

Ser Asn Arg Val Val Asp Leu Met Ala His Met Ala Ser Lys Glu
325 330 335

<210> SEQ ID NO 75
<211> LENGTH: 1017
<212> TYPE: PRT
<213> ORGANISM: Homo sapiens

<400> SEQUENCE: 75

Met Val Phe Ser Val Arg Gln Cys Gly His Val Gly Arg Thr Glu Glu
1 5 10 15

Val Leu Leu Thr Phe Lys Ile Phe Leu Val Ile Ile Cys Leu His Val
20 25 30

Val Leu Val Thr Ser Leu Glu Glu Asp Thr Asp Asn Ser Ser Leu Ser
35 40 45

Pro Pro Pro Ala Lys Leu Ser Val Val Ser Phe Ala Pro Ser Ser Asn
50 55 60

Gly Thr Pro Glu Val Glu Thr Thr Ser Leu Asn Asp Val Thr Leu Ser
65 70 75 80

Leu Leu Pro Ser Asn Glu Thr Glu Lys Thr Lys Ile Thr Ile Val Lys
85 90 95

Thr Phe Asn Ala Ser Gly Val Lys Pro Gln Arg Asn Ile Cys Asn Leu
100 105 110

Ser Ser Ile Cys Asn Asp Ser Ala Phe Phe Arg Gly Glu Ile Met Phe
115 120 125

Gln Tyr Asp Lys Glu Ser Thr Val Pro Gln Asn Gln His Ile Thr Asn
130 135 140

Gly Thr Leu Thr Gly Val Leu Ser Leu Ser Glu Leu Lys Arg Ser Glu
145 150 155 160

Leu Asn Lys Thr Leu Gln Thr Leu Ser Glu Thr Tyr Phe Ile Met Cys
165 170 175

Ala Thr Ala Glu Ala Gln Ser Thr Leu Asn Cys Thr Phe Thr Ile Lys
180 185 190

Leu Asn Asn Thr Met Asn Ala Cys Ala Val Ile Ala Ala Leu Glu Arg
195 200 205

Val Lys Ile Arg Pro Met Glu His Cys Cys Cys Ser Val Arg Ile Pro
210 215 220

Cys Pro Ser Ser Pro Glu Glu Leu Glu Lys Leu Gln Cys Asp Leu Gln
225 230 235 240

Asp Pro Ile Val Cys Leu Ala Asp His Pro Arg Gly Pro Pro Phe Ser
245 250 255

Ser Ser Gln Ser Ile Pro Val Val Pro Arg Ala Thr Val Leu Ser Gln
260 265 270

Val Pro Lys Ala Thr Ser Phe Ala Glu Pro Pro Asp Tyr Ser Pro Val
275 280 285

Thr His Asn Val Pro Ser Pro Ile Gly Glu Ile Gln Pro Leu Ser Pro
290 295 300

Gln Pro Ser Ala Pro Ile Ala Ser Ser Pro Ala Ile Asp Met Pro Pro
305 310 315 320

Gln Ser Glu Thr Ile Ser Ser Pro Met Pro Gln Thr His Val Ser Gly
325 330 335

Thr Pro Pro Pro Val Lys Ala Ser Phe Ser Ser Pro Thr Val Ser Ala
340 345 350

Pro Ala Asn Val Asn Thr Thr Ser Ala Pro Pro Val Gln Thr Asp Ile
355 360 365

Val Asn Thr Ser Ser Ile Ser Asp Leu Glu Asn Gln Val Leu Gln Met
370 375 380

Glu Lys Ala Leu Ser Leu Gly Ser Leu Glu Pro Asn Leu Ala Gly Glu
385 390 395 400

Met Ile Asn Gln Val Ser Arg Leu Leu His Ser Pro Pro Asp Met Leu
405 410 415

```
Ala Pro Leu Ala Gln Arg Leu Leu Lys Val Val Asp Asp Ile Gly Leu
            420                 425                 430

Gln Leu Asn Phe Ser Asn Thr Thr Ile Ser Leu Thr Ser Pro Ser Leu
        435                 440                 445

Ala Leu Ala Val Ile Arg Val Asn Ala Ser Ser Phe Asn Thr Thr Thr
    450                 455                 460

Phe Val Ala Gln Asp Pro Ala Asn Leu Gln Val Ser Leu Glu Thr Gln
465                 470                 475                 480

Ala Pro Glu Asn Ser Ile Gly Thr Ile Thr Leu Pro Ser Ser Leu Met
                485                 490                 495

Asn Asn Leu Pro Ala His Asp Met Glu Leu Ala Ser Arg Val Gln Phe
            500                 505                 510

Asn Phe Phe Glu Thr Pro Ala Leu Phe Gln Asp Pro Ser Leu Glu Asn
        515                 520                 525

Leu Ser Leu Ile Ser Tyr Val Ile Ser Ser Ser Val Ala Asn Leu Thr
    530                 535                 540

Val Arg Asn Leu Thr Arg Asn Val Thr Val Thr Leu Lys His Ile Asn
545                 550                 555                 560

Pro Ser Gln Asp Glu Leu Thr Val Arg Cys Val Phe Trp Asp Leu Gly
                565                 570                 575

Arg Asn Gly Gly Arg Gly Gly Trp Ser Asp Asn Gly Cys Ser Val Lys
            580                 585                 590

Asp Arg Arg Leu Asn Glu Thr Ile Cys Thr Cys Ser His Leu Thr Ser
        595                 600                 605

Phe Gly Val Leu Leu Asp Leu Ser Arg Thr Ser Val Leu Pro Ala Gln
    610                 615                 620

Met Met Ala Leu Thr Phe Ile Thr Tyr Ile Gly Cys Gly Leu Ser Ser
625                 630                 635                 640

Ile Phe Leu Ser Val Thr Leu Val Thr Tyr Ile Ala Phe Glu Lys Ile
                645                 650                 655

Arg Arg Asp Tyr Pro Ser Lys Ile Leu Ile Gln Leu Cys Ala Ala Leu
            660                 665                 670

Leu Leu Leu Asn Leu Val Phe Leu Leu Asp Ser Trp Ile Ala Leu Tyr
        675                 680                 685

Lys Met Gln Gly Leu Cys Ile Ser Val Ala Val Phe Leu His Tyr Phe
    690                 695                 700

Leu Leu Val Ser Phe Thr Trp Met Gly Leu Glu Ala Phe His Met Tyr
705                 710                 715                 720

Leu Ala Leu Val Lys Val Phe Asn Thr Tyr Ile Arg Lys Tyr Ile Leu
                725                 730                 735

Lys Phe Cys Ile Val Gly Trp Gly Val Pro Ala Val Val Val Thr Ile
            740                 745                 750

Ile Leu Thr Ile Ser Pro Asp Asn Tyr Gly Leu Gly Ser Tyr Gly Lys
        755                 760                 765

Phe Pro Asn Gly Ser Pro Asp Asp Phe Cys Trp Ile Asn Asn Asn Ala
    770                 775                 780

Val Phe Tyr Ile Thr Val Val Gly Tyr Phe Cys Val Ile Phe Leu Leu
785                 790                 795                 800

Asn Val Ser Met Phe Ile Val Val Leu Val Gln Leu Cys Arg Ile Lys
                805                 810                 815

Lys Lys Lys Gln Leu Gly Ala Gln Arg Lys Thr Ser Ile Gln Asp Leu
            820                 825                 830
```

```
Arg Ser Ile Ala Gly Leu Thr Phe Leu Leu Gly Ile Thr Trp Gly Phe
        835                 840                 845

Ala Phe Phe Ala Trp Gly Pro Val Asn Val Thr Phe Met Tyr Leu Phe
    850                 855                 860

Ala Ile Phe Asn Thr Leu Gln Gly Phe Phe Ile Phe Ile Phe Tyr Cys
865                 870                 875                 880

Val Ala Lys Glu Asn Val Arg Lys Gln Trp Arg Arg Tyr Leu Cys Cys
                885                 890                 895

Gly Lys Leu Arg Leu Ala Glu Asn Ser Asp Trp Ser Lys Thr Ala Thr
            900                 905                 910

Asn Gly Leu Lys Lys Gln Thr Val Asn Gln Gly Val Ser Ser Ser Ser
        915                 920                 925

Asn Ser Leu Gln Ser Ser Ser Asn Ser Thr Asn Ser Thr Thr Leu Leu
    930                 935                 940

Val Asn Asn Asp Cys Ser Val His Ala Ser Gly Asn Gly Asn Ala Ser
945                 950                 955                 960

Thr Glu Arg Asn Gly Val Ser Phe Ser Val Gln Asn Gly Asp Val Cys
                965                 970                 975

Leu His Asp Phe Thr Gly Lys Gln His Met Phe Asn Glu Lys Glu Asp
            980                 985                 990

Ser Cys Asn Gly Lys Gly Arg Met  Ala Leu Arg Arg Thr  Ser Lys Arg
        995                 1000                1005

Gly Ser  Leu His Phe Ile Glu  Gln Met
    1010                1015


<210> SEQ ID NO 76
<211> LENGTH: 641
<212> TYPE: PRT
<213> ORGANISM: Homo sapiens

<400> SEQUENCE: 76

Met Ala Lys Ala Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190
```

```
Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
    370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
            420                 425                 430

Asp Asn Gln Pro Gly Val Leu Ile Gln Val Tyr Glu Gly Glu Arg Ala
        435                 440                 445

Met Thr Lys Asp Asn Asn Leu Leu Gly Arg Phe Glu Leu Ser Gly Ile
    450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510

Glu Glu Ile Glu Arg Met Val Gln Glu Ala Glu Lys Tyr Lys Ala Glu
        515                 520                 525

Asp Glu Val Gln Arg Glu Arg Val Ser Ala Lys Asn Ala Leu Glu Ser
    530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Lys Val Leu Asp Lys Cys Gln Glu
                565                 570                 575

Val Ile Ser Trp Leu Asp Ala Asn Thr Leu Ala Glu Lys Asp Glu Phe
            580                 585                 590

Glu His Lys Arg Lys Glu Leu Glu Gln Val Cys Asn Pro Ile Ile Ser
        595                 600                 605
```

```
Gly Leu Tyr Gln Gly Ala Gly Gly Pro Gly Pro Gly Gly Phe Gly Ala
    610                 615                 620

Gln Gly Pro Lys Gly Gly Ser Gly Ser Gly Pro Thr Ile Glu Glu Val
625                 630                 635                 640

Asp


<210> SEQ ID NO 77
<211> LENGTH: 646
<212> TYPE: PRT
<213> ORGANISM: Homo sapiens

<400> SEQUENCE: 77

Met Ser Lys Gly Pro Ala Val Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Met Asn Pro Thr
    50                  55                  60

Asn Thr Val Phe Asp Ala Lys Arg Leu Ile Gly Arg Arg Phe Asp Asp
65                  70                  75                  80

Ala Val Val Gln Ser Asp Met Lys His Trp Pro Phe Met Val Val Asn
                85                  90                  95

Asp Ala Gly Arg Pro Lys Val Gln Val Glu Tyr Lys Gly Glu Thr Lys
            100                 105                 110

Ser Phe Tyr Pro Glu Glu Val Ser Ser Met Val Leu Thr Lys Met Lys
        115                 120                 125

Glu Ile Ala Glu Ala Tyr Leu Gly Lys Thr Val Thr Asn Ala Val Val
    130                 135                 140

Thr Val Pro Ala Tyr Phe Asn Asp Ser Gln Arg Gln Ala Thr Lys Asp
145                 150                 155                 160

Ala Gly Thr Ile Ala Gly Leu Asn Val Leu Arg Ile Ile Asn Glu Pro
                165                 170                 175

Thr Ala Ala Ala Ile Ala Tyr Gly Leu Asp Lys Lys Val Gly Ala Glu
            180                 185                 190

Arg Asn Val Leu Ile Phe Asp Leu Gly Gly Gly Thr Phe Asp Val Ser
        195                 200                 205

Ile Leu Thr Ile Glu Asp Gly Ile Phe Glu Val Lys Ser Thr Ala Gly
    210                 215                 220

Asp Thr His Leu Gly Gly Glu Asp Phe Asp Asn Arg Met Val Asn His
225                 230                 235                 240

Phe Ile Ala Glu Phe Lys Arg Lys His Lys Lys Asp Ile Ser Glu Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Ile Glu Ile Asp Ser Leu Tyr
        275                 280                 285

Glu Gly Ile Asp Phe Tyr Thr Ser Ile Thr Arg Ala Arg Phe Glu Glu
    290                 295                 300

Leu Asn Ala Asp Leu Phe Arg Gly Thr Leu Asp Pro Val Glu Lys Ala
305                 310                 315                 320

Leu Arg Asp Ala Lys Leu Asp Lys Ser Gln Ile His Asp Ile Val Leu
                325                 330                 335
```

Val Gly Gly Ser Thr Arg Ile Pro Lys Ile Gln Lys Leu Leu Gln Asp
340 345 350

Phe Phe Asn Gly Lys Glu Leu Asn Lys Ser Ile Asn Pro Asp Glu Ala
355 360 365

Val Ala Tyr Gly Ala Ala Val Gln Ala Ala Ile Leu Ser Gly Asp Lys
370 375 380

Ser Glu Asn Val Gln Asp Leu Leu Leu Leu Asp Val Thr Pro Leu Ser
385 390 395 400

Leu Gly Ile Glu Thr Ala Gly Gly Val Met Thr Val Leu Ile Lys Arg
405 410 415

Asn Thr Thr Ile Pro Thr Lys Gln Thr Gln Thr Phe Thr Thr Tyr Ser
420 425 430

Asp Asn Gln Pro Gly Val Leu Ile Gln Val Tyr Glu Gly Glu Arg Ala
435 440 445

Met Thr Lys Asp Asn Asn Leu Leu Gly Lys Phe Glu Leu Thr Gly Ile
450 455 460

Pro Pro Ala Pro Arg Gly Val Pro Gln Ile Glu Val Thr Phe Asp Ile
465 470 475 480

Asp Ala Asn Gly Ile Leu Asn Val Ser Ala Val Asp Lys Ser Thr Gly
485 490 495

Lys Glu Asn Lys Ile Thr Ile Thr Asn Asp Lys Gly Arg Leu Ser Lys
500 505 510

Glu Asp Ile Glu Arg Met Val Gln Glu Ala Glu Lys Tyr Lys Ala Glu
515 520 525

Asp Glu Lys Gln Arg Asp Lys Val Ser Ser Lys Asn Ser Leu Glu Ser
530 535 540

Tyr Ala Phe Asn Met Lys Ala Thr Val Glu Asp Glu Lys Leu Gln Gly
545 550 555 560

Lys Ile Asn Asp Glu Asp Lys Gln Lys Ile Leu Asp Lys Cys Asn Glu
565 570 575

Ile Ile Asn Trp Leu Asp Lys Asn Gln Thr Ala Glu Lys Glu Glu Phe
580 585 590

Glu His Gln Gln Lys Glu Leu Glu Lys Val Cys Asn Pro Ile Ile Thr
595 600 605

Lys Leu Tyr Gln Ser Ala Gly Gly Met Pro Gly Gly Met Pro Gly Gly
610 615 620

Phe Pro Gly Gly Gly Ala Pro Pro Ser Gly Gly Ala Ser Ser Gly Pro
625 630 635 640

Thr Ile Glu Glu Val Asp
645

<210> SEQ ID NO 78
<211> LENGTH: 632
<212> TYPE: PRT
<213> ORGANISM: Homo sapiens

<400> SEQUENCE: 78

Ala Asp Leu Ile Asn Asn Leu Gly Thr Ile Ala Lys Ser Gly Thr Lys
1 5 10 15

Ala Phe Met Glu Ala Leu Gln Ala Gly Ala Asp Ile Ser Met Ile Gly
20 25 30

Gln Phe Gly Val Gly Phe Tyr Ser Ala Tyr Leu Val Ala Glu Lys Val
35 40 45

Thr Val Ile Thr Lys His Asn Asp Asp Glu Gln Tyr Ala Trp Glu Ser
50 55 60

```
Ser Ala Gly Gly Ser Phe Thr Val Arg Thr Asp Thr Gly Glu Pro Met
65                  70                  75                  80

Gly Arg Gly Thr Lys Val Ile Leu His Leu Lys Glu Asp Gln Thr Glu
                85                  90                  95

Tyr Leu Glu Glu Arg Arg Ile Lys Glu Ile Val Lys Lys His Ser Gln
            100                 105                 110

Phe Ile Gly Tyr Pro Ile Thr Leu Phe Val Glu Lys Glu Arg Asp Lys
        115                 120                 125

Glu Val Ser Asp Asp Glu Ala Glu Glu Lys Glu Asp Lys Glu Glu Glu
    130                 135                 140

Lys Glu Lys Glu Glu Lys Glu Ser Glu Asp Lys Pro Glu Ile Glu Asp
145                 150                 155                 160

Val Gly Ser Asp Glu Glu Glu Glu Lys Lys Asp Gly Asp Lys Lys Lys
                165                 170                 175

Lys Lys Lys Ile Lys Glu Lys Tyr Ile Asp Gln Glu Glu Leu Asn Lys
            180                 185                 190

Thr Lys Pro Ile Trp Thr Arg Asn Pro Asp Asp Ile Thr Asn Glu Glu
        195                 200                 205

Tyr Gly Glu Phe Tyr Lys Ser Leu Thr Asn Asp Trp Glu Asp His Leu
    210                 215                 220

Ala Val Lys His Phe Ser Val Glu Gly Gln Leu Glu Phe Arg Ala Leu
225                 230                 235                 240

Leu Phe Val Pro Arg Arg Ala Pro Phe Asp Leu Phe Glu Asn Arg Lys
                245                 250                 255

Lys Lys Asn Asn Ile Lys Leu Tyr Val Arg Arg Val Phe Ile Met Asp
            260                 265                 270

Asn Cys Glu Glu Leu Ile Pro Glu Tyr Leu Asn Phe Ile Arg Gly Val
        275                 280                 285

Val Asp Ser Glu Asp Leu Pro Leu Asn Ile Ser Arg Glu Met Leu Gln
    290                 295                 300

Gln Ser Lys Ile Leu Lys Val Ile Arg Lys Asn Leu Val Lys Lys Cys
305                 310                 315                 320

Leu Glu Leu Phe Thr Glu Leu Ala Glu Asp Lys Glu Asn Tyr Lys Lys
                325                 330                 335

Phe Tyr Glu Gln Phe Ser Lys Asn Ile Lys Leu Gly Ile His Glu Asp
            340                 345                 350

Ser Gln Asn Arg Lys Lys Leu Ser Glu Leu Leu Arg Tyr Tyr Thr Ser
        355                 360                 365

Ala Ser Gly Asp Glu Met Val Ser Leu Lys Asp Tyr Cys Thr Arg Met
    370                 375                 380

Lys Glu Asn Gln Lys His Ile Tyr Tyr Ile Thr Gly Glu Thr Lys Asp
385                 390                 395                 400

Gln Val Ala Asn Ser Ala Phe Val Glu Arg Leu Arg Lys His Gly Leu
                405                 410                 415

Glu Val Ile Tyr Met Ile Glu Pro Ile Asp Glu Tyr Cys Val Gln Gln
            420                 425                 430

Leu Lys Glu Phe Glu Gly Lys Thr Leu Val Ser Val Thr Lys Glu Gly
        435                 440                 445

Leu Glu Leu Pro Glu Asp Glu Glu Glu Lys Lys Lys Gln Glu Glu Lys
    450                 455                 460

Lys Thr Lys Phe Glu Asn Leu Cys Lys Ile Met Lys Asp Ile Leu Glu
465                 470                 475                 480
```

```
Lys Lys Val Glu Lys Val Val Val Ser Asn Arg Leu Val Thr Ser Pro
                485                 490                 495

Cys Cys Ile Val Thr Ser Thr Tyr Gly Trp Thr Ala Asn Met Glu Arg
            500                 505                 510

Ile Met Lys Ala Gln Ala Leu Arg Asp Asn Ser Thr Met Gly Tyr Met
        515                 520                 525

Ala Ala Lys Lys His Leu Glu Ile Asn Pro Asp His Ser Ile Ile Glu
    530                 535                 540

Thr Leu Arg Gln Lys Ala Glu Ala Asp Lys Asn Asp Lys Ser Val Lys
545                 550                 555                 560

Asp Leu Val Ile Leu Leu Tyr Glu Thr Ala Leu Leu Ser Ser Gly Phe
                565                 570                 575

Ser Leu Glu Asp Pro Gln Thr His Ala Asn Arg Ile Tyr Arg Met Ile
            580                 585                 590

Lys Leu Gly Leu Gly Ile Asp Glu Asp Asp Pro Thr Ala Asp Asp Thr
        595                 600                 605

Ser Ala Ala Val Thr Glu Glu Met Pro Pro Leu Glu Gly Asp Asp Asp
    610                 615                 620

Thr Ser Arg Met Glu Glu Val Asp
625                 630


<210> SEQ ID NO 79
<211> LENGTH: 824
<212> TYPE: PRT
<213> ORGANISM: Homo sapiens

<400> SEQUENCE: 79

Met Pro Glu Glu Thr Gln Thr Gln Asp Gln Pro Met Glu Glu Glu Glu
1               5                   10                  15

Val Glu Thr Phe Ala Phe Gln Ala Glu Ile Ala Gln Leu Met Ser Leu
            20                  25                  30

Ile Ile Asn Thr Phe Tyr Ser Asn Lys Glu Ile Phe Leu Arg Glu Leu
        35                  40                  45

Ile Ser Asn Ser Ser Asp Ala Leu Asp Lys Ile Arg Tyr Glu Ser Leu
    50                  55                  60

Thr Asp Pro Ser Lys Leu Asp Ser Gly Lys Glu Leu His Ile Asn Leu
65                  70                  75                  80

Ile Pro Asn Lys Gln Asp Arg Thr Leu Thr Ile Val Asp Thr Gly Ile
                85                  90                  95

Gly Met Thr Lys Met Pro Glu Glu Val His His Gly Glu Glu Glu Val
            100                 105                 110

Glu Thr Phe Ala Phe Gln Ala Glu Ile Ala Gln Leu Met Ser Leu Ile
        115                 120                 125

Ile Asn Thr Phe Tyr Ser Asn Lys Glu Ile Phe Leu Arg Glu Leu Ile
    130                 135                 140

Ser Asn Ala Ser Asp Ala Leu Asp Lys Ile Arg Tyr Glu Ser Leu Thr
145                 150                 155                 160

Asp Pro Ser Lys Leu Asp Ser Gly Lys Glu Leu Lys Ile Asp Ile Ile
                165                 170                 175

Pro Asn Pro Gln Glu Arg Thr Leu Thr Leu Val Asp Thr Gly Ile Gly
            180                 185                 190

Met Thr Lys Ala Asp Leu Ile Asn Asn Leu Gly Thr Ile Ala Lys Ser
        195                 200                 205

Gly Thr Lys Ala Phe Met Glu Ala Leu Gln Ala Gly Ala Asp Ile Ser
    210                 215                 220
```

```
Met Ile Gly Gln Phe Gly Val Gly Phe Tyr Ser Ala Tyr Leu Val Ala
225                 230                 235                 240

Glu Lys Val Val Val Ile Thr Lys His Asn Asp Asp Glu Gln Tyr Ala
                245                 250                 255

Trp Glu Ser Ser Ala Gly Gly Ser Phe Thr Val Arg Ala Asp His Gly
            260                 265                 270

Glu Pro Ile Gly Arg Gly Thr Lys Val Ile Leu His Leu Lys Glu Asp
        275                 280                 285

Gln Thr Glu Tyr Leu Glu Glu Arg Arg Val Lys Glu Val Val Lys Lys
    290                 295                 300

His Ser Gln Phe Ile Gly Tyr Pro Ile Thr Leu Tyr Leu Glu Lys Glu
305                 310                 315                 320

Arg Glu Lys Glu Ile Ser Asp Asp Glu Ala Glu Glu Glu Lys Gly Glu
                325                 330                 335

Lys Glu Glu Glu Asp Lys Asp Asp Glu Glu Lys Pro Lys Ile Glu Asp
            340                 345                 350

Val Gly Ser Asp Glu Glu Asp Asp Ser Gly Lys Asp Lys Lys Lys Lys
        355                 360                 365

Thr Lys Lys Ile Lys Glu Lys Tyr Ile Asp Gln Glu Glu Leu Asn Lys
    370                 375                 380

Thr Lys Pro Ile Trp Thr Arg Asn Pro Asp Asp Ile Thr Gln Glu Glu
385                 390                 395                 400

Tyr Gly Glu Phe Tyr Lys Ser Leu Thr Asn Asp Trp Glu Asp His Leu
                405                 410                 415

Ala Val Lys His Phe Ser Val Glu Gly Gln Leu Glu Phe Arg Ala Leu
            420                 425                 430

Leu Phe Ile Pro Arg Arg Ala Pro Phe Asp Leu Phe Glu Asn Lys Lys
        435                 440                 445

Lys Lys Asn Asn Ile Lys Leu Tyr Val Arg Arg Val Phe Ile Met Asp
    450                 455                 460

Ser Cys Asp Glu Leu Ile Pro Glu Tyr Leu Asn Phe Ile Arg Gly Val
465                 470                 475                 480

Val Asp Ser Glu Asp Leu Pro Leu Asn Ile Ser Arg Glu Met Leu Gln
                485                 490                 495

Gln Ser Lys Ile Leu Lys Val Ile Arg Lys Asn Ile Val Lys Lys Cys
            500                 505                 510

Leu Glu Leu Phe Ser Glu Leu Ala Glu Asp Lys Glu Asn Tyr Lys Lys
        515                 520                 525

Phe Tyr Glu Ala Phe Ser Lys Asn Leu Lys Leu Gly Ile His Glu Asp
    530                 535                 540

Ser Thr Asn Arg Arg Arg Leu Ser Glu Leu Leu Arg Tyr His Thr Ser
545                 550                 555                 560

Gln Ser Gly Asp Glu Met Thr Ser Leu Ser Glu Tyr Val Ser Arg Met
                565                 570                 575

Lys Glu Thr Gln Lys Ser Ile Tyr Tyr Ile Thr Gly Glu Ser Lys Glu
            580                 585                 590

Gln Val Ala Asn Ser Ala Phe Val Glu Arg Val Arg Lys Arg Gly Phe
        595                 600                 605

Glu Val Val Tyr Met Thr Glu Pro Ile Asp Glu Tyr Cys Val Gln Gln
    610                 615                 620

Leu Lys Glu Phe Asp Gly Lys Ser Leu Val Ser Val Thr Lys Glu Gly
625                 630                 635                 640
```

```
Leu Glu Leu Pro Glu Asp Glu Glu Glu Lys Lys Lys Met Glu Glu Ser
                645                 650                 655

Lys Ala Lys Phe Glu Asn Leu Cys Lys Leu Met Lys Glu Ile Leu Asp
            660                 665                 670

Lys Lys Val Glu Lys Val Thr Ile Ser Asn Arg Leu Val Ser Ser Pro
        675                 680                 685

Cys Cys Ile Val Thr Ser Thr Tyr Gly Trp Thr Ala Asn Met Glu Arg
    690                 695                 700

Ile Met Lys Ala Gln Ala Leu Arg Asp Asn Ser Thr Met Gly Tyr Met
705                 710                 715                 720

Met Ala Lys Lys His Leu Glu Ile Asn Pro Asp His Pro Ile Val Glu
                725                 730                 735

Thr Leu Arg Gln Lys Ala Glu Ala Asp Lys Asn Asp Lys Ala Val Lys
            740                 745                 750

Asp Leu Val Val Leu Leu Phe Glu Thr Ala Leu Leu Ser Ser Gly Phe
        755                 760                 765

Ser Leu Glu Asp Pro Gln Thr His Ser Asn Arg Ile Tyr Arg Met Ile
    770                 775                 780

Lys Leu Gly Leu Gly Ile Asp Glu Asp Glu Val Ala Ala Glu Glu Pro
785                 790                 795                 800

Asn Ala Ala Val Pro Asp Glu Ile Pro Pro Leu Glu Gly Asp Glu Asp
                805                 810                 815

Ala Ser Arg Met Glu Glu Val Asp
            820
```

<210> SEQ ID NO 80
<211> LENGTH: 374
<212> TYPE: PRT
<213> ORGANISM: Homo sapiens

<400> SEQUENCE: 80

```
Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190
```

Val Leu Asn Ala Ser Val Thr Ser Pro Leu Leu Glu Gly Asn Leu Val
195 200 205

Thr Leu Ser Cys Glu Thr Lys Leu Leu Leu Gln Arg Pro Gly Leu Gln
210 215 220

Leu Tyr Phe Ser Phe Tyr Met Gly Ser Lys Thr Leu Arg Gly Arg Asn
225 230 235 240

Thr Ser Ser Glu Tyr Gln Ile Leu Thr Ala Arg Arg Glu Asp Ser Gly
245 250 255

Leu Tyr Trp Cys Glu Ala Ala Thr Glu Asp Gly Asn Val Leu Lys Arg
260 265 270

Ser Pro Glu Leu Glu Leu Gln Val Leu Gly Leu Gln Leu Pro Thr Pro
275 280 285

Val Trp Phe His Val Leu Phe Tyr Leu Ala Val Gly Ile Met Phe Leu
290 295 300

Val Asn Thr Val Leu Trp Val Thr Ile Arg Lys Glu Leu Lys Arg Lys
305 310 315 320

Lys Lys Trp Asp Leu Glu Ile Ser Leu Asp Ser Gly His Glu Lys Lys
325 330 335

Val Ile Ser Ser Leu Gln Glu Asp Arg His Leu Glu Glu Glu Leu Lys
340 345 350

Cys Gln Glu Gln Lys Glu Glu Gln Leu Gln Glu Gly Val His Arg Lys
355 360 365

Glu Pro Gln Gly Ala Thr
370

<210> SEQ ID NO 81
<211> LENGTH: 525
<212> TYPE: PRT
<213> ORGANISM: Homo sapiens

<400> SEQUENCE: 81

Met Lys Ala Leu Ile Ala Ala Leu Leu Leu Ile Thr Leu Gln Tyr Ser
1 5 10 15

Cys Ala Val Ser Pro Thr Asp Cys Ser Ala Val Glu Pro Glu Ala Glu
20 25 30

Lys Ala Leu Asp Leu Ile Asn Lys Arg Arg Arg Asp Gly Tyr Leu Phe
35 40 45

Gln Leu Leu Arg Ile Ala Asp Ala His Leu Asp Arg Val Glu Asn Thr
50 55 60

Thr Val Tyr Tyr Leu Val Leu Asp Val Gln Glu Ser Asp Cys Ser Val
65 70 75 80

Leu Ser Arg Lys Tyr Trp Asn Asp Cys Glu Pro Pro Asp Ser Arg Arg
85 90 95

Pro Ser Glu Ile Val Ile Gly Gln Cys Lys Val Ile Ala Thr Arg His
100 105 110

Ser His Glu Ser Gln Asp Leu Arg Val Ile Asp Phe Asn Cys Thr Thr
115 120 125

Ser Ser Val Ser Ser Ala Leu Ala Asn Thr Lys Asp Ser Pro Val Leu
130 135 140

Ile Asp Phe Phe Glu Asp Thr Glu Arg Tyr Arg Lys Gln Ala Asn Lys
145 150 155 160

Ala Leu Glu Lys Tyr Lys Glu Glu Asn Asp Asp Phe Ala Ser Phe Arg
165 170 175

Val Asp Arg Ile Glu Arg Val Ala Arg Val Arg Gly Gly Glu Gly Thr

```
            180                 185                 190

Gly Tyr Phe Val Asp Phe Ser Val Arg Asn Cys Pro Arg His His Phe
        195                 200                 205

Pro Arg His Pro Asn Val Phe Gly Phe Cys Arg Ala Asp Leu Phe Tyr
    210                 215                 220

Asp Val Glu Ala Leu Asp Leu Glu Ser Pro Lys Asn Leu Val Ile Asn
225                 230                 235                 240

Cys Glu Val Phe Asp Pro Gln Glu His Glu Asn Ile Asn Gly Val Pro
                245                 250                 255

Pro His Leu Gly His Pro Phe His Trp Gly Gly His Glu Arg Ser Ser
            260                 265                 270

Thr Thr Lys Pro Pro Phe Lys Pro His Gly Ser Arg Asp His His His
        275                 280                 285

Pro His Lys Pro His Glu His Gly Pro Pro Pro Pro Pro Asp Glu Arg
    290                 295                 300

Asp His Ser His Gly Pro Pro Leu Pro Gln Gly Pro Pro Pro Leu Leu
305                 310                 315                 320

Pro Met Ser Cys Ser Ser Cys Gln His Ala Thr Phe Gly Thr Asn Gly
                325                 330                 335

Ala Gln Arg His Ser His Asn Asn Asn Ser Ser Asp Leu His Pro His
            340                 345                 350

Lys His His Ser His Glu Gln His Pro His Gly His His Pro His Ala
        355                 360                 365

His His Pro His Glu His Asp Thr His Arg Gln His Pro His Gly His
    370                 375                 380

His Pro His Gly His His Pro His Gly His His Pro His Gly His His
385                 390                 395                 400

Pro His Gly His His Pro His Cys His Asp Phe Gln Asp Tyr Gly Pro
                405                 410                 415

Cys Asp Pro Pro Pro His Asn Gln Gly His Cys Cys His Gly His Gly
            420                 425                 430

Pro Pro Pro Gly His Leu Arg Arg Arg Gly Pro Gly Lys Gly Pro Arg
        435                 440                 445

Pro Phe His Cys Arg Gln Ile Gly Ser Val Tyr Arg Leu Pro Pro Leu
    450                 455                 460

Arg Lys Gly Glu Val Leu Pro Leu Pro Glu Ala Asn Phe Pro Ser Phe
465                 470                 475                 480

Pro Leu Pro His His Lys His Pro Leu Lys Pro Asp Asn Gln Pro Phe
                485                 490                 495

Pro Gln Ser Val Ser Glu Ser Cys Pro Gly Lys Phe Lys Ser Gly Phe
            500                 505                 510

Pro Gln Val Ser Met Phe Phe Thr His Thr Phe Pro Lys
        515                 520                 525


<210> SEQ ID NO 82
<211> LENGTH: 509
<212> TYPE: PRT
<213> ORGANISM: Homo sapiens

<400> SEQUENCE: 82

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30
```

```
Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
```

-continued

```
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu Cys Ile Cys
            500                 505
```

<210> SEQ ID NO 83
<211> LENGTH: 214
<212> TYPE: PRT
<213> ORGANISM: Homo sapiens

<400> SEQUENCE: 83

```
Met Arg Pro Lys Thr Gly Gln Val Gly Cys Glu Thr Pro Glu Glu Leu
1               5                   10                  15

Gly Pro Gly Pro Arg Gln Arg Trp Pro Leu Leu Leu Leu Gly Leu Ala
            20                  25                  30

Met Val Ala His Gly Leu Leu Arg Pro Met Val Ala Pro Gln Ser Gly
        35                  40                  45

Asp Pro Asp Pro Gly Ala Ser Val Gly Ser Ser Arg Ser Ser Leu Arg
    50                  55                  60

Ser Leu Trp Gly Arg Leu Leu Leu Gln Pro Ser Pro Gln Arg Ala Asp
65                  70                  75                  80

Pro Arg Cys Trp Pro Arg Gly Phe Trp Ser Glu Pro Gln Ser Leu Cys
                85                  90                  95

Tyr Val Phe Gly Thr Gly Thr Lys Val Thr Val Leu Gly Gln Pro Lys
            100                 105                 110

Ala Asn Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 84
<211> LENGTH: 313
<212> TYPE: PRT
<213> ORGANISM: Homo sapiens

<400> SEQUENCE: 84

```
Met Asn Gln Leu Ser Phe Leu Leu Phe Leu Ile Ala Thr Thr Arg Gly
1               5                   10                  15

Trp Ser Thr Asp Glu Ala Asn Thr Tyr Phe Lys Glu Trp Thr Cys Ser
            20                  25                  30

Ser Ser Pro Ser Leu Pro Arg Ser Cys Lys Glu Ile Lys Asp Glu Cys
        35                  40                  45

Pro Ser Ala Phe Asp Gly Leu Tyr Phe Leu Arg Thr Glu Asn Gly Val
```

```
    50                  55                  60

Ile Tyr Gln Thr Phe Cys Asp Met Thr Ser Gly Gly Gly Gly Trp Thr
65                  70                  75                  80

Leu Val Ala Ser Val His Glu Asn Asp Met Arg Gly Lys Cys Thr Val
                85                  90                  95

Gly Asp Arg Trp Ser Ser Gln Gln Gly Ser Lys Ala Val Tyr Pro Glu
            100                 105                 110

Gly Asp Gly Asn Trp Ala Asn Tyr Asn Thr Phe Gly Ser Ala Glu Ala
        115                 120                 125

Ala Thr Ser Asp Asp Tyr Lys Asn Pro Gly Tyr Tyr Asp Ile Gln Ala
    130                 135                 140

Lys Asp Leu Gly Ile Trp His Val Pro Asn Lys Ser Pro Met Gln His
145                 150                 155                 160

Trp Arg Asn Ser Ser Leu Leu Arg Tyr Arg Thr Asp Thr Gly Phe Leu
                165                 170                 175

Gln Thr Leu Gly His Asn Leu Phe Gly Ile Tyr Gln Lys Tyr Pro Val
            180                 185                 190

Lys Tyr Gly Glu Gly Lys Cys Trp Thr Asp Asn Gly Pro Val Ile Pro
        195                 200                 205

Val Val Tyr Asp Phe Gly Asp Ala Gln Lys Thr Ala Ser Tyr Tyr Ser
    210                 215                 220

Pro Tyr Gly Gln Arg Glu Phe Thr Ala Gly Phe Val Gln Phe Arg Val
225                 230                 235                 240

Phe Asn Asn Glu Arg Ala Ala Asn Ala Leu Cys Ala Gly Met Arg Val
                245                 250                 255

Thr Gly Cys Asn Thr Glu His His Cys Ile Gly Gly Gly Gly Tyr Phe
            260                 265                 270

Pro Glu Ala Ser Pro Gln Gln Cys Gly Asp Phe Ser Gly Phe Asp Trp
        275                 280                 285

Ser Gly Tyr Gly Thr His Val Gly Tyr Ser Ser Ser Arg Glu Ile Thr
    290                 295                 300

Glu Ala Ala Val Leu Leu Phe Tyr Arg
305                 310


<210> SEQ ID NO 85
<211> LENGTH: 325
<212> TYPE: PRT
<213> ORGANISM: Homo sapiens

<400> SEQUENCE: 85

Met Leu Ser Met Leu Arg Thr Met Thr Arg Leu Cys Phe Leu Leu Phe
1               5                   10                  15

Phe Ser Val Ala Thr Ser Gly Cys Ser Ala Ala Ala Ala Ser Ser Leu
            20                  25                  30

Glu Met Leu Ser Arg Glu Phe Glu Thr Cys Ala Phe Ser Phe Ser Ser
        35                  40                  45

Leu Pro Arg Ser Cys Lys Glu Ile Lys Glu Arg Cys His Ser Ala Gly
    50                  55                  60

Asp Gly Leu Tyr Phe Leu Arg Thr Lys Asn Gly Val Val Tyr Gln Thr
65                  70                  75                  80

Phe Cys Asp Met Thr Ser Gly Gly Gly Gly Trp Thr Leu Val Ala Ser
                85                  90                  95

Val His Glu Asn Asp Met Arg Gly Lys Cys Thr Val Gly Asp Arg Trp
            100                 105                 110
```

Ser Ser Gln Gln Gly Asn Lys Ala Asp Tyr Pro Glu Gly Asp Gly Asn
115 120 125

Trp Ala Asn Tyr Asn Thr Phe Gly Ser Ala Glu Ala Ala Thr Ser Asp
130 135 140

Asp Tyr Lys Asn Pro Gly Tyr Tyr Asp Ile Gln Ala Lys Asp Leu Gly
145 150 155 160

Ile Trp His Val Pro Asn Lys Ser Pro Met Gln His Trp Arg Asn Ser
165 170 175

Ala Leu Leu Arg Tyr Arg Thr Asn Thr Gly Phe Leu Gln Arg Leu Gly
180 185 190

His Asn Leu Phe Gly Ile Tyr Gln Lys Tyr Pro Val Lys Tyr Arg Ser
195 200 205

Gly Lys Cys Trp Asn Asp Asn Gly Pro Ala Ile Pro Val Val Tyr Asp
210 215 220

Phe Gly Asp Ala Lys Lys Thr Ala Ser Tyr Tyr Ser Pro Tyr Gly Gln
225 230 235 240

Arg Glu Phe Val Ala Gly Phe Val Gln Phe Arg Val Phe Asn Asn Glu
245 250 255

Arg Ala Ala Asn Ala Leu Cys Ala Gly Ile Lys Val Thr Gly Cys Asn
260 265 270

Thr Glu His His Cys Ile Gly Gly Gly Gly Phe Phe Pro Gln Gly Lys
275 280 285

Pro Arg Gln Cys Gly Asp Phe Ser Ala Phe Asp Trp Asp Gly Tyr Gly
290 295 300

Thr His Val Lys Ser Ser Cys Ser Arg Glu Ile Thr Glu Ala Ala Val
305 310 315 320

Leu Leu Phe Tyr Arg
325

<210> SEQ ID NO 86
<211> LENGTH: 745
<212> TYPE: PRT
<213> ORGANISM: Homo sapiens

<400> SEQUENCE: 86

Met Glu Val Met Asn Leu Met Glu Gln Pro Ile Lys Val Thr Glu Trp
1 5 10 15

Gln Gln Thr Tyr Thr Tyr Asp Ser Gly Ile His Ser Gly Ala Asn Thr
20 25 30

Cys Val Pro Ser Val Ser Ser Lys Gly Ile Met Glu Glu Asp Glu Ala
35 40 45

Cys Gly Arg Gln Tyr Thr Leu Lys Lys Thr Thr Thr Tyr Thr Gln Gly
50 55 60

Val Pro Pro Ser Gln Gly Asp Leu Glu Tyr Gln Met Ser Thr Thr Ala
65 70 75 80

Arg Ala Lys Arg Val Arg Glu Ala Met Cys Pro Gly Val Ser Gly Glu
85 90 95

Asp Ser Ser Leu Leu Leu Ala Thr Gln Val Glu Gly Gln Ala Thr Asn
100 105 110

Leu Gln Arg Leu Ala Glu Pro Ser Gln Leu Leu Lys Ser Ala Ile Val
115 120 125

His Leu Ile Asn Tyr Gln Asp Asp Ala Glu Leu Ala Thr Arg Ala Leu
130 135 140

Pro Glu Leu Thr Lys Leu Leu Asn Asp Glu Asp Pro Val Val Val Thr
145 150 155 160

```
Lys Ala Ala Met Ile Val Asn Gln Leu Ser Lys Lys Glu Ala Ser Arg
                165                 170                 175

Arg Ala Leu Met Gly Ser Pro Gln Leu Val Ala Ala Val Val Arg Thr
            180                 185                 190

Met Gln Asn Thr Ser Asp Leu Asp Thr Ala Arg Cys Thr Thr Ser Ile
        195                 200                 205

Leu His Asn Leu Ser His His Arg Glu Gly Leu Leu Ala Ile Phe Lys
    210                 215                 220

Ser Gly Gly Ile Pro Ala Leu Val Arg Met Leu Ser Ser Pro Val Glu
225                 230                 235                 240

Ser Val Leu Phe Tyr Ala Ile Thr Thr Leu His Asn Leu Leu Leu Tyr
                245                 250                 255

Gln Glu Gly Ala Lys Met Ala Val Arg Leu Ala Asp Gly Leu Gln Lys
            260                 265                 270

Met Val Pro Leu Leu Asn Lys Asn Asn Pro Lys Phe Leu Ala Ile Thr
        275                 280                 285

Thr Asp Cys Leu Gln Leu Leu Ala Tyr Gly Asn Gln Glu Ser Lys Leu
    290                 295                 300

Ile Ile Leu Ala Asn Gly Gly Pro Gln Ala Leu Val Gln Ile Met Arg
305                 310                 315                 320

Asn Tyr Ser Tyr Glu Lys Leu Leu Trp Thr Thr Ser Arg Val Leu Lys
                325                 330                 335

Val Leu Ser Val Cys Pro Ser Asn Lys Pro Ala Ile Val Glu Ala Gly
            340                 345                 350

Gly Met Gln Ala Leu Gly Lys His Leu Thr Ser Asn Ser Pro Arg Leu
        355                 360                 365

Val Gln Asn Cys Leu Trp Thr Leu Arg Asn Leu Ser Asp Val Ala Thr
    370                 375                 380

Lys Gln Glu Gly Leu Glu Ser Val Leu Lys Ile Leu Val Asn Gln Leu
385                 390                 395                 400

Ser Val Asp Asp Val Asn Val Leu Thr Cys Ala Thr Gly Thr Leu Ser
                405                 410                 415

Asn Leu Thr Cys Asn Asn Ser Lys Asn Lys Thr Leu Val Thr Gln Asn
            420                 425                 430

Ser Gly Val Glu Ala Leu Ile His Ala Ile Leu Arg Ala Gly Asp Lys
        435                 440                 445

Asp Asp Ile Thr Glu Pro Ala Val Cys Ala Leu Arg His Leu Thr Ser
    450                 455                 460

Arg His Pro Glu Ala Glu Met Ala Gln Asn Ser Val Arg Leu Asn Tyr
465                 470                 475                 480

Gly Ile Pro Ala Ile Val Lys Leu Leu Asn Gln Pro Asn Gln Trp Pro
                485                 490                 495

Leu Val Lys Ala Thr Ile Gly Leu Ile Arg Asn Leu Ala Leu Cys Pro
            500                 505                 510

Ala Asn His Ala Pro Leu Gln Glu Ala Ala Val Ile Pro Arg Leu Val
        515                 520                 525

Gln Leu Leu Val Lys Ala His Gln Asp Ala Gln Arg His Val Ala Ala
    530                 535                 540

Gly Thr Gln Gln Pro Tyr Thr Asp Gly Val Arg Met Glu Glu Ile Val
545                 550                 555                 560

Glu Gly Cys Thr Gly Ala Leu His Ile Leu Ala Arg Asp Pro Met Asn
                565                 570                 575
```

```
Arg Met Glu Ile Phe Arg Leu Asn Thr Ile Pro Leu Phe Val Gln Leu
            580                 585                 590

Leu Tyr Ser Ser Val Glu Asn Ile Gln Arg Val Ala Ala Gly Val Leu
        595                 600                 605

Cys Glu Leu Ala Gln Asp Lys Glu Ala Ala Asp Ala Ile Asp Ala Glu
    610                 615                 620

Gly Ala Ser Ala Pro Leu Met Glu Leu Leu His Ser Arg Asn Glu Gly
625                 630                 635                 640

Thr Ala Thr Tyr Ala Ala Ala Val Leu Phe Arg Ile Ser Glu Asp Lys
                645                 650                 655

Asn Pro Asp Tyr Arg Lys Arg Val Ser Val Glu Leu Thr Asn Ser Leu
            660                 665                 670

Phe Lys His Asp Pro Ala Ala Trp Glu Ala Ala Gln Ser Met Ile Pro
        675                 680                 685

Ile Asn Glu Pro Tyr Gly Asp Asp Met Asp Ala Thr Tyr Arg Pro Met
    690                 695                 700

Tyr Ser Ser Asp Val Pro Leu Asp Pro Leu Glu Met His Met Asp Met
705                 710                 715                 720

Asp Gly Asp Tyr Pro Ile Asp Thr Tyr Ser Asp Gly Leu Arg Pro Pro
                725                 730                 735

Tyr Pro Thr Ala Asp His Met Leu Ala
            740                 745
```

<210> SEQ ID NO 87
<211> LENGTH: 261
<212> TYPE: PRT
<213> ORGANISM: Homo sapiens

<400> SEQUENCE: 87

```
Met Trp Asp Leu Val Leu Ser Ile Ala Leu Ser Val Gly Cys Thr Gly
1               5                   10                  15

Ala Val Pro Leu Ile Gln Ser Arg Ile Val Gly Gly Trp Glu Cys Glu
            20                  25                  30

Lys His Ser Gln Pro Trp Gln Val Ala Val Tyr Ser His Gly Trp Ala
        35                  40                  45

His Cys Gly Gly Val Leu Val His Pro Gln Trp Val Leu Thr Ala Ala
    50                  55                  60

His Cys Leu Lys Lys Asn Ser Gln Val Trp Leu Gly Arg His Asn Leu
65                  70                  75                  80

Phe Glu Pro Glu Asp Thr Gly Gln Arg Val Pro Val Ser His Ser Phe
                85                  90                  95

Pro His Pro Leu Tyr Asn Met Ser Leu Leu Lys His Gln Ser Leu Arg
            100                 105                 110

Pro Asp Glu Asp Ser Ser His Asp Leu Met Leu Leu Arg Leu Ser Glu
        115                 120                 125

Pro Ala Lys Ile Thr Asp Val Val Lys Val Leu Gly Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Arg Pro Arg Ser Leu Gln Cys Val Ser Leu
                165                 170                 175

His Leu Leu Ser Asn Asp Met Cys Ala Arg Ala Tyr Ser Glu Lys Val
            180                 185                 190

Thr Glu Phe Met Leu Cys Ala Gly Leu Trp Thr Gly Gly Lys Asp Thr
        195                 200                 205
```

Cys Gly Gly Asp Ser Gly Gly Pro Leu Val Cys Asn Gly Val Leu Gln
    210                 215                 220

Gly Ile Thr Ser Trp Gly Pro Glu Pro Cys Ala Leu Pro Glu Lys Pro
225                 230                 235                 240

Ala Val Tyr Thr Lys Val Val His Tyr Arg Lys Trp Ile Lys Asp Thr
                245                 250                 255

Ile Ala Ala Asn Pro
            260

<210> SEQ ID NO 88
<211> LENGTH: 1939
<212> TYPE: PRT
<213> ORGANISM: Homo sapiens

<400> SEQUENCE: 88

Met Ser Ser Asp Ser Glu Met Ala Ile Phe Gly Glu Ala Ala Pro Phe
1               5                   10                  15

Leu Arg Lys Ser Glu Arg Glu Arg Ile Glu Ala Gln Asn Lys Pro Phe
            20                  25                  30

Asp Ala Lys Thr Ser Val Phe Val Val Asp Pro Lys Glu Ser Phe Val
        35                  40                  45

Lys Ala Thr Val Gln Ser Arg Glu Gly Gly Lys Val Thr Ala Lys Thr
    50                  55                  60

Glu Ala Gly Ala Thr Val Thr Val Lys Asp Asp Gln Val Phe Pro Met
65                  70                  75                  80

Asn Pro Pro Lys Tyr Asp Lys Ile Glu Asp Met Ala Met Met Thr His
                85                  90                  95

Leu His Glu Pro Ala Val Leu Tyr Asn Leu Lys Glu Arg Tyr Ala Ala
            100                 105                 110

Trp Met Ile Tyr Thr Tyr Ser Gly Leu Phe Cys Val Thr Val Asn Pro
        115                 120                 125

Tyr Lys Trp Leu Pro Val Tyr Asn Ala Glu Val Val Thr Ala Tyr Arg
    130                 135                 140

Gly Lys Lys Arg Gln Glu Ala Pro Pro His Ile Phe Ser Ile Ser Asp
145                 150                 155                 160

Asn Ala Tyr Gln Phe Met Leu Thr Asp Arg Glu Asn Gln Ser Ile Leu
                165                 170                 175

Ile Thr Gly Glu Ser Gly Ala Gly Lys Thr Val Asn Thr Lys Arg Val
            180                 185                 190

Ile Gln Tyr Phe Ala Thr Ile Ala Val Thr Gly Glu Lys Lys Lys Glu
        195                 200                 205

Glu Val Thr Ser Gly Lys Met Gln Gly Thr Leu Glu Asp Gln Ile Ile
    210                 215                 220

Ser Ala Asn Pro Leu Leu Glu Ala Phe Gly Asn Ala Lys Thr Val Arg
225                 230                 235                 240

Asn Asp Asn Ser Ser Arg Phe Gly Lys Phe Ile Arg Ile His Phe Gly
                245                 250                 255

Thr Thr Gly Lys Leu Ala Ser Ala Asp Ile Glu Thr Tyr Leu Leu Glu
            260                 265                 270

Lys Ser Arg Val Thr Phe Gln Leu Lys Ala Glu Arg Ser Tyr His Ile
        275                 280                 285

Phe Tyr Gln Ile Met Ser Asn Lys Lys Pro Asp Leu Ile Glu Met Leu
    290                 295                 300

Leu Ile Thr Thr Asn Pro Tyr Asp Tyr Ala Phe Val Ser Gln Gly Glu

```
305                 310                 315                 320

Ile Thr Val Pro Ser Ile Asp Asp Gln Glu Glu Leu Met Ala Thr Asp
                325                 330                 335

Ser Ala Ile Glu Ile Leu Gly Phe Thr Ser Asp Glu Arg Val Ser Ile
            340                 345                 350

Tyr Lys Leu Thr Gly Ala Val Met His Tyr Gly Asn Met Lys Phe Lys
        355                 360                 365

Gln Lys Gln Arg Glu Glu Gln Ala Glu Pro Asp Gly Thr Glu Val Ala
    370                 375                 380

Asp Lys Ala Ala Tyr Leu Gln Asn Leu Asn Ser Ala Asp Leu Leu Lys
385                 390                 395                 400

Ala Leu Cys Tyr Pro Arg Val Lys Val Gly Asn Glu Tyr Val Thr Lys
                405                 410                 415

Gly Gln Thr Val Gln Gln Val Tyr Asn Ala Val Gly Ala Leu Ala Lys
            420                 425                 430

Ala Val Tyr Asp Lys Met Phe Leu Trp Met Val Thr Arg Ile Asn Gln
        435                 440                 445

Gln Leu Asp Thr Lys Gln Pro Arg Gln Tyr Phe Ile Gly Val Leu Asp
    450                 455                 460

Ile Ala Gly Phe Glu Ile Phe Asp Phe Asn Ser Leu Glu Gln Leu Cys
465                 470                 475                 480

Ile Asn Phe Thr Asn Glu Lys Leu Gln Gln Phe Phe Asn His His Met
                485                 490                 495

Phe Val Leu Glu Gln Glu Glu Tyr Lys Lys Glu Gly Ile Glu Trp Thr
            500                 505                 510

Phe Ile Asp Phe Gly Met Asp Leu Ala Ala Cys Ile Glu Leu Ile Glu
        515                 520                 525

Lys Pro Met Gly Ile Phe Ser Ile Leu Glu Glu Glu Cys Met Phe Pro
    530                 535                 540

Lys Ala Thr Asp Thr Ser Phe Lys Asn Lys Leu Tyr Glu Gln His Leu
545                 550                 555                 560

Gly Lys Ser Asn Asn Phe Gln Lys Pro Lys Pro Ala Lys Gly Lys Pro
                565                 570                 575

Glu Ala His Phe Ser Leu Ile His Tyr Ala Gly Thr Val Asp Tyr Asn
            580                 585                 590

Ile Ala Gly Trp Leu Asp Lys Asn Lys Asp Pro Leu Asn Glu Thr Val
        595                 600                 605

Val Gly Leu Tyr Gln Lys Ser Ala Met Lys Thr Leu Ala Leu Leu Phe
    610                 615                 620

Val Gly Ala Thr Gly Ala Glu Ala Glu Ala Gly Gly Gly Lys Lys Gly
625                 630                 635                 640

Gly Lys Lys Lys Gly Ser Ser Phe Gln Thr Val Ser Ala Leu Phe Arg
                645                 650                 655

Glu Asn Leu Asn Lys Leu Met Thr Asn Leu Arg Ser Thr His Pro His
            660                 665                 670

Phe Val Arg Cys Ile Ile Pro Asn Glu Thr Lys Thr Pro Gly Ala Met
        675                 680                 685

Glu His Glu Leu Val Leu His Gln Leu Arg Cys Asn Gly Val Leu Glu
    690                 695                 700

Gly Ile Arg Ile Cys Arg Lys Gly Phe Pro Ser Arg Ile Leu Tyr Ala
705                 710                 715                 720

Asp Phe Lys Gln Arg Tyr Lys Val Leu Asn Ala Ser Ala Ile Pro Glu
                725                 730                 735
```

```
Gly Gln Phe Ile Asp Ser Lys Lys Ala Ser Glu Lys Leu Leu Gly Ser
            740                 745                 750

Ile Asp Ile Asp His Thr Gln Tyr Lys Phe Gly His Thr Lys Val Phe
        755                 760                 765

Phe Lys Ala Gly Leu Leu Gly Leu Leu Glu Glu Met Arg Asp Glu Lys
    770                 775                 780

Leu Ala Gln Leu Ile Thr Arg Thr Gln Ala Met Cys Arg Gly Phe Leu
785                 790                 795                 800

Ala Arg Val Glu Tyr Gln Lys Met Val Glu Arg Arg Glu Ser Ile Phe
                805                 810                 815

Cys Ile Gln Tyr Asn Val Arg Ala Phe Met Asn Val Lys His Trp Pro
            820                 825                 830

Trp Met Lys Leu Tyr Phe Lys Ile Lys Pro Leu Leu Lys Ser Ala Glu
        835                 840                 845

Thr Glu Lys Glu Met Ala Asn Met Lys Glu Glu Phe Glu Lys Thr Lys
    850                 855                 860

Glu Glu Leu Ala Lys Thr Glu Ala Lys Arg Lys Glu Leu Glu Glu Lys
865                 870                 875                 880

Met Val Thr Leu Met Gln Glu Lys Asn Asp Leu Gln Leu Gln Val Gln
                885                 890                 895

Ala Glu Ala Asp Ser Leu Ala Asp Ala Glu Glu Arg Cys Asp Gln Leu
            900                 905                 910

Ile Lys Thr Lys Ile Gln Leu Glu Ala Lys Ile Lys Glu Val Thr Glu
        915                 920                 925

Arg Ala Glu Asp Glu Glu Glu Ile Asn Ala Glu Leu Thr Ala Lys Lys
    930                 935                 940

Arg Lys Leu Glu Asp Glu Cys Ser Glu Leu Lys Lys Asp Ile Asp Asp
945                 950                 955                 960

Leu Glu Leu Thr Leu Ala Lys Val Glu Lys Glu Lys His Ala Thr Glu
                965                 970                 975

Asn Lys Val Lys Asn Leu Thr Glu Glu Met Ala Gly Leu Asp Glu Thr
            980                 985                 990

Ile Ala Lys Leu Thr Lys Glu Lys  Lys Ala Leu Gln Glu  Ala His Gln
        995                 1000                1005

Gln Thr  Leu Asp Asp Leu Gln  Ala Glu Glu Asp Lys  Val Asn Thr
    1010                1015                1020

Leu Thr  Lys Ala Lys Ile Lys  Leu Glu Gln Gln Val  Asp Asp Leu
    1025                1030                1035

Glu Gly  Ser Leu Glu Gln Glu  Lys Lys Ile Arg Met  Asp Leu Glu
    1040                1045                1050

Arg Ala  Lys Arg Lys Leu Glu  Gly Asp Leu Lys Leu  Ala Gln Glu
    1055                1060                1065

Ser Thr  Met Asp Ile Glu Asn  Asp Lys Gln Gln Leu  Asp Glu Lys
    1070                1075                1080

Leu Lys  Lys Lys Glu Phe Glu  Met Ser Gly Leu Gln  Ser Lys Ile
    1085                1090                1095

Glu Asp  Glu Gln Ala Leu Gly  Met Gln Leu Gln Lys  Lys Ile Lys
    1100                1105                1110

Glu Leu  Gln Ala Arg Ile Glu  Glu Leu Glu Glu Glu  Ile Glu Ala
    1115                1120                1125

Glu Arg  Ala Ser Arg Ala Lys  Ala Glu Lys Gln Arg  Ser Asp Leu
    1130                1135                1140
```

```
Ser Arg  Glu Leu Glu Glu Ile  Ser Glu Arg Leu Glu  Glu Ala Gly
    1145                 1150                 1155

Gly Ala  Thr Ser Ala Gln Ile  Glu Met Asn Lys Lys  Arg Glu Ala
    1160                 1165                 1170

Glu Phe  Gln Lys Met Arg Arg  Asp Leu Glu Glu Ala  Thr Leu Gln
    1175                 1180                 1185

His Glu  Ala Thr Ala Ala Thr  Leu Arg Lys Lys His  Ala Asp Ser
    1190                 1195                 1200

Val Ala  Glu Leu Gly Glu Gln  Ile Asp Asn Leu Gln  Arg Val Lys
    1205                 1210                 1215

Gln Lys  Leu Glu Lys Glu Lys  Ser Glu Met Lys Met  Glu Ile Asp
    1220                 1225                 1230

Asp Leu  Ala Ser Asn Met Glu  Thr Val Ser Lys Ala  Lys Gly Asn
    1235                 1240                 1245

Leu Glu  Lys Met Cys Arg Ala  Leu Glu Asp Gln Leu  Ser Glu Ile
    1250                 1255                 1260

Lys Thr  Lys Glu Glu Glu Gln  Gln Arg Leu Ile Asn  Asp Leu Thr
    1265                 1270                 1275

Ala Gln  Arg Ala Arg Leu Gln  Thr Glu Ser Gly Glu  Tyr Ser Arg
    1280                 1285                 1290

Gln Leu  Asp Glu Lys Asp Thr  Leu Val Ser Gln Leu  Ser Arg Gly
    1295                 1300                 1305

Lys Gln  Ala Phe Thr Gln Gln  Ile Glu Glu Leu Lys  Arg Gln Leu
    1310                 1315                 1320

Glu Glu  Glu Ile Lys Ala Lys  Ser Ala Leu Ala His  Ala Leu Gln
    1325                 1330                 1335

Ser Ser  Arg His Asp Cys Asp  Leu Leu Arg Glu Gln  Tyr Glu Glu
    1340                 1345                 1350

Glu Gln  Glu Ala Lys Ala Glu  Leu Gln Arg Ala Met  Ser Lys Ala
    1355                 1360                 1365

Asn Ser  Glu Val Ala Gln Trp  Arg Thr Lys Tyr Glu  Thr Asp Ala
    1370                 1375                 1380

Ile Gln  Arg Thr Glu Glu Leu  Glu Glu Ala Lys Lys  Lys Leu Ala
    1385                 1390                 1395

Gln Arg  Leu Gln Asp Ala Glu  Glu His Val Glu Ala  Val Asn Ala
    1400                 1405                 1410

Lys Cys  Ala Ser Leu Glu Lys  Thr Lys Gln Arg Leu  Gln Asn Glu
    1415                 1420                 1425

Val Glu  Asp Leu Met Ile Asp  Val Glu Arg Thr Asn  Ala Ala Cys
    1430                 1435                 1440

Ala Ala  Leu Asp Lys Lys Gln  Arg Asn Phe Asp Lys  Ile Leu Ala
    1445                 1450                 1455

Glu Trp  Lys Gln Lys Cys Glu  Glu Thr His Ala Glu  Leu Glu Ala
    1460                 1465                 1470

Ser Gln  Lys Glu Ser Arg Ser  Leu Ser Thr Glu Leu  Phe Lys Ile
    1475                 1480                 1485

Lys Asn  Ala Tyr Glu Glu Ser  Leu Asp Gln Leu Glu  Thr Leu Lys
    1490                 1495                 1500

Arg Glu  Asn Lys Asn Leu Gln  Gln Glu Ile Ser Asp  Leu Thr Glu
    1505                 1510                 1515

Gln Ile  Ala Glu Gly Gly Lys  Arg Ile His Glu Leu  Glu Lys Ile
    1520                 1525                 1530

Lys Lys  Gln Val Glu Gln Glu  Lys Ser Glu Leu Gln  Ala Ala Leu
```

```
    1535                1540                1545

Glu Glu  Ala Glu Ala Ser Leu  Glu His Glu Glu Gly  Lys Ile Leu
    1550                1555                1560

Arg Ile  Gln Leu Glu Leu Asn  Gln Val Lys Ser Glu  Val Asp Arg
    1565                1570                1575

Lys Ile  Ala Glu Lys Asp Glu  Glu Ile Asp Gln Met  Lys Arg Asn
    1580                1585                1590

His Ile  Arg Ile Val Glu Ser  Met Gln Ser Thr Leu  Asp Ala Glu
    1595                1600                1605

Ile Arg  Ser Arg Asn Asp Ala  Ile Arg Leu Lys Lys  Lys Met Glu
    1610                1615                1620

Gly Asp  Leu Asn Glu Met Glu  Ile Gln Leu Asn His  Ala Asn Arg
    1625                1630                1635

Met Ala  Ala Glu Ala Leu Arg  Asn Tyr Arg Asn Thr  Gln Ala Ile
    1640                1645                1650

Leu Lys  Asp Thr Gln Leu His  Leu Asp Asp Ala Leu  Arg Ser Gln
    1655                1660                1665

Glu Asp  Leu Lys Glu Gln Leu  Ala Met Val Glu Arg  Arg Ala Asn
    1670                1675                1680

Leu Leu  Gln Ala Glu Ile Glu  Glu Leu Arg Ala Thr  Leu Glu Gln
    1685                1690                1695

Thr Glu  Arg Ser Arg Lys Ile  Ala Glu Gln Glu Leu  Leu Asp Ala
    1700                1705                1710

Ser Glu  Arg Val Gln Leu Leu  His Thr Gln Asn Thr  Ser Leu Ile
    1715                1720                1725

Asn Thr  Lys Lys Lys Leu Glu  Thr Asp Ile Ser Gln  Ile Gln Gly
    1730                1735                1740

Glu Met  Glu Asp Ile Ile Gln  Glu Ala Arg Asn Ala  Glu Glu Lys
    1745                1750                1755

Ala Lys  Lys Ala Ile Thr Asp  Ala Ala Met Met Ala  Glu Glu Leu
    1760                1765                1770

Lys Lys  Glu Gln Asp Thr Ser  Ala His Leu Glu Arg  Met Lys Lys
    1775                1780                1785

Asn Leu  Glu Gln Thr Val Lys  Asp Leu Gln His Arg  Leu Asp Glu
    1790                1795                1800

Ala Glu  Gln Leu Ala Leu Lys  Gly Gly Lys Lys Gln  Ile Gln Lys
    1805                1810                1815

Leu Glu  Ala Arg Val Arg Glu  Leu Glu Gly Glu Val  Glu Ser Glu
    1820                1825                1830

Gln Lys  Arg Asn Val Glu Ala  Val Lys Gly Leu Arg  Lys His Glu
    1835                1840                1845

Arg Lys  Val Lys Glu Leu Thr  Tyr Gln Thr Glu Glu  Asp Arg Lys
    1850                1855                1860

Asn Ile  Leu Arg Leu Gln Asp  Leu Val Asp Lys Leu  Gln Ala Lys
    1865                1870                1875

Val Lys  Ser Tyr Lys Arg Gln  Ala Glu Glu Ala Glu  Glu Gln Ser
    1880                1885                1890

Asn Val  Asn Leu Ser Lys Phe  Arg Arg Ile Gln His  Glu Leu Glu
    1895                1900                1905

Glu Ala  Glu Glu Arg Ala Asp  Ile Ala Glu Ser Gln  Val Asn Lys
    1910                1915                1920

Leu Arg  Val Lys Ser Arg Glu  Val His Thr Lys Ile  Ile Ser Glu
    1925                1930                1935
```

Glu

<210> SEQ ID NO 89
<211> LENGTH: 1941
<212> TYPE: PRT
<213> ORGANISM: Homo sapiens

<400> SEQUENCE: 89

Met Ser Ser Asp Ser Glu Leu Ala Val Phe Gly Glu Ala Ala Pro Phe
1               5                   10                  15

Leu Arg Lys Ser Glu Arg Glu Arg Ile Glu Ala Gln Asn Arg Pro Phe
            20                  25                  30

Asp Ala Lys Thr Ser Val Phe Val Ala Glu Pro Lys Glu Ser Phe Val
        35                  40                  45

Lys Gly Thr Ile Gln Ser Arg Glu Gly Gly Lys Val Thr Val Lys Thr
    50                  55                  60

Glu Gly Gly Ala Thr Leu Thr Val Lys Asp Asp Gln Val Phe Pro Met
65                  70                  75                  80

Asn Pro Pro Lys Tyr Asp Lys Ile Glu Asp Met Ala Met Met Thr His
                85                  90                  95

Leu His Glu Pro Ala Val Leu Tyr Asn Leu Lys Glu Arg Tyr Ala Ala
            100                 105                 110

Trp Met Ile Tyr Thr Tyr Ser Gly Leu Phe Cys Val Thr Val Asn Pro
        115                 120                 125

Tyr Lys Trp Leu Pro Val Tyr Lys Pro Glu Val Val Thr Ala Tyr Arg
    130                 135                 140

Gly Lys Lys Arg Gln Glu Ala Pro Pro His Ile Phe Ser Ile Ser Asp
145                 150                 155                 160

Asn Ala Tyr Gln Phe Met Leu Thr Asp Arg Glu Asn Gln Ser Ile Leu
                165                 170                 175

Ile Thr Gly Glu Ser Gly Ala Gly Lys Thr Val Asn Thr Lys Arg Val
            180                 185                 190

Ile Gln Tyr Phe Ala Thr Ile Ala Val Thr Gly Glu Lys Lys Lys Glu
        195                 200                 205

Glu Ile Thr Ser Gly Lys Ile Gln Gly Thr Leu Glu Asp Gln Ile Ile
    210                 215                 220

Ser Ala Asn Pro Leu Leu Glu Ala Phe Gly Asn Ala Lys Thr Val Arg
225                 230                 235                 240

Asn Asp Asn Ser Ser Arg Phe Gly Lys Phe Ile Arg Ile His Phe Gly
                245                 250                 255

Thr Thr Gly Lys Leu Ala Ser Ala Asp Ile Glu Thr Tyr Leu Leu Glu
            260                 265                 270

Lys Ser Arg Val Val Phe Gln Leu Lys Ala Glu Arg Ser Tyr His Ile
        275                 280                 285

Phe Tyr Gln Ile Thr Ser Asn Lys Lys Pro Glu Leu Ile Glu Met Leu
    290                 295                 300

Leu Ile Thr Thr Asn Pro Tyr Asp Tyr Pro Phe Val Ser Gln Gly Glu
305                 310                 315                 320

Ile Ser Val Ala Ser Ile Asp Asp Gln Glu Glu Leu Met Ala Thr Asp
                325                 330                 335

Ser Ala Ile Asp Ile Leu Gly Phe Thr Asn Glu Glu Lys Val Ser Ile
            340                 345                 350

Tyr Lys Leu Thr Gly Ala Val Met His Tyr Gly Asn Leu Lys Phe Lys
        355                 360                 365

```
Gln Lys Gln Arg Glu Glu Gln Ala Glu Pro Asp Gly Thr Glu Val Ala
    370                 375                 380

Asp Lys Ala Ala Tyr Leu Gln Ser Leu Asn Ser Ala Asp Leu Leu Lys
385                 390                 395                 400

Ala Leu Cys Tyr Pro Arg Val Lys Val Gly Asn Glu Tyr Val Thr Lys
                405                 410                 415

Gly Gln Thr Val Glu Gln Val Ser Asn Ala Val Gly Ala Leu Ala Lys
            420                 425                 430

Ala Val Tyr Glu Lys Met Phe Leu Trp Met Val Ala Arg Ile Asn Gln
        435                 440                 445

Gln Leu Asp Thr Lys Gln Pro Arg Gln Tyr Phe Ile Gly Val Leu Asp
    450                 455                 460

Ile Ala Gly Phe Glu Ile Phe Asp Phe Asn Ser Leu Glu Gln Leu Cys
465                 470                 475                 480

Ile Asn Phe Thr Asn Glu Lys Leu Gln Gln Phe Phe Asn His His Met
                485                 490                 495

Phe Val Leu Glu Gln Glu Glu Tyr Lys Lys Glu Gly Ile Glu Trp Thr
            500                 505                 510

Phe Ile Asp Phe Gly Met Asp Leu Ala Ala Cys Ile Glu Leu Ile Glu
        515                 520                 525

Lys Pro Met Gly Ile Phe Ser Ile Leu Glu Glu Glu Cys Met Phe Pro
    530                 535                 540

Lys Ala Thr Asp Thr Ser Phe Lys Asn Lys Leu Tyr Asp Gln His Leu
545                 550                 555                 560

Gly Lys Ser Ala Asn Phe Gln Lys Pro Lys Val Val Lys Gly Lys Ala
                565                 570                 575

Glu Ala His Phe Ala Leu Ile His Tyr Ala Gly Val Val Asp Tyr Asn
            580                 585                 590

Ile Thr Gly Trp Leu Glu Lys Asn Lys Asp Pro Leu Asn Glu Thr Val
        595                 600                 605

Val Gly Leu Tyr Gln Lys Ser Ala Met Lys Thr Leu Ala Gln Leu Phe
    610                 615                 620

Ser Gly Ala Gln Thr Ala Glu Gly Glu Gly Ala Gly Gly Gly Ala Lys
625                 630                 635                 640

Lys Gly Gly Lys Lys Lys Gly Ser Ser Phe Gln Thr Val Ser Ala Leu
                645                 650                 655

Phe Arg Glu Asn Leu Asn Lys Leu Met Thr Asn Leu Arg Ser Thr His
            660                 665                 670

Pro His Phe Val Arg Cys Ile Ile Pro Asn Glu Thr Lys Thr Pro Gly
        675                 680                 685

Ala Met Glu His Glu Leu Val Leu His Gln Leu Arg Cys Asn Gly Val
    690                 695                 700

Leu Glu Gly Ile Arg Ile Cys Arg Lys Gly Phe Pro Ser Arg Ile Leu
705                 710                 715                 720

Tyr Ala Asp Phe Lys Gln Arg Tyr Lys Val Leu Asn Ala Ser Ala Ile
                725                 730                 735

Pro Glu Gly Gln Phe Ile Asp Ser Lys Lys Ala Ser Glu Lys Leu Leu
            740                 745                 750

Ala Ser Ile Asp Ile Asp His Thr Gln Tyr Lys Phe Gly His Thr Lys
        755                 760                 765

Val Phe Phe Lys Ala Gly Leu Leu Gly Leu Leu Glu Glu Met Arg Asp
    770                 775                 780
```

```
Asp Lys Leu Ala Gln Leu Ile Thr Arg Thr Gln Ala Arg Cys Arg Gly
785                 790                 795                 800

Phe Leu Ala Arg Val Glu Tyr Gln Arg Met Val Glu Arg Arg Glu Ala
                805                 810                 815

Ile Phe Cys Ile Gln Tyr Asn Ile Arg Ser Phe Met Asn Val Lys His
            820                 825                 830

Trp Pro Trp Met Lys Leu Phe Phe Lys Ile Lys Pro Leu Leu Lys Ser
        835                 840                 845

Ala Glu Thr Glu Lys Glu Met Ala Thr Met Lys Glu Glu Phe Gln Lys
    850                 855                 860

Ile Lys Asp Glu Leu Ala Lys Ser Glu Ala Lys Arg Lys Glu Leu Glu
865                 870                 875                 880

Glu Lys Met Val Thr Leu Leu Lys Glu Lys Asn Asp Leu Gln Leu Gln
                885                 890                 895

Val Gln Ala Glu Ala Glu Gly Leu Ala Asp Ala Glu Glu Arg Cys Asp
            900                 905                 910

Gln Leu Ile Lys Thr Lys Ile Gln Leu Glu Ala Lys Ile Lys Glu Val
        915                 920                 925

Thr Glu Arg Ala Glu Asp Glu Glu Glu Ile Asn Ala Glu Leu Thr Ala
    930                 935                 940

Lys Lys Arg Lys Leu Glu Asp Glu Cys Ser Glu Leu Lys Lys Asp Ile
945                 950                 955                 960

Asp Asp Leu Glu Leu Thr Leu Ala Lys Val Glu Lys Glu Lys His Ala
                965                 970                 975

Thr Glu Asn Lys Val Lys Asn Leu Thr Glu Glu Met Ala Gly Leu Asp
            980                 985                 990

Glu Thr Ile Ala Lys Leu Thr Lys  Glu Lys Lys Ala Leu  Gln Glu Ala
        995                 1000                1005

His Gln  Gln Thr Leu Asp Asp  Leu Gln Ala Glu Glu  Asp Lys Val
    1010                1015                1020

Asn Thr  Leu Thr Lys Ala Lys  Ile Lys Leu Glu Gln  Gln Val Asp
    1025                1030                1035

Asp Leu  Glu Gly Ser Leu Glu  Gln Glu Lys Lys Leu  Arg Met Asp
    1040                1045                1050

Leu Glu  Arg Ala Lys Arg Lys  Leu Glu Gly Asp Leu  Lys Leu Ala
    1055                1060                1065

Gln Glu  Ser Ile Met Asp Ile  Glu Asn Glu Lys Gln  Gln Leu Asp
    1070                1075                1080

Glu Lys  Leu Lys Lys Lys Glu  Phe Glu Ile Ser Asn  Leu Gln Ser
    1085                1090                1095

Lys Ile  Glu Asp Glu Gln Ala  Leu Gly Ile Gln Leu  Gln Lys Lys
    1100                1105                1110

Ile Lys  Glu Leu Gln Ala Arg  Ile Glu Glu Leu Glu  Glu Glu Ile
    1115                1120                1125

Glu Ala  Glu Arg Ala Ser Arg  Ala Lys Ala Glu Lys  Gln Arg Ser
    1130                1135                1140

Asp Leu  Ser Arg Glu Leu Glu  Glu Ile Ser Glu Arg  Leu Glu Glu
    1145                1150                1155

Ala Gly  Gly Ala Thr Ser Ala  Gln Ile Glu Met Asn  Lys Lys Arg
    1160                1165                1170

Glu Ala  Glu Phe Gln Lys Met  Arg Arg Asp Leu Glu  Glu Ala Thr
    1175                1180                1185

Leu Gln  His Glu Ala Thr Ala  Ala Thr Leu Arg Lys  Lys His Ala
```

```
    1190                1195                1200

Asp Ser  Val Ala Glu Leu Gly  Glu Gln Ile Asp Asn  Leu Gln Arg
    1205                1210                1215

Val Lys  Gln Lys Leu Glu Lys  Glu Lys Ser Glu Met  Lys Met Glu
    1220                1225                1230

Ile Asp  Asp Leu Ala Ser Asn  Val Glu Thr Val Ser  Lys Ala Lys
    1235                1240                1245

Gly Asn  Leu Glu Lys Met Cys  Arg Thr Leu Glu Asp  Gln Leu Ser
    1250                1255                1260

Glu Leu  Lys Ser Lys Glu Glu  Glu Gln Gln Arg Leu  Ile Asn Asp
    1265                1270                1275

Leu Thr  Ala Gln Arg Gly Arg  Leu Gln Thr Glu Ser  Gly Glu Phe
    1280                1285                1290

Ser Arg  Gln Leu Asp Glu Lys  Glu Ala Leu Val Ser  Gln Leu Ser
    1295                1300                1305

Arg Gly  Lys Gln Ala Phe Thr  Gln Gln Ile Glu Glu  Leu Lys Arg
    1310                1315                1320

Gln Leu  Glu Glu Glu Ile Lys  Ala Lys Asn Ala Leu  Ala His Ala
    1325                1330                1335

Leu Gln  Ser Ser Arg His Asp  Cys Asp Leu Leu Arg  Glu Gln Tyr
    1340                1345                1350

Glu Glu  Glu Gln Glu Ser Lys  Ala Glu Leu Gln Arg  Ala Leu Ser
    1355                1360                1365

Lys Ala  Asn Thr Glu Val Ala  Gln Trp Arg Thr Lys  Tyr Glu Thr
    1370                1375                1380

Asp Ala  Ile Gln Arg Thr Glu  Glu Leu Glu Glu Ala  Lys Lys Lys
    1385                1390                1395

Leu Ala  Gln Arg Leu Gln Ala  Ala Glu Glu His Val  Glu Ala Val
    1400                1405                1410

Asn Ala  Lys Cys Ala Ser Leu  Glu Lys Thr Lys Gln  Arg Leu Gln
    1415                1420                1425

Asn Glu  Val Glu Asp Leu Met  Leu Asp Val Glu Arg  Thr Asn Ala
    1430                1435                1440

Ala Cys  Ala Ala Leu Asp Lys  Lys Gln Arg Asn Phe  Asp Lys Ile
    1445                1450                1455

Leu Ala  Glu Trp Lys Gln Lys  Cys Glu Glu Thr His  Ala Glu Leu
    1460                1465                1470

Glu Ala  Ser Gln Lys Glu Ala  Arg Ser Leu Gly Thr  Glu Leu Phe
    1475                1480                1485

Lys Ile  Lys Asn Ala Tyr Glu  Glu Ser Leu Asp Gln  Leu Glu Thr
    1490                1495                1500

Leu Lys  Arg Glu Asn Lys Asn  Leu Gln Gln Glu Ile  Ser Asp Leu
    1505                1510                1515

Thr Glu  Gln Ile Ala Glu Gly  Gly Lys Arg Ile His  Glu Leu Glu
    1520                1525                1530

Lys Ile  Lys Lys Gln Val Glu  Gln Glu Lys Cys Glu  Leu Gln Ala
    1535                1540                1545

Ala Leu  Glu Glu Ala Glu Ala  Ser Leu Glu His Glu  Glu Gly Lys
    1550                1555                1560

Ile Leu  Arg Ile Gln Leu Glu  Leu Asn Gln Val Lys  Ser Glu Val
    1565                1570                1575

Asp Arg  Lys Ile Ala Glu Lys  Asp Glu Glu Ile Asp  Gln Leu Lys
    1580                1585                1590
```

Arg Asn His Ile Arg Ile Val Glu Ser Met Gln Ser Thr Leu Asp
1595 1600 1605

Ala Glu Ile Arg Ser Arg Asn Asp Ala Ile Arg Leu Lys Lys Lys
1610 1615 1620

Met Glu Gly Asp Leu Asn Glu Met Glu Ile Gln Leu Asn His Ala
1625 1630 1635

Asn Arg Met Ala Ala Glu Ala Leu Arg Asn Tyr Arg Asn Thr Gln
1640 1645 1650

Gly Ile Leu Lys Asp Thr Gln Ile His Leu Asp Asp Ala Leu Arg
1655 1660 1665

Ser Gln Glu Asp Leu Lys Glu Gln Leu Ala Met Val Glu Arg Arg
1670 1675 1680

Ala Asn Leu Leu Gln Ala Glu Ile Glu Glu Leu Arg Ala Thr Leu
1685 1690 1695

Glu Gln Thr Glu Arg Ser Arg Lys Ile Ala Glu Gln Glu Leu Leu
1700 1705 1710

Asp Ala Ser Glu Arg Val Gln Leu Leu His Thr Gln Asn Thr Ser
1715 1720 1725

Leu Ile Asn Thr Lys Lys Lys Leu Glu Thr Asp Ile Ser Gln Met
1730 1735 1740

Gln Gly Glu Met Glu Asp Ile Leu Gln Glu Ala Arg Asn Ala Glu
1745 1750 1755

Glu Lys Ala Lys Lys Ala Ile Thr Asp Ala Ala Met Met Ala Glu
1760 1765 1770

Glu Leu Lys Lys Glu Gln Asp Thr Ser Ala His Leu Glu Arg Met
1775 1780 1785

Lys Lys Asn Met Glu Gln Thr Val Lys Asp Leu Gln Leu Arg Leu
1790 1795 1800

Asp Glu Ala Glu Gln Leu Ala Leu Lys Gly Gly Lys Lys Gln Ile
1805 1810 1815

Gln Lys Leu Glu Ala Arg Val Arg Glu Leu Glu Gly Glu Val Glu
1820 1825 1830

Ser Glu Gln Lys Arg Asn Ala Glu Ala Val Lys Gly Leu Arg Lys
1835 1840 1845

His Glu Arg Arg Val Lys Glu Leu Thr Tyr Gln Thr Glu Glu Asp
1850 1855 1860

Arg Lys Asn Ile Leu Arg Leu Gln Asp Leu Val Asp Lys Leu Gln
1865 1870 1875

Ala Lys Val Lys Ser Tyr Lys Arg Gln Ala Glu Glu Ala Glu Glu
1880 1885 1890

Gln Ser Asn Thr Asn Leu Ala Lys Phe Arg Lys Leu Gln His Glu
1895 1900 1905

Leu Glu Glu Ala Glu Glu Arg Ala Asp Ile Ala Glu Ser Gln Val
1910 1915 1920

Asn Lys Leu Arg Val Lys Ser Arg Glu Val His Thr Lys Val Ile
1925 1930 1935

Ser Glu Glu
1940

<210> SEQ ID NO 90
<211> LENGTH: 6669
<212> TYPE: PRT
<213> ORGANISM: Homo sapiens

<400> SEQUENCE: 90

```
Met Ala Asp Asp Glu Asp Tyr Glu Glu Val Val Glu Tyr Tyr Thr Glu
1               5                   10                  15

Glu Val Val Tyr Glu Glu Val Pro Gly Glu Thr Ile Thr Lys Ile Tyr
            20                  25                  30

Glu Thr Thr Thr Thr Arg Thr Ser Asp Tyr Glu Gln Ser Glu Thr Ser
        35                  40                  45

Lys Pro Ala Leu Ala Gln Pro Ala Leu Ala Gln Pro Ala Ser Ala Lys
    50                  55                  60

Pro Val Glu Arg Arg Lys Val Ile Arg Lys Lys Val Asp Pro Ser Lys
65                  70                  75                  80

Phe Met Thr Pro Tyr Ile Ala His Ser Gln Lys Met Gln Asp Leu Phe
                85                  90                  95

Ser Pro Asn Lys Tyr Lys Glu Lys Phe Glu Lys Thr Lys Gly Gln Pro
            100                 105                 110

Tyr Ala Ser Thr Thr Asp Thr Pro Glu Leu Arg Arg Ile Lys Lys Val
        115                 120                 125

Gln Asp Gln Leu Ser Glu Val Lys Tyr Arg Met Asp Gly Asp Val Ala
    130                 135                 140

Lys Thr Ile Cys His Val Asp Glu Lys Ala Lys Asp Ile Glu His Ala
145                 150                 155                 160

Lys Lys Val Ser Gln Gln Val Ser Lys Val Leu Tyr Lys Gln Asn Trp
                165                 170                 175

Glu Asp Thr Lys Asp Lys Tyr Leu Leu Pro Pro Asp Ala Pro Glu Leu
            180                 185                 190

Val Gln Ala Val Lys Asn Thr Ala Met Phe Ser Lys Lys Leu Tyr Thr
        195                 200                 205

Glu Asp Trp Glu Ala Asp Lys Ser Leu Phe Tyr Pro Tyr Asn Asp Ser
    210                 215                 220

Pro Glu Leu Arg Arg Val Ala Gln Ala Gln Lys Ala Leu Ser Asp Val
225                 230                 235                 240

Ala Tyr Lys Lys Gly Leu Ala Glu Gln Gln Ala Gln Phe Thr Pro Leu
                245                 250                 255

Ala Asp Pro Pro Asp Ile Glu Phe Ala Lys Lys Val Thr Asn Gln Val
            260                 265                 270

Ser Lys Gln Lys Tyr Lys Glu Asp Tyr Glu Asn Lys Ile Lys Gly Lys
        275                 280                 285

Trp Ser Glu Thr Pro Cys Phe Glu Val Ala Asn Ala Arg Met Asn Ala
    290                 295                 300

Asp Asn Ile Ser Thr Arg Lys Tyr Gln Glu Asp Phe Glu Asn Met Lys
305                 310                 315                 320

Asp Gln Ile Tyr Phe Met Gln Thr Glu Thr Pro Glu Tyr Lys Met Asn
                325                 330                 335

Lys Lys Ala Gly Val Ala Ala Ser Lys Val Lys Tyr Lys Glu Asp Tyr
            340                 345                 350

Glu Lys Asn Lys Gly Lys Ala Asp Tyr Asn Val Leu Pro Ala Ser Glu
        355                 360                 365

Asn Pro Gln Leu Arg Gln Leu Lys Ala Ala Gly Asp Ala Leu Ser Asp
    370                 375                 380

Lys Leu Tyr Lys Glu Asn Tyr Glu Lys Thr Lys Ala Lys Ser Ile Asn
385                 390                 395                 400

Tyr Cys Glu Thr Pro Lys Phe Lys Leu Asp Thr Val Leu Gln Asn Phe
                405                 410                 415
```

```
Ser Ser Asp Lys Lys Tyr Lys Asp Ser Tyr Leu Lys Asp Ile Leu Gly
            420                 425                 430

His Tyr Val Gly Ser Phe Glu Asp Pro Tyr His Ser His Cys Met Lys
        435                 440                 445

Val Thr Ala Gln Asn Ser Asp Lys Asn Tyr Lys Ala Glu Tyr Glu Glu
    450                 455                 460

Asp Arg Gly Lys Gly Phe Phe Pro Gln Thr Ile Thr Gln Glu Tyr Glu
465                 470                 475                 480

Ala Ile Lys Lys Leu Asp Gln Cys Lys Asp His Thr Tyr Lys Val His
                485                 490                 495

Pro Asp Lys Thr Lys Phe Thr Gln Val Thr Asp Ser Pro Val Leu Leu
            500                 505                 510

Gln Ala Gln Val Asn Ser Lys Gln Leu Ser Asp Leu Asn Tyr Lys Ala
        515                 520                 525

Lys His Glu Ser Glu Lys Phe Lys Cys His Ile Pro Pro Asp Thr Pro
    530                 535                 540

Ala Phe Ile Gln His Lys Val Asn Ala Tyr Asn Leu Ser Asp Asn Leu
545                 550                 555                 560

Tyr Lys Gln Asp Trp Glu Lys Ser Lys Ala Lys Lys Phe Asp Ile Lys
                565                 570                 575

Val Asp Ala Ile Pro Leu Leu Ala Ala Lys Ala Asn Thr Lys Asn Thr
            580                 585                 590

Ser Asp Val Met Tyr Lys Lys Asp Tyr Glu Lys Asn Lys Gly Lys Met
        595                 600                 605

Ile Gly Val Leu Ser Ile Asn Asp Asp Pro Lys Met Leu His Ser Leu
    610                 615                 620

Lys Val Ala Lys Asn Gln Ser Asp Arg Leu Tyr Lys Glu Asn Tyr Glu
625                 630                 635                 640

Lys Thr Lys Ala Lys Ser Met Asn Tyr Cys Glu Thr Pro Lys Tyr Gln
                645                 650                 655

Leu Asp Thr Gln Leu Lys Asn Phe Ser Glu Ala Arg Tyr Lys Asp Leu
            660                 665                 670

Tyr Val Lys Asp Val Leu Gly His Tyr Val Gly Ser Met Glu Asp Pro
        675                 680                 685

Tyr His Thr His Cys Met Lys Val Ala Ala Gln Asn Ser Asp Lys Ser
    690                 695                 700

Tyr Lys Ala Glu Tyr Glu Glu Asp Lys Gly Lys Cys Tyr Phe Pro Gln
705                 710                 715                 720

Thr Ile Thr Gln Glu Tyr Glu Ala Ile Lys Lys Leu Asp Gln Cys Lys
                725                 730                 735

Asp His Thr Tyr Lys Val His Pro Asp Lys Thr Lys Phe Thr Ala Val
            740                 745                 750

Thr Asp Ser Pro Val Leu Leu Gln Ala Gln Leu Asn Thr Lys Gln Leu
        755                 760                 765

Ser Asp Leu Asn Tyr Lys Ala Lys His Glu Gly Glu Lys Phe Lys Cys
    770                 775                 780

His Ile Pro Ala Asp Ala Pro Gln Phe Ile Gln His Arg Val Asn Ala
785                 790                 795                 800

Tyr Asn Leu Ser Asp Asn Val Tyr Lys Gln Asp Trp Glu Lys Ser Lys
                805                 810                 815

Ala Lys Lys Phe Asp Ile Lys Val Asp Ala Ile Pro Leu Leu Ala Ala
            820                 825                 830
```

```
Lys Ala Asn Thr Lys Asn Thr Ser Asp Val Met Tyr Lys Lys Asp Tyr
        835                 840                 845

Glu Lys Ser Lys Gly Lys Met Ile Gly Ala Leu Ser Ile Asn Asp Asp
    850                 855                 860

Pro Lys Met Leu His Ser Leu Lys Thr Ala Lys Asn Gln Ser Asp Arg
865                 870                 875                 880

Glu Tyr Arg Lys Asp Tyr Glu Lys Ser Lys Thr Ile Tyr Thr Ala Pro
                885                 890                 895

Leu Asp Met Leu Gln Val Thr Gln Ala Lys Lys Ser Gln Ala Ile Ala
            900                 905                 910

Ser Asp Val Asp Tyr Lys His Ile Leu His Ser Tyr Ser Tyr Pro Pro
        915                 920                 925

Asp Ser Ile Asn Val Asp Leu Ala Lys Lys Ala Tyr Ala Leu Gln Ser
    930                 935                 940

Asp Val Glu Tyr Lys Ala Asp Tyr Asn Ser Trp Met Lys Gly Cys Gly
945                 950                 955                 960

Trp Val Pro Phe Gly Ser Leu Glu Met Glu Lys Ala Lys Arg Ala Ser
                965                 970                 975

Asp Ile Leu Asn Glu Lys Lys Tyr Arg Gln His Pro Asp Thr Leu Lys
            980                 985                 990

Phe Thr Ser Ile Glu Asp Ala Pro  Ile Thr Val Gln Ser  Lys Ile Asn
        995                 1000                1005

Gln Ala  Gln Arg Ser Asp Ile  Ala Tyr Lys Ala Lys  Gly Glu Glu
    1010                1015                1020

Ile Ile  His Lys Tyr Asn Leu  Pro Pro Asp Leu Pro  Gln Phe Ile
    1025                1030                1035

Gln Ala  Lys Val Asn Ala Tyr  Asn Ile Ser Glu Asn  Met Tyr Lys
    1040                1045                1050

Ala Asp  Leu Lys Asp Leu Ser  Lys Lys Gly Tyr Asp  Leu Arg Thr
    1055                1060                1065

Asp Ala  Ile Pro Ile Arg Ala  Ala Lys Ala Ala Arg  Gln Ala Ala
    1070                1075                1080

Ser Asp  Val Gln Tyr Lys Lys  Asp Tyr Glu Lys Ala  Lys Gly Lys
    1085                1090                1095

Met Val  Gly Phe Gln Ser Leu  Gln Asp Asp Pro Lys  Leu Val His
    1100                1105                1110

Tyr Met  Asn Val Ala Lys Ile  Gln Ser Asp Arg Glu  Tyr Lys Lys
    1115                1120                1125

Asp Tyr  Glu Lys Thr Lys Ser  Lys Tyr Asn Thr Pro  His Asp Met
    1130                1135                1140

Phe Asn  Val Val Ala Ala Lys  Lys Ala Gln Asp Val  Val Ser Asn
    1145                1150                1155

Val Asn  Tyr Lys His Ser Leu  His His Tyr Thr Tyr  Leu Pro Asp
    1160                1165                1170

Ala Met  Asp Leu Glu Leu Ser  Lys Asn Met Met Gln  Ile Gln Ser
    1175                1180                1185

Asp Asn  Val Tyr Lys Glu Asp  Tyr Asn Asn Trp Met  Lys Gly Ile
    1190                1195                1200

Gly Trp  Ile Pro Ile Gly Ser  Leu Asp Val Glu Lys  Val Lys Lys
    1205                1210                1215

Ala Gly  Asp Ala Leu Asn Glu  Lys Lys Tyr Arg Gln  His Pro Asp
    1220                1225                1230

Thr Leu  Lys Phe Thr Ser Ile  Val Asp Ser Pro Val  Met Val Gln
```

```
    1235                1240                1245

Ala Lys  Gln Asn Thr Lys Gln  Val Ser Asp Ile Leu  Tyr Lys Ala
    1250                1255                1260

Lys Gly  Glu Asp Val Lys His  Lys Tyr Thr Met Ser  Pro Asp Leu
    1265                1270                1275

Pro Gln  Phe Leu Gln Ala Lys  Cys Asn Ala Tyr Asn  Ile Ser Asp
    1280                1285                1290

Val Cys  Tyr Lys Arg Asp Trp  Tyr Asp Leu Ile Ala  Lys Gly Asn
    1295                1300                1305

Asn Val  Leu Gly Asp Ala Ile  Pro Ile Thr Ala Ala  Lys Ala Ser
    1310                1315                1320

Arg Asn  Ile Ala Ser Asp Tyr  Lys Tyr Lys Glu Ala  Tyr Glu Lys
    1325                1330                1335

Ser Lys  Gly Lys His Val Gly  Phe Arg Ser Leu Gln  Asp Asp Pro
    1340                1345                1350

Lys Leu  Val His Tyr Met Asn  Val Ala Lys Leu Gln  Ser Asp Arg
    1355                1360                1365

Glu Tyr  Lys Lys Asn Tyr Glu  Asn Thr Lys Thr Ser  Tyr His Thr
    1370                1375                1380

Pro Gly  Asp Met Val Ser Ile  Thr Ala Ala Lys Met  Ala Gln Asp
    1385                1390                1395

Val Ala  Thr Asn Val Asn Tyr  Lys Gln Pro Leu His  His Tyr Thr
    1400                1405                1410

Tyr Leu  Pro Asp Ala Met Ser  Leu Glu His Thr Arg  Asn Val Asn
    1415                1420                1425

Gln Ile  Gln Ser Asp Asn Val  Tyr Lys Asp Glu Tyr  Asn Ser Phe
    1430                1435                1440

Leu Lys  Gly Ile Gly Trp Ile  Pro Ile Gly Ser Leu  Glu Val Glu
    1445                1450                1455

Lys Val  Lys Lys Ala Gly Asp  Ala Leu Asn Glu Arg  Lys Tyr Arg
    1460                1465                1470

Gln His  Pro Asp Thr Val Lys  Phe Thr Ser Val Pro  Asp Ser Met
    1475                1480                1485

Gly Met  Val Leu Ala Gln His  Asn Thr Lys Gln Leu  Ser Asp Leu
    1490                1495                1500

Asn Tyr  Lys Val Glu Gly Glu  Lys Leu Lys His Lys  Tyr Thr Ile
    1505                1510                1515

Asp Pro  Glu Leu Pro Gln Phe  Ile Gln Ala Lys Val  Asn Ala Leu
    1520                1525                1530

Asn Met  Ser Asp Ala His Tyr  Lys Ala Asp Trp Lys  Lys Thr Ile
    1535                1540                1545

Ala Lys  Gly Tyr Asp Leu Arg  Pro Asp Ala Ile Pro  Ile Val Ala
    1550                1555                1560

Ala Lys  Ser Ser Arg Asn Ile  Ala Ser Asp Cys Lys  Tyr Lys Glu
    1565                1570                1575

Ala Tyr  Glu Lys Ala Lys Gly  Lys Gln Val Gly Phe  Leu Ser Leu
    1580                1585                1590

Gln Asp  Asp Pro Lys Leu Val  His Tyr Met Asn Val  Ala Lys Ile
    1595                1600                1605

Gln Ser  Asp Arg Glu Tyr Lys  Lys Gly Tyr Glu Ala  Ser Lys Thr
    1610                1615                1620

Lys Tyr  His Thr Pro Leu Asp  Met Val Ser Val Thr  Ala Ala Lys
    1625                1630                1635
```

Lys Ser Gln Glu Val Ala Thr Asn Ala Asn Tyr Arg Gln Ser Tyr
1640 1645 1650

His His Tyr Thr Leu Leu Pro Asp Ala Leu Asn Val Glu His Ser
1655 1660 1665

Arg Asn Ala Met Gln Ile Gln Ser Asp Asn Leu Tyr Lys Ser Asp
1670 1675 1680

Phe Thr Asn Trp Met Lys Gly Ile Gly Trp Val Pro Ile Glu Ser
1685 1690 1695

Leu Glu Val Glu Lys Ala Lys Lys Ala Gly Glu Ile Leu Ser Glu
1700 1705 1710

Lys Lys Tyr Arg Gln His Pro Glu Lys Leu Lys Phe Thr Tyr Ala
1715 1720 1725

Met Asp Thr Met Glu Gln Ala Leu Asn Lys Ser Asn Lys Leu Asn
1730 1735 1740

Met Asp Lys Arg Leu Tyr Thr Glu Lys Trp Asn Lys Asp Lys Thr
1745 1750 1755

Thr Ile His Val Met Pro Asp Thr Pro Asp Ile Leu Leu Ser Arg
1760 1765 1770

Val Asn Gln Ile Thr Met Ser Asp Lys Leu Tyr Lys Ala Gly Trp
1775 1780 1785

Glu Glu Glu Lys Lys Lys Gly Tyr Asp Leu Arg Pro Asp Ala Ile
1790 1795 1800

Ala Ile Lys Ala Ala Arg Ala Ser Arg Asp Ile Ala Ser Asp Tyr
1805 1810 1815

Lys Tyr Lys Lys Ala Tyr Glu Gln Ala Lys Gly Lys His Ile Gly
1820 1825 1830

Phe Arg Ser Leu Glu Asp Asp Pro Lys Leu Val His Phe Met Gln
1835 1840 1845

Val Ala Lys Met Gln Ser Asp Arg Glu Tyr Lys Lys Gly Tyr Glu
1850 1855 1860

Lys Ser Lys Thr Ser Phe His Thr Pro Val Asp Met Leu Ser Val
1865 1870 1875

Val Ala Ala Lys Lys Ser Gln Glu Val Ala Thr Asn Ala Asn Tyr
1880 1885 1890

Arg Asn Val Ile His Thr Tyr Asn Met Leu Pro Asp Ala Met Ser
1895 1900 1905

Phe Glu Leu Ala Lys Asn Met Met Gln Ile Gln Ser Asp Asn Gln
1910 1915 1920

Tyr Lys Ala Asp Tyr Ala Asp Phe Met Lys Gly Ile Gly Trp Leu
1925 1930 1935

Pro Leu Gly Ser Leu Glu Ala Glu Lys Asn Lys Lys Ala Met Glu
1940 1945 1950

Ile Ile Ser Glu Lys Lys Tyr Arg Gln His Pro Asp Thr Leu Lys
1955 1960 1965

Tyr Ser Thr Leu Met Asp Ser Met Asn Met Val Leu Ala Gln Asn
1970 1975 1980

Asn Ala Lys Ile Met Asn Glu His Leu Tyr Lys Gln Ala Trp Glu
1985 1990 1995

Ala Asp Lys Thr Lys Val His Ile Met Pro Asp Ile Pro Gln Ile
2000 2005 2010

Ile Leu Ala Lys Ala Asn Ala Ile Asn Met Ser Asp Lys Leu Tyr
2015 2020 2025

```
Lys Leu  Ser Leu Glu Glu Ser  Lys Lys Lys Gly Tyr  Asp Leu Arg
    2030                 2035                 2040

Pro Asp  Ala Ile Pro Ile Lys  Ala Ala Lys Ala Ser  Arg Asp Ile
    2045                 2050                 2055

Ala Ser  Asp Tyr Lys Tyr Lys  Tyr Asn Tyr Glu Lys  Gly Lys Gly
    2060                 2065                 2070

Lys Met  Val Gly Phe Arg Ser  Leu Glu Asp Asp Pro  Lys Leu Val
    2075                 2080                 2085

His Ser  Met Gln Val Ala Lys  Met Gln Ser Asp Arg  Glu Tyr Lys
    2090                 2095                 2100

Lys Asn  Tyr Glu Asn Thr Lys  Thr Ser Tyr His Thr  Pro Ala Asp
    2105                 2110                 2115

Met Leu  Ser Val Thr Ala Ala  Lys Asp Ala Gln Ala  Asn Ile Thr
    2120                 2125                 2130

Asn Thr  Asn Tyr Lys His Leu  Ile His Lys Tyr Ile  Leu Leu Pro
    2135                 2140                 2145

Asp Ala  Met Asn Ile Glu Leu  Thr Arg Asn Met Asn  Arg Ile Gln
    2150                 2155                 2160

Ser Asp  Asn Glu Tyr Lys Gln  Asp Tyr Asn Glu Trp  Tyr Lys Gly
    2165                 2170                 2175

Leu Gly  Trp Ser Pro Ala Gly  Ser Leu Glu Val Glu  Lys Ala Lys
    2180                 2185                 2190

Lys Ala  Thr Glu Tyr Ala Ser  Asp Gln Lys Tyr Arg  Gln His Pro
    2195                 2200                 2205

Ser Asn  Phe Gln Phe Lys Lys  Leu Thr Asp Ser Met  Asp Met Val
    2210                 2215                 2220

Leu Ala  Lys Gln Asn Ala His  Thr Met Asn Lys His  Leu Tyr Thr
    2225                 2230                 2235

Ile Asp  Trp Asn Lys Asp Lys  Thr Lys Ile His Val  Met Pro Asp
    2240                 2245                 2250

Thr Pro  Asp Ile Leu Gln Ala  Lys Gln Asn Gln Thr  Leu Tyr Ser
    2255                 2260                 2265

Gln Lys  Leu Tyr Lys Leu Gly  Trp Glu Glu Ala Leu  Lys Lys Gly
    2270                 2275                 2280

Tyr Asp  Leu Pro Val Asp Ala  Ile Ser Val Gln Leu  Ala Lys Ala
    2285                 2290                 2295

Ser Arg  Asp Ile Ala Ser Asp  Tyr Lys Tyr Lys Gln  Gly Tyr Arg
    2300                 2305                 2310

Lys Gln  Leu Gly His His Val  Gly Phe Arg Ser Leu  Gln Asp Asp
    2315                 2320                 2325

Pro Lys  Leu Val Leu Ser Met  Asn Val Ala Lys Met  Gln Ser Glu
    2330                 2335                 2340

Arg Glu  Tyr Lys Lys Asp Phe  Glu Lys Trp Lys Thr  Lys Phe Ser
    2345                 2350                 2355

Ser Pro  Val Asp Met Leu Gly  Val Val Leu Ala Lys  Lys Cys Gln
    2360                 2365                 2370

Glu Leu  Val Ser Asp Val Asp  Tyr Lys Asn Tyr Leu  His Gln Trp
    2375                 2380                 2385

Thr Cys  Leu Pro Asp Gln Asn  Asp Val Val Gln Ala  Lys Lys Val
    2390                 2395                 2400

Tyr Glu  Leu Gln Ser Glu Asn  Leu Tyr Lys Ser Asp  Leu Glu Trp
    2405                 2410                 2415

Leu Arg  Gly Ile Gly Trp Ser  Pro Leu Gly Ser Leu  Glu Ala Glu
```

-continued

```
    2420                2425                2430

Lys Asn  Lys Arg Ala Ser Glu  Ile Ile Ser Glu Lys  Lys Tyr Arg
    2435                2440                2445

Gln Pro  Pro Asp Arg Asn Lys  Phe Thr Ser Ile Pro  Asp Ala Met
    2450                2455                2460

Asp Ile  Val Leu Ala Lys Thr  Asn Ala Lys Asn Arg  Ser Asp Arg
    2465                2470                2475

Leu Tyr  Arg Glu Ala Trp Asp  Lys Asp Lys Thr Gln  Ile His Ile
    2480                2485                2490

Met Pro  Asp Thr Pro Asp Ile  Val Leu Ala Lys Ala  Asn Leu Ile
    2495                2500                2505

Asn Thr  Ser Asp Lys Leu Tyr  Arg Met Gly Tyr Glu  Glu Leu Lys
    2510                2515                2520

Arg Lys  Gly Tyr Asp Leu Pro  Val Asp Ala Ile Pro  Ile Lys Ala
    2525                2530                2535

Ala Lys  Ala Ser Arg Glu Ile  Ala Ser Glu Tyr Lys  Tyr Lys Glu
    2540                2545                2550

Gly Phe  Arg Lys Gln Leu Gly  His His Ile Gly Ala  Arg Asn Ile
    2555                2560                2565

Glu Asp  Asp Pro Lys Met Met  Trp Ser Met His Val  Ala Lys Ile
    2570                2575                2580

Gln Ser  Asp Arg Glu Tyr Lys  Lys Asp Phe Glu Lys  Trp Lys Thr
    2585                2590                2595

Lys Phe  Ser Ser Pro Val Asp  Met Leu Gly Val Val  Leu Ala Lys
    2600                2605                2610

Lys Cys  Gln Thr Leu Val Ser  Asp Val Asp Tyr Lys  Asn Tyr Leu
    2615                2620                2625

His Gln  Trp Thr Cys Leu Pro  Asp Gln Ser Asp Val  Ile His Ala
    2630                2635                2640

Arg Gln  Ala Tyr Asp Leu Gln  Ser Asp Asn Leu Tyr  Lys Ser Asp
    2645                2650                2655

Leu Gln  Trp Leu Lys Gly Ile  Gly Trp Met Thr Ser  Gly Ser Leu
    2660                2665                2670

Glu Asp  Glu Lys Asn Lys Arg  Ala Thr Gln Ile Leu  Ser Asp His
    2675                2680                2685

Val Tyr  Arg Gln His Pro Asp  Gln Phe Lys Phe Ser  Ser Leu Met
    2690                2695                2700

Asp Ser  Ile Pro Met Val Leu  Ala Lys Asn Asn Ala  Ile Thr Met
    2705                2710                2715

Asn His  Arg Leu Tyr Thr Glu  Ala Trp Asp Lys Asp  Lys Thr Thr
    2720                2725                2730

Val His  Ile Met Pro Asp Thr  Pro Glu Val Leu Leu  Ala Lys Gln
    2735                2740                2745

Asn Lys  Val Asn Tyr Ser Glu  Lys Leu Tyr Lys Leu  Gly Leu Glu
    2750                2755                2760

Glu Ala  Lys Arg Lys Gly Tyr  Asp Met Arg Val Asp  Ala Ile Pro
    2765                2770                2775

Ile Lys  Ala Ala Lys Ala Ser  Arg Asp Ile Ala Ser  Glu Phe Lys
    2780                2785                2790

Tyr Lys  Glu Gly Tyr Arg Lys  Gln Leu Gly His His  Ile Gly Ala
    2795                2800                2805

Arg Ala  Ile Arg Asp Asp Pro  Lys Met Met Trp Ser  Met His Val
    2810                2815                2820
```

Ala Lys Ile Gln Ser Asp Arg Glu Tyr Lys Lys Asp Phe Glu Lys
2825 2830 2835

Trp Lys Thr Lys Phe Ser Ser Pro Val Asp Met Leu Gly Val Val
2840 2845 2850

Leu Ala Lys Lys Cys Gln Thr Leu Val Ser Asp Val Asp Tyr Lys
2855 2860 2865

Asn Tyr Leu His Gln Trp Thr Cys Leu Pro Asp Gln Ser Asp Val
2870 2875 2880

Ile His Ala Arg Gln Ala Tyr Asp Leu Gln Ser Asp Asn Met Tyr
2885 2890 2895

Lys Ser Asp Leu Gln Trp Met Arg Gly Ile Gly Trp Val Ser Ile
2900 2905 2910

Gly Ser Leu Asp Val Glu Lys Cys Lys Arg Ala Thr Glu Ile Leu
2915 2920 2925

Ser Asp Lys Ile Tyr Arg Gln Pro Pro Asp Arg Phe Lys Phe Thr
2930 2935 2940

Ser Val Thr Asp Ser Leu Glu Gln Val Leu Ala Lys Asn Asn Ala
2945 2950 2955

Ile Thr Met Asn Lys Arg Leu Tyr Thr Glu Ala Trp Asp Lys Asp
2960 2965 2970

Lys Thr Gln Ile His Ile Met Pro Asp Thr Pro Glu Ile Met Leu
2975 2980 2985

Ala Arg Gln Asn Lys Ile Asn Tyr Ser Glu Thr Leu Tyr Lys Leu
2990 2995 3000

Ala Asn Glu Glu Ala Lys Lys Lys Gly Tyr Asp Leu Arg Ser Asp
3005 3010 3015

Ala Ile Pro Ile Val Ala Ala Lys Ala Ser Arg Asp Val Ile Ser
3020 3025 3030

Asp Tyr Lys Tyr Lys Asp Gly Tyr Arg Lys Gln Leu Gly His His
3035 3040 3045

Ile Gly Ala Arg Asn Ile Glu Asp Asp Pro Lys Met Met Trp Ser
3050 3055 3060

Met His Val Ala Lys Ile Gln Ser Asp Arg Glu Tyr Lys Lys Asp
3065 3070 3075

Phe Glu Lys Trp Lys Thr Lys Phe Ser Ser Pro Val Asp Met Leu
3080 3085 3090

Gly Val Val Leu Ala Lys Lys Cys Gln Thr Leu Val Ser Asp Val
3095 3100 3105

Asp Tyr Lys Asn Tyr Leu His Glu Trp Thr Cys Leu Pro Asp Gln
3110 3115 3120

Asn Asp Val Ile His Ala Arg Gln Ala Tyr Asp Leu Gln Ser Asp
3125 3130 3135

Asn Ile Tyr Lys Ser Asp Leu Gln Trp Leu Arg Gly Ile Gly Trp
3140 3145 3150

Val Pro Ile Gly Ser Met Asp Val Val Lys Cys Lys Arg Ala Ala
3155 3160 3165

Glu Ile Leu Ser Asp Asn Ile Tyr Arg Gln Pro Pro Asp Lys Leu
3170 3175 3180

Lys Phe Thr Ser Val Thr Asp Ser Leu Glu Gln Val Leu Ala Lys
3185 3190 3195

Asn Asn Ala Leu Asn Met Asn Lys Arg Leu Tyr Thr Glu Ala Trp
3200 3205 3210

```
Asp Lys  Asp Lys Thr Gln Val  His Ile Met Pro Asp  Thr Pro Glu
    3215                 3220                 3225

Ile Met  Leu Ala Arg Gln Asn  Lys Ile Asn Tyr Ser  Glu Ser Leu
    3230                 3235                 3240

Tyr Arg  Gln Ala Met Glu Glu  Ala Lys Lys Glu Gly  Tyr Asp Leu
    3245                 3250                 3255

Arg Ser  Asp Ala Ile Pro Ile  Val Ala Ala Lys Ala  Ser Arg Asp
    3260                 3265                 3270

Ile Ala  Ser Asp Tyr Lys Tyr  Lys Glu Ala Tyr Arg  Lys Gln Leu
    3275                 3280                 3285

Gly His  His Ile Gly Ala Arg  Ala Val His Asp Asp  Pro Lys Ile
    3290                 3295                 3300

Met Trp  Ser Leu His Ile Ala  Lys Val Gln Ser Asp  Arg Glu Tyr
    3305                 3310                 3315

Lys Lys  Asp Phe Glu Lys Tyr  Lys Thr Arg Tyr Ser  Ser Pro Val
    3320                 3325                 3330

Asp Met  Leu Gly Ile Val Leu  Ala Lys Lys Cys Gln  Thr Leu Val
    3335                 3340                 3345

Ser Asp  Val Asp Tyr Lys His  Pro Leu His Glu Trp  Ile Cys Leu
    3350                 3355                 3360

Pro Asp  Gln Asn Asp Ile Ile  His Ala Arg Lys Ala  Tyr Asp Leu
    3365                 3370                 3375

Gln Ser  Asp Asn Leu Tyr Lys  Ser Asp Leu Glu Trp  Met Lys Gly
    3380                 3385                 3390

Ile Gly  Trp Val Pro Ile Asp  Ser Leu Glu Val Val  Arg Ala Lys
    3395                 3400                 3405

Arg Ala  Gly Glu Leu Leu Ser  Asp Thr Ile Tyr Arg  Gln Arg Pro
    3410                 3415                 3420

Glu Thr  Leu Lys Phe Thr Ser  Ile Thr Asp Thr Pro  Glu Gln Val
    3425                 3430                 3435

Leu Ala  Lys Asn Asn Ala Leu  Asn Met Asn Lys Arg  Leu Tyr Thr
    3440                 3445                 3450

Glu Ala  Trp Asp Asn Asp Lys  Lys Thr Ile His Val  Met Pro Asp
    3455                 3460                 3465

Thr Pro  Glu Ile Met Leu Ala  Lys Leu Asn Arg Ile  Asn Tyr Ser
    3470                 3475                 3480

Asp Lys  Leu Tyr Lys Leu Ala  Leu Glu Glu Ser Lys  Lys Glu Gly
    3485                 3490                 3495

Tyr Asp  Leu Arg Leu Asp Ala  Ile Pro Ile Gln Ala  Ala Lys Ala
    3500                 3505                 3510

Ser Arg  Asp Ile Ala Ser Asp  Tyr Lys Tyr Lys Glu  Gly Tyr Arg
    3515                 3520                 3525

Lys Gln  Leu Gly His His Ile  Gly Ala Arg Asn Ile  Lys Asp Asp
    3530                 3535                 3540

Pro Lys  Met Met Trp Ser Ile  His Val Ala Lys Ile  Gln Ser Asp
    3545                 3550                 3555

Arg Glu  Tyr Lys Lys Glu Phe  Glu Lys Trp Lys Thr  Lys Phe Ser
    3560                 3565                 3570

Ser Pro  Val Asp Met Leu Gly  Val Val Leu Ala Lys  Lys Cys Gln
    3575                 3580                 3585

Ile Leu  Val Ser Asp Ile Asp  Tyr Lys His Pro Leu  His Glu Trp
    3590                 3595                 3600

Thr Cys  Leu Pro Asp Gln Asn  Asp Val Ile Gln Ala  Arg Lys Ala
```

```
    3605                3610                3615

Tyr Asp  Leu Gln Ser Asp Ala  Ile Tyr Lys Ser Asp  Leu Glu Trp
    3620                3625                3630

Leu Arg  Gly Ile Gly Trp Val  Pro Ile Gly Ser Val  Glu Val Glu
    3635                3640                3645

Lys Val  Lys Arg Ala Gly Glu  Ile Leu Ser Asp Arg  Lys Tyr Arg
    3650                3655                3660

Gln Pro  Ala Asp Gln Leu Lys  Phe Thr Cys Ile Thr  Asp Thr Pro
    3665                3670                3675

Glu Ile  Val Leu Ala Lys Asn  Asn Ala Leu Thr Met  Ser Lys His
    3680                3685                3690

Leu Tyr  Thr Glu Ala Trp Asp  Ala Asp Lys Thr Ser  Ile His Val
    3695                3700                3705

Met Pro  Asp Thr Pro Asp Ile  Leu Leu Ala Lys Ser  Asn Ser Ala
    3710                3715                3720

Asn Ile  Ser Gln Lys Leu Tyr  Thr Lys Gly Trp Asp  Glu Ser Lys
    3725                3730                3735

Met Lys  Asp Tyr Asp Leu Arg  Ala Asp Ala Ile Ser  Ile Lys Ser
    3740                3745                3750

Ala Lys  Ala Ser Arg Asp Ile  Ala Ser Asp Tyr Lys  Tyr Lys Glu
    3755                3760                3765

Ala Tyr  Glu Lys Gln Lys Gly  His His Ile Gly Ala  Gln Ser Ile
    3770                3775                3780

Glu Asp  Asp Pro Lys Ile Met  Cys Ala Ile His Ala  Gly Lys Ile
    3785                3790                3795

Gln Ser  Glu Arg Glu Tyr Lys  Lys Glu Phe Gln Lys  Trp Lys Thr
    3800                3805                3810

Lys Phe  Ser Ser Pro Val Asp  Met Leu Ser Ile Leu  Leu Ala Lys
    3815                3820                3825

Lys Cys  Gln Thr Leu Val Thr  Asp Ile Asp Tyr Arg  Asn Tyr Leu
    3830                3835                3840

His Glu  Trp Thr Cys Met Pro  Asp Gln Asn Asp Ile  Ile Gln Ala
    3845                3850                3855

Lys Lys  Ala Tyr Asp Leu Gln  Ser Asp Ala Leu Tyr  Lys Ala Asp
    3860                3865                3870

Leu Glu  Trp Leu Arg Gly Ile  Gly Trp Met Pro Gln  Gly Ser Pro
    3875                3880                3885

Glu Val  Leu Arg Val Lys Asn  Ala Gln Asn Ile Phe  Cys Asp Ser
    3890                3895                3900

Val Tyr  Arg Thr Pro Val Val  Asn Leu Lys Tyr Thr  Ser Ile Val
    3905                3910                3915

Asp Thr  Pro Glu Val Val Leu  Ala Lys Ser Asn Ala  Glu Asn Ile
    3920                3925                3930

Ser Ile  Pro Lys Tyr Arg Glu  Val Trp Asp Lys Asp  Lys Thr Ser
    3935                3940                3945

Ile His  Ile Met Pro Asp Thr  Pro Glu Ile Asn Leu  Ala Arg Ala
    3950                3955                3960

Asn Ala  Leu Asn Val Ser Asn  Lys Leu Tyr Arg Glu  Gly Trp Asp
    3965                3970                3975

Glu Met  Lys Ala Gly Cys Asp  Val Arg Leu Asp Ala  Ile Pro Ile
    3980                3985                3990

Gln Ala  Ala Lys Ala Ser Arg  Glu Ile Ala Ser Asp  Tyr Lys Tyr
    3995                4000                4005
```

Lys Leu Asp His Glu Lys Gln Lys Gly His Tyr Val Gly Thr Leu
4010 4015 4020

Thr Ala Arg Asp Asp Asn Lys Ile Arg Trp Ala Leu Ile Ala Asp
4025 4030 4035

Lys Leu Gln Asn Glu Arg Glu Tyr Arg Leu Asp Trp Ala Lys Trp
4040 4045 4050

Lys Ala Lys Ile Gln Ser Pro Val Asp Met Leu Ser Ile Leu His
4055 4060 4065

Ser Lys Asn Ser Gln Ala Leu Val Ser Asp Met Asp Tyr Arg Asn
4070 4075 4080

Tyr Leu His Gln Trp Thr Cys Met Pro Asp Gln Asn Asp Val Ile
4085 4090 4095

Gln Ala Lys Lys Ala Tyr Glu Leu Gln Ser Asp Asn Val Tyr Lys
4100 4105 4110

Ala Asp Leu Glu Trp Leu Arg Gly Ile Gly Trp Met Pro Asn Asp
4115 4120 4125

Ser Val Ser Val Asn His Ala Lys His Ala Ala Asp Ile Phe Ser
4130 4135 4140

Glu Lys Lys Tyr Arg Thr Lys Ile Glu Thr Leu Asn Phe Thr Pro
4145 4150 4155

Val Asp Asp Arg Val Asp Tyr Val Thr Ala Lys Gln Ser Gly Glu
4160 4165 4170

Ile Leu Asp Asp Ile Lys Tyr Arg Lys Asp Trp Asn Ala Thr Lys
4175 4180 4185

Ser Lys Tyr Thr Leu Thr Glu Thr Pro Leu Leu His Thr Ala Gln
4190 4195 4200

Glu Ala Ala Arg Ile Leu Asp Gln Tyr Leu Tyr Lys Glu Gly Trp
4205 4210 4215

Glu Arg Gln Lys Ala Thr Gly Tyr Ile Leu Pro Pro Asp Ala Val
4220 4225 4230

Pro Phe Val His Ala His His Cys Asn Asp Val Gln Ser Glu Leu
4235 4240 4245

Lys Tyr Lys Ala Glu His Val Lys Gln Lys Gly His Tyr Val Gly
4250 4255 4260

Val Pro Thr Met Arg Asp Asp Pro Lys Leu Val Trp Phe Glu His
4265 4270 4275

Ala Gly Gln Ile Gln Asn Glu Arg Leu Tyr Lys Glu Asp Tyr His
4280 4285 4290

Lys Thr Lys Ala Lys Ile Asn Ile Pro Ala Asp Met Val Ser Val
4295 4300 4305

Leu Ala Ala Lys Gln Gly Gln Thr Leu Val Ser Asp Ile Asp Tyr
4310 4315 4320

Arg Asn Tyr Leu His Gln Trp Met Cys His Pro Asp Gln Asn Asp
4325 4330 4335

Val Ile Gln Ala Arg Lys Ala Tyr Asp Leu Gln Ser Asp Asn Val
4340 4345 4350

Tyr Arg Ala Asp Leu Glu Trp Leu Arg Gly Ile Gly Trp Ile Pro
4355 4360 4365

Leu Asp Ser Val Asp His Val Arg Val Thr Lys Asn Gln Glu Met
4370 4375 4380

Met Ser Gln Ile Lys Tyr Lys Lys Asn Ala Leu Glu Asn Tyr Pro
4385 4390 4395

```
Asn Phe Arg Ser Val Val Asp Pro Pro Glu Ile Val Leu Ala Lys
    4400                4405                4410

Ile Asn Ser Val Asn Gln Ser Asp Val Lys Tyr Lys Glu Thr Phe
    4415                4420                4425

Asn Lys Ala Lys Gly Lys Tyr Thr Phe Ser Pro Asp Thr Pro His
    4430                4435                4440

Ile Ser His Ser Lys Asp Met Gly Lys Leu Tyr Ser Thr Ile Leu
    4445                4450                4455

Tyr Lys Gly Ala Trp Glu Gly Thr Lys Ala Tyr Gly Tyr Thr Leu
    4460                4465                4470

Asp Glu Arg Tyr Ile Pro Ile Val Gly Ala Lys His Ala Asp Leu
    4475                4480                4485

Val Asn Ser Glu Leu Lys Tyr Lys Glu Thr Tyr Glu Lys Gln Lys
    4490                4495                4500

Gly His Tyr Leu Ala Gly Lys Val Ile Gly Glu Phe Pro Gly Val
    4505                4510                4515

Val His Cys Leu Asp Phe Gln Lys Met Arg Ser Ala Leu Asn Tyr
    4520                4525                4530

Arg Lys His Tyr Glu Asp Thr Lys Ala Asn Val His Ile Pro Asn
    4535                4540                4545

Asp Met Met Asn His Val Leu Ala Lys Arg Cys Gln Tyr Ile Leu
    4550                4555                4560

Ser Asp Leu Glu Tyr Arg His Tyr Phe His Gln Trp Thr Ser Leu
    4565                4570                4575

Leu Glu Glu Pro Asn Val Ile Arg Val Arg Asn Ala Gln Glu Ile
    4580                4585                4590

Leu Ser Asp Asn Val Tyr Lys Asp Asp Leu Asn Trp Leu Lys Gly
    4595                4600                4605

Ile Gly Cys Tyr Val Trp Asp Thr Pro Gln Ile Leu His Ala Lys
    4610                4615                4620

Lys Ser Tyr Asp Leu Gln Ser Gln Leu Gln Tyr Thr Ala Ala Gly
    4625                4630                4635

Lys Glu Asn Leu Gln Asn Tyr Asn Leu Val Thr Asp Thr Pro Leu
    4640                4645                4650

Tyr Val Thr Ala Val Gln Ser Gly Ile Asn Ala Ser Glu Val Lys
    4655                4660                4665

Tyr Lys Glu Asn Tyr His Gln Ile Lys Asp Lys Tyr Thr Thr Val
    4670                4675                4680

Leu Glu Thr Val Asp Tyr Asp Arg Thr Arg Asn Leu Lys Asn Leu
    4685                4690                4695

Tyr Ser Ser Asn Leu Tyr Lys Glu Ala Trp Asp Arg Val Lys Ala
    4700                4705                4710

Thr Ser Tyr Ile Leu Pro Ser Ser Thr Leu Ser Leu Thr His Ala
    4715                4720                4725

Lys Asn Gln Lys His Leu Ala Ser His Ile Lys Tyr Arg Glu Glu
    4730                4735                4740

Tyr Glu Lys Phe Lys Ala Leu Tyr Thr Leu Pro Arg Ser Val Asp
    4745                4750                4755

Asp Asp Pro Asn Thr Ala Arg Cys Leu Arg Val Gly Lys Leu Asn
    4760                4765                4770

Ile Asp Arg Leu Tyr Arg Ser Val Tyr Glu Lys Asn Lys Met Lys
    4775                4780                4785

Ile His Ile Val Pro Asp Met Val Glu Met Val Thr Ala Lys Asp
```

4790 4795 4800

Ser Gln Lys Lys Val Ser Glu Ile Asp Tyr Arg Leu Arg Leu His
4805 4810 4815

Glu Trp Ile Cys His Pro Asp Leu Gln Val Asn Asp His Val Arg
4820 4825 4830

Lys Val Thr Asp Gln Ile Ser Asp Ile Val Tyr Lys Asp Asp Leu
4835 4840 4845

Asn Trp Leu Lys Gly Ile Gly Cys Tyr Val Trp Asp Thr Pro Glu
4850 4855 4860

Ile Leu His Ala Lys His Ala Tyr Asp Leu Arg Asp Asp Ile Lys
4865 4870 4875

Tyr Lys Ala His Met Leu Lys Thr Arg Asn Asp Tyr Lys Leu Val
4880 4885 4890

Thr Asp Thr Pro Val Tyr Val Gln Ala Val Lys Ser Gly Lys Gln
4895 4900 4905

Leu Ser Asp Ala Val Tyr His Tyr Asp Tyr Val His Ser Val Arg
4910 4915 4920

Gly Lys Val Ala Pro Thr Thr Lys Thr Val Asp Leu Asp Arg Ala
4925 4930 4935

Leu His Ala Tyr Lys Leu Gln Ser Ser Asn Leu Tyr Lys Thr Ser
4940 4945 4950

Leu Arg Thr Leu Pro Thr Gly Tyr Arg Leu Pro Gly Asp Thr Pro
4955 4960 4965

His Phe Lys His Ile Lys Asp Thr Arg Tyr Met Ser Ser Tyr Phe
4970 4975 4980

Lys Tyr Lys Glu Ala Tyr Glu His Thr Lys Ala Tyr Gly Tyr Thr
4985 4990 4995

Leu Gly Pro Lys Asp Val Pro Phe Val His Val Arg Arg Val Asn
5000 5005 5010

Asn Val Thr Ser Glu Arg Leu Tyr Arg Glu Leu Tyr His Lys Leu
5015 5020 5025

Lys Asp Lys Ile His Thr Thr Pro Asp Thr Pro Glu Ile Arg Gln
5030 5035 5040

Val Lys Lys Thr Gln Glu Ala Val Ser Glu Leu Ile Tyr Lys Ser
5045 5050 5055

Asp Phe Phe Lys Met Gln Gly His Met Ile Ser Leu Pro Tyr Thr
5060 5065 5070

Pro Gln Val Ile His Cys Arg Tyr Val Gly Asp Ile Thr Ser Asp
5075 5080 5085

Ile Lys Tyr Lys Glu Asp Leu Gln Val Leu Lys Gly Phe Gly Cys
5090 5095 5100

Phe Leu Tyr Asp Thr Pro Asp Met Val Arg Ser Arg His Leu Arg
5105 5110 5115

Lys Leu Trp Ser Asn Tyr Leu Tyr Thr Asp Lys Ala Arg Lys Met
5120 5125 5130

Arg Asp Lys Tyr Lys Val Val Leu Asp Thr Pro Glu Tyr Arg Lys
5135 5140 5145

Val Gln Glu Leu Lys Thr His Leu Ser Glu Leu Val Tyr Arg Ala
5150 5155 5160

Ala Gly Lys Lys Gln Lys Ser Ile Phe Thr Ser Val Pro Asp Thr
5165 5170 5175

Pro Asp Leu Leu Arg Ala Lys Arg Gly Gln Lys Leu Gln Ser Gln
5180 5185 5190

```
Tyr Leu  Tyr Val Glu Leu Ala  Thr Lys Glu Arg Pro  His His His
    5195                 5200                 5205

Ala Gly  Asn Gln Thr Thr Ala  Leu Lys His Ala Lys  Asp Val Lys
    5210                 5215                 5220

Asp Met  Val Ser Glu Lys Lys  Tyr Lys Ile Gln Tyr  Glu Lys Met
    5225                 5230                 5235

Lys Asp  Lys Tyr Thr Pro Val  Pro Asp Thr Pro Ile  Leu Ile Arg
    5240                 5245                 5250

Ala Lys  Arg Ala Tyr Trp Asn  Ala Ser Asp Leu Arg  Tyr Lys Glu
    5255                 5260                 5265

Thr Phe  Gln Lys Thr Lys Gly  Lys Tyr His Thr Val  Lys Asp Ala
    5270                 5275                 5280

Leu Asp  Ile Val Tyr His Arg  Lys Val Thr Asp Asp  Ile Ser Lys
    5285                 5290                 5295

Ile Lys  Tyr Lys Glu Asn Tyr  Met Ser Gln Leu Gly  Ile Trp Arg
    5300                 5305                 5310

Ser Ile  Pro Asp Arg Pro Glu  His Phe His His Arg  Ala Val Thr
    5315                 5320                 5325

Asp Thr  Val Ser Asp Val Lys  Tyr Lys Glu Asp Leu  Thr Trp Leu
    5330                 5335                 5340

Lys Gly  Ile Gly Cys Tyr Ala  Tyr Asp Thr Pro Asp  Phe Thr Leu
    5345                 5350                 5355

Ala Glu  Lys Asn Lys Thr Leu  Tyr Ser Lys Tyr Lys  Tyr Lys Glu
    5360                 5365                 5370

Val Phe  Glu Arg Thr Lys Ser  Asp Phe Lys Tyr Val  Ala Asp Ser
    5375                 5380                 5385

Pro Ile  Asn Arg His Phe Lys  Tyr Ala Thr Gln Leu  Met Asn Glu
    5390                 5395                 5400

Lys Lys  Tyr Arg Ala Asp Tyr  Glu Gln Arg Lys Asp  Lys Tyr His
    5405                 5410                 5415

Leu Val  Val Asp Glu Pro Arg  His Leu Leu Ala Lys  Thr Ala Gly
    5420                 5425                 5430

Asp Gln  Ile Ser Gln Ile Lys  Tyr Arg Lys Asn Tyr  Glu Lys Ser
    5435                 5440                 5445

Lys Asp  Lys Phe Thr Ser Ile  Val Asp Thr Pro Glu  His Leu Arg
    5450                 5455                 5460

Thr Thr  Lys Val Asn Lys Gln  Ile Ser Asp Ile Leu  Tyr Lys Leu
    5465                 5470                 5475

Glu Tyr  Asn Lys Ala Lys Pro  Arg Gly Tyr Thr Thr  Ile His Asp
    5480                 5485                 5490

Thr Pro  Met Leu Leu His Val  Arg Lys Val Lys Asp  Glu Val Ser
    5495                 5500                 5505

Asp Leu  Lys Tyr Lys Glu Val  Tyr Gln Arg Asn Lys  Ser Asn Cys
    5510                 5515                 5520

Thr Ile  Glu Pro Asp Ala Val  His Ile Lys Ala Ala  Lys Asp Ala
    5525                 5530                 5535

Tyr Lys  Val Asn Thr Asn Leu  Asp Tyr Lys Lys Gln  Tyr Glu Ala
    5540                 5545                 5550

Asn Lys  Ala His Trp Lys Trp  Thr Pro Asp Arg Pro  Asp Phe Leu
    5555                 5560                 5565

Gln Ala  Ala Lys Ser Ser Leu  Gln Gln Ser Asp Phe  Glu Tyr Lys
    5570                 5575                 5580
```

```
Leu Asp Arg Glu Phe Leu Lys Gly Cys Lys Leu Ser Val Thr Asp
    5585                5590                5595

Asp Lys Asn Thr Val Leu Ala Leu Arg Asn Thr Leu Ile Glu Ser
    5600                5605                5610

Asp Leu Lys Tyr Lys Glu Lys His Val Lys Glu Arg Gly Thr Cys
    5615                5620                5625

His Ala Val Pro Asp Thr Pro Gln Ile Leu Leu Ala Lys Thr Val
    5630                5635                5640

Ser Asn Leu Val Ser Glu Asn Lys Tyr Lys Asp His Val Lys Lys
    5645                5650                5655

His Leu Ala Gln Gly Ser Tyr Thr Thr Leu Pro Glu Thr Arg Asp
    5660                5665                5670

Thr Val His Val Lys Glu Val Thr Lys His Val Ser Asp Thr Asn
    5675                5680                5685

Tyr Lys Lys Lys Phe Val Lys Glu Lys Gly Lys Ser Asn Tyr Ser
    5690                5695                5700

Ile Met Leu Glu Pro Pro Glu Val Lys His Ala Met Glu Val Ala
    5705                5710                5715

Lys Lys Gln Ser Asp Val Ala Tyr Arg Lys Asp Ala Lys Glu Asn
    5720                5725                5730

Leu His Tyr Thr Thr Val Ala Asp Arg Pro Asp Ile Lys Lys Ala
    5735                5740                5745

Thr Gln Ala Ala Lys Gln Ala Ser Glu Val Glu Tyr Arg Ala Lys
    5750                5755                5760

His Arg Lys Glu Gly Ser His Gly Leu Ser Met Leu Gly Arg Pro
    5765                5770                5775

Asp Ile Glu Met Ala Lys Lys Ala Ala Lys Leu Ser Ser Gln Val
    5780                5785                5790

Lys Tyr Arg Glu Asn Phe Asp Lys Glu Lys Gly Lys Thr Pro Lys
    5795                5800                5805

Tyr Asn Pro Lys Asp Ser Gln Leu Tyr Lys Val Met Lys Asp Ala
    5810                5815                5820

Asn Asn Leu Ala Ser Glu Val Lys Tyr Lys Ala Asp Leu Lys Lys
    5825                5830                5835

Leu His Lys Pro Val Thr Asp Met Lys Glu Ser Leu Ile Met Asn
    5840                5845                5850

His Val Leu Asn Thr Ser Gln Leu Ala Ser Ser Tyr Gln Tyr Lys
    5855                5860                5865

Lys Lys Tyr Glu Lys Ser Lys Gly His Tyr His Thr Ile Pro Asp
    5870                5875                5880

Asn Leu Glu Gln Leu His Leu Lys Glu Ala Thr Glu Leu Gln Ser
    5885                5890                5895

Ile Val Lys Tyr Lys Glu Lys Tyr Glu Lys Glu Arg Gly Lys Pro
    5900                5905                5910

Met Leu Asp Phe Glu Thr Pro Thr Tyr Ile Thr Ala Lys Glu Ser
    5915                5920                5925

Gln Gln Met Gln Ser Gly Lys Glu Tyr Arg Lys Asp Tyr Glu Glu
    5930                5935                5940

Ser Ile Lys Gly Arg Asn Leu Thr Gly Leu Glu Val Thr Pro Ala
    5945                5950                5955

Leu Leu His Val Lys Tyr Ala Thr Lys Ile Ala Ser Glu Lys Glu
    5960                5965                5970

Tyr Arg Lys Asp Leu Glu Glu Ser Ile Arg Gly Lys Gly Leu Thr
```

```
    5975                5980                5985

Glu Met  Glu Asp Thr Pro Asp  Met Leu Arg Ala Lys  Asn Ala Thr
    5990                5995                6000

Gln Ile  Leu Asn Glu Lys Glu  Tyr Lys Arg Asp Leu  Glu Leu Glu
    6005                6010                6015

Val Lys  Gly Arg Gly Leu Asn  Ala Met Ala Asn Glu  Thr Pro Asp
    6020                6025                6030

Phe Met  Arg Ala Arg Asn Ala  Thr Asp Ile Ala Ser  Gln Ile Lys
    6035                6040                6045

Tyr Lys  Gln Ser Ala Glu Met  Glu Lys Ala Asn Phe  Thr Ser Val
    6050                6055                6060

Val Asp  Thr Pro Glu Ile Ile  His Ala Gln Gln Val  Lys Asn Leu
    6065                6070                6075

Ser Ser  Gln Lys Lys Tyr Lys  Glu Asp Ala Glu Lys  Ser Met Ser
    6080                6085                6090

Tyr Tyr  Glu Thr Val Leu Asp  Thr Pro Glu Ile Gln  Arg Val Arg
    6095                6100                6105

Glu Asn  Gln Lys Asn Phe Ser  Leu Leu Gln Tyr Gln  Cys Asp Leu
    6110                6115                6120

Lys Asn  Ser Lys Gly Lys Ile  Thr Val Val Gln Asp  Thr Pro Glu
    6125                6130                6135

Ile Leu  Arg Val Lys Glu Asn  Gln Lys Asn Phe Ser  Ser Val Leu
    6140                6145                6150

Tyr Lys  Glu Asp Val Ser Pro  Gly Thr Ala Ile Gly  Lys Thr Pro
    6155                6160                6165

Glu Met  Met Arg Val Lys Gln  Thr Gln Asp His Ile  Ser Ser Val
    6170                6175                6180

Lys Tyr  Lys Glu Ala Ile Gly  Gln Gly Thr Pro Ile  Pro Asp Leu
    6185                6190                6195

Pro Glu  Val Lys Arg Val Lys  Glu Thr Gln Lys His  Ile Ser Ser
    6200                6205                6210

Val Met  Tyr Lys Glu Asn Leu  Gly Thr Gly Ile Pro  Thr Thr Val
    6215                6220                6225

Thr Pro  Glu Ile Glu Arg Val  Lys Arg Asn Gln Glu  Asn Phe Ser
    6230                6235                6240

Ser Val  Leu Tyr Lys Glu Asn  Leu Gly Lys Gly Ile  Pro Thr Pro
    6245                6250                6255

Ile Thr  Pro Glu Met Glu Arg  Val Lys Arg Asn Gln  Glu Asn Phe
    6260                6265                6270

Ser Ser  Val Leu Tyr Lys Glu  Asn Met Gly Lys Gly  Thr Pro Leu
    6275                6280                6285

Ala Val  Thr Pro Glu Met Glu  Arg Val Lys His Asn  Gln Glu Asn
    6290                6295                6300

Ile Ser  Ser Val Leu Tyr Lys  Glu Asn Val Gly Lys  Ala Thr Ala
    6305                6310                6315

Thr Pro  Val Thr Pro Glu Met  Gln Arg Val Lys Arg  Asn Gln Glu
    6320                6325                6330

Asn Ile  Ser Ser Val Leu Tyr  Lys Glu Asn Leu Gly  Lys Ala Thr
    6335                6340                6345

Pro Thr  Pro Phe Thr Pro Glu  Met Glu Arg Val Lys  Arg Asn Gln
    6350                6355                6360

Glu Asn  Phe Ser Ser Val Leu  Tyr Lys Glu Asn Met  Arg Lys Ala
    6365                6370                6375
```

Thr Pro Thr Pro Val Thr Pro Glu Met Glu Arg Ala Lys Arg Asn
6380 6385 6390

Gln Glu Asn Ile Ser Ser Val Leu Tyr Ser Asp Ser Phe Arg Lys
6395 6400 6405

Gln Ile Gln Gly Lys Ala Ala Tyr Val Leu Asp Thr Pro Glu Met
6410 6415 6420

Arg Arg Val Arg Glu Thr Gln Arg His Ile Ser Thr Val Lys Tyr
6425 6430 6435

His Glu Asp Phe Glu Lys His Lys Gly Cys Phe Thr Pro Val Val
6440 6445 6450

Thr Asp Pro Ile Thr Glu Arg Val Lys Lys Asn Met Gln Asp Phe
6455 6460 6465

Ser Asp Ile Asn Tyr Arg Gly Ile Gln Arg Lys Val Val Glu Met
6470 6475 6480

Glu Gln Lys Arg Asn Asp Gln Asp Gln Glu Thr Ile Thr Gly Leu
6485 6490 6495

Arg Val Trp Arg Thr Asn Pro Gly Ser Val Phe Asp Tyr Asp Pro
6500 6505 6510

Ala Glu Asp Asn Ile Gln Ser Arg Ser Leu His Met Ile Asn Val
6515 6520 6525

Gln Ala Gln Arg Arg Ser Arg Glu Gln Ser Arg Ser Ala Ser Ala
6530 6535 6540

Leu Ser Ile Ser Gly Gly Glu Glu Lys Ser Glu His Ser Glu Ala
6545 6550 6555

Pro Asp His His Leu Ser Thr Tyr Ser Asp Gly Gly Val Phe Ala
6560 6565 6570

Val Ser Thr Ala Tyr Lys His Ala Lys Thr Thr Glu Leu Pro Gln
6575 6580 6585

Gln Arg Ser Ser Ser Val Ala Thr Gln Gln Thr Thr Val Ser Ser
6590 6595 6600

Ile Pro Ser His Pro Ser Thr Ala Gly Lys Ile Phe Arg Ala Met
6605 6610 6615

Tyr Asp Tyr Met Ala Ala Asp Ala Asp Glu Val Ser Phe Lys Asp
6620 6625 6630

Gly Asp Ala Ile Ile Asn Val Gln Ala Ile Asp Glu Gly Trp Met
6635 6640 6645

Tyr Gly Thr Val Gln Arg Thr Gly Arg Thr Gly Met Leu Pro Ala
6650 6655 6660

Asn Tyr Val Glu Ala Ile
6665

<210> SEQ ID NO 91
<211> LENGTH: 868
<212> TYPE: PRT
<213> ORGANISM: Homo sapiens

<400> SEQUENCE: 91

Met Ala Thr Phe Ile Ser Val Gln Leu Lys Lys Thr Ser Glu Val Asp
1 5 10 15

Leu Ala Lys Pro Leu Val Lys Phe Ile Gln Gln Thr Tyr Pro Ser Gly
20 25 30

Gly Glu Glu Gln Ala Gln Tyr Cys Arg Ala Ala Glu Glu Leu Ser Lys
35 40 45

Leu Arg Arg Ala Ala Val Gly Arg Pro Leu Asp Lys His Glu Gly Ala

```
    50                  55                  60

Leu Glu Thr Leu Leu Arg Tyr Tyr Asp Gln Ile Cys Ser Ile Glu Pro
65                  70                  75                  80

Lys Phe Pro Phe Ser Glu Asn Gln Ile Cys Leu Thr Phe Thr Trp Lys
                85                  90                  95

Asp Ala Phe Asp Lys Gly Ser Leu Phe Gly Gly Ser Val Lys Leu Ala
            100                 105                 110

Leu Ala Ser Leu Gly Tyr Glu Lys Ser Cys Val Leu Phe Asn Cys Ala
        115                 120                 125

Ala Leu Ala Ser Gln Ile Ala Ala Glu Gln Asn Leu Asp Asn Asp Glu
    130                 135                 140

Gly Leu Lys Ile Ala Ala Lys His Tyr Gln Phe Ala Ser Gly Ala Phe
145                 150                 155                 160

Leu His Ile Lys Glu Thr Val Leu Ser Ala Leu Ser Arg Glu Pro Thr
                165                 170                 175

Val Asp Ile Ser Pro Asp Thr Val Gly Thr Leu Ser Leu Ile Met Leu
            180                 185                 190

Ala Gln Ala Gln Glu Val Phe Phe Leu Lys Ala Thr Arg Asp Lys Met
        195                 200                 205

Lys Asp Ala Ile Ile Ala Lys Leu Ala Asn Gln Ala Ala Asp Tyr Phe
    210                 215                 220

Gly Asp Ala Phe Lys Gln Cys Gln Tyr Lys Asp Thr Leu Pro Lys Glu
225                 230                 235                 240

Val Phe Pro Val Leu Ala Ala Lys His Cys Ile Met Gln Ala Asn Ala
                245                 250                 255

Glu Tyr His Gln Ser Ile Leu Ala Lys Gln Gln Lys Lys Phe Gly Glu
            260                 265                 270

Glu Ile Ala Arg Leu Gln His Ala Ala Glu Leu Ile Lys Thr Val Ala
        275                 280                 285

Ser Arg Tyr Asp Glu Tyr Val Asn Val Lys Asp Phe Ser Asp Lys Ile
    290                 295                 300

Asn Arg Ala Leu Ala Ala Ala Lys Lys Asp Asn Asp Phe Ile Tyr His
305                 310                 315                 320

Asp Arg Val Pro Asp Leu Lys Asp Leu Asp Pro Ile Gly Lys Ala Thr
                325                 330                 335

Leu Val Lys Ser Thr Pro Val Asn Val Pro Ile Ser Gln Lys Phe Thr
            340                 345                 350

Asp Leu Phe Glu Lys Met Val Pro Val Ser Val Gln Gln Ser Leu Ala
        355                 360                 365

Ala Tyr Asn Gln Arg Lys Ala Asp Leu Val Asn Arg Ser Ile Ala Gln
    370                 375                 380

Met Arg Glu Ala Thr Thr Leu Ala Asn Gly Val Leu Ala Ser Leu Asn
385                 390                 395                 400

Leu Pro Ala Ala Ile Glu Asp Val Ser Gly Asp Thr Val Pro Gln Ser
                405                 410                 415

Ile Leu Thr Lys Ser Arg Ser Val Ile Glu Gln Gly Gly Ile Gln Thr
            420                 425                 430

Val Asp Gln Leu Ile Lys Glu Leu Pro Glu Leu Leu Gln Arg Asn Arg
        435                 440                 445

Glu Ile Leu Asp Glu Ser Leu Arg Leu Leu Asp Glu Glu Glu Ala Thr
    450                 455                 460

Asp Asn Asp Leu Arg Ala Lys Phe Lys Glu Arg Trp Gln Arg Thr Pro
465                 470                 475                 480
```

Ser Asn Glu Leu Tyr Lys Pro Leu Arg Ala Glu Gly Thr Asn Phe Arg
485 490 495

Thr Val Leu Asp Lys Ala Val Gln Ala Asp Gly Gln Val Lys Glu Cys
500 505 510

Tyr Gln Ser His Arg Asp Thr Ile Val Leu Leu Cys Lys Pro Glu Pro
515 520 525

Glu Leu Asn Ala Ala Ile Pro Ser Ala Asn Pro Ala Lys Thr Met Gln
530 535 540

Gly Ser Glu Val Val Asn Val Leu Lys Ser Leu Leu Ser Asn Leu Asp
545 550 555 560

Glu Val Lys Lys Glu Arg Glu Gly Leu Glu Asn Asp Leu Lys Ser Val
565 570 575

Asn Phe Asp Met Thr Ser Lys Phe Leu Thr Ala Leu Ala Gln Asp Gly
580 585 590

Val Ile Asn Glu Glu Ala Leu Ser Val Thr Glu Leu Asp Arg Val Tyr
595 600 605

Gly Gly Leu Thr Thr Lys Val Gln Glu Ser Leu Lys Lys Gln Glu Gly
610 615 620

Leu Leu Lys Asn Ile Gln Val Ser His Gln Glu Phe Ser Lys Met Lys
625 630 635 640

Gln Ser Asn Asn Glu Ala Asn Leu Arg Glu Glu Val Leu Lys Asn Leu
645 650 655

Ala Thr Ala Tyr Asp Asn Phe Val Glu Leu Val Ala Asn Leu Lys Glu
660 665 670

Gly Thr Lys Phe Tyr Asn Glu Leu Thr Glu Ile Leu Val Arg Phe Gln
675 680 685

Asn Lys Cys Ser Asp Ile Val Phe Ala Arg Lys Thr Glu Arg Asp Glu
690 695 700

Leu Leu Lys Asp Leu Gln Gln Ser Ile Ala Arg Glu Pro Ser Ala Pro
705 710 715 720

Ser Ile Pro Thr Pro Ala Tyr Gln Ser Ser Pro Ala Gly Gly His Ala
725 730 735

Pro Thr Pro Pro Thr Pro Ala Pro Arg Thr Met Pro Pro Thr Lys Pro
740 745 750

Gln Pro Pro Ala Arg Pro Pro Pro Pro Val Leu Pro Ala Asn Arg Ala
755 760 765

Pro Ser Ala Thr Ala Pro Ser Pro Val Gly Ala Gly Thr Ala Ala Pro
770 775 780

Ala Pro Ser Gln Thr Pro Gly Ser Ala Pro Pro Pro Gln Ala Gln Gly
785 790 795 800

Pro Pro Tyr Pro Thr Tyr Pro Gly Tyr Pro Gly Tyr Cys Gln Met Pro
805 810 815

Met Pro Met Gly Tyr Asn Pro Tyr Ala Tyr Gly Gln Tyr Asn Met Pro
820 825 830

Tyr Pro Pro Val Tyr His Gln Ser Pro Gly Gln Ala Pro Tyr Pro Gly
835 840 845

Pro Gln Gln Pro Ser Tyr Pro Phe Pro Gln Pro Pro Gln Gln Ser Tyr
850 855 860

Tyr Pro Gln Gln
865

<210> SEQ ID NO 92
<211> LENGTH: 146

<212> TYPE: PRT
<213> ORGANISM: Homo sapiens

<400> SEQUENCE: 92

Met Arg Leu Leu Gln Leu Leu Phe Arg Ala Ser Pro Ala Thr Leu Leu
1 5 10 15

Leu Val Leu Cys Leu Gln Leu Gly Ala Asn Lys Ala Gln Asp Asn Thr
20 25 30

Arg Lys Ile Ile Ile Lys Asn Phe Asp Ile Pro Lys Ser Val Arg Pro
35 40 45

Asn Asp Glu Val Thr Ala Val Leu Ala Val Gln Thr Glu Leu Lys Glu
50 55 60

Cys Met Val Val Lys Thr Tyr Leu Ile Ser Ser Ile Pro Leu Gln Gly
65 70 75 80

Ala Phe Asn Tyr Lys Tyr Thr Ala Cys Leu Cys Asp Asp Asn Pro Lys
85 90 95

Thr Phe Tyr Trp Asp Phe Tyr Thr Asn Arg Thr Val Gln Ile Ala Ala
100 105 110

Val Val Asp Val Ile Arg Glu Leu Gly Ile Cys Pro Asp Asp Ala Ala
115 120 125

Val Ile Pro Ile Lys Asn Asn Arg Phe Tyr Thr Ile Glu Ile Leu Lys
130 135 140

Val Glu
145

<210> SEQ ID NO 93
<211> LENGTH: 261
<212> TYPE: PRT
<213> ORGANISM: Homo sapiens

<400> SEQUENCE: 93

Met Trp Val Pro Val Val Phe Leu Thr Leu Ser Val Thr Trp Ile Gly
1 5 10 15

Ala Ala Pro Leu Ile Leu Ser Arg Ile Val Gly Gly Trp Glu Cys Glu
20 25 30

Lys His Ser Gln Pro Trp Gln Val Leu Val Ala Ser Arg Gly Arg Ala
35 40 45

Val Cys Gly Gly Val Leu Val His Pro Gln Trp Val Leu Thr Ala Ala
50 55 60

His Cys Ile Arg Asn Lys Ser Val Ile Leu Leu Gly Arg His Ser Leu
65 70 75 80

Phe His Pro Glu Asp Thr Gly Gln Val Phe Gln Val Ser His Ser Phe
85 90 95

Pro His Pro Leu Tyr Asp Met Ser Leu Leu Lys Asn Arg Phe Leu Arg
100 105 110

Pro Gly Asp Asp Ser Ser His Asp Leu Met Leu Leu Arg Leu Ser Glu
115 120 125

Pro Ala Glu Leu Thr Asp Ala Val Lys Val Met Asp Leu Pro Thr Gln
130 135 140

Glu Pro Ala Leu Gly Thr Thr Cys Tyr Ala Ser Gly Trp Gly Ser Ile
145 150 155 160

Glu Pro Glu Glu Phe Leu Thr Pro Lys Lys Leu Gln Cys Val Asp Leu
165 170 175

His Val Ile Ser Asn Asp Val Cys Ala Gln Val His Pro Gln Lys Val
180 185 190

```
Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
    210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260


<210> SEQ ID NO 94
<211> LENGTH: 386
<212> TYPE: PRT
<213> ORGANISM: Homo sapiens

<400> SEQUENCE: 94

Met Arg Ala Ala Pro Leu Leu Leu Ala Arg Ala Ala Ser Leu Ser Leu
1               5                   10                  15

Gly Phe Leu Phe Leu Leu Phe Phe Trp Leu Asp Arg Ser Val Leu Ala
            20                  25                  30

Lys Glu Leu Lys Phe Val Thr Leu Val Phe Arg His Gly Asp Arg Ser
        35                  40                  45

Pro Ile Asp Thr Phe Pro Thr Asp Pro Ile Lys Glu Ser Ser Trp Pro
    50                  55                  60

Gln Gly Phe Gly Gln Leu Thr Gln Leu Gly Met Glu Gln His Tyr Glu
65                  70                  75                  80

Leu Gly Glu Tyr Ile Arg Lys Arg Tyr Arg Lys Phe Leu Asn Glu Ser
                85                  90                  95

Tyr Lys His Glu Gln Val Tyr Ile Arg Ser Thr Asp Val Asp Arg Thr
            100                 105                 110

Leu Met Ser Ala Met Thr Asn Leu Ala Ala Leu Phe Pro Pro Glu Gly
        115                 120                 125

Val Ser Ile Trp Asn Pro Ile Leu Leu Trp Gln Pro Ile Pro Val His
    130                 135                 140

Thr Val Pro Leu Ser Glu Asp Gln Leu Leu Tyr Leu Pro Phe Arg Asn
145                 150                 155                 160

Cys Pro Arg Phe Gln Glu Leu Glu Ser Glu Thr Leu Lys Ser Glu Glu
                165                 170                 175

Phe Gln Lys Arg Leu His Pro Tyr Lys Asp Phe Ile Ala Thr Leu Gly
            180                 185                 190

Lys Leu Ser Gly Leu His Gly Gln Asp Leu Phe Gly Ile Trp Ser Lys
        195                 200                 205

Val Tyr Asp Pro Leu Tyr Cys Glu Ser Val His Asn Phe Thr Leu Pro
    210                 215                 220

Ser Trp Ala Thr Glu Asp Thr Met Thr Lys Leu Arg Glu Leu Ser Glu
225                 230                 235                 240

Leu Ser Leu Leu Ser Leu Tyr Gly Ile His Lys Gln Lys Glu Lys Ser
                245                 250                 255

Arg Leu Gln Gly Gly Val Leu Val Asn Glu Ile Leu Asn His Met Lys
            260                 265                 270

Arg Ala Thr Gln Ile Pro Ser Tyr Lys Lys Leu Ile Met Tyr Ser Ala
        275                 280                 285

His Asp Thr Thr Val Ser Gly Leu Gln Met Ala Leu Asp Val Tyr Asn
    290                 295                 300
```

Gly Leu Leu Pro Pro Tyr Ala Ser Cys His Leu Thr Glu Leu Tyr Phe
305 310 315 320

Glu Lys Gly Glu Tyr Phe Val Glu Met Tyr Tyr Arg Asn Glu Thr Gln
325 330 335

His Glu Pro Tyr Pro Leu Met Leu Pro Gly Cys Ser Pro Ser Cys Pro
340 345 350

Leu Glu Arg Phe Ala Glu Leu Val Gly Pro Val Ile Pro Gln Asp Trp
355 360 365

Ser Thr Glu Cys Met Thr Thr Asn Ser His Gln Gly Thr Glu Asp Ser
370 375 380

Thr Asp
385

<210> SEQ ID NO 95
<211> LENGTH: 693
<212> TYPE: PRT
<213> ORGANISM: Homo sapiens

<400> SEQUENCE: 95

Met Ala Ala Leu Gly Val Gln Ser Ile Asn Trp Gln Thr Ala Phe Asn
1 5 10 15

Arg Gln Ala His His Thr Asp Lys Phe Ser Ser Gln Glu Leu Ile Leu
20 25 30

Arg Arg Gly Gln Asn Phe Gln Val Leu Met Ile Met Asn Lys Gly Leu
35 40 45

Gly Ser Asn Glu Arg Leu Glu Phe Ile Val Ser Thr Gly Pro Tyr Pro
50 55 60

Ser Glu Ser Ala Met Thr Lys Ala Val Phe Pro Leu Ser Asn Gly Ser
65 70 75 80

Ser Gly Gly Trp Ser Ala Val Leu Gln Ala Ser Asn Gly Asn Thr Leu
85 90 95

Thr Ile Ser Ile Ser Ser Pro Ala Ser Ala Pro Ile Gly Arg Tyr Thr
100 105 110

Met Ala Leu Gln Ile Phe Ser Gln Gly Gly Ile Ser Ser Val Lys Leu
115 120 125

Gly Thr Phe Ile Leu Leu Phe Asn Pro Trp Leu Asn Val Asp Ser Val
130 135 140

Phe Met Gly Asn His Ala Glu Arg Glu Glu Tyr Val Gln Glu Asp Ala
145 150 155 160

Gly Ile Ile Phe Val Gly Ser Thr Asn Arg Ile Gly Met Ile Gly Trp
165 170 175

Asn Phe Gly Gln Phe Glu Glu Asp Ile Leu Ser Ile Cys Leu Ser Ile
180 185 190

Leu Asp Arg Ser Leu Asn Phe Arg Arg Asp Ala Ala Thr Asp Val Ala
195 200 205

Ser Arg Asn Asp Pro Lys Tyr Val Gly Arg Val Leu Ser Ala Met Ile
210 215 220

Asn Ser Asn Asp Asp Asn Gly Val Leu Ala Gly Asn Trp Ser Gly Thr
225 230 235 240

Tyr Thr Gly Gly Arg Asp Pro Arg Ser Trp Asn Gly Ser Val Glu Ile
245 250 255

Leu Lys Asn Trp Lys Lys Ser Gly Phe Ser Pro Val Arg Tyr Gly Gln
260 265 270

Cys Trp Val Phe Ala Gly Thr Leu Asn Thr Ala Leu Arg Ser Leu Gly

```
        275                 280                 285

Ile Pro Ser Arg Val Ile Thr Asn Phe Asn Ser Ala His Asp Thr Asp
    290                 295                 300

Arg Asn Leu Ser Val Asp Val Tyr Tyr Asp Pro Met Gly Asn Pro Leu
305                 310                 315                 320

Asp Lys Gly Ser Asp Ser Val Trp Asn Phe His Val Trp Asn Glu Gly
                325                 330                 335

Trp Phe Val Arg Ser Asp Leu Gly Pro Ser Tyr Gly Gly Trp Gln Val
            340                 345                 350

Leu Asp Ala Thr Pro Gln Glu Arg Ser Gln Gly Val Phe Gln Cys Gly
        355                 360                 365

Pro Ala Ser Val Ile Gly Val Arg Glu Gly Asp Val Gln Leu Asn Phe
    370                 375                 380

Asp Met Pro Phe Ile Phe Ala Glu Val Asn Ala Asp Arg Ile Thr Trp
385                 390                 395                 400

Leu Tyr Asp Asn Thr Thr Gly Lys Gln Trp Lys Asn Ser Val Asn Ser
                405                 410                 415

His Thr Ile Gly Arg Tyr Ile Ser Thr Lys Ala Val Gly Ser Asn Ala
            420                 425                 430

Arg Met Asp Val Thr Asp Lys Tyr Lys Tyr Pro Glu Gly Ser Asp Gln
        435                 440                 445

Glu Arg Gln Val Phe Gln Lys Ala Leu Gly Lys Leu Lys Pro Asn Thr
    450                 455                 460

Pro Phe Ala Ala Thr Ser Ser Met Gly Leu Glu Thr Glu Glu Gln Glu
465                 470                 475                 480

Pro Ser Ile Ile Gly Lys Leu Lys Val Ala Gly Met Leu Ala Val Gly
                485                 490                 495

Lys Glu Val Asn Leu Val Leu Leu Leu Lys Asn Leu Ser Arg Asp Thr
            500                 505                 510

Lys Thr Val Thr Val Asn Met Thr Ala Trp Thr Ile Ile Tyr Asn Gly
        515                 520                 525

Thr Leu Val His Glu Val Trp Lys Asp Ser Ala Thr Met Ser Leu Asp
    530                 535                 540

Pro Glu Glu Glu Ala Glu His Pro Ile Lys Ile Ser Tyr Ala Gln Tyr
545                 550                 555                 560

Glu Lys Tyr Leu Lys Ser Asp Asn Met Ile Arg Ile Thr Ala Val Cys
                565                 570                 575

Lys Val Pro Asp Glu Ser Glu Val Val Val Glu Arg Asp Ile Ile Leu
            580                 585                 590

Asp Asn Pro Thr Leu Thr Leu Glu Val Leu Asn Glu Ala Arg Val Arg
        595                 600                 605

Lys Pro Val Asn Val Gln Met Leu Phe Ser Asn Pro Leu Asp Glu Pro
    610                 615                 620

Val Arg Asp Cys Val Leu Met Val Glu Gly Ser Gly Leu Leu Leu Gly
625                 630                 635                 640

Asn Leu Lys Ile Asp Val Pro Thr Leu Gly Pro Lys Glu Gly Ser Arg
                645                 650                 655

Val Arg Phe Asp Ile Leu Pro Ser Arg Ser Gly Thr Lys Gln Leu Leu
            660                 665                 670

Ala Asp Phe Ser Cys Asn Lys Phe Pro Ala Ile Lys Ala Met Leu Ser
        675                 680                 685

Ile Asp Val Ala Glu
    690
```

<210> SEQ ID NO 96
<211> LENGTH: 259
<212> TYPE: PRT
<213> ORGANISM: Homo sapiens

<400> SEQUENCE: 96

Met Asn Ile Leu Ala Pro Val Arg Arg Asp Arg Val Leu Ala Glu Leu
1 5 10 15

Pro Gln Cys Leu Arg Lys Glu Ala Ala Leu His Gly His Lys Asp Phe
20 25 30

His Pro Arg Val Thr Cys Ala Cys Gln Glu His Arg Thr Gly Thr Val
35 40 45

Gly Phe Lys Ile Ser Lys Val Ile Val Val Gly Asp Leu Ser Val Gly
50 55 60

Lys Thr Cys Leu Ile Asn Arg Phe Cys Lys Asp Thr Phe Asp Lys Asn
65 70 75 80

Tyr Lys Ala Thr Ile Gly Val Asp Phe Glu Met Glu Arg Phe Glu Val
85 90 95

Leu Gly Ile Pro Phe Ser Leu Gln Leu Trp Asp Thr Ala Gly Gln Glu
100 105 110

Arg Phe Lys Cys Ile Ala Ser Thr Tyr Tyr Arg Gly Ala Gln Ala Ile
115 120 125

Ile Ile Val Phe Asn Leu Asn Asp Val Ala Ser Leu Glu His Thr Lys
130 135 140

Gln Trp Leu Ala Asp Ala Leu Lys Glu Asn Asp Pro Ser Ser Val Leu
145 150 155 160

Leu Phe Leu Val Gly Ser Lys Lys Asp Leu Ser Thr Pro Ala Gln Tyr
165 170 175

Ala Leu Met Glu Lys Asp Ala Leu Gln Val Ala Gln Glu Met Lys Ala
180 185 190

Glu Tyr Trp Ala Val Ser Ser Leu Thr Gly Glu Asn Val Arg Glu Phe
195 200 205

Phe Phe Arg Val Ala Ala Leu Thr Phe Glu Ala Asn Val Leu Ala Glu
210 215 220

Leu Glu Lys Ser Gly Ala Arg Arg Ile Gly Asp Val Val Arg Ile Asn
225 230 235 240

Ser Asp Asp Ser Asn Leu Tyr Leu Thr Ala Ser Lys Lys Lys Pro Thr
245 250 255

Cys Cys Pro

<210> SEQ ID NO 97
<211> LENGTH: 462
<212> TYPE: PRT
<213> ORGANISM: Homo sapiens

<400> SEQUENCE: 97

Met Lys Pro Asn Ile Ile Phe Val Leu Ser Leu Leu Leu Ile Leu Glu
1 5 10 15

Lys Gln Ala Ala Val Met Gly Gln Lys Gly Gly Ser Lys Gly Arg Leu
20 25 30

Pro Ser Glu Phe Ser Gln Phe Pro His Gly Gln Lys Gly Gln His Tyr
35 40 45

Ser Gly Gln Lys Gly Lys Gln Gln Thr Glu Ser Lys Gly Ser Phe Ser
50 55 60

```
Ile Gln Tyr Thr Tyr His Val Asp Ala Asn Asp His Asp Gln Ser Arg
65                  70                  75                  80

Lys Ser Gln Gln Tyr Asp Leu Asn Ala Leu His Lys Thr Thr Lys Ser
                85                  90                  95

Gln Arg His Leu Gly Gly Ser Gln Gln Leu Leu His Asn Lys Gln Glu
            100                 105                 110

Gly Arg Asp His Asp Lys Ser Lys Gly His Phe His Arg Val Val Ile
        115                 120                 125

His His Lys Gly Gly Lys Ala His Arg Gly Thr Gln Asn Pro Ser Gln
    130                 135                 140

Asp Gln Gly Asn Ser Pro Ser Gly Lys Gly Ile Ser Ser Gln Tyr Ser
145                 150                 155                 160

Asn Thr Glu Glu Arg Leu Trp Val His Gly Leu Ser Lys Glu Gln Thr
                165                 170                 175

Ser Val Ser Gly Ala Gln Lys Gly Arg Lys Gln Gly Gly Ser Gln Ser
            180                 185                 190

Ser Tyr Val Leu Gln Thr Glu Glu Leu Val Ala Asn Lys Gln Gln Arg
        195                 200                 205

Glu Thr Lys Asn Ser His Gln Asn Lys Gly His Tyr Gln Asn Val Val
    210                 215                 220

Glu Val Arg Glu Glu His Ser Ser Lys Val Gln Thr Ser Leu Cys Pro
225                 230                 235                 240

Ala His Gln Asp Lys Leu Gln His Gly Ser Lys Asp Ile Phe Ser Thr
                245                 250                 255

Gln Asp Glu Leu Leu Val Tyr Asn Lys Asn Gln His Gln Thr Lys Asn
            260                 265                 270

Leu Asn Gln Asp Gln Gln His Gly Arg Lys Ala Asn Lys Ile Ser Tyr
        275                 280                 285

Gln Ser Ser Ser Thr Glu Glu Arg Arg Leu His Tyr Gly Glu Asn Gly
    290                 295                 300

Val Gln Lys Asp Val Ser Gln Ser Ser Ile Tyr Ser Gln Thr Glu Glu
305                 310                 315                 320

Lys Ala Gln Gly Lys Ser Gln Lys Gln Ile Thr Ile Pro Ser Gln Glu
                325                 330                 335

Gln Glu His Ser Gln Lys Ala Asn Lys Ile Ser Tyr Gln Ser Ser Ser
            340                 345                 350

Thr Glu Glu Arg Arg Leu His Tyr Gly Glu Asn Gly Val Gln Lys Asp
        355                 360                 365

Val Ser Gln Arg Ser Ile Tyr Ser Gln Thr Glu Lys Leu Val Ala Gly
    370                 375                 380

Lys Ser Gln Ile Gln Ala Pro Asn Pro Lys Gln Glu Pro Trp His Gly
385                 390                 395                 400

Glu Asn Ala Lys Gly Glu Ser Gly Gln Ser Thr Asn Arg Glu Gln Asp
                405                 410                 415

Leu Leu Ser His Glu Gln Lys Gly Arg His Gln His Gly Ser His Gly
            420                 425                 430

Gly Leu Asp Ile Val Ile Ile Glu Gln Glu Asp Asp Ser Asp Arg His
        435                 440                 445

Leu Ala Gln His Leu Asn Asn Asp Arg Asn Pro Leu Phe Thr
    450                 455                 460
```

<210> SEQ ID NO 98
<211> LENGTH: 582
<212> TYPE: PRT

<213> ORGANISM: Homo sapiens

<400> SEQUENCE: 98

```
Met Lys Ser Ile Ile Leu Phe Val Leu Ser Leu Leu Leu Ile Leu Glu
1               5                   10                  15

Lys Gln Ala Ala Val Met Gly Gln Lys Gly Gly Ser Lys Gly Gln Leu
            20                  25                  30

Pro Ser Gly Ser Ser Gln Phe Pro His Gly Gln Lys Gly Gln His Tyr
        35                  40                  45

Phe Gly Gln Lys Asp Gln Gln His Thr Lys Ser Lys Gly Ser Phe Ser
    50                  55                  60

Ile Gln His Thr Tyr His Val Asp Ile Asn Asp His Asp Trp Thr Arg
65                  70                  75                  80

Lys Ser Gln Gln Tyr Asp Leu Asn Ala Leu His Lys Ala Thr Lys Ser
                85                  90                  95

Lys Gln His Leu Gly Gly Ser Gln Gln Leu Leu Asn Tyr Lys Gln Glu
            100                 105                 110

Gly Arg Asp His Asp Lys Ser Lys Gly His Phe His Met Ile Val Ile
        115                 120                 125

His His Lys Gly Gly Gln Ala His His Gly Thr Gln Asn Pro Ser Gln
    130                 135                 140

Asp Gln Gly Asn Ser Pro Ser Gly Lys Gly Leu Ser Ser Gln Cys Ser
145                 150                 155                 160

Asn Thr Glu Lys Arg Leu Trp Val His Gly Leu Ser Lys Glu Gln Ala
                165                 170                 175

Ser Ala Ser Gly Ala Gln Lys Gly Arg Thr Gln Gly Gly Ser Gln Ser
            180                 185                 190

Ser Tyr Val Leu Gln Thr Glu Glu Leu Val Val Asn Lys Gln Gln Arg
        195                 200                 205

Glu Thr Lys Asn Ser His Gln Asn Lys Gly His Tyr Gln Asn Val Val
    210                 215                 220

Asp Val Arg Glu Glu His Ser Ser Lys Leu Gln Thr Ser Leu His Pro
225                 230                 235                 240

Ala His Gln Asp Arg Leu Gln His Gly Pro Lys Asp Ile Phe Thr Thr
                245                 250                 255

Gln Asp Glu Leu Leu Val Tyr Asn Lys Asn Gln His Gln Thr Lys Asn
            260                 265                 270

Leu Ser Gln Asp Gln Glu His Gly Arg Lys Ala His Lys Ile Ser Tyr
        275                 280                 285

Pro Ser Ser Arg Thr Glu Glu Arg Gln Leu His His Gly Glu Lys Ser
    290                 295                 300

Val Gln Lys Asp Val Ser Lys Gly Ser Ile Ser Ile Gln Thr Glu Glu
305                 310                 315                 320

Lys Ile His Gly Lys Ser Gln Asn Gln Val Thr Ile His Ser Gln Asp
                325                 330                 335

Gln Glu His Gly His Lys Glu Asn Lys Ile Ser Tyr Gln Ser Ser Ser
            340                 345                 350

Thr Glu Glu Arg His Leu Asn Cys Gly Glu Lys Gly Ile Gln Lys Gly
        355                 360                 365

Val Ser Lys Gly Ser Ile Ser Ile Gln Thr Glu Glu Gln Ile His Gly
    370                 375                 380

Lys Ser Gln Asn Gln Val Arg Ile Pro Ser Gln Ala Gln Glu Tyr Gly
385                 390                 395                 400
```

His Lys Glu Asn Lys Ile Ser Tyr Gln Ser Ser Ser Thr Glu Glu Arg
405 410 415

Arg Leu Asn Ser Gly Glu Lys Asp Val Gln Lys Gly Val Ser Lys Gly
420 425 430

Ser Ile Ser Ile Gln Thr Glu Glu Lys Ile His Gly Lys Ser Gln Asn
435 440 445

Gln Val Thr Ile Pro Ser Gln Asp Gln Glu His Gly His Lys Glu Asn
450 455 460

Lys Met Ser Tyr Gln Ser Ser Ser Thr Glu Glu Arg Arg Leu Asn Tyr
465 470 475 480

Gly Gly Lys Ser Thr Gln Lys Asp Val Ser Gln Ser Ser Ile Ser Phe
485 490 495

Gln Ile Glu Lys Leu Val Glu Gly Lys Ser Gln Ile Gln Thr Pro Asn
500 505 510

Pro Asn Gln Asp Gln Trp Ser Gly Gln Asn Ala Lys Gly Lys Ser Gly
515 520 525

Gln Ser Ala Asp Ser Lys Gln Asp Leu Leu Ser His Glu Gln Lys Gly
530 535 540

Arg Tyr Lys Gln Glu Ser Ser Glu Ser His Asn Ile Val Ile Thr Glu
545 550 555 560

His Glu Val Ala Gln Asp Asp His Leu Thr Gln Gln Tyr Asn Glu Asp
565 570 575

Arg Asn Pro Ile Ser Thr
580

<210> SEQ ID NO 99
<211> LENGTH: 514
<212> TYPE: PRT
<213> ORGANISM: Homo sapiens

<400> SEQUENCE: 99

Met Val Leu Asp Leu Asp Leu Phe Arg Val Asp Lys Gly Gly Asp Pro
1 5 10 15

Ala Leu Ile Arg Glu Thr Gln Glu Lys Arg Phe Lys Asp Pro Gly Leu
20 25 30

Val Asp Gln Leu Val Lys Ala Asp Ser Glu Trp Arg Arg Cys Arg Phe
35 40 45

Arg Ala Asp Asn Leu Asn Lys Leu Lys Asn Leu Cys Ser Lys Thr Ile
50 55 60

Gly Glu Lys Met Lys Lys Lys Glu Pro Val Gly Asp Asp Glu Ser Val
65 70 75 80

Pro Glu Asn Val Leu Ser Phe Asp Asp Leu Thr Ala Asp Ala Leu Ala
85 90 95

Asn Leu Lys Val Ser Gln Ile Lys Lys Val Arg Leu Leu Ile Asp Glu
100 105 110

Ala Ile Leu Lys Cys Asp Ala Glu Arg Ile Lys Leu Glu Ala Glu Arg
115 120 125

Phe Glu Asn Leu Arg Glu Ile Gly Asn Leu Leu His Pro Ser Val Pro
130 135 140

Ile Ser Asn Asp Glu Asp Val Asp Asn Lys Val Glu Arg Ile Trp Gly
145 150 155 160

Asp Cys Thr Val Arg Lys Lys Tyr Ser His Val Asp Leu Val Val Met
165 170 175

Val Asp Gly Phe Glu Gly Glu Lys Gly Ala Val Val Ala Gly Ser Arg
180 185 190

Gly Tyr Phe Leu Lys Gly Val Leu Val Phe Leu Glu Gln Ala Leu Ile
195 200 205

Gln Tyr Ala Leu Arg Thr Leu Gly Ser Arg Gly Tyr Ile Pro Ile Tyr
210 215 220

Thr Pro Phe Phe Met Arg Lys Glu Val Met Gln Glu Val Ala Gln Leu
225 230 235 240

Ser Gln Phe Asp Glu Glu Leu Tyr Lys Val Ile Gly Lys Gly Ser Glu
245 250 255

Lys Ser Asp Asp Asn Ser Tyr Asp Glu Lys Tyr Leu Ile Ala Thr Ser
260 265 270

Glu Gln Pro Ile Ala Ala Leu His Arg Asp Glu Trp Leu Arg Pro Glu
275 280 285

Asp Leu Pro Ile Lys Tyr Ala Gly Leu Ser Thr Cys Phe Arg Gln Glu
290 295 300

Val Gly Ser His Gly Arg Asp Thr Arg Gly Ile Phe Arg Val His Gln
305 310 315 320

Phe Glu Lys Ile Glu Gln Phe Val Tyr Ser Ser Pro His Asp Asn Lys
325 330 335

Ser Trp Glu Met Phe Glu Glu Met Ile Thr Thr Ala Glu Glu Phe Tyr
340 345 350

Gln Ser Leu Gly Ile Pro Tyr His Ile Val Asn Ile Val Ser Gly Ser
355 360 365

Leu Asn His Ala Ala Ser Lys Lys Leu Asp Leu Glu Ala Trp Phe Pro
370 375 380

Gly Ser Gly Ala Phe Arg Glu Leu Val Ser Cys Ser Asn Cys Thr Asp
385 390 395 400

Tyr Gln Ala Arg Arg Leu Arg Ile Arg Tyr Gly Gln Thr Lys Lys Met
405 410 415

Met Asp Lys Val Glu Phe Val His Met Leu Asn Ala Thr Met Cys Ala
420 425 430

Thr Thr Arg Thr Ile Cys Ala Ile Leu Glu Asn Tyr Gln Thr Glu Lys
435 440 445

Gly Ile Thr Val Pro Glu Lys Leu Lys Glu Phe Met Pro Pro Gly Leu
450 455 460

Gln Glu Leu Ile Pro Phe Val Lys Pro Ala Pro Ile Glu Gln Glu Pro
465 470 475 480

Ser Lys Lys Gln Lys Lys Gln His Glu Gly Ser Lys Lys Lys Ala Ala
485 490 495

Ala Arg Asp Val Thr Leu Glu Asn Arg Leu Gln Asn Met Glu Val Thr
500 505 510

Asp Ala

<210> SEQ ID NO 100
<211> LENGTH: 356
<212> TYPE: PRT
<213> ORGANISM: Homo sapiens

<400> SEQUENCE: 100

Met Ala Ala Ala Ala Lys Pro Asn Asn Leu Ser Leu Val Val His Gly
1 5 10 15

Pro Gly Asp Leu Arg Leu Glu Asn Tyr Pro Ile Pro Glu Pro Gly Pro
20 25 30

Asn Glu Val Leu Leu Arg Met His Ser Val Gly Ile Cys Gly Ser Asp
35 40 45

Val His Tyr Trp Glu Tyr Gly Arg Ile Gly Asn Phe Ile Val Lys Lys
    50                  55                  60

Pro Met Val Leu Gly His Glu Ala Ser Gly Thr Val Glu Lys Val Gly
65                  70                  75                  80

Ser Ser Val Lys His Leu Lys Pro Gly Asp Arg Val Ala Ile Glu Pro
                85                  90                  95

Gly Ala Pro Arg Glu Asn Asp Glu Phe Cys Lys Met Gly Arg Tyr Asn
            100                 105                 110

Leu Ser Pro Ser Ile Phe Phe Cys Ala Thr Pro Pro Asp Asp Gly Asn
        115                 120                 125

Leu Cys Arg Phe Tyr Lys His Asn Ala Ala Phe Cys Tyr Lys Leu Pro
    130                 135                 140

Asp Asn Val Thr Phe Glu Glu Gly Ala Leu Ile Glu Pro Leu Ser Val
145                 150                 155                 160

Gly Ile His Ala Cys Arg Arg Gly Gly Val Thr Leu Gly His Lys Val
                165                 170                 175

Leu Val Cys Gly Ala Gly Pro Ile Gly Met Val Thr Leu Leu Val Ala
            180                 185                 190

Lys Ala Met Gly Ala Ala Gln Val Val Val Thr Asp Leu Ser Ala Thr
        195                 200                 205

Arg Leu Ser Lys Ala Lys Glu Ile Gly Ala Asp Leu Val Leu Gln Ile
    210                 215                 220

Ser Lys Glu Ser Pro Gln Glu Ile Ala Arg Lys Val Glu Gly Gln Leu
225                 230                 235                 240

Gly Cys Lys Pro Glu Val Thr Ile Glu Cys Thr Gly Ala Glu Ala Ser
                245                 250                 255

Ile Gln Ala Gly Ile Tyr Ala Thr Arg Ser Gly Gly Asn Leu Val Leu
            260                 265                 270

Val Gly Leu Gly Ser Glu Met Thr Thr Val Pro Leu Leu His Ala Ala
        275                 280                 285

Ile Arg Glu Val Asp Ile Lys Gly Val Phe Arg Tyr Cys Asn Thr Trp
    290                 295                 300

Pro Val Ala Ile Ser Met Leu Ala Ser Lys Ser Val Asn Val Lys Pro
305                 310                 315                 320

Leu Val Thr His Arg Phe Pro Leu Glu Lys Ala Leu Glu Ala Phe Glu
                325                 330                 335

Thr Phe Lys Lys Gly Leu Gly Leu Lys Ile Met Leu Lys Cys Pro Ser
            340                 345                 350

Asp Gln Asn Pro
        355

<210> SEQ ID NO 101
<211> LENGTH: 449
<212> TYPE: PRT
<213> ORGANISM: Homo sapiens

<400> SEQUENCE: 101

Met Arg Glu Cys Ile Ser Ile His Val Gly Gln Ala Gly Val Gln Ile
1               5                   10                  15

Gly Asn Ala Cys Trp Glu Leu Tyr Cys Leu Glu His Gly Ile Gln Pro
            20                  25                  30

Asp Gly Gln Met Pro Ser Asp Lys Thr Ile Gly Gly Gly Asp Asp Ser
        35                  40                  45

Phe Asn Thr Phe Phe Ser Glu Thr Gly Ala Gly Lys His Val Pro Arg

```
    50                  55                  60

Ala Val Phe Val Asp Leu Glu Pro Thr Val Ile Asp Glu Val Arg Thr
65                  70                  75                  80

Gly Thr Tyr Arg Gln Leu Phe His Pro Glu Gln Leu Ile Thr Gly Lys
                85                  90                  95

Glu Asp Ala Ala Asn Asn Tyr Ala Arg Gly His Tyr Thr Ile Gly Lys
            100                 105                 110

Glu Ile Ile Asp Leu Val Leu Asp Arg Ile Arg Lys Leu Ala Asp Gln
        115                 120                 125

Cys Thr Gly Leu Gln Gly Phe Leu Val Phe His Ser Phe Gly Gly Gly
    130                 135                 140

Thr Gly Ser Gly Phe Thr Ser Leu Leu Met Glu Arg Leu Ser Val Asp
145                 150                 155                 160

Tyr Gly Lys Lys Ser Lys Leu Glu Phe Ser Ile Tyr Pro Ala Pro Gln
                165                 170                 175

Val Ser Thr Ala Val Val Glu Pro Tyr Asn Ser Ile Leu Thr Thr His
            180                 185                 190

Thr Thr Leu Glu His Ser Asp Cys Ala Phe Met Val Asp Asn Glu Ala
        195                 200                 205

Ile Tyr Asp Ile Cys Arg Arg Asn Leu Asp Ile Glu Arg Pro Thr Tyr
    210                 215                 220

Thr Asn Leu Asn Arg Leu Ile Ser Gln Ile Val Ser Ser Ile Thr Ala
225                 230                 235                 240

Ser Leu Arg Phe Asp Gly Ala Leu Asn Val Asp Leu Thr Glu Phe Gln
                245                 250                 255

Thr Asn Leu Val Pro Tyr Pro Arg Ile His Phe Pro Leu Ala Thr Tyr
            260                 265                 270

Ala Pro Val Ile Ser Ala Glu Lys Ala Tyr His Glu Gln Leu Thr Val
        275                 280                 285

Ala Glu Ile Thr Asn Ala Cys Phe Glu Pro Ala Asn Gln Met Val Lys
    290                 295                 300

Cys Asp Pro Arg His Gly Lys Tyr Met Ala Cys Cys Leu Leu Tyr Arg
305                 310                 315                 320

Gly Asp Val Val Pro Lys Asp Val Asn Ala Ala Ile Ala Thr Ile Lys
                325                 330                 335

Thr Lys Arg Thr Ile Gln Phe Val Asp Trp Cys Pro Thr Gly Phe Lys
            340                 345                 350

Val Gly Ile Asn Tyr Gln Pro Pro Thr Val Val Pro Gly Gly Asp Leu
        355                 360                 365

Ala Lys Val Gln Arg Ala Val Cys Met Leu Ser Asn Thr Thr Ala Val
    370                 375                 380

Ala Glu Ala Trp Ala Arg Leu Asp His Lys Phe Asp Leu Met Tyr Ala
385                 390                 395                 400

Lys Arg Ala Phe Val His Trp Tyr Val Gly Glu Gly Met Glu Glu Gly
                405                 410                 415

Glu Phe Ser Glu Ala Arg Glu Asp Met Ala Ala Leu Glu Lys Asp Tyr
            420                 425                 430

Glu Glu Val Gly Ala Asp Ser Ala Asp Gly Glu Asp Glu Gly Glu Glu
        435                 440                 445

Tyr

<210> SEQ ID NO 102
<211> LENGTH: 449
```

<212> TYPE: PRT
<213> ORGANISM: Homo sapiens

<400> SEQUENCE: 102

Met Arg Glu Cys Ile Ser Ile His Val Gly Gln Ala Gly Val Gln Ile
1 5 10 15

Gly Asn Ala Cys Trp Glu Leu Tyr Cys Leu Glu His Gly Ile Gln Pro
20 25 30

Asp Gly Gln Met Pro Ser Asp Lys Thr Ile Gly Gly Gly Asp Asp Ser
35 40 45

Phe Asn Thr Phe Phe Ser Glu Thr Gly Ala Gly Lys His Val Pro Arg
50 55 60

Ala Val Phe Val Asp Leu Glu Pro Thr Val Ile Asp Glu Val Arg Thr
65 70 75 80

Gly Thr Tyr Arg Gln Leu Phe His Pro Glu Gln Leu Ile Thr Gly Lys
85 90 95

Glu Asp Ala Ala Asn Asn Tyr Ala Arg Gly His Tyr Thr Ile Gly Lys
100 105 110

Glu Ile Ile Asp Leu Val Leu Asp Arg Ile Arg Lys Leu Ala Asp Gln
115 120 125

Cys Thr Gly Leu Gln Gly Phe Leu Val Phe His Ser Phe Gly Gly Gly
130 135 140

Thr Gly Ser Gly Phe Thr Ser Leu Leu Met Glu Arg Leu Ser Val Asp
145 150 155 160

Tyr Gly Lys Lys Ser Lys Leu Glu Phe Ser Ile Tyr Pro Ala Pro Gln
165 170 175

Val Ser Thr Ala Val Val Glu Pro Tyr Asn Ser Ile Leu Thr Thr His
180 185 190

Thr Thr Leu Glu His Ser Asp Cys Ala Phe Met Val Asp Asn Glu Ala
195 200 205

Ile Tyr Asp Ile Cys Arg Arg Asn Leu Asp Ile Glu Arg Pro Thr Tyr
210 215 220

Thr Asn Leu Asn Arg Leu Ile Ser Gln Ile Val Ser Ser Ile Thr Ala
225 230 235 240

Ser Leu Arg Phe Asp Gly Ala Leu Asn Val Asp Leu Thr Glu Phe Gln
245 250 255

Thr Asn Leu Val Pro Tyr Pro Arg Ile His Phe Pro Leu Ala Thr Tyr
260 265 270

Ala Pro Val Ile Ser Ala Glu Lys Ala Tyr His Glu Gln Leu Thr Val
275 280 285

Ala Glu Ile Thr Asn Ala Cys Phe Glu Pro Ala Asn Gln Met Val Lys
290 295 300

Cys Asp Pro Arg His Gly Lys Tyr Met Ala Cys Cys Leu Leu Tyr Arg
305 310 315 320

Gly Asp Val Val Pro Lys Asp Val Asn Ala Ala Ile Ala Thr Ile Lys
325 330 335

Thr Lys Arg Thr Ile Gln Phe Val Asp Trp Cys Pro Thr Gly Phe Lys
340 345 350

Val Gly Ile Asn Tyr Gln Pro Pro Thr Val Val Pro Gly Gly Asp Leu
355 360 365

Ala Lys Val Gln Arg Ala Val Cys Met Leu Ser Asn Thr Thr Ala Val
370 375 380

Ala Glu Ala Trp Ala Arg Leu Asp His Lys Phe Asp Leu Met Tyr Ala
385 390 395 400

```
Lys Arg Ala Phe Val His Trp Tyr Val Gly Glu Gly Met Glu Glu Gly
                405                 410                 415

Glu Phe Ser Glu Ala Arg Glu Asp Met Ala Ala Leu Glu Lys Asp Tyr
            420                 425                 430

Glu Glu Val Gly Ala Asp Ser Ala Asp Gly Glu Asp Glu Gly Glu Glu
        435                 440                 445

Tyr


<210> SEQ ID NO 103
<211> LENGTH: 448
<212> TYPE: PRT
<213> ORGANISM: Homo sapiens

<400> SEQUENCE: 103

Met Arg Glu Cys Ile Ser Val His Val Gly Gln Ala Gly Val Gln Met
1               5                   10                  15

Gly Asn Ala Cys Trp Glu Leu Tyr Cys Leu Glu His Gly Ile Gln Pro
            20                  25                  30

Asp Gly Gln Met Pro Ser Asp Lys Thr Ile Gly Gly Gly Asp Asp Ser
        35                  40                  45

Phe Thr Thr Phe Phe Cys Glu Thr Gly Ala Gly Lys His Val Pro Arg
    50                  55                  60

Ala Val Phe Val Asp Leu Glu Pro Thr Val Ile Asp Glu Ile Arg Asn
65                  70                  75                  80

Gly Pro Tyr Arg Gln Leu Phe His Pro Glu Gln Leu Ile Thr Gly Lys
                85                  90                  95

Glu Asp Ala Ala Asn Asn Tyr Ala Arg Gly His Tyr Thr Ile Gly Lys
            100                 105                 110

Glu Ile Ile Asp Pro Val Leu Asp Arg Ile Arg Lys Leu Ser Asp Gln
        115                 120                 125

Cys Thr Gly Leu Gln Gly Phe Leu Val Phe His Ser Phe Gly Gly Gly
    130                 135                 140

Thr Gly Ser Gly Phe Thr Ser Leu Leu Met Glu Arg Leu Ser Val Asp
145                 150                 155                 160

Tyr Gly Lys Lys Ser Lys Leu Glu Phe Ser Ile Tyr Pro Ala Pro Gln
                165                 170                 175

Val Ser Thr Ala Val Val Glu Pro Tyr Asn Ser Ile Leu Thr Thr His
            180                 185                 190

Thr Thr Leu Glu His Ser Asp Cys Ala Phe Met Val Asp Asn Glu Ala
        195                 200                 205

Ile Tyr Asp Ile Cys Arg Arg Asn Leu Asp Ile Glu Arg Pro Thr Tyr
    210                 215                 220

Thr Asn Leu Asn Arg Leu Ile Ser Gln Ile Val Ser Ser Ile Thr Ala
225                 230                 235                 240

Ser Leu Arg Phe Asp Gly Ala Leu Asn Val Asp Leu Thr Glu Phe Gln
                245                 250                 255

Thr Asn Leu Val Pro Tyr Pro Arg Ile His Phe Pro Leu Ala Thr Tyr
            260                 265                 270

Ala Pro Val Ile Ser Ala Glu Lys Ala Tyr His Glu Gln Leu Ser Val
        275                 280                 285

Ala Glu Ile Thr Asn Ala Cys Phe Glu Pro Ala Asn Gln Met Val Lys
    290                 295                 300

Cys Asp Pro Arg His Gly Lys Tyr Met Ala Cys Cys Leu Leu Tyr Arg
305                 310                 315                 320
```

Gly Asp Val Val Pro Lys Asp Val Asn Ala Ala Ile Ala Ala Ile Lys
325 330 335

Thr Lys Arg Ser Ile Gln Phe Val Asp Trp Cys Pro Thr Gly Phe Lys
340 345 350

Val Gly Ile Asn Tyr Gln Pro Pro Thr Val Val Pro Gly Gly Asp Leu
355 360 365

Ala Lys Val Gln Arg Ala Val Cys Met Leu Ser Asn Thr Thr Ala Ile
370 375 380

Ala Glu Ala Trp Ala Arg Leu Asp His Lys Phe Asp Leu Met Tyr Ala
385 390 395 400

Lys Arg Ala Phe Val His Trp Tyr Val Gly Glu Gly Met Glu Glu Gly
405 410 415

Glu Phe Ser Glu Ala Arg Glu Asp Met Ala Ala Leu Glu Lys Asp Tyr
420 425 430

Glu Glu Val Gly Ile Asp Ser Tyr Glu Asp Glu Asp Glu Gly Glu Glu
435 440 445

<210> SEQ ID NO 104
<211> LENGTH: 444
<212> TYPE: PRT
<213> ORGANISM: Homo sapiens

<400> SEQUENCE: 104

Met Arg Glu Ile Val His Ile Gln Ala Gly Gln Cys Gly Asn Gln Ile
1 5 10 15

Gly Ala Lys Phe Trp Glu Val Ile Ser Asp Glu His Gly Ile Asp Pro
20 25 30

Thr Gly Thr Tyr His Gly Asp Ser Asp Leu Gln Leu Asp Arg Ile Ser
35 40 45

Val Tyr Tyr Asn Glu Ala Thr Gly Gly Lys Tyr Val Pro Arg Ala Ile
50 55 60

Leu Val Asp Leu Glu Pro Gly Thr Met Asp Ser Val Arg Ser Gly Pro
65 70 75 80

Phe Gly Gln Ile Phe Arg Pro Asp Asn Phe Val Phe Gly Gln Ser Gly
85 90 95

Ala Gly Asn Asn Trp Ala Lys Gly His Tyr Thr Glu Gly Ala Glu Leu
100 105 110

Val Asp Ser Val Leu Asp Val Val Arg Lys Glu Ala Glu Ser Cys Asp
115 120 125

Cys Leu Gln Gly Phe Gln Leu Thr His Ser Leu Gly Gly Gly Thr Gly
130 135 140

Ser Gly Met Gly Thr Leu Leu Ile Ser Lys Ile Arg Glu Glu Tyr Pro
145 150 155 160

Asp Arg Ile Met Asn Thr Phe Ser Val Val Pro Ser Pro Lys Val Ser
165 170 175

Asp Thr Val Val Glu Pro Tyr Asn Ala Thr Leu Ser Val His Gln Leu
180 185 190

Val Glu Asn Thr Asp Glu Thr Tyr Cys Ile Asp Asn Glu Ala Leu Tyr
195 200 205

Asp Ile Cys Phe Arg Thr Leu Lys Leu Thr Thr Pro Thr Tyr Gly Asp
210 215 220

Leu Asn His Leu Val Ser Ala Thr Met Ser Gly Val Thr Thr Cys Leu
225 230 235 240

Arg Phe Pro Gly Gln Leu Asn Ala Asp Leu Arg Lys Leu Ala Val Asn

-continued

```
                245                 250                 255

Met Val Pro Phe Pro Arg Leu His Phe Phe Met Pro Gly Phe Ala Pro
            260                 265                 270

Leu Thr Ser Arg Gly Ser Gln Gln Tyr Arg Ala Leu Thr Val Pro Glu
        275                 280                 285

Leu Thr Gln Gln Val Phe Asp Ala Lys Asn Met Met Ala Ala Cys Asp
    290                 295                 300

Pro Arg His Gly Arg Tyr Leu Thr Val Ala Ala Val Phe Arg Gly Arg
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala
            340                 345                 350

Val Cys Asp Ile Pro Pro Arg Gly Leu Lys Met Ala Val Thr Phe Ile
        355                 360                 365

Gly Asn Ser Thr Ala Ile Gln Glu Leu Phe Lys Arg Ile Ser Glu Gln
    370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
            420                 425                 430

Glu Glu Asp Phe Gly Glu Glu Ala Glu Glu Glu Ala
        435                 440
```